US011597926B2

(12) United States Patent
Bleicher et al.

(10) Patent No.: US 11,597,926 B2
(45) **Date of Patent: *Mar. 7, 2023**

(54) THIOPHOSPHORAMIDITES

(71) Applicant: ROCHE INNOVATION CENTER COPENHAGEN A/S, Hørsholm (DK)

(72) Inventors: Konrad Bleicher, Basel (CH); Joerg Duschmalé, Basel (CH); Martina Brigitte Duschmalé, Basel (CH); Henrik Frydenlund Hansen, Hørsholm (DK); Troels Koch, Hørsholm (DK); Meiling Li, Basel (CH); Adrian Schaeublin, Basel (CH); Xi Shu, Hubei (CN); Yong Wu, Hubei (CN)

(73) Assignee: ROCHE INNOVATION CENTER COPENHAGEN A/S, Hørsholm (DK)

( * ) Notice: Subject to any disclaimer, the term of this patent is extended or adjusted under 35 U.S.C. 154(b) by 156 days.

This patent is subject to a terminal disclaimer.

(21) Appl. No.: 15/733,302

(22) PCT Filed: Dec. 21, 2018

(86) PCT No.: PCT/EP2018/086457

§ 371 (c)(1),
(2) Date: Jun. 22, 2020

(87) PCT Pub. No.: WO2019/122277

PCT Pub. Date: Jun. 27, 2019

(65) Prior Publication Data

US 2021/0115438 A1 Apr. 22, 2021

(30) Foreign Application Priority Data

Dec. 22, 2017 (WO) ................ PCT/CN2017/118043
Oct. 3, 2018 (EP) .................................... 18198487

(51) Int. Cl.

| | |
|---|---|
| ***C07H 19/10*** | (2006.01) |
| ***C07H 19/20*** | (2006.01) |
| ***C07H 21/04*** | (2006.01) |
| ***C12N 15/113*** | (2010.01) |
| ***C07H 1/00*** | (2006.01) |

(52) U.S. Cl.

CPC ............. *C12N 15/113* (2013.01); *C07H 1/00* (2013.01); *C07H 19/10* (2013.01); *C07H 19/20* (2013.01); *C07H 21/04* (2013.01); *C12N 2310/11* (2013.01); *C12N 2310/313* (2013.01); *C12N 2310/3231* (2013.01); *C12N 2310/341* (2013.01); *C12N 2330/30* (2013.01)

(58) Field of Classification Search

None
See application file for complete search history.

(56) References Cited

U.S. PATENT DOCUMENTS

2017/0319614 A1* 11/2017 Hossbach ................. A61P 9/00

FOREIGN PATENT DOCUMENTS

| | | | |
|---|---|---|---|
| CA | 2036287 | A1 | 12/1991 |
| EP | 3620519 | A1 | 3/2020 |
| JP | 06-009682 | A | 1/1994 |
| WO | 93/07883 | A1 | 4/1993 |
| WO | 98/39352 | A1 | 9/1998 |
| WO | 99/14226 | A2 | 3/1999 |
| WO | 2000/047599 | A1 | 8/2000 |
| WO | 00/66604 | A2 | 11/2000 |
| WO | 01/23613 | A1 | 4/2001 |
| WO | 2004/046160 | A2 | 6/2004 |
| WO | 2007/090071 | A2 | 8/2007 |
| WO | 2007/134181 | A2 | 11/2007 |
| WO | 2007/146511 | A2 | 12/2007 |
| WO | 2008/049085 | A1 | 4/2008 |
| WO | 2008/113832 | A2 | 9/2008 |

(Continued)

OTHER PUBLICATIONS

Iwamoto, N., et al., "Control of Phosphorothioate Stereochemistry Substantially Increases the Efficacy of Antisense Oligonucleotides," 2017, Nature Biotechnology, vol. 35, No. 9, pp. 845-855,11 pages.
Jastrzebska et al., "Thermal Stability and Conformation of Antiparallel Duplexes Formed by P-stereodefined Phosphorothioate DNA/LNA Chimeric Oligomers with DNA and RNA Matrices," 2015, Organic & Biomolecular Chemistry, vol. 13, No. 39, pp. 10032-10040, 9 pages.

(Continued)

*Primary Examiner* — Traviss C Mcintosh, III
(74) *Attorney, Agent, or Firm* — Holland & Hart LLP

(57) ABSTRACT

The present invention relates to a compound of formula (II) or (IIb) Wherein X, Y, $R^x$, $R^y$, $R^5$ and Nu are as defined in the description and in the claims. The compound of formula (II) can be used in the manufacture of oligonucleotides.

(II)

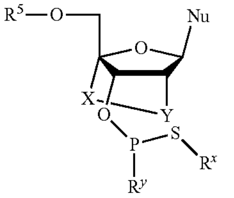

(IIb)

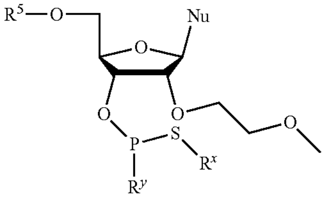

20 Claims, 23 Drawing Sheets

Specification includes a Sequence Listing.

(56) References Cited

FOREIGN PATENT DOCUMENTS

| | | | |
|---|---|---|---|
| WO | 2008/150729 | A2 | 12/2008 |
| WO | 2008/154401 | A2 | 12/2008 |
| WO | 2009/006478 | A2 | 1/2009 |
| WO | 2009/043353 | A2 | 4/2009 |
| WO | 2009/067647 | A1 | 5/2009 |
| WO | 2009/090182 | A1 | 7/2009 |
| WO | 2010/036698 | A1 | 4/2010 |
| WO | 20160079183 | A1 | 5/2010 |
| WO | 2010/077578 | A1 | 7/2010 |
| WO | 2011/017521 | A2 | 2/2011 |
| WO | 2011/156202 | A1 | 12/2011 |
| WO | 2012/109395 | A1 | 8/2012 |
| WO | 2013/033230 | A1 | 3/2013 |
| WO | 2013/036868 | A1 | 3/2013 |
| WO | 2013/154798 | A1 | 10/2013 |
| WO | 2014/076195 | A1 | 5/2014 |
| WO | 2014/076196 | A1 | 5/2014 |
| WO | 2014/168548 | A2 | 10/2014 |
| WO | 2014/179620 | A1 | 11/2014 |
| WO | 2014/207232 | A1 | 12/2014 |
| WO | 2016/127000 | A1 | 8/2016 |
| WO | 2016/127002 | A1 | 8/2016 |
| WO | 2016/172598 | A1 | 10/2016 |
| WO | 2017/067970 | A1 | 4/2017 |
| WO | 2017/173034 | A1 | 10/2017 |
| WO | 20170198775 | A1 | 11/2017 |
| WO | 2017/216340 | A1 | 12/2017 |
| WO | 2018/002105 | A1 | 1/2018 |
| WO | 2018/102397 | A1 | 6/2018 |

OTHER PUBLICATIONS

Karwowski et al., "Stereocontrolled Synthesis of LNA Dinucleoside Phosphorothioate by the Oxathiaphospholane approach," 2001, Bioorganic & Medicinal Chemistry Letters, vol. 11, No. 8, Amsterdam, NL, pp. 1001-1003, 3 pages.

Rahman, et al., "Synthesis and properties of 2', 4'-BNANC, a second generation of BNA", Nucleic Acids Symposium Series, vol. 49, No. 1, 2005, pp. 5-6, 2 pages.

Volk et al., "Development of Phosphorothioate DNA and DNA Thioaptamers", Biomedicines, 2017, vol. 5, No. 41, pp. 1-20, 20 pages.

Wiesler, W.T. et al., "Synthesis of Phosphorodithioate DNA via Sulfar-linked Base-Labile Protecting Groups," 1996, The Journal of Organic Chemistry, vol. 61, No. 13, pp. 4272-4281, 10 pages.

Yang, X., "Solid-Phase Synthesis of Oligodeoxynucleotide Analogs Containing Phosphorodithioate Linkages" 2016, Current Protocols in Nucleic Acid Chemistry, 2016, Hoboken, NJ, vol. Supp. 66, pp. 4.71.1-4.71.14, 14 pages.

International Search Report issued in PCT/EP2018/086457, dated Mar. 19, 2019, 6 pages.

Written Opinion of International Preliminary Examining Authority issued in PCT/EP2018/086457, dated Feb. 17, 2020, 8 pages.

Rahman et al., "Synthesis and properties of 2',4'BNANC, a second generation BNA", Nucleic Acids Symposium No. 49, 2005, pp. 5-6.

"Xianbin Yang, et al, ""Aptamers containing thymidine 3'-O-phosphorodithioates: Synthesis and binding to nuclear factor-?B"", Bioorganic & Medicinal Chemistry Letters, vol. 9, Issue 23, Dec. 1999, pp. 3357-3362".

A M Krieg et al, "Oligodeoxynucleotide modifications determine the magnitude of B cell stimulation by CpG motifs", Antisense Nucleic Acid Drug Dev, vol. 6(2), 1996, pp. 133-139.

Bergstrom DE, "Unnatural nucleosides with unusual base pairing properties", Current Protocols in Nucleic Acid Chemistry, 2009, Suppl. 37 1.4.1, 32 pgs.

Cahn, R.S., et al., Specification of Molecular Chirality, Angewandte Chemie International Edition, 1966, vol. 5, No. 4, pp. 385-415.

F. Eckstein et al, "Phosphorothioate Oligodeoxynucleotides: What Is Their Origin and What Is Unique About Them?", Antisense and Nucleic Acid Drug Development vol. 10, No. 2, Jan. 2009, pp. 117-121.

Fluiter et al., Mol. Biosyst., 2009, 10, 1039.

Glen F Deleavey, et al, "Designing Chemically Modified Oligonucleotides for Targeted Gene Silencing", Chemistry & Biology, vol. 19, Issue 8, Aug. 2012, pp. 937-954.

Hansen et al., "Entropy titration. A Calorimetric Method for the Determination of t..G0 (K), t..H0 and t..S0 1," Chemical Communications. 36-38, (1965) (3 pages).

Havens et al, "Splice-switching antisense oligonucleotides as therapeutic drugs", Nucleic Acids Research, vol. 44, No. 14, 2016, pp. 6549-6563.

Hirao et al., "Natural versus Artificial Creation of Base Pairs in DNA: Origin of Nucleobases from the Perspectives of Unnatural Base Pair Studies," Ace Chem Res. 45(12): 2055-2065 (2012) (11 pages).

Holdgate et al., "Measurements of Binding Thermodynamics in Drug Discovery," Drug Discov Today. 10(22):1543-1550 (2005) (8 pages).

International Preliminary Report on Patentability received for PCT Patent Application No. PCT/EP2018/086457, dated Feb. 17, 2020, 7 pages.

James P. Vaughn, et al, "Inhibition of the erbB-2 Tyrosine Kinase Receptor in Breast Cancer Cells by Phosphoromonothioate and Phosphorodithioate Antisense Oligonucleotides", Nucleic Acids Research, vol. 24, Issue 22, Nov. 1996, pp. 4558-4564.

Jean-Louis Mergny, et al, "Analysis of Thermal Melting Curves", Oligonucleotidesvol. 13, No. 6, 2003, pp. 515-537.

Jun Qin, et al, "Functions and Applications of Exosomes", Acta Poloniae Pharmaceutica ñ Drug Research, vol. 71 No. 4, Aug. 2014, pp. 537-543.

Mangos et al., "Efficient RNase H-directed Cleavage of RNA Promoted by Antisense DNA or 2'F-ANA Constructs Containing Acyclic Nucleotide Inserts," J Am Chem Soc. 125(3):654-661 (2003) (8 pages).

Manoharan, "Oligonucleotide Conjugates as Potential Antisense Drugs with Improved Uptake, Biodistribution, Targeted Delivery, and Mechanism of Action," Antisense and Nucleic Acid Drug Dev. 12(2):103-128 (2004) (26 pages).

McTigue et al., "Sequence-Dependent Thermodynamic Parameters for Locked Nucleic Acid (LNA)-DNA Duplex Formation," Biochemistry. 43(18):5388-5405 (2004) (18 pages).

Mitsuoka et al., "A bridged nucleic acid, 2',4'-BNA COC: synthesis of fully modified oligonucleotides bearing thymine, 5 methylcytosine, adenine and guanine 2',4'-BNA COC monomers and RNA-selective nucleic-acid recognition," Nucleic Acids Research, Mar. 2009, 37(4):1225-1238, 14 pgs.

Morita K et al., "2'-O,4'-C-Ethylene-Bridged Nucleic Acids (ENA): Highly Nuclease-Resistant and Thermodynamically Stable Oligonucleotides for Antisense Drug," Bioorganic & Medicinal Chemistry Letters, 2002, vol. 12, pp. 73-76, 4 pages.

Mridul K. Ghosh, et al, "Evaluation of some properties of a phosphorodithioate oligodeoxyribonucleotide for antisense application", Nucleic Acids Research, vol. 21, Issue 24, Dec. 1993, pp. 5761-5766.

N. Oka et al, "Solid-Phase Synthesis of Stereoregular Oligodeoxyribonucleoside Phosphorothioates Using Bicyclic Oxazaphospholidine Derivatives as Monomer Units", J. Am. Chem. Soc. 2008, 130, 47, 16031-16037.

S M Freier, et al, "The ups and downs of nucleic acid duplex stability: structure-stability studies on chemically-modified DNA:RNA duplexes", Nucleic Acids Res., vol. 25(22), Nov. 1997, pp. 4429-4443.

S. T. Crooke, Antisense drug technology: principles, strategies, and applications, 2nd ed., 2008.

S. T. Crooke, ed., Ch. 16, Marcel Dekker, Inc., 2001.

Samir El Andaloussi, et al, "Exosomes for targeted siRNA delivery across biological barriers", Adv Drug Deliv Rev., vol. 65(3), Mar. 2013, pp. 391-397.

Santalucia J Jr., "A Unified View of Polymer, Dumbbell, and Oligonucleotide DNA Nearest-neiqhbor Thermodynamics," Proc Natl Acad Sci US A. 95(4):1460-1465 (1998) (6 pages).

Seth et al., "Synthesis and Biophysical Evaluation of 2',4'-Constrained 2'0-Methoxyethyl and 2',4'-Constrained 2'0-Ethvl Nucleic Acid Analo!!lles," J. Org. Chem., 2010, 75:1569-1581.

(56) References Cited

OTHER PUBLICATIONS

Sugimoto et al., "Thermodynamic Parameters to Predict Stability of RNA/DNA Hybrid Duplexes," Biochemistry. 34(35): 11211-11216 (1995) (6 pages).
Uhlmann; Curr. Opinion in Drug Development, 2000, 3(2), 293-213.
Vester B et al., "Chemically modified oligonucleotides with efficient RNase H response," Bioorganic & Medicinal chemistry Letters, 2008, vol. 18, pp. 2296-2300, 5 pages.
X. Yang, Curr Protoc Nucleic Acid Chem 2017, 70, 4.77.71-74.77.13.
Xianbin Yang, et al, "Gene Silencing Activity of siRNA Molecules Containing Phosphorodithioate Substitutions", ACS Chem. Biol., vol. 7, Apr. 2012, pp. 1214-1220.
Kumar, R., et al., The first analogues of LNA (Locked Nucleic Acids): Phosphorothioate-LNA and 2'-thio-LNA, Bioorganic & Medicinal Chemistry Letters, vol. 8, No. 16, 1998, pp. 2219-2222.
Sekine, M., et al., Synthesis of Artificial Nucleic Acids Functionalized by Fixation of Conformation, Journal of Synthetic Organic Chemistry, vol. 58, No. 1, 2000, pp. 2-13. (English Abstract submitted).
Veedu, R., et al., Locked Nucleic Acids: Promising Nucleic Acid Analogs for Therapeutic Applications, Chemistry & Biodiversity, vol. 7, No. 3, 2010, pp. 536-542.
Gemba, Pharmaceutical Society of Japan, vol. 48, No. 7, pp. 663-667, 5 pgs.
Noguchi, Pharmaceutical Society of Japan, vol. 27, No. 4, pp. 350-351, 2 pgs.

* cited by examiner

| Sequence | 10 000nM ICC (nM) | 2 000nM ICC (nM) | 400nM ICC (nM) | 80nM ICC (nM) | 16nM ICC (nM) | 3.2nM ICC (nM) | 0.64nM ICC (nM) | 0.128nM ICC (nM) |
|---|---|---|---|---|---|---|---|---|
| GCa*ttggtatTCA | 24.6 | 16.5 | 10.2 | 3.5 | 0.8 | 0.4 | 0.3 | 0.3 |
| Gcat*tggtatTCA | 66.7 | 27.0 | 14.9 | 3.4 | 1.0 | 0.4 | 0.4 | 0.3 |
| Gcatt*ggtatTCA | 151.7 | 40.0 | 15.6 | 2.9 | 0.9 | 0.4 | 0.3 | 0.3 |
| Gcattg*gtatTCA | 50.6 | 26.4 | 11.9 | 3.8 | 0.9 | 0.3 | 0.2 | 0.2 |
| GCattgg*tatTCA | 61.5 | 38.6 | 15.0 | 3.5 | 0.8 | 0.5 | 0.3 | 0.3 |
| GCattggt*atTCA | 98.9 | 53.6 | 17.3 | 4.1 | 1.1 | 0.6 | 0.4 | 0.3 |
| GCattggta*tTCA | 88.6 | 54.0 | 10.7 | 2.7 | 0.7 | 0.3 | 0.2 | 0.2 |
| GCattggtat*TCA | 41.2 | 31.2 | 12.7 | 2.7 | 0.7 | 0.5 | 0.4 | 0.4 |
| GCattggtatTCA | 16.0 | 13.5 | 6.9 | 1.7 | 0.5 | 0.3 | 0.2 | 0.2 |

Nomenclature:
G=LNA-G
a=DNA-A
*=non-briging dithioate linkage

Figure 9B

| Sequence | 3000 nM mRNA (nM) | 1000 nM mRNA (nM) | 300 nM mRNA (nM) | 100 nM mRNA (nM) | 30 nM mRNA (nM) | 10 nM mRNA (nM) | 3 nM mRNA (nM) | 1 nM mRNA (nM) | 0.3 nM mRNA (nM) | 0 nM mRNA (nM) |
|---|---|---|---|---|---|---|---|---|---|---|
| GCattggtatTC*A | 2.97 | 2.01 | 4.89 | 12.65 | 24.49 | 44.07 | 82.75 | 99.86 | 104.26 | 101.40 |
| G*CattggtatTCA | 2.35 | 2.69 | 4.42 | 11.25 | 30.44 | 47.00 | 96.90 | 102.94 | 98.68 | 99.41 |
| G*CattggtatTC*A | 2.24 | 2.53 | 4.01 | 9.41 | 18.79 | 35.49 | 72.17 | 85.99 | 89.17 | 96.57 |
| G*CattggtatT*C*A | 3.90 | 4.10 | 4.44 | 8.62 | 17.46 | 43.47 | 52.39 | 89.74 | 66.49 | 100.90 |
| G*C*attggtatTC*A | 3.12 | 3.38 | 11.19 | 8.69 | 31.17 | 45.81 | 61.95 | 94.17 | 86.34 | 112.19 |
| G*C*attggtatT*C*A | 3.62 | 4.41 | 4.99 | 6.65 | 21.42 | 36.31 | 62.62 | 98.43 | 95.86 | 100.04 |
| GCattggtatTCA | 3.64 | 3.01 | 5.15 | 11.15 | 33.04 | 45.24 | 63.96 | 70.73 | 76.51 | 87.77 |

Nomenclature:
G=LNA-G
a=DNA-A
*=non-briging dithicate linkage

Figure 10B

THIOPHOSPHORAMIDITES

Reference to a Sequence Listing Submitted via EFS-WEB The content of the ASCII text file of the sequence listing named "P34610 Sequence Listing.txt" which was created on Jun. 16, 2020 and is 77,824 bytes in size submitted electronically via EFS-Web with this U.S. National Phase application is incorporated by reference in its entirety.

CROSS REFERENCE TO RELATED APPLICATIONS

This application is a U.S. National Entry and claims priority to PCT International Patent Application No. PCT/EP2018/086457, filed Dec. 21, 2018, and entitled "NOVEL THIOPHOSPHORAMIDITES", which claims priority to European Patent Application No. 18198487.3 filed Oct. 3, 2018 and PCT Patent Application No. PCT/CN2017/118043 filed Dec. 22, 2017, the entire disclosures of which are incorporated herein by this reference.

BACKGROUND

The use of synthetic oligonucleotides as therapeutic agents has witnessed remarkable progress over recent decades leading to the development of molecules acting by diverse mechanisms including RNase H activating gapmers, splice switching oligonucleotides, microRNA inhibitors, siRNA or aptamers (S. T. Crooke, *Antisense drug technology: principles, strategies, and applications,* 2nd ed. ed., Boca Raton, Fla.: CRC Press, 2008). However, oligonucleotides are inherently unstable towards nucleolytic degradation in biological systems. Furthermore, they show a highly unfavorable pharmacokinetic behavior. In order to improve on these drawbacks a wide variety of chemical modifications have been investigated in recent decades. Arguably one of the most successful modification is the introduction of phosphorothioate linkages, where one of the non-bridging phosphate oxygen atoms is replaced with a sulfur atom (F. Eckstein, *Antisense and Nucleic Acid Drug Development* 2009, 10, 117-121.). Such phosphorothioate oligodeoxynucleotides show an increased protein binding as well as a distinctly higher stability to nucleolytic degradation and thus a substantially higher half-live in plasma, tissues and cells than their unmodified phosphodiester analogues. These crucial features have allowed for the development of the first generation of oligonucleotide therapeutics as well as opened the door for their further improvement through later generation modifications such as Locked Nucleic Acids (LNAs). Replacement of a phosphodiester linkage with a phosphorothioate, however, creates a chiral center at the phosphorous atom. As a consequence, all approved phosphorothioate oligonucleotide therapeutics are used as mixtures of a huge amount of diastereoisomeric compounds, which all potentially have different (and possibly opposing) physiochemical and pharmacological properties.

While the stereospecific synthesis of single stereochemically defined phosphorothioate oligonucleotides is now possible (N. Oka, M. Yamamoto, T. Sato, T. Wada, *J. Am. Chem. Soc.* 2008, 130, 16031-16037) it remains a challenge to identify the stereoisomer with optimal properties within the huge number of possible diastereoisomers. In this context, the reduction of the diastereoisomeric complexity by the use of non-chiral thiophosphate linkages is of great interest. For example, the symmetrical non-bridging dithioate modification (see e.g. W. T. Wiesler, M. H. Caruthers, *J. Org. Chem.* 1996, 61, 4272-4281), where both non-bridging oxygen atoms within the phosphate linkage are replaced by sulfur has been applied to immunostimulatory oligonucleotides (A. M. Krieg, S. Matson, E. Fisher, *Antisense Nucleic Acid Drug Dev.* 1996, 6, 133-139), siRNA (e.g. X. Yang, M. Sierant, M. Janicka, L. Peczek, C. Martinez, T. Hassell, N. Li, X. Li, T. Wang, B. Nawrot, *ACS Chem. Biol.* 2012, 7, 1214-1220) and aptamers (e.g. X. Yang, S. Fennewald, B. A. Luxon, J. Aronson, N. K. Herzog, D. G. Gorenstein, *Bioorg. Med. Chem. Lett.* 1999, 9, 3357-3362). Interestingly, attempts to make use of this non-chiral modification in the context of antisense oligonucleotides have met with limited success to date (see e.g. M. K. Ghosh, K. Ghosh, O. Dahl, J. S. Cohen, *Nucleic Acids Res.* 1993, 21, 5761-5766. and J. P. Vaughn, J. Stekler, S. Demirdji, J. K. Mills, M. H. Caruthers, J. D. Iglehart, J. R. Marks, *Nucleic Acids Res.* 1996, 24, 4558-4564).

To our surprise we have now found that non-bridging phosphorodithioates can be introduced into oligonucleotide, in particular to oligonucleotide gapmers or mixmers in general and LNA-DNA-LNA gapmers or LNA/DNA mixmers in particular. The modification is well tolerated and the resulting molecules show great potential for therapeutic applications, while every non-bridging phosphorodithioate modification reduces the size of the overall library of possible diastereoisomers by 50%. When the modification is placed in the LNA flanks of gapmers, the resulting oligonucleotides turn out to be generally more potent than the corresponding all-phosphorothioate parent. In general, the modification is additionally well tolerated within the gap region and even more surprisingly can lead to an improved potency as well, when positioned appropriately.

We have thus surprisingly found that the invention provides oligonucleotides with improved physiochemical and pharmacological properties, including, for example, improved potency. In some aspects, the oligonucleotide of the invention retains the activity or efficacy, and may be as potent or is more potent, than the identical compound where the phosphodithioate linkages of formula (IA or IBIB) are replaced with the conventional stereorandom phosphorothioate linkages (phosphorothioate reference compound). Every introduction of the non-bridging phosphorodithioate modification removes one of the chiral centers at phosphorous and thereby reduces the diastereoisomeric complexity of the compound by 50%. Additionally, whenever a dithioate modification is introduced, the oligonucleotide appears to be taken up dramatically better into cells, in particular into hepatocytes, muscle cells, heart cells for example.

The introduction of non-bridging dithioate modifications into the LNA flanks of gapmers appears to be particularly beneficial, leading to molecules demonstrating a higher target reduction and a substantially better uptake behavior, higher stability and good safetly profile.

The chemical synthesis of non-bridging phosphorodithioate linkages in oligonucleotides is best achieved by solid phase oligonucleotide synthesis techniques using appropriate thiophosphoramidite building blocks. The successful application of such thiophosphoramidites has been described for regular DNA (X. Yang, *Curr Protoc Nucleic Acid Chem* 2016, 66, 4.71.71-74.71.14.) as well as RNA (X. Yang, *Curr Protoc Nucleic Acid Chem* 2017, 70, 4.77.71-74.77.13.) and the required building blocks are available from commercial sources. Interestingly, the more challenging synthesis of the corresponding LNA thiophosphoramidites has not been reported. Within this application, we also report the successful synthesis of all four LNA thiophosphoramidites and their incorporation into oligonucleotides.

STATEMENT OF THE INVENTION

The invention relates to an oligonucleotide comprising at least one phosphorodithioate internucleoside linkage of formula (I)

(I)

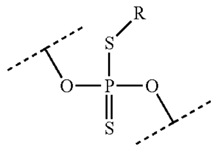

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a LNA nucleoside and wherein R is hydrogen or a phosphate protecting group. The invention further relates in particular to a gapmer oligonucleotide comprising a phosphorodithioate internucleoside linkage of formula (I). The invention also relates to a process for the manufacture of an oligonucleotide according to the invention and to a LNA nucleoside monomer useful in particular in the manufacture of on oligonucleotide according to the invention.

The invention relates to an oligonucleotide comprising at least one phosphorodithioate internucleoside linkage of formula (IA) or (IB)

(IA)

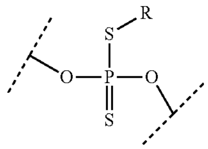

(IB)

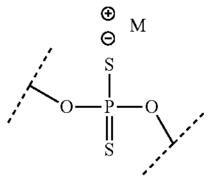

wherein one of the two oxygen atoms is linked to the 3'carbon atom of an adjacent nucleoside ($A^1$) and the other one is linked to the 5'carbon atom of another adjacent nucleoside ($A^2$), and wherein in (IA) R is hydrogen or a phosphate protecting group, and in (IB) M+ is a cation, such as a metal cation, such as an alkali metal cation, such as a Na+ or K+ cation; or M+ is an ammonium cation.

Alternatively stated M is a metal, such as an alkali metal, such as Na or K; or M is $NH_4$.

The invention provides an antisense oligonucleotide comprising a phosphorodithioate internucleoside linkage, of formula IA or IB as described herein. The oligonucleotide of the invention is preferably a single stranded antisense oligonucleotide, which comprises one or more 2'sugar modified nucleosides, such as one or more LNA nucleosides or one or more 2' MOE nucleosides. The antisense oligonucleotide of the invention is capable of modulating the expression of a target nucleic acid, such as a target pre-mRNA, or target microRNA in a cell which is expressing the target RNA—in vivo or in vitro. In some embodiments, the single stranded antisense oligonucleotide further comprises phosphorothioate internucleoside linkages. The single stranded antisense oligonucleotide may, for example may be in the form of a gapmer oligonucleotide, a mixmer oligonucleotide or a totalmer oligonucleotide. The single stranded antisense oligonucleotide mixmer may be for use in modulating a splicing event in a target pre-mRNA. The single stranded antisense oligonucleotide mixmer may be for use in inhibiting the expression of a target microRNA.

The invention further refers to the use of the oligonucleotide of the invention, such as the single stranded antisense oligonucleotide as a therapeutic.

The invention further relates in particular to a mixmer oligonucleotide comprising a phosphorodithioate internucleoside linkage of formula (IA or IB). The invention further relates in particular to a totalmer oligonucleotide comprising a phosphorodithioate internucleoside linkage of formula (IA or IB).

The invention also relates to a process for the manufacture of an oligonucleotide according to the invention and to a LNA nucleoside monomer useful in particular in the manufacture of on oligonucleotide according to the invention.

The invention also relates to a process for the manufacture of an oligonucleotide according to the invention and to a MOE nucleoside monomer useful in particular in the manufacture of on oligonucleotide according to the invention.

The invention further provides novel MOE and LNA monomers which may be used in the manufacture of on oligonucleotide according to the invention.

During oligonucleotide synthesis, the use of a protective R group is often used. After oligonucleotide synthesis, the protecting group is typically exchanged for either a hydrogen atom or cation like an alkali metal or an ammonium cation, such as when the oligonucleotide is in the form of a salt. The salt typically contains a cation, such as a metal cation, e.g. sodium or potassium cation or an ammonium cation. With regards antisense oligonucleotides, preferably R is hydrogen, or the the antisense oligonucleotide is in the form of a salt (as shown in IB).

The phosphorodithioate internucleoside linkage of formula (IB) may, for example, be selected from the group consisting of:

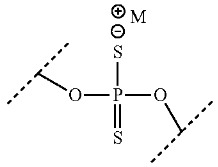

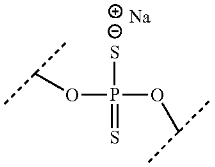

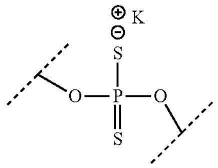

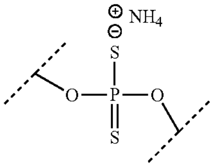

wherein M+ is a is a cation, such as a metal cation, such as an alkali metal cation, such as a Na+ or K+ cation; or M+ is an ammonium cation. The oligonucleotide of the invention may therefore be in the form of an oligonucleotide salt, an alkali metal salt, such as a sodium salt, a potassium salt or an ammonium salt.

Alternatively represented, the oligonucleotide of the invention may comprise a phosphorodithioate internucleoside linkage of formula IA' or IB'

(IA')

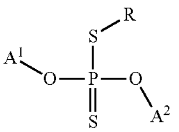

(IB')

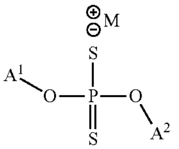

The invention further relates in particular to a gapmer oligonucleotide comprising a phosphorodithioate internucleoside linkage of formula (I), for formula IA or IB, or formula IA' or formula IB'.

The invention further relates in particular to a mixmer oligonucleotide comprising a phosphorodithioate internucleoside linkage of formula (I), for formula IA or IB, or formula IA' or formula IB'.

The invention further relates in particular to a totalmer oligonucleotide comprising a phosphorodithioate internucleoside linkage of formula (I), for formula IA or IB, or formula IA' or formula IB'.

In preferred embodiments of the oligonucleotide of the invention at least one of the two nucleosides ($A^1$) and ($A^2$) is a LNA nucleoside.

In preferred embodiments of the oligonucleotide of the invention at least one of the two nucleosides ($A^1$) and ($A^2$) is a 2'-O-MOE nucleoside.

In preferred embodiments of the oligonucleotide of the invention, the oligonucleotide is a single stranded antisense oligonucleotide, at least one of the two nucleosides ($A^1$) and ($A^2$) is a LNA nucleoside.

In preferred embodiments of the oligonucleotide of the invention the oligonucleotide is a single stranded antisense oligonucleotide, and at least one of the two nucleosides ($A^1$) and ($A^2$) is a 2'-O-MOE nucleoside.

The invention provides an antisense oligonucleotide, for inhibition of a target RNA in a cell, wherein the antisense gapmer oligonucleotide comprises at least one phosphorodithioate internucleoside linkage of formula (IA) or (IB)

(IA)

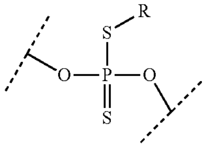

(IB)

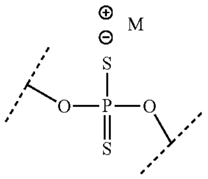

wherein in (IA) R is hydrogen or a phosphate protecting group, and in (IB) M+ is a cation, such as a metal cation, such as an alkali metal cation, such as a Na+ or K+ cation; or M+ is an ammonium cation, wherein the antisense oligonucleotide is or comprises an antisense gapmer oligonucleotide (referred to herein as a gapmer or a gapmer ligonucleotide), The antisense oligonucleotide of the invention may therefore comprise or consist of a gapmer.

The invention provides for an antisense oligonucleotide comprising at least one phosphorodithioate internucleoside linkage formula (IA) or (IB)

(IA)

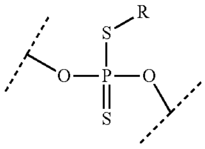

(IB)

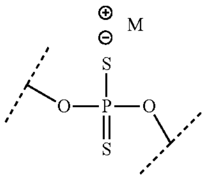

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a LNA nucleoside and and wherein in (IA) R is hydrogen or a phosphate protecting group, and in (IB) M+ is a cation, such as a metal cation, such as an alkali metal cation, such as a Na+ or K+ cation; or M+ is an ammonium cation, wherein $A^2$ is the 3' terminal nucleoside of the oligonucleotide.

The invention provides for an antisense oligonucleotide comprising at least one phosphorodithioate internucleoside linkage of formula (IA) or (IB)18

(IA)

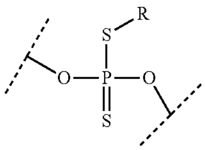

(IB)

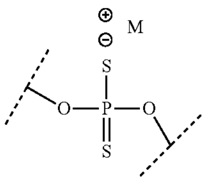

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a LNA nucleoside and and wherein in (IA) R is hydrogen or a phosphate protecting group, and in (IB) M+ is a cation, such as a metal cation, such as an alkali metal cation, such as a Na+ or K+ cation; or M+ is an ammonium cation, wherein $A^1$ is the 5' terminal nucleoside of the oligonucleotide.

The invention provides for an antisense oligonucleotide comprising at least one phosphorodithioate internucleoside linkage of formula (IA) or (IB)

(IA)

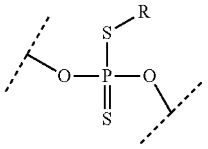

(IB)

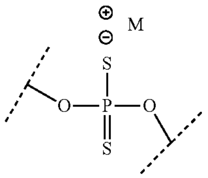

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a 2-O-MOE nucleoside and wherein in (IA) R is hydrogen or a phosphate protecting group, and in (IB) M+ is a cation, such as a metal cation, such as an alkali metal cation, such as a Na+ or K+ cation; or M+ is an ammonium cation, wherein $A^2$ is the 3' terminal nucleoside of the oligonucleotide.

The invention provides for an antisense oligonucleotide comprising at least one phosphorodithioate internucleoside linkage of formula (IA) or )IB)

(IA)

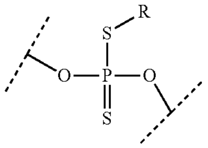

(IB)

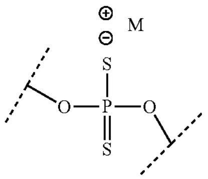

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a 2-O-MOE nucleoside and wherein in (IA) R is hydrogen or a phosphate protecting group, and in (IB) M+ is a cation, such as a metal cation, such as an alkali metal cation, such as a Na+ or K+ cation; or M+ is an ammonium cation, wherein $A^1$ is the 5' terminal nucleoside of the oligonucleotide.

The invention provides for an antisense oligonucleotide comprising at least one phosphorodithioate internucleoside linkage of formula (IA) or (IB)

(IA)

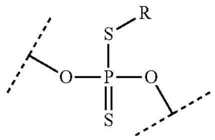

(IB)

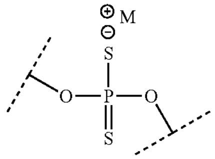

wherein one of the two oxygen atoms is linked to the 3'carbon atom of an adjacent nucleoside (A) and the other one is linked to the 5'carbon atom of another adjacent nucleoside ($A^2$), wherein at least one of the two nucleosides (A) and ($A^2$) is a 2' sugar modified nucleoside and and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein $A^2$ is the 3' terminal nucleoside of the oligonucleotide.

The invention provides for an antisense oligonucleotide comprising at least one phosphorodithioate internucleoside linkage of formula (IA) or (IB)

(IA)

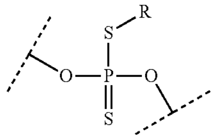

(IB)

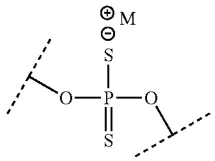

wherein one of the two oxygen atoms is linked to the 3'carbon atom of an adjacent nucleoside ($A^1$) and the other one is linked to the 5'carbon atom of another adjacent nucleoside ($A^2$), wherein at least one of the two nucleosides ($A^1$) and ($A^2$) is a 2' sugar modified nucleoside and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein $A^1$ is the 5' terminal nucleoside of the oligonucleotide.

The 2' sugar modified nucleoside may be independently selected from the group consisting of 2' sugar modified nucleoside selected from the group consisting of 2'-alkoxy-RNA, 2'-alkoxyalkoxy-RNA, 2'-amino-DNA, 2'-fluoro-RNA, 2'-fluoro-ANA and an LNA nucleoside.

The invention provides for a single stranded antisense oligonucleotide comprising at least one phosphorodithioate internucleoside linkage of formula (IA) or (IB)

(IA)

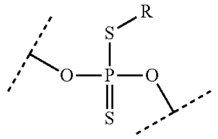

(IB)

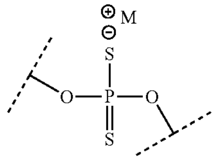

wherein one of the two oxygen atoms is linked to the 3'carbon atom of an adjacent nucleoside ($A^1$) and the other one is linked to the 5'carbon atom of another adjacent nucleoside ($A^2$), and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded oligonucleotide further comprises at least one stereodefined phosphorothioate internucleoside linkage, (Sp, S) or (Rp, R)

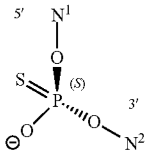 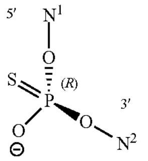

wherein N1 and N2 are nucleosides.

The invention also provides for a single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

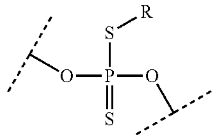

(IB)

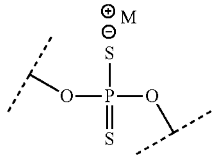

wherein one of the two oxygen atoms is linked to the 3'carbon atom of an adjacent nucleoside (A1) and the other one is linked to the 5'carbon atom of another adjacent nucleoside (A2) and wherein R is hydrogen or a phosphate protecting group.

The invention also provides for a single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

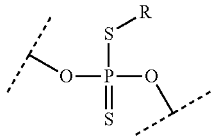

(IB)

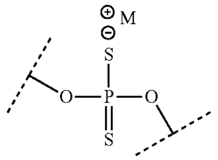

wherein one of the two oxygen atoms is linked to the 3'carbon atom of an adjacent nucleoside (A1) and the other one is linked to the 5'carbon atom of another adjacent nucleoside (A2); and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded antisense oligonucleotide is for use in modulating the splicing of a pre-mRNA target RNA.

The invention also provides for a single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

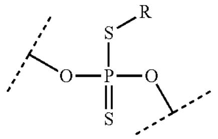

(IB)

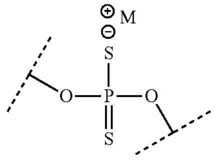

wherein one of the two oxygen atoms is linked to the 3'carbon atom of an adjacent nucleoside (A1) and the other one is linked to the 5'carbon atom of another adjacent nucleoside (A2); and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded antisense oligonucleotide is for use in inhibiting the expression of a long-non coding RNA. See WO 2012/065143 for examples of IncRNAs which may be targeted by the compounds of the invention.

The invention also provides for a single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

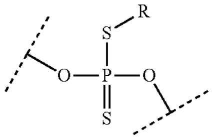

(IB)

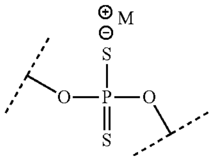

wherein one of the two oxygen atoms is linked to the 3'carbon atom of an adjacent nucleoside (A1) and the other one is linked to the 5'carbon atom of another adjacent nucleoside (A2); and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded antisense oligonucleotide is for use in inhibiting the expression of a human mRNA or pre-mRNA target.

The invention also provides for a single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

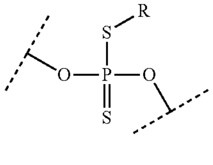

-continued (IB)

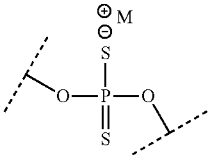

wherein one of the two oxygen atoms is linked to the 3'carbon atom of an adjacent nucleoside (A1) and the other one is linked to the 5'carbon atom of another adjacent nucleoside (A2); and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded antisense oligonucleotide is for use in inhibiting the expression of a viral RNA target. Suitable the viral RNA target may be HCV or HBV for example.

The invention also provides for a single stranded antisense oligonucleotide, for modulation of a RNA target in a cell, wherein the antisense oligonucleotide comprises or consists of a contiguous nucleotide sequence of 7-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA)

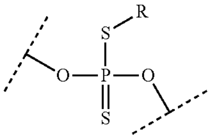

(IB)

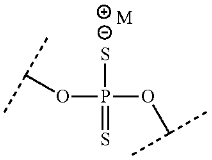

wherein one of the two oxygen atoms is linked to the 3'carbon atom of an adjacent nucleoside (A1) and the other one is linked to the 5'carbon atom of another adjacent nucleoside (A2); and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded antisense oligonucleotide is for use in inhibiting the expression of a microRNA.

For targeting a RNA target, e.g. a pre-mRNA target, an mRNA target, a viral RNA target, a microRNA or a long non coding RNA target, the oligonucleotide of the invention is suitably capable of inhibiting the expression of the target RNA. This is achieved by the complementarity between tha antisense oligonucleotide and the target RNA. Inhibition of the RNA target may be achieved by reducing the level of the RNA target or by blocking the function of the RNA target. RNA inhibition of an RNA target may suitably be achieved via recruitment of a cellular RNAse such as RNaseH, e.g. via the use of a gapmer, or may be achieved via a non nuclease mediated mechanism, such as a steric blocking mechanism (such as for microRNA inhibition, for splice modulating of pre-mRNAs, or for blocking the interaction between a long non coding RNA and chromatin).

The invention also relates to a process for the manufacture of an oligonucleotide according to the invention and to a LNA or MOE nucleoside monomer useful in particular in the manufacture of an oligonucleotide according to the invention.

The invention provides for a pharmaceutically acceptable salt of an oligonucleotide according to the invention, or a conjugate thereof, in particular a sodium or a potassium salt or an ammonium salt.

The invention provides for a conjugate comprising an oligonucleotide, or a pharmaceutically acceptable salt, thereof, and at least one conjugate moiety covalently attached to said oligonucleotide or said pharmaceutically acceptable salt, optionally via a linker moiety.

The invention provides for a pharmaceutical composition comprising an oligonucleotide, pharmaceutically acceptable salt or conjugate according to the invention and a therapeutically inert carrier.

The invention provides for an oligonucleotide, a pharmaceutically acceptable salt or a conjugate according to any the invention for use as a therapeutically active substance.

The invention provides for a method for the modulation of a target RNA in a cell which is expressing said RNA, said method comprising the step of administering an effective amount of the oligonucleotide, pharmaceutically acceptable salt, conjugate or composition according to the invention to the cell, wherein the oligonucleotide is complementary to the target RNA.

The invention provides for a method of modulation of a splicing of a target pre-RNA in a cell which is expressing said target pre-mRNA, said method comprising the step of administering an effective amount of the oligonucleotide, pharmaceutically acceptable salt, conjugate or composition according to the invention to the cell, wherein the oligonucleotide is complementary to the target RNA and is capable of modulating a splicing event in the pre-mRNA.

The invention provides for the use of an oligonucleotide, pharmaceutical salt, conjugate, or composition of the invention for inhibition of a pre-mRNA, an mRNA, or a long-non coding RNA in a cell, such as in a human cell.

The above methods or uses may be an in vitro method or an in vivo method.

The invention provides for the use of an oligonucleotide, pharmaceutical salt, conjugate, or composition of the invention in the manufacture of a medicament.

The invention provides for the use of a phosphorodithioate internucleoside linkage of formula IA or IB, for use for enhancing the in vitro or in vivo stability of a single stranded phosphorothioate antisense oligonucleotide.

The invention provides for the use of a phosphorodithioate internucleoside linkage of formula IA or IB, for use for enhancing the in vitro or in vivo duration of action a single stranded phosphorothioate antisense oligonucleotide.

The invention provides for the use of a phosphorodithioate internucleoside linkage of formula IA or IB, for use for enhancing cellular uptake or tissue distribution of a single stranded phosphorothioate antisense oligonucleotide.

The invention provides for the use of a phosphorodithioate internucleoside linkage of formula IA or IB, for use for enhancing uptake of a single stranded phosphorothioate antisense oligonucleotide into a tissue selected from the group consisting of skeletal muscle, heart, epithelial cells, including retinal epithelial cells (e.g. for Htra1 targeting compounds), livre, kidney, or spleen.

For in vivo use a single stranded phosphorothioate antisense oligonucleotide may be a therapeutic oligonucleotide.

FIGURES

FIG. 1 shows the target mRNA levels in primary rat hepatocytes after 24 and 74 hours of administration of oligonucleotide gapmers having a single phosphorodithioate internucleoside linkage according the invention in the gap.

FIG. 2 shows the target mRNA levels in primary rat hepatocytes after 24 and 74 hours of administration of oligonucleotide gapmers having multiple phosphorodithioate internucleoside linkages according the invention in the gap.

FIG. 3 shows the target mRNA levels in primary rat hepatocytes after 24 and 74 hours of administration of oligonucleotide gapmers having multiple phosphorodithioate internucleoside linkages according the invention in the gap.

FIG. 4 shows the target mRNA levels in primary rat hepatocytes after 24 and 74 hours of administration of oligonucleotide gapmers having phosphorodithioate internucleoside linkages according the invention in the flanks.

Figure 7:
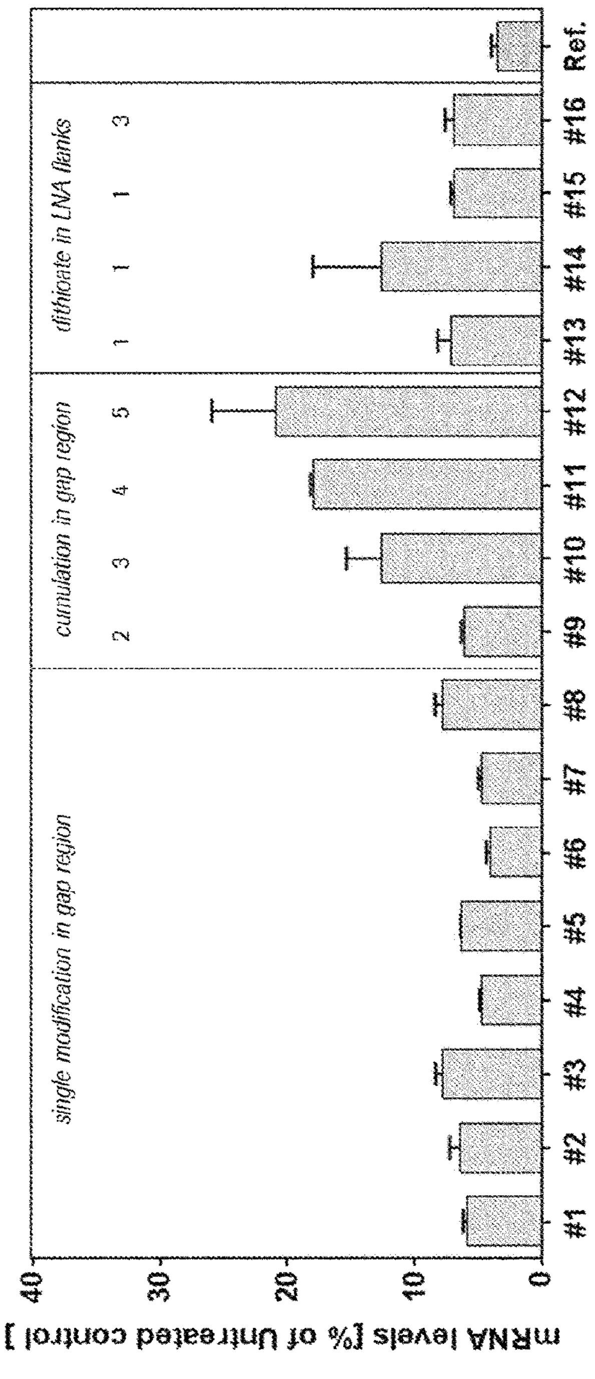

FIG. 7: Exploring achiral phosphodithioate in the gap and flank regions of gapmers—residual mRNA levels after treatment of primary rat hepatocytes.

Figure 8:
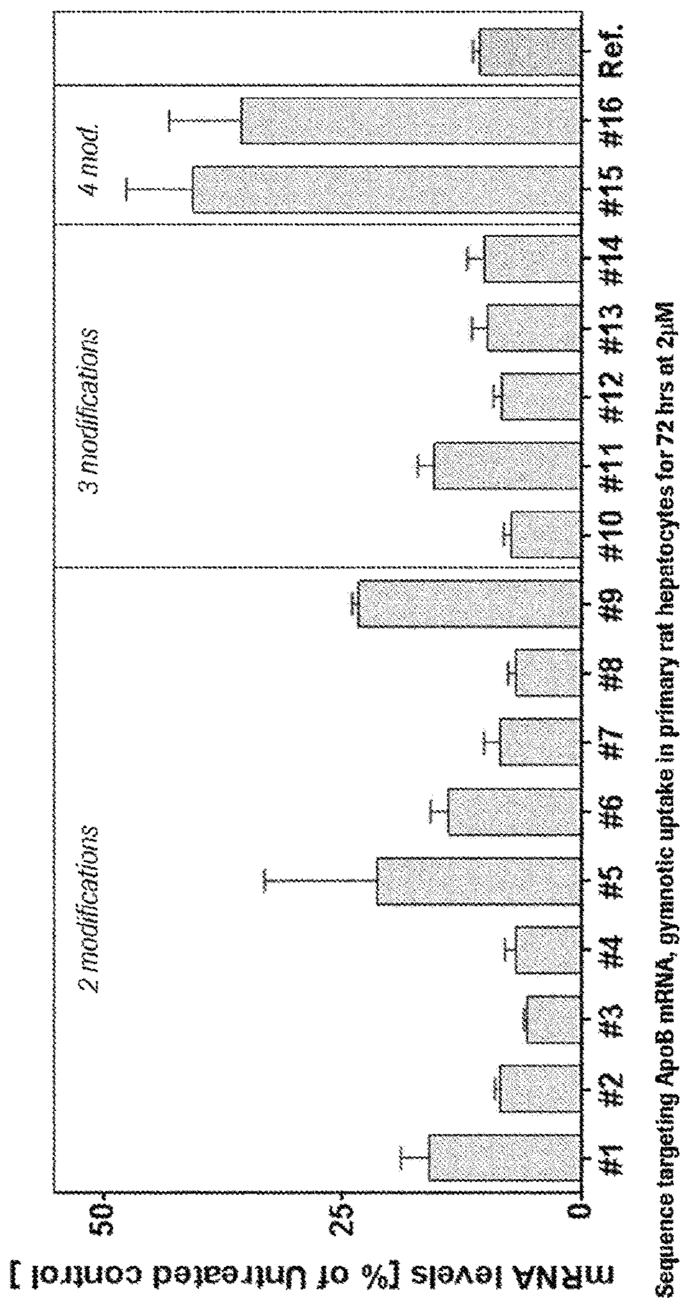

FIG. 8: Exploring positional dependency and optimization of achiral phosphodithioate in the gap regions of gapmers—residual mRNA levels after treatment of primary rat hepatocytes.

Figure 9A:
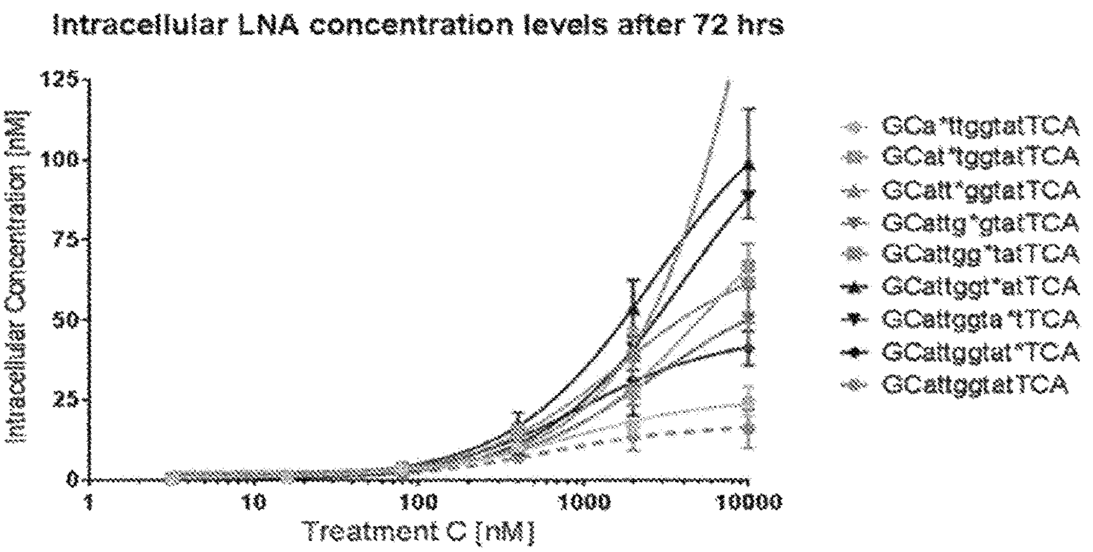

FIGS. 9A and 9B: Exploring achiral phosphodithioate in the gap regions of gapmers—effect on cellular uptake.

Figure 10A:
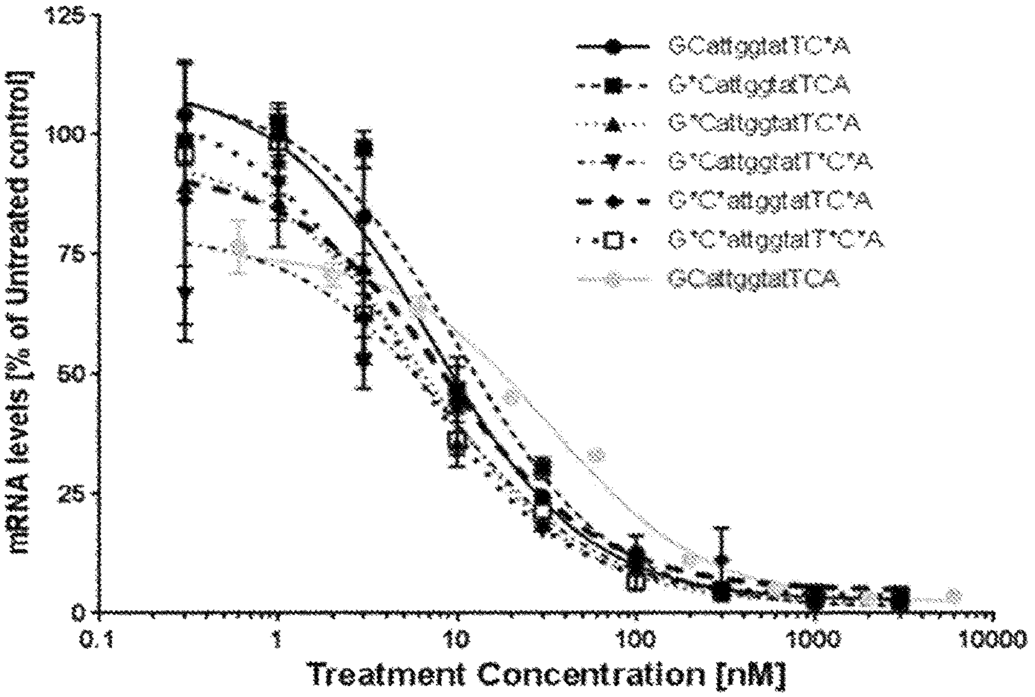

FIGS. 10A and 10B: Introduction of achiral phosphorodithioate in the flank regions of gapmers provides increased potency, with a correlation between phosphorothioate load with increased potency (4 linkages>3 linkages>2 linkages>1 linkage>no phosphorodithioate linkages in the flanks).

Figure 11:
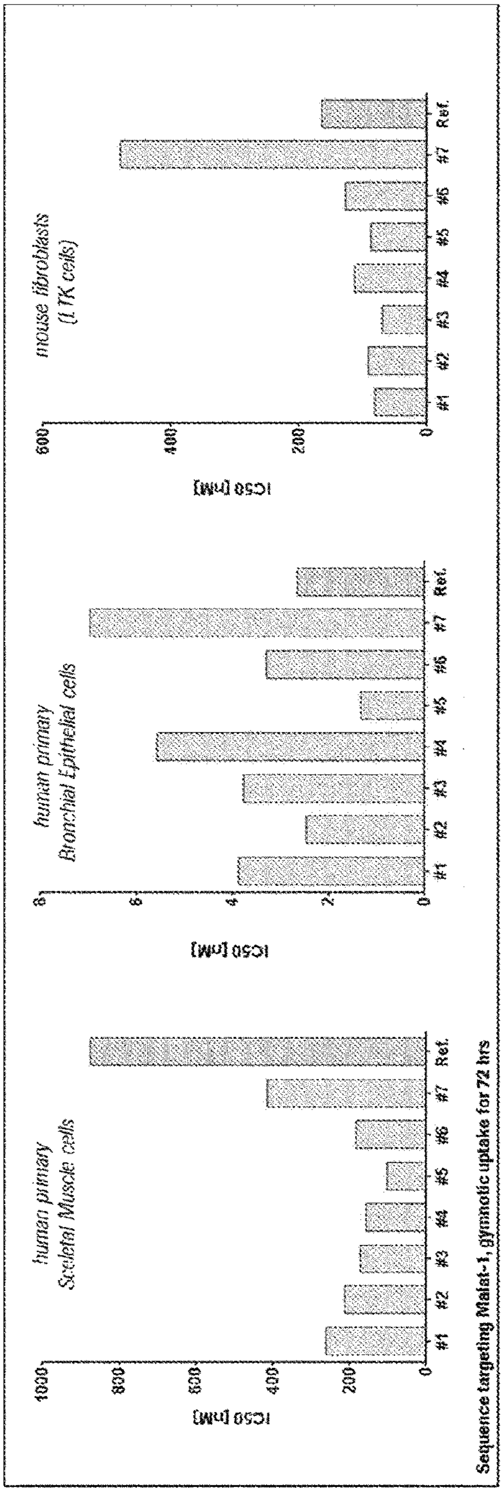

FIG. 11: IC50 values in difference cell types.

Figure 12:
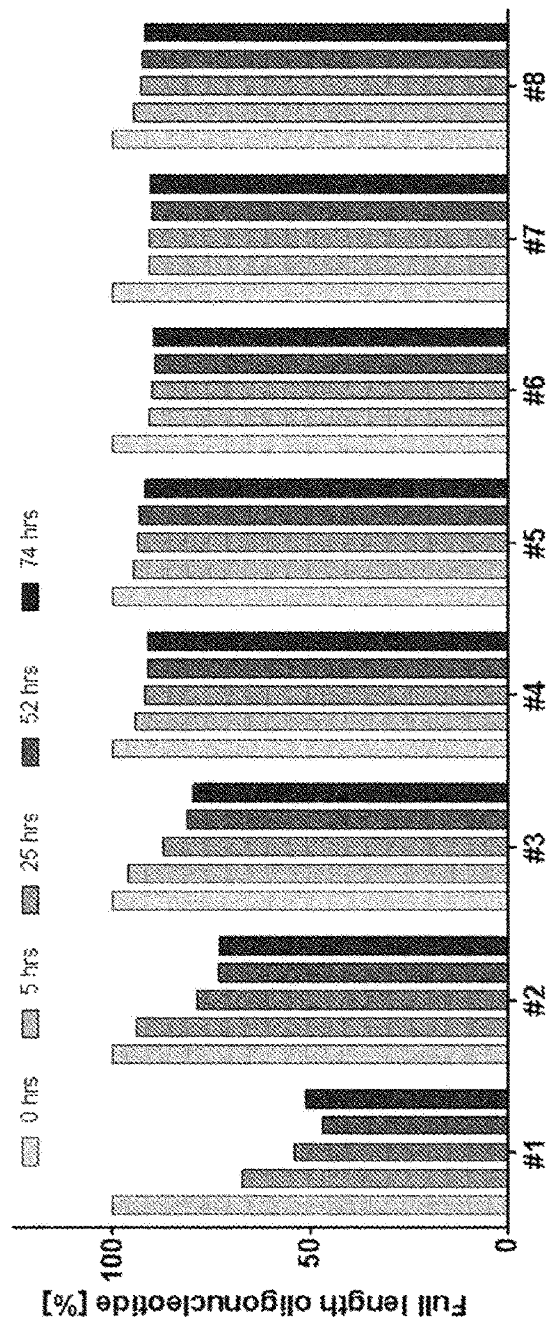

FIG. 12: In vitro rat serum stability of 3' end protected LNA oligonucleotides.

Figure 13:
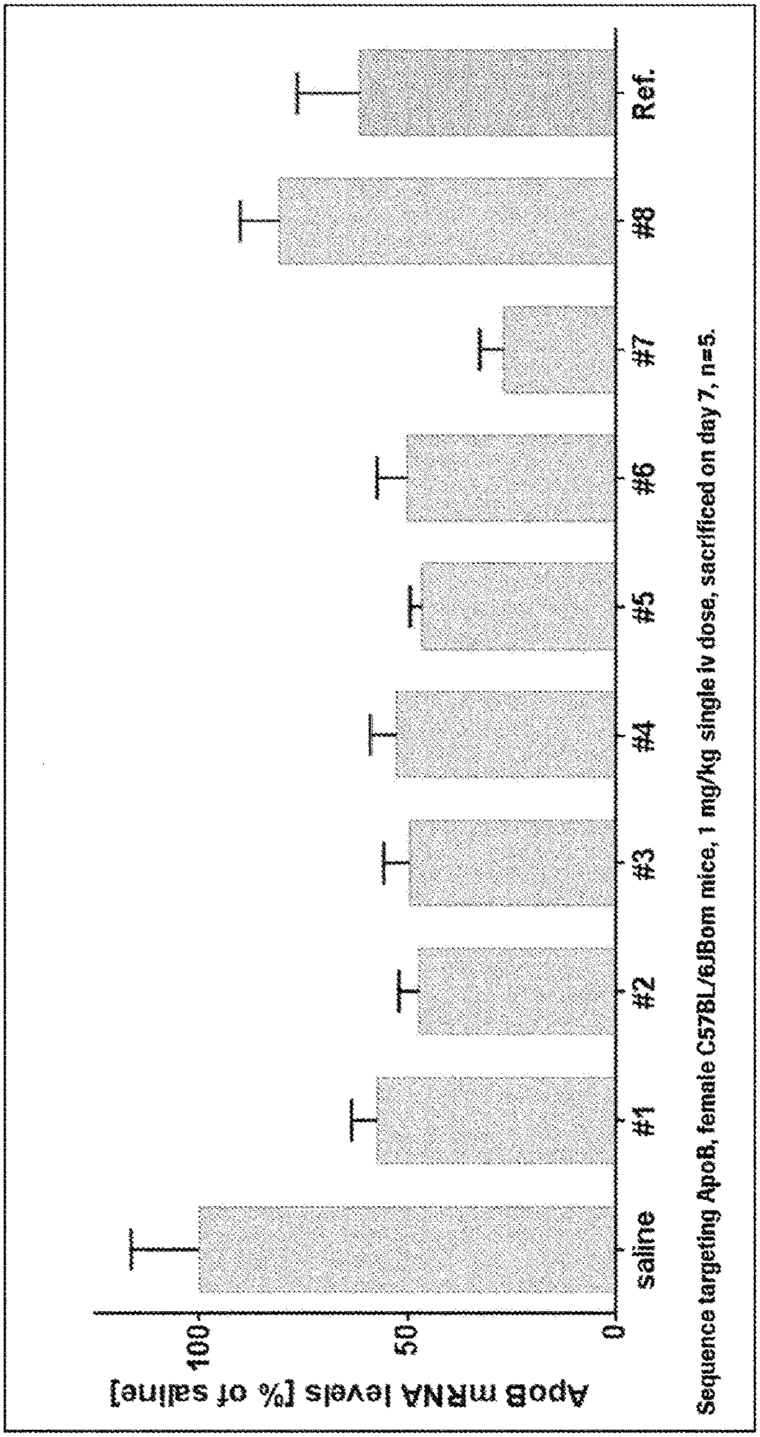

FIG. 13: In vivo evaluation of gapmers containing achiral phosphorodithioate linkages in the flanks and the gap regions—Target inhibition.

Figure 14A:
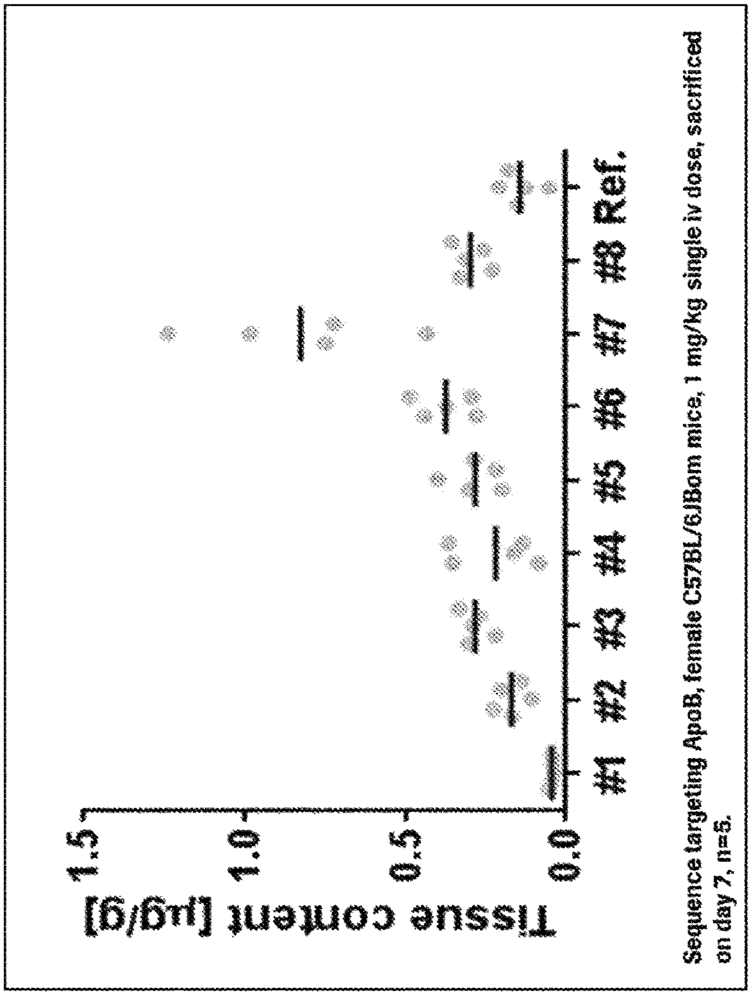

FIG. 14A: In vivo evaluation of gapmers containing achiral phosphorodithioate linkages in the flanks and the gap regions—Tissue uptake.

Figure 14B:
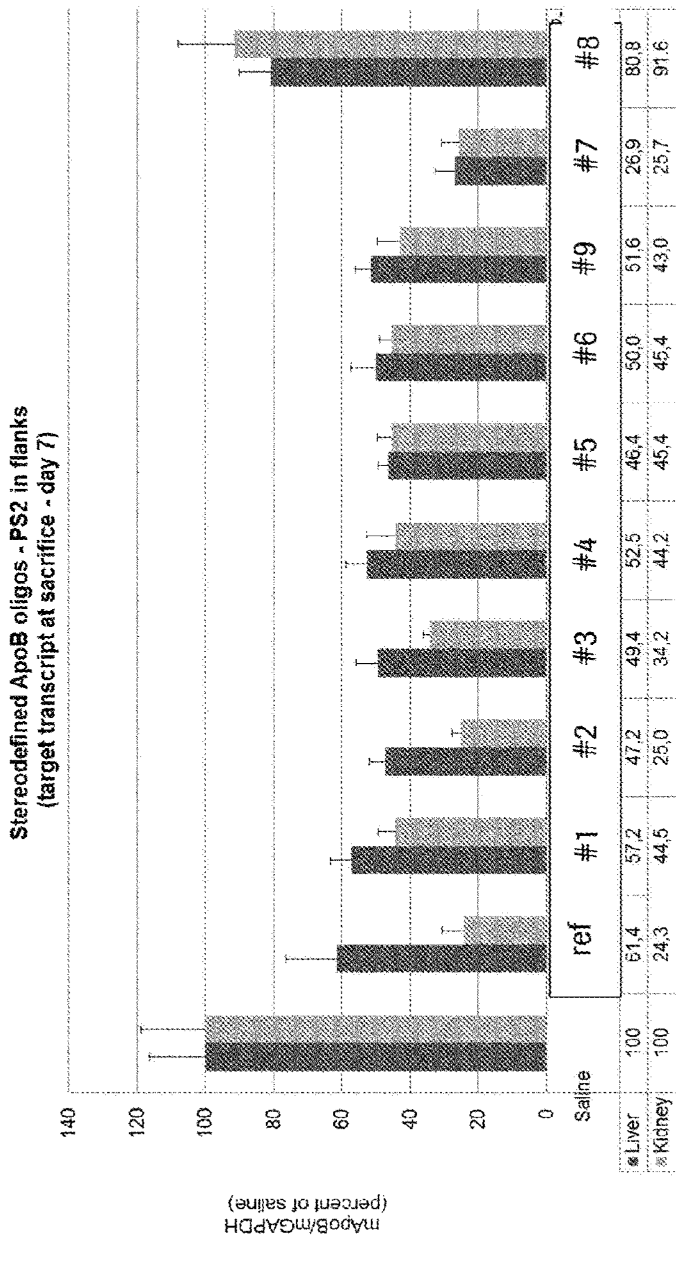

FIG. 14B: In vivo evaluation of gapmers containing achiral phosphorodithioate linkages in the flanks and the gap regions—Liver/kidney ratio.

Figure 15A:
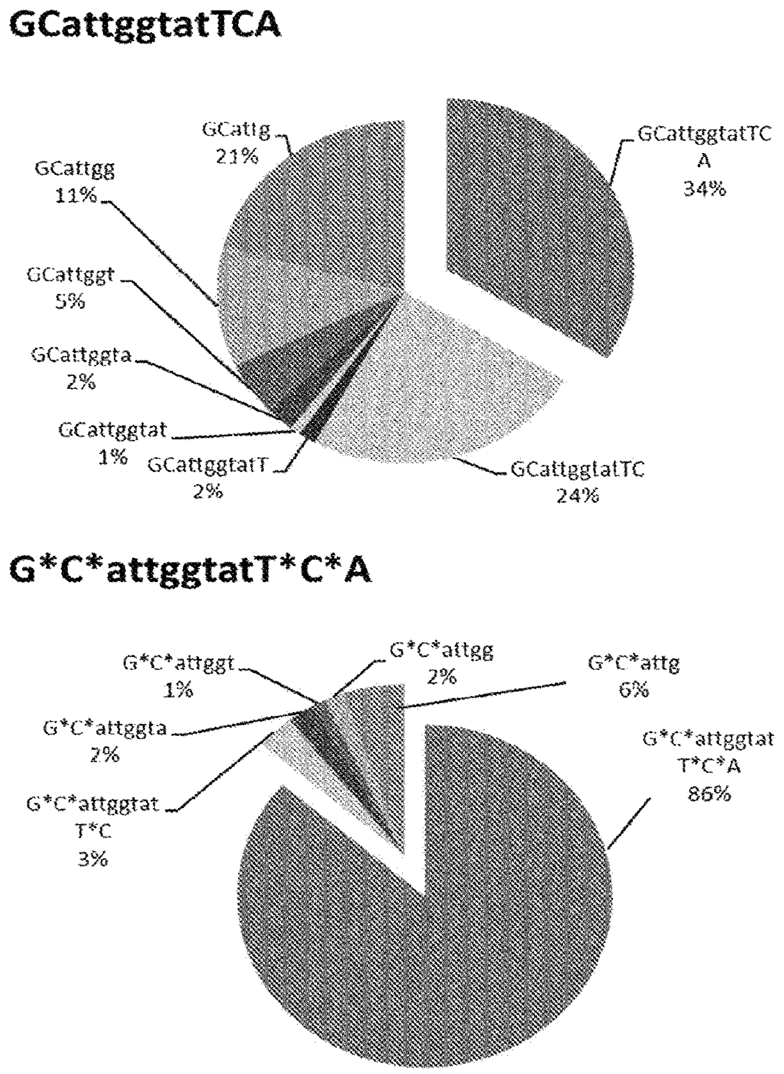
Figure 15B:
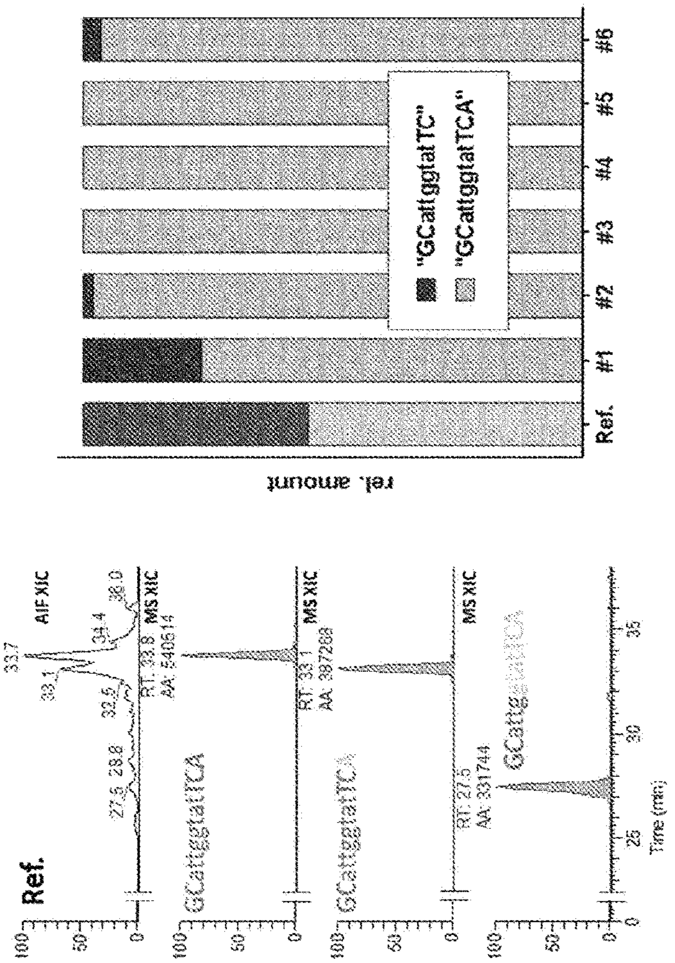

FIGS. 15A and 15B: In vivo evaluation of gapmers containing achiral phosphorodithioate linkages in the flanks and the gap regions—metabolite analysis.

Figure 16:
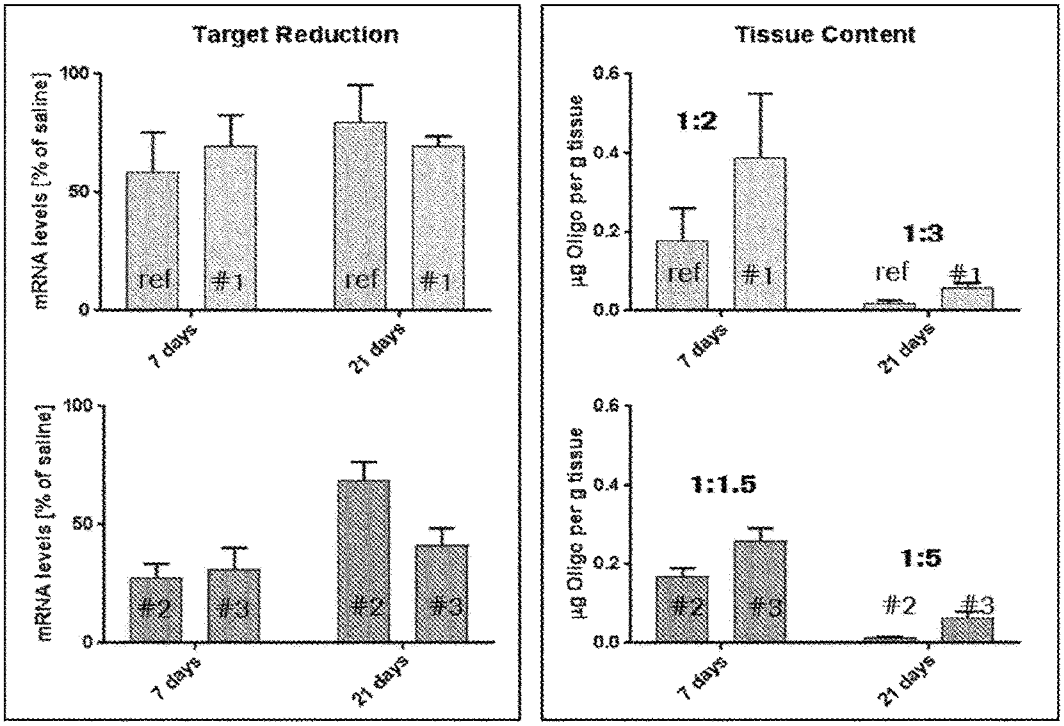

FIG. 16: The prolonged duration of action with antisense oligonucleotides comprising achiral phosphorodithioate internucleoside linkages can be further enhanced by combination with stereodefined phosphorothioate internucleoside linkages.

Figure 17A:
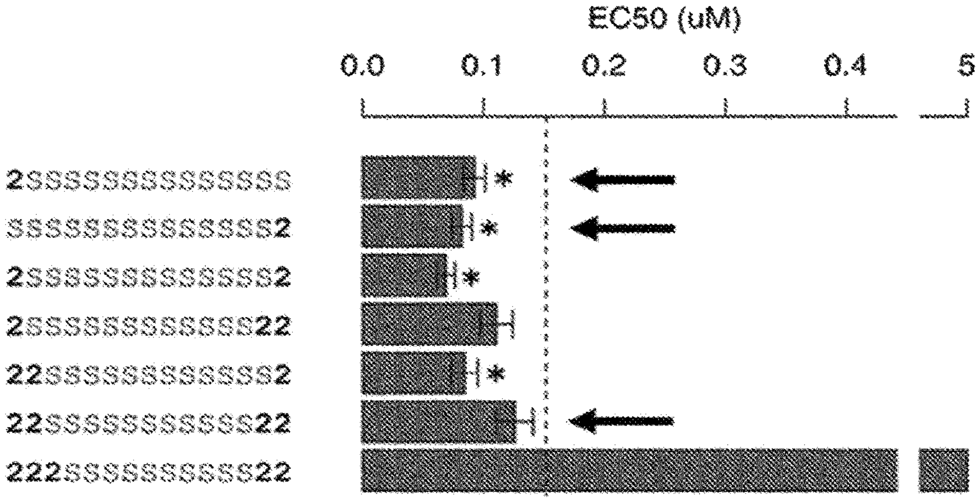

FIG. 17A: In vitro EC50 determination of achiral phosphorodithioate gapmers targeting MALAT-1.

Figure 17B:
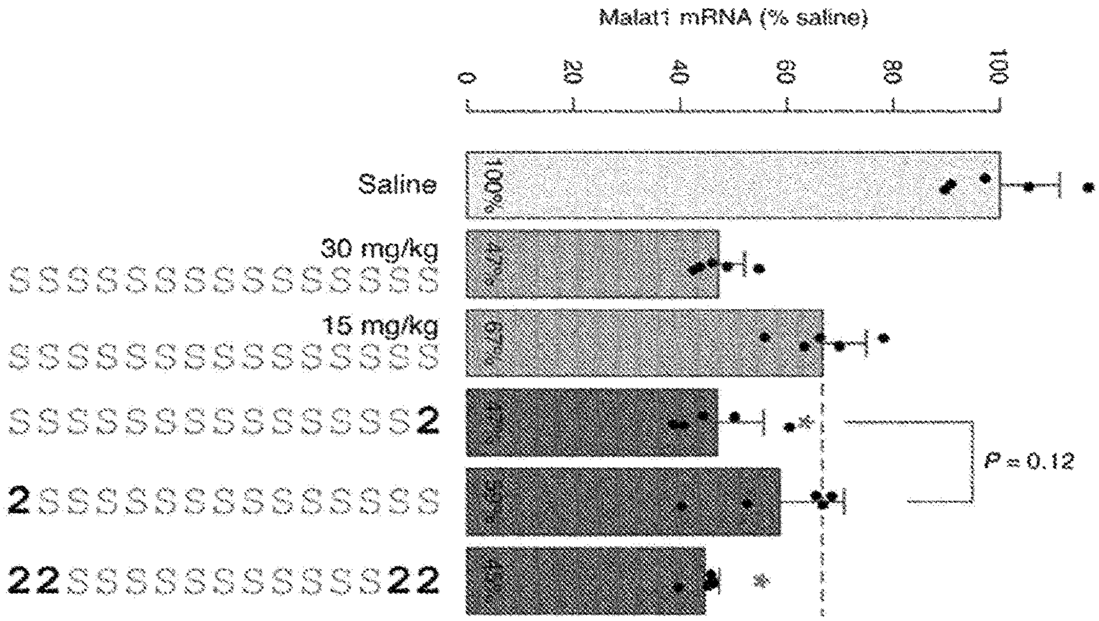

FIG. 17B: In vivo potency of achiral phosphorodithioate gapmers targeting MALAT-1.

Figure 17C:
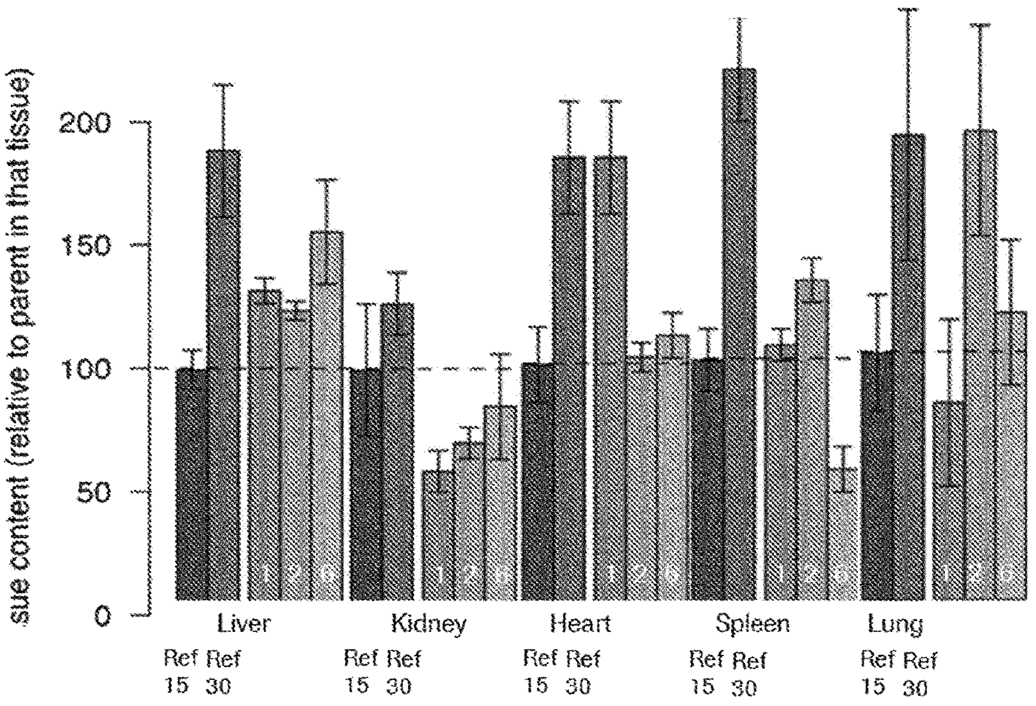

FIG. 17C: In vivo study of achiral phosphorodithioate gapmers targeting MALAT-1-tissue content FIG. 18A: In vitro study of achiral monophosphorothioate modified gapmer oligonucleotides targeting ApoB. Activity data.

Figure 18A:
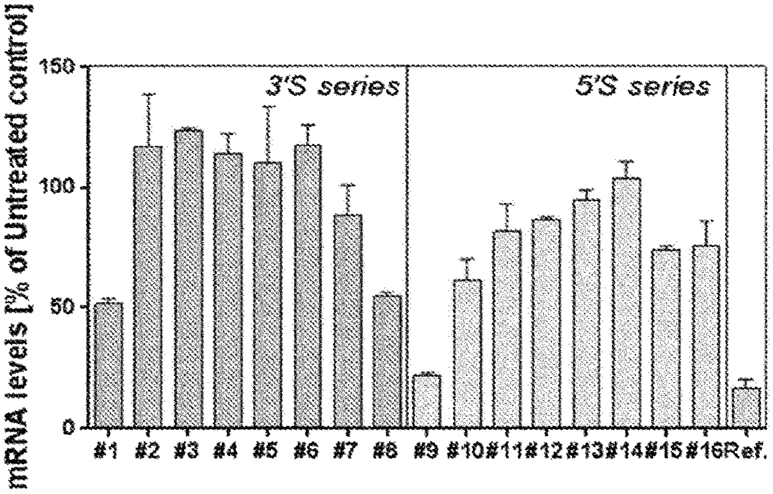
Figure 18B:
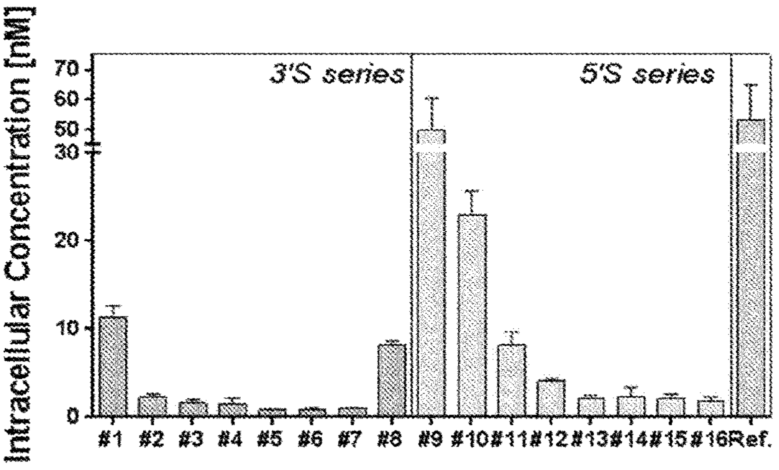

FIG. 18B: In vitro study of achiral monophosphorothioate modified gapmer oligonucleotides targeting ApoB. Cellular content data.

Figure 19A:
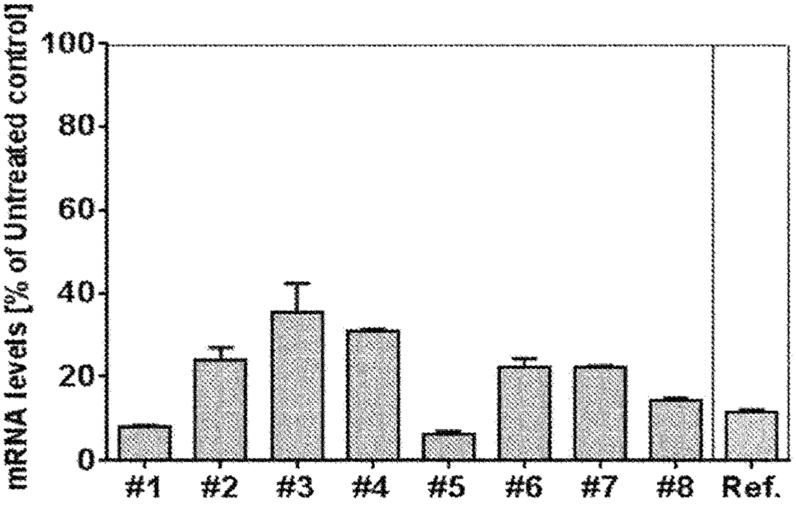

FIG. 19A: In vitro study of chiral phosphorodithioate modified gapmer oligonucleotides targeting ApoB. Activity data.

Figure 19B:
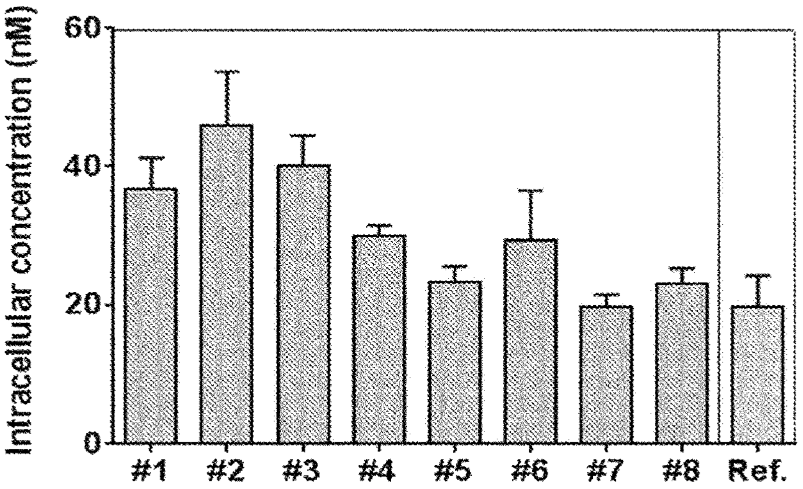

FIG. 19B: In vitro study of chiral phosphorodithioate modified gapmer oligonucleotides targeting ApoB. Cellular content data.

Figure 20:
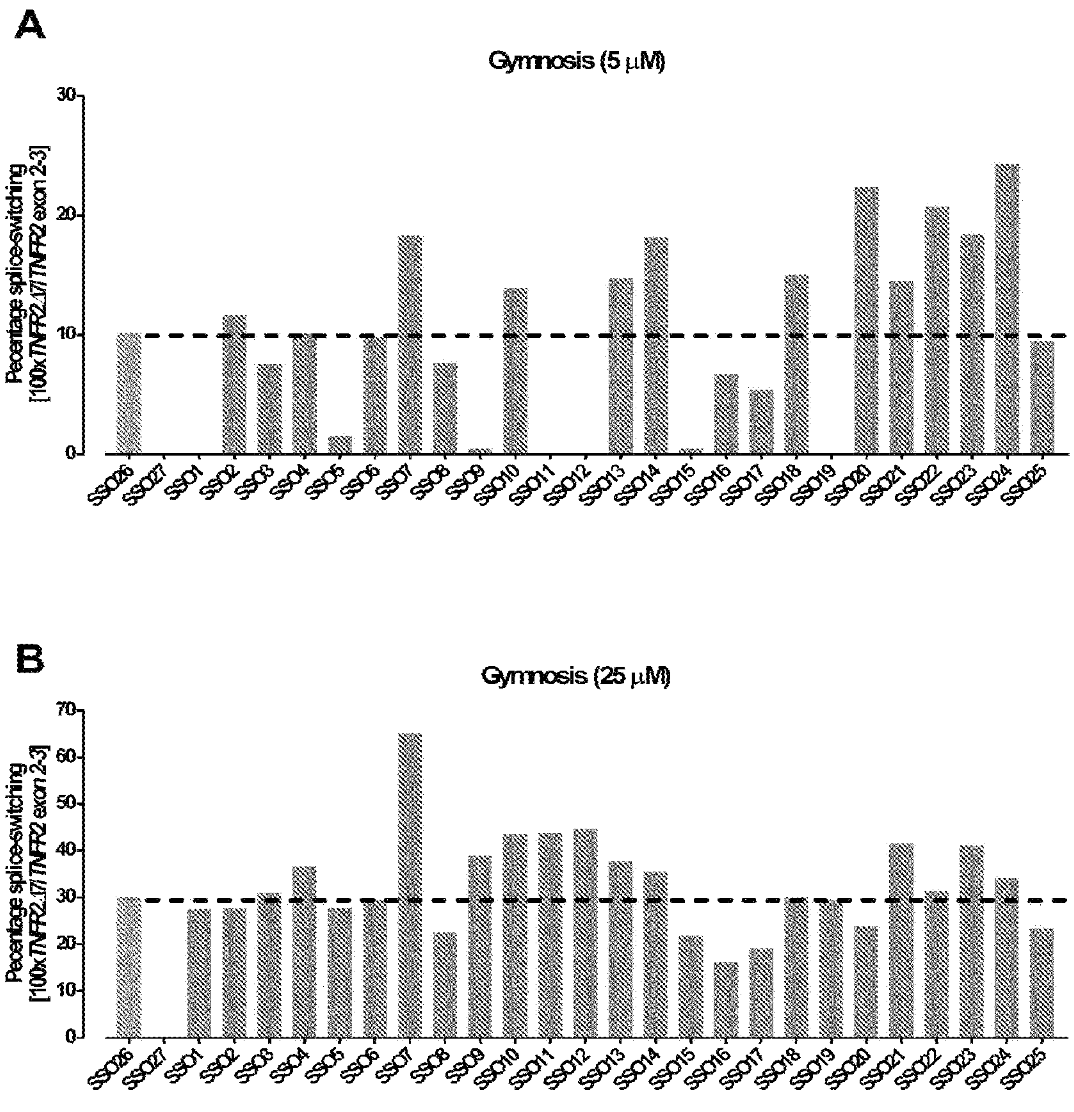

FIG. 20: Effects of achiral phosphorodithioates (P2S) internucleoside linkages present in splice-switching oligonucleotide targeting the 3' splice site of TNFRSF1B. Human Colo 205 cells was seeded in a 96 well plate and subjected to 5 μM (A) and 25 μM (B) of oligo, respectively. The percentage of exon 7 skipping was analyzed by droplet digital PCR using probes targeting the exon 6-8 junction and compared to the total amount of TNFRSF1B by the assay targeting exon 2-3. SSO #26 is the parent oligo, and SSO #27 is a negative control not targeting TNFRSF1B.

Figure 21:
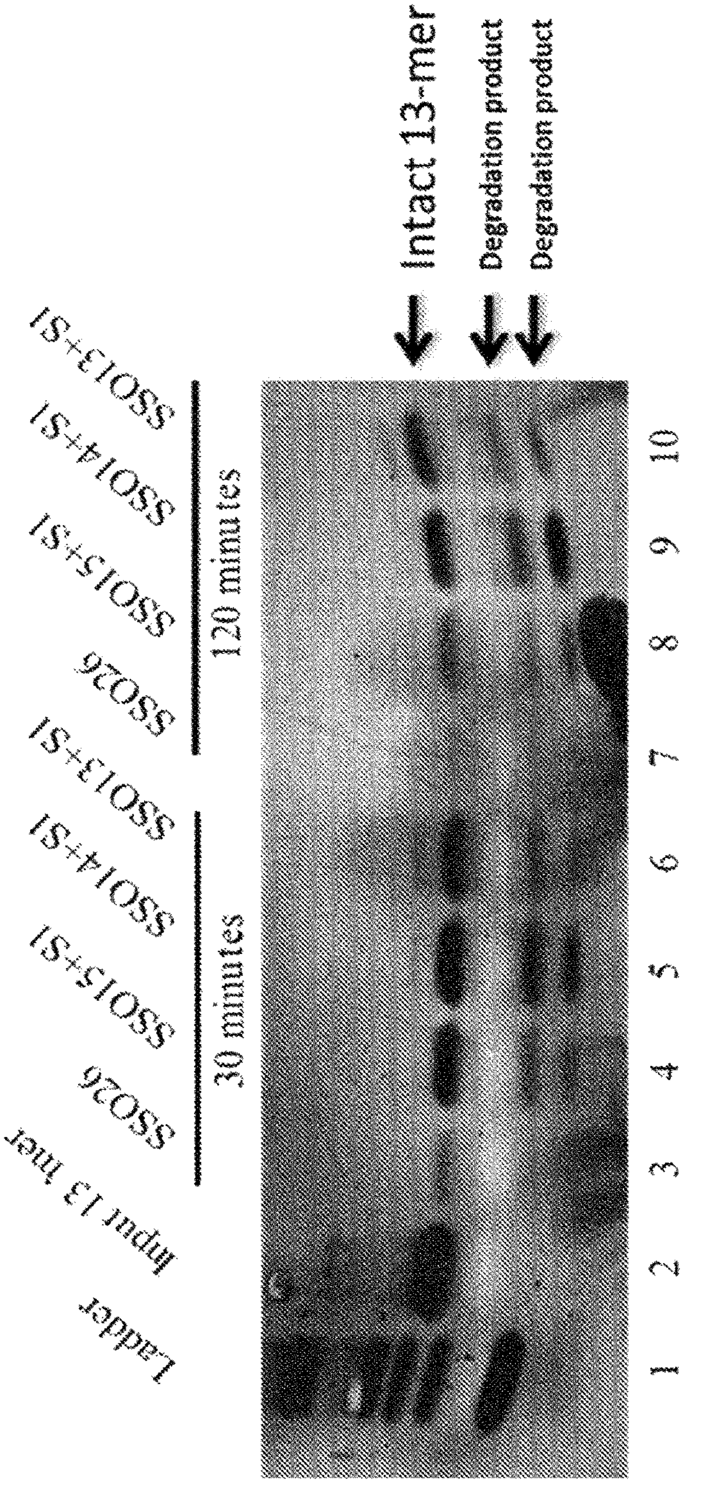

FIG. 21: Stability assay using S1 nuclease. Dithioate containing oligos were incubated with S nuclease for 30 and 120 minutes, respectively. The oligos were visualized on a 15% TBE-Urea gel. As marker of the migration of intact oligos (SSO #14) was included without being subjected to S nuclease.

DEFINITIONS

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl, cyclohexyl, cycloheptyl and cyclooctyl, more particularly cyclopropyl and cyclobutyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy. Methoxyethoxy is a particular example of "alkoxyalkoxy".

The term "oxy", alone or in combination, signifies the —O— group.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination, signifies a straight-chain or branched hydrocarbon residue comprising a triple bond and up to 8, particularly 2 carbon atoms.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl or trifluoromethyl. Fluoromethyl, difluoromethyl and trifluoromethyl are particular "haloalkyl".

The term "halocycloalkyl", alone or in combination, denotes a cycloalkyl group as defined above substituted with at least one halogen, particularly substituted with one to five halogens, particularly one to three halogens. Particular example of "halocycloalkyl" are halocyclopropyl, in particular fluorocyclopropyl, difluorocyclopropyl and trifluorocyclopropyl.

The terms "hydroxyl" and "hydroxy", alone or in combination, signify the —OH group.

The terms "thiohydroxyl" and "thiohydroxy", alone or in combination, signify the —SH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—$NH_2$), the secondary amino group (—NH—), or the tertiary amino group (—N—).

The term "alkylamino", alone or in combination, signifies an amino group as defined above substituted with one or two alkyl groups as defined above.

The term "sulfonyl", alone or in combination, means the —$SO_2$ group.

The term "sulfinyl", alone or in combination, signifies the —SO— group.

The term "sulfanyl", alone or in combination, signifies the —S— group.

The term "cyano", alone or in combination, signifies the —CN group.

The term "azido", alone or in combination, signifies the —$N_3$ group.

The term "nitro", alone or in combination, signifies the $NO_2$ group.

The term "formyl", alone or in combination, signifies the —C(O)H group.

The term "carbamoyl", alone or in combination, signifies the —C(O)$NH_2$ group.

The term "cabamido", alone or in combination, signifies the —NH—C(O)—$NH_2$ group.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl or acridinyl.

The term "heterocyclyl", alone or in combination, signifies a monovalent saturated or partly unsaturated mono- or bicyclic ring system of 4 to 12, in particular 4 to 9 ring atoms, comprising 1, 2, 3 or 4 ring heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples for monocyclic saturated heterocyclyl are azetidinyl, pyrrolidinyl, tetrahydro-furanyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The oligonucleotide of the invention can also be present in the form of zwitterions. Particularly preferred pharmaceutically acceptable salts of the invention are the sodium, lithium, potassium and trialkylammonium salts.

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

"Phosphate protecting group" is a protecting group of the phosphate group. Examples of phosphate protecting group are 2-cyanoethyl and methyl. A particular example of phosphate protecting group is 2-cyanoethyl.

"Hydroxyl protecting group" is a protecting group of the hydroxyl group and is also used to protect thiol groups. Examples of hydroxyl protecting groups are acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl) phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), methyl ethers and ethoxyethyl ethers (EE). Particular examples of hydroxyl protecting group are DMT and TMT, in particular DMT.

"Thiohydroxyl protecting group" is a protecting group of the thiohydroxyl group. Examples of thiohydroxyl protecting groups are those of the "hydroxyl protecting group".

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self complementarity is less than 50% across of the full length of the oligonucleotide.

Modulation of Expression

The term "modulation of expression" as used herein is to be understood as an overall term for an oligonucleotide's ability to alter the expression of or alter the level of the target nucleic acid. Modulation of expression may be determined by comparison to expression or level of the target nucleic acid prior to administration of the oligonucleotide, or modulation of expression may be determined by reference to a control experiment where the oligonucleotide of the invention is not administered. It is generally understood that the control is an individual or target cell treated with a saline composition or an individual or target cell treated with a non-targeting oligonucleotide (mock).

One type of modulation is the ability of an oligonucleotide's ability to inhibit, down-regulate, reduce, suppress, remove, stop, block, prevent, lessen, lower, avoid or terminate expression of the target nucleic acid e.g. by degradation of the target nucleic acid (e.g. via RNaseH1 mediated degradation) or blockage of transcription. Another type of modulation is an oligonucleotide's ability to restore, increase or enhance expression of the target RNA, e.g. modulating the splicing event on a target pre-mRNA, or via blockage of inhibitory mechanisms such as microRNA repression of an mRNA.

Contiguous Nucleotide Sequence

The term "contiguous nucleotide sequence" refers to the region of the oligonucleotide which is complementary to, such as fully complementary to, the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group to the contiguous nucleotide sequence, e.g. region D or D'. The nucleotide linker region may or may not be complementary to the target nucleic acid. The antisense oligonucleotide mixmer referred to herein may comprise or may consist of the contiguous nucleotide sequence.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides, such as region F and F'.

In an embodiment, the oligonucleotide comprises one or more internucleoside linkages modified from the natural phosphodiester, such one or more modified internucleoside linkages that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are nuclease resistant internucleoside linkages. In some embodiments all of the internucleoside linkages of the oligonucleotide, or contiguous nucleotide sequence thereof, are nuclease resistant internucleoside linkages. It will be recognized that, in some embodiments the nucleosides which link the oligonucleotide of the invention to a non-nucleotide functional group, such as a conjugate, may be phosphodiester.

A preferred modified internucleoside linkage for use in the oligonucleotide of the invention is phosphorothioate.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80% or such as at least 90% of the internucleoside linkages in the oligonucleotide, or contiguous nucleotide sequence thereof, are phosphorothioate. In some embodiments, other than the phosphorodithioate internucleoside linkages, all of the internucleoside linkages of the oligonucleotide, or contiguous nucleotide sequence thereof, are phosphorothioate. In some embodiments, the oligonucleotide of the invention comprises both phosphorothioate internucleoside linkages and at least one phosphodiester linkage, such as 2, 3 or 4 phosphodiester linkages, in addition to the phosphorodithioate linkage(s). In a gapmer oligonucleotide, phosphodiester linkages, when present, are suitably not located between contiguous DNA nucleosides in the gap region G.

Nuclease resistant linkages, such as phosphorothioate linkages, are particularly useful in oligonucleotide regions capable of recruiting nuclease when forming a duplex with the target nucleic acid, such as region G for gapmers. Phosphorothioate linkages may, however, also be useful in non-nuclease recruiting regions and/or affinity enhancing regions such as regions F and F' for gapmers. Gapmer oligonucleotides may, in some embodiments comprise one or more phosphodiester linkages in region F or F', or both region F and F', which the internucleoside linkage in region G may be fully phosphorothioate.

Advantageously, all the internucleoside linkages in the contiguous nucleotide sequence of the oligonucleotide, or all the internucleoside linkages of the oligonucleotide, are phosphorothioate linkages.

It is recognized that, as disclosed in EP 2 742 135, antisense oligonucleotides may comprise other internucleoside linkages (other than phosphodiester and phosphorothioate), for example alkyl phosphonate/methyl phosphonate internucleosides, which according to EP 2 742 135 may for example be tolerated in an otherwise DNA phosphorothioate the gap region.

Stereorandom Phosphorothioate Linkages

Phosphorothioate linkages are internucleoside phosphate linkages where one of the non-bridging oxygens has been substituted with a sulfur. The substitution of one of the non-bridging oxygens with a sulfur introduces a chiral center, and as such within a single phosphorothioate oligonucleotide, each phosphorothioate internucleoside linkage will be either in the S (Sp) or R (Rp) stereoisoforms. Such internucleoside linkages are referred to as "chiral internucleoside linkages". By comparison, phosphodiester internucleoside linkages are non-chiral as they have two non-terminal oxygen atoms.

The designation of the chirality of a stereocenter is determined by standard Cahn-Ingold-Prelog rules (CIP priority rules) first published in Cahn, R. S.; Ingold, C. K.; Prelog, V. (1966) "Specification of Molecular Chirality" Angewandte Chemie International Edition 5 (4): 385-415. doi:10.1002/anie.196603851.

During standard oligonucleotide synthesis the stereoselectivity of the coupling and the following sulfurization is not controlled. For this reason the stereochemistry of each phosphorothioate internucleoside linkages is randomly Sp or Rp, and as such a phosphorothioate oligonucleotide produced by traditional oligonucleotide synthesis actually can exist in as many as 2' different phosphorothioate diastereoisomers, where X is the number of phosphorothioate internucleoside linkages. Such oligonucleotides are referred to as stereorandom phosphorothioate oligonucleotides herein, and do not contain any stereodefined internucleoside linkages. Stereorandom phosphorothioate oligonucleotides are therefore mixtures of individual diastereoisomers originating from the non-stereodefined synthesis. In this context the mixture is defined as up to 2' different phosphorothioate diastereoisomers.

Stereodefined Internucleoside Linkages

A stereodefined internucleoside linkage is a chiral internucleoside linkage having a diastereoisomeric excess for one of its two diastereomeric forms, Rp or Sp.

It should be recognized that stereoselective oligonucleotide synthesis methods used in the art typically provide at least about 90% or at least about 95% diastereoselectivity at each chiral internucleoside linkage, and as such up to about 10%, such as about 5% of oligonucleotide molecules may have the alternative diastereoisomeric form.

In some embodiments the diastereoisomeric ratio of each stereodefined chiral internucleoside linkage is at least about 90:10. In some embodiments the diastereoisomeric ratio of each chiral internucleoside linkage is at least about 95:5.

The stereodefined phosphorothioate linkage is a particular example of stereodefined internucleoside linkage.

Stereodefined Phosphorothioate Linkage

A stereodefined phosphorothioate linkage is a phosphorothioate linkage having a diastereomeric excess for one of its two diastereosiomeric forms, Rp or Sp.

The Rp and Sp configurations of the phosphorothioate internucleoside linkages are presented below

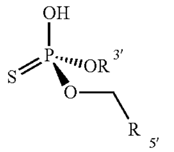
Sp

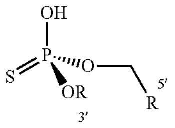
Rp

Where the 3' R group represents the 3' position of the adjacent nucleoside (a 5' nucleoside), and the 5' R group represents the 5' position of the adjacent nucleoside (a 3' nucleoside).

Rp internucleoside linkages may also be represented as srP, and Sp internucleoside linkages may be represented as ssP herein.

In a particular embodiment, the diastereomeric ratio of each stereodefined phosphorothioate linkage is at least about 90:10 or at least 95:5.

In some embodiments the diastereomeric ratio of each stereodefined phosphorothioate linkage is at least about 97:3. In some embodiments the diastereomeric ratio of each stereodefined phosphorothioate linkage is at least about 98:2. In some embodiments the diastereomeric ratio of each stereodefined phosphorothioate linkage is at least about 99:1.

In some embodiments a stereodefined internucleoside linkage is in the same diastereomeric form (Rp or Sp) in at least 97%, such as at least 98%, such as at least 99%, or (essentially) all of the oligonucleotide molecules present in a population of the oligonucleotide molecule.

Diastereomeric purity can be measured in a model system only having an achiral backbone (i.e. phosphodiesters). It is possible to measure the diastereomeric purity of each monomer by e.g. coupling a monomer having a stereodefine internucleoside linkage to the following model-system "5' t-po-t-po-t-po 3'". The result of this will then give: 5'

DMTr-t-srp-t-po-t-po-t-po 3' or 5' DMTr-t-ssp-t-po-t-po-t-po 3' which can be separated using HPLC. The diastereomeric purity is determined by integrating the UV signal from the two possible diastereoisomers and giving a ratio of these e.g. 98:2, 99:1 or >99:1.

It will be understood that the diastereomeric purity of a specific single diastereoisomer (a single stereodefined oligonucleotide molecule) will be a function of the coupling selectivity for the defined stereocenter at each internucleoside position, and the number of stereodefined internucleoside linkages to be introduced. By way of example, if the coupling selectivity at each position is 97%, the resulting purity of the stereodefined oligonucleotide with 15 stereodefined internucleoside linkages will be $0.97^{15}$, i.e. 63% of the desired diastereoisomer as compared to 37% of the other diastereoisomers. The purity of the defined diastereoisomer may after synthesis be improved by purification, for example by HPLC, such as ion exchange chromatography or reverse phase chromatography.

In some embodiments, a stereodefined oligonucleotide refers to a population of an oligonucleotide wherein at least about 40%, such as at least about 50% of the population is of the desired diastereoisomer.

Alternatively stated, in some embodiments, a stereodefined oligonucleotide refers to a population of oligonucleotides wherein at least about 40%, such as at least about 50%, of the population consists of the desired (specific) stereodefined internucleoside linkage motifs (also termed stereodefined motif).

For stereodefined oligonucleotides which comprise both stereorandom and stereodefined internucleoside chiral centers, the purity of the stereodefined oligonucleotide is determined with reference to the % of the population of the oligonucleotide which retains the desired stereodefined internucleoside linkage motif(s), the stereorandom linkages being disregarded in the calculation.

Nucleobase

The term nucleobase includes the purine (e.g. adenine and guanine) and pyrimidine (e.g. uracil, thymine and cytosine) moieties present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Stereodefined Oligonucleotide

A stereodefined oligonucleotide is an oligonucleotide wherein at least one of the internucleoside linkages is a stereodefined internucleoside linkage.

A stereodefined phosphorothioate oligonucleotide is an oligonucleotide wherein at least one of the internucleoside linkages is a stereodefined phosphorothioate internucleoside linkage.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides in a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences dividing by the total number of nucleotides in the oligonucleotide and multiplying by 100. Percent Identity=(Matches×100)/Length of aligned region. Preferably, insertions and deletions are not allowed in the calculation of % complementarity of a contiguous nucleotide sequence.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature (Tm) defined as the temperature at which half of the oligonucleotides are duplexed with the target nucleic acid. At physiological conditions Tm is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by ΔG°=−RTln($K_d$), where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Nat Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO 2011/017521) or tricyclic nucleic acids (WO 2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-fluoro-RNA and 2'-F-ANA nucleoside. Further examples can be found in e.g. Freier & Altmann; Nucl. Acid Res., 1997, 25, 4429-4443 and Uhlmann; Curr. Opinion in Drug Development, 2000, 3(2), 293-213 and Deleavey and Damha, Chemistry and Biology 2012, 19, 937. Below are illustrations of some 2' substituted modified nucleosides.

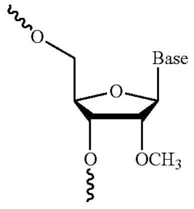

2′-O-Me

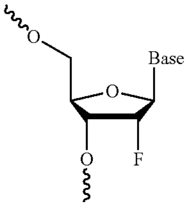

2′F-RNA

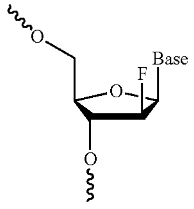

2′F-ANA

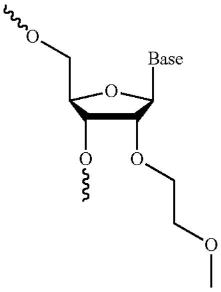

2′-O-MOE

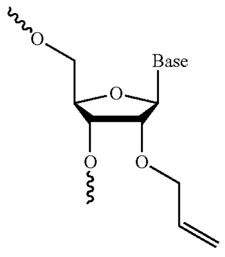

2′-O-Allyl

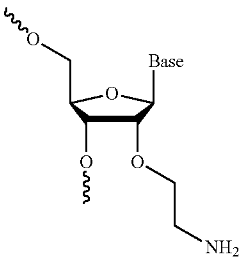

2′-O-Ethylamine

In relation to the present invention 2' substituted does not include 2' bridged molecules like LNA.

Locked Nucleic Acid Nucleosides (LNA Nucleosides)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81 and Mitsuoka et al., Nucleic Acids Research 2009, 37(4), 1225-1238.

The 2'-4' bridge comprises 2 to 4 bridging atoms and is in particular of formula —X—Y—, X being linked to C4' and Y linked to C2', wherein X is oxygen, sulfur, $—CR^aR^b—$, $—C(R^a){=}C(R^b)—$, $—C(=CR^aR^b)—$, $—C(R^a){=}N—$, $—Si(R^a)_2—$, $—SO_2—$, $—NR^a—$; $—O—NR^a—$, $—NR^a—O—$, —C(=J)-, Se, $—O—NR^a—$, $—NR^a—CR^aR^b—$, $—N(R^a)—O—$ or $—O—CR^aR^b—$;

Y is oxygen, sulfur, $—(CR^aR^b)_n—$, $—CR^aR^b—O—CR^aR^b—$, $—C(R^a){=}C(R^b)—$, $—C(R^a){=}N—$, $—Si(R^a)_2—$, $—SO_2—$, $—NR^a—$, —C(=J)-, Se, $—O—NR^a—$, $—NR^a—CR^aR^b—$, $—N(R^a)—O—$ or $—O—CR^aR^b—$;

with the proviso that —X—Y— is not —O—O—, $Si(R^a)_2—Si(R^a)_2—$, $—SO_2—SO_2—$, $—C(R^a){=}C(R^b)—C(R^a){=}C(R^b)$, $—C(R^a){=}N—C(R^a){=}N—$, $—C(R^a){=}N—C(R^a){=}C(R^b)$, $—C(R^a){=}C(R^b)—C(R^a){=}N—$ or —Se—Se—;

J is oxygen, sulfur, $=CH_2$ or $=N(R^a)$;

$R^a$ and $R^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, $—OC(=X^a)R^c$, $—OC(=X^a)NR^cR^d$ and $—NR^eC(=X^a)NR^cR^d$;

or two geminal $R^a$ and $R^b$ together form optionally substituted methylene;

or two geminal $R^a$ and $R^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocylyl, aryl and heteroaryl;

$X^a$ is oxygen, sulfur or —NR;

$R^c$, $R^d$ and $R^e$ are independently selected from hydrogen and alkyl; and n is 1, 2 or 3.

In a further particular embodiment of the invention, X is oxygen, sulfur, $—NR^a—$, $—CR^aR^b—$ or $—C(=CR^aR^b)—$, particularly oxygen, sulfur, —NH—, $—CH_2—$ or $—C(=CH_2)—$, more particularly oxygen.

In another particular embodiment of the invention, Y is $—CR^aR^b—$, $—CR^aR^b—CR^aR^b—$ or $—CR^aR^b—CR^aR^b—CR^aR^b—$, particularly $—CH_2—CHCH_3—$, $—CHCH_3—CH_2—$, $—CH_2—CH_2—$ or $—CH_2—CH_2—CH_2—$.

In a particular embodiment of the invention, —X—Y— is $—O—(CR^aR^b)_n—$, $—S—CR^aR^b—$, $—N(R^a)CR^aR^b—$, $—CR^aR^b—CR^aR^b—$, $—O—CR^aR^b—O—CR^aR^b—$, $—CR^aR^b—O—CR^aR^b—$, $—C(=CR^aR^b)—CR^aR^b—$, $—N(R^a)CR^aR^b—$, $—O—N(R^a)—CR^aR^b—$ or $—N(R^a)—O—CR^aR^b—$.

In a particular embodiment of the invention, $R^a$ and $R^b$ are independently selected from the group consisting of hydrogen, halogen, hydroxyl, alkyl and alkoxyalkyl, in particular hydrogen, halogen, alkyl and alkoxyalkyl.

In another embodiment of the invention, $R^a$ and $R^b$ are independently selected from the group consisting of hydrogen, fluoro, hydroxyl, methyl and $—CH_2—O—CH_3$, in particular hydrogen, fluoro, methyl and $—CH_2—O—CH_3$.

Advantageously, one of $R^a$ and $R^b$ of —X—Y— is as defined above and the other ones are all hydrogen at the same time.

In a further particular embodiment of the invention, $R^a$ is hydrogen or alkyl, in particular hydrogen or methyl.

In another particular embodiment of the invention, $R^b$ is hydrogen or or alkyl, in particular hydrogen or methyl.

In a particular embodiment of the invention, one or both of $R^a$ and $R^b$ are hydrogen.

In a particular embodiment of the invention, only one of $R^a$ and $R^b$ is hydrogen.

In one particular embodiment of the invention, one of $R^a$ and $R^b$ is methyl and the other one is hydrogen.

In a particular embodiment of the invention, $R^a$ and $R^b$ are both methyl at the same time.

In a particular embodiment of the invention, —X—Y— is $—O—CH_2—$, $—S—CH_2—$, $—S—CH(CH_3)—$, $—NH—CH_2—$, $—O—CH_2CH_2—$, $—O—CH(CH_2—O—CH_3)—$, $—O—CH(CH_2CH_3)—$, $—O—CH(CH_3)—$, $—O—CH_2—O—CH_2—$, $—O—CH_2—O—CH_2—$, $—CH_2—O—CH_2—$, $—C(=CH_2)CH_2—$, $—C(=CH_2)CH(CH_3)—$, $—N(OCH_3)CH_2—$ or $—N(CH_3)CH_2—$;

In a particular embodiment of the invention, —X—Y— is $—O—CR^aR^b—$ wherein $R^a$ and $R^b$ are independently selected from the group consisting of hydrogen, alkyl and alkoxyalkyl, in particular hydrogen, methyl and $—CH_2—O—CH_3$.

In a particular embodiment, —X—Y— is $—O—CH_2—$ or $—CH(CH_3)—$, particularly $—O—CH_2—$.

The 2'-4' bridge may be positioned either below the plane of the ribose ring (beta-D-configuration), or above the plane of the ring (alpha-L-configuration), as illustrated in formula (A) and formula (B) respectively.

The LNA nucleoside according to the invention is in particular of formula (B1) or (B2)

(B1)

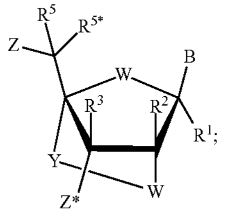

(B2)

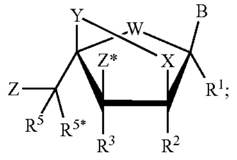

wherein

W is oxygen, sulfur, —N($R^a$)— or —C$R^aR^b$—, in particular oxygen;

B is a nucleobase or a modified nucleobase;

Z is an internucleoside linkage to an adjacent nucleoside or a 5'-terminal group;

Z* is an internucleoside linkage to an adjacent nucleoside or a 3'-terminal group;

$R^1$, $R^2$, $R^3$, $R^5$ and $R^{5*}$ are independently selected from hydrogen, halogen, alkyl, haloalkyl, alkenyl, alkynyl, hydroxy, alkoxy, alkoxyalkyl, azido, alkenyloxy, carboxyl, alkoxycarbonyl, alkylcarbonyl, formyl and aryl; and X, Y, $R^a$ and $R^b$ are as defined above.

In a particular embodiment, in the definition of —X—Y—, $R^a$ is hydrogen or alkyl, in particular hydrogen or methyl. In another particular embodiment, in the definition of —X—Y—, $R^b$ is hydrogen or alkyl, in particular hydrogen or methyl. In a further particular embodiment, in the definition of —X—Y—, one or both of $R^a$ and $R^b$ are hydrogen. In a particular embodiment, in the definition of —X—Y—, only one of $R^a$ and $R^b$ is hydrogen. In one particular embodiment, in the definition of —X—Y—, one of $R^a$ and $R^b$ is methyl and the other one is hydrogen. In a particular embodiment, in the definition of —X—Y—, $R^a$ and $R^b$ are both methyl at the same time.

In a further particular embodiment, in the definition of X, $R^a$ is hydrogen or alkyl, in particular hydrogen or methyl. In another particular embodiment, in the definition of X, $R^b$ is hydrogen or alkyl, in particular hydrogen or methyl. In a particular embodiment, in the definition of X, one or both of $R^a$ and $R^b$ are hydrogen. In a particular embodiment, in the definition of X, only one of $R^a$ and $R^b$ is hydrogen. In one particular embodiment, in the definition of X, one of $R^a$ and $R^b$ is methyl and the other one is hydrogen. In a particular embodiment, in the definition of X, $R^a$ and $R^b$ are both methyl at the same time.

In a further particular embodiment, in the definition of Y, $R^a$ is hydrogen or alkyl, in particular hydrogen or methyl. In another particular embodiment, in the definition of Y, $R^b$ is hydrogen or alkyl, in particular hydrogen or methyl. In a particular embodiment, in the definition of Y, one or both of $R^a$ and $R^b$ are hydrogen. In a particular embodiment, in the definition of Y, only one of $R^a$ and $R^b$ is hydrogen. In one particular embodiment, in the definition of Y, one of $R^a$ and $R^b$ is methyl and the other one is hydrogen. In a particular embodiment, in the definition of Y, $R^a$ and $R^b$ are both methyl at the same time.

In a particular embodiment of the invention $R^1$, $R^2$, $R^3$, $R^5$ and $R^{5*}$ are independently selected from hydrogen and alkyl, in particular hydrogen and methyl.

In a further particular advantageous embodiment of the invention, $R^1$, $R^2$, $R^3$, $R^5$ and $R^{5*}$ are all hydrogen at the same time.

In another particular embodiment of the invention, $R^1$, $R^2$, $R^3$, are all hydrogen at the same time, one of $R^5$ and $R^{5*}$ is hydrogen and the other one is as defined above, in particular alkyl, more particularly methyl.

In a particular embodiment of the invention, $R^5$ and $R^{5*}$ are independently selected from hydrogen, halogen, alkyl, alkoxyalkyl and azido, in particular from hydrogen, fluoro, methyl, methoxyethyl and azido. In particular advantageous embodiments of the invention, one of $R^5$ and $R^{5*}$ is hydrogen and the other one is alkyl, in particular methyl, halogen, in particular fluoro, alkoxyalkyl, in particular methoxyethyl or azido; or $R^5$ and $R^{5*}$ are both hydrogen or halogen at the same time, in particular both hydrogen of fluoro at the same time. In such particular embodiments, W can advantageously be oxygen, and —X—Y— advantageously —O—$CH_2$—.

In a particular embodiment of the invention, —X—Y— is —O—$CH_2$—, W is oxygen and $R^1$, $R^2$, $R^3$, $R^5$ and $R^{5*}$ are all hydrogen at the same time. Such LNA nucleosides are disclosed in WO 99/014226, WO 00/66604, WO 98/039352 and WO 2004/046160 which are all hereby incorporated by reference, and include what are commonly known in the art as beta-D-oxy LNA and alpha-L-oxy LNA nucleosides.

In another particular embodiment of the invention, —X—Y— is —S—$CH_2$—, W is oxygen and $R^1$, $R^2$, $R^3$, $R^5$ and $R^{5*}$ are all hydrogen at the same time. Such thio LNA nucleosides are disclosed in WO 99/014226 and WO 2004/046160 which are hereby incorporated by reference.

In another particular embodiment of the invention, —X—Y— is —NH—$CH_2$—, W is oxygen and $R^1$, $R^2$, $R^3$, $R^5$ and $R^{5*}$ are all hydrogen at the same time. Such amino LNA nucleosides are disclosed in WO 99/014226 and WO 2004/046160 which are hereby incorporated by reference.

In another particular embodiment of the invention, —X—Y— is —O—$CH_2CH_2$— or —O$CH_2CH_2CH_2$—, W is oxygen, and $R^1$, $R^2$, $R^3$, $R^5$ and $R^{5*}$ are all hydrogen at the same time. Such LNA nucleosides are disclosed in WO 00/047599 and Morita et al., Bioorganic & Med. Chem. Lett. 12, 73-76, which are hereby incorporated by reference, and include what are commonly known in the art as 2'-O-4'C-ethylene bridged nucleic acids (ENA).

In another particular embodiment of the invention, —X—Y— is —O—$CH_2$—, W is oxygen, $R^1$, $R^2$, $R^3$ are all hydrogen at the same time, one of $R^5$ and $R^{5*}$ is hydrogen and the other one is not hydrogen, such as alkyl, for example methyl. Such 5' substituted LNA nucleosides are disclosed in WO 2007/134181 which is hereby incorporated by reference.

In another particular embodiment of the invention, —X—Y— is —O—C$R^aR^b$—, wherein one or both of $R^a$ and $R^b$ are not hydrogen, in particular alkyl such as methyl, W is oxygen, $R^1$, $R^2$, $R^3$ are all hydrogen at the same time, one of $R^5$ and $R^{5*}$ is hydrogen and the other one is not hydrogen, in particular alkyl, for example methyl. Such bis modified LNA nucleosides are disclosed in WO 2010/077578 which is hereby incorporated by reference.

In another particular embodiment of the invention, —X—Y— is —O—CH$R^a$—, W is oxygen and $R^1$, $R^2$, $R^3$, $R^5$ and $R^{5*}$ are all hydrogen at the same time. Such 6'-substituted LNA nucleosides are disclosed in WO 2010/036698 and WO 2007/090071 which are both hereby incorporated by reference. In such 6'-substituted LNA nucleosides, $R^a$ is in particular $C_1$-$C_6$ alkyl, such as methyl.

In another particular embodiment of the invention, —X—Y— is —O—CH($CH_2$—O—$CH_3$)— ("2' O-methoxyethyl bicyclic nucleic acid", Seth et al. J. Org. Chem. 2010, Vol 75(5) pp. 1569-81).

In another particular embodiment of the invention, —X—Y— is —O—CH($CH_2CH_3$)—;

In another particular embodiment of the invention, —X—Y— is —O—CH($CH_2$—O—$CH_3$)—, W is oxygen and $R^1$, $R^2$, $R^3$, $R^5$ and $R^{5*}$ are all hydrogen at the same time. Such LNA nucleosides are also known in the art as cyclic MOEs (cMOE) and are disclosed in WO 2007/090071.

In another particular embodiment of the invention, —X—Y— is —O—CH($CH_3$)— ("2'O-ethyl bicyclic nucleic acid", Seth at al., J. Org. Chem. 2010, Vol 75(5) pp. 1569-81).

In another particular embodiment of the invention, —X—Y— is —O—$CH_2$—O—$CH_2$— (Seth et al., J. Org. Chem 2010 op. cit.)

In another particular embodiment of the invention, —X—Y— is —O—CH($CH_3$)—, W is oxygen and $R^1$, $R^2$, $R^3$, $R^5$ and $R^{5*}$ are all hydrogen at the same time. Such 6'-methyl LNA nucleosides are also known in the art as cET nucleosides, and may be either (S)-cET or (R)-cET diastereoisomers, as disclosed in WO 2007/090071 (beta-D) and WO 2010/036698 (alpha-L) which are both hereby incorporated by reference.

In another particular embodiment of the invention, —X—Y— is —O—$CR^aR^b$—, wherein neither $R^a$ nor $R^b$ is hydrogen, W is oxygen and $R^1$, $R^2$, $R^3$, $R^5$ and $R^{5*}$ are all hydrogen at the same time. In a particular embodiment, $R^a$ and $R^b$ are both alkyl at the same time, in particular both methyl at the same time. Such 6'-di-substituted LNA nucleosides are disclosed in WO 2009/006478 which is hereby incorporated by reference.

In another particular embodiment of the invention, —X—Y— is —S—$CHR^a$—, W is oxygen and $R^1$, $R^2$, $R^3$, $R^5$ and $R^{5*}$ are all hydrogen at the same time. Such 6'-substituted thio LNA nucleosides are disclosed in WO 2011/156202 which is hereby incorporated by reference. In a particular embodiment of such 6'-substituted thio LNA, $R^a$ is alkyl, in particular methyl.

In a particular embodiment of the invention, —X—Y— is —C(=$CH_2$)C($R^aR^b$)—, —C(=CHF)C($R^aR^b$)— or —C(=$CF_2$)C($R^aR^b$)—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. $R^a$ and $R^b$ are in particular both hydrogen or methyl at the same time or one of $R^a$ and $R^b$ is hydrogen and the other one is methyl. Such vinyl carbo LNA nucleosides are disclosed in WO 2008/154401 and WO 2009/067647 which are both hereby incorporated by reference.

In a particular embodiment of the invention, —X—Y— is —N($OR^a$)—$CH_2$—, W is oxygen and $R^1$, $R^2$, $R^3$, $R^5$ and $R^{5*}$ are all hydrogen at the same time. In a particular embodiment, $R^a$ is alkyl such as methyl. Such LNA nucleosides are also known as N substituted LNAs and are disclosed in WO 2008/150729 which is hereby incorporated by reference.

In a particular embodiment of the invention, —X—Y— is —O—N($R^a$)—, —N($R^a$)—O—, —$NR^a$—$CR^aR^b$—$CR^aR^b$— or —$NR^a$—$CR^aR^b$—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. In a particular embodiment, $R^a$ is alkyl, such as methyl, $R^b$ is hydrogen or methyl, in particular hydrogen. (Seth et al., J. Org. Chem 2010 op. cit.).

In a particular embodiment of the invention, —X—Y— is —O—N($CH_3$)— (Seth et al., J. Org. Chem 2010 op. cit.).

In a particular embodiment of the invention, $R^5$ and $R^{5*}$ are both hydrogen at the same time. In another particular embodiment of the invention, one of $R^5$ and $R^{5*}$ is hydrogen and the other one is alkyl, such as methyl. In such embodiments, $R^1$, $R^2$ and $R^3$ can be in particular hydrogen and —X—Y— can be in particular —O—$CH_2$— or —O—CHC($R^a$)$_3$, such as —O—CH($CH_3$)—.

In a particular embodiment of the invention, —X—Y— is —$CR^aR^b$—O—$CR^aR^b$—, such as —$CH_2$—O—$CH_2$—, W is oxygen and $R^1$, $R^2$, $R^3$, $R^5$ and $R^{5*}$ are all hydrogen at the same time. In such particular embodiments, $R^a$ can be in particular alkyl such as methyl, $R^b$ hydrogen or methyl, in particular hydrogen. Such LNA nucleosides are also known as conformationally restricted nucleotides (CRNs) and are disclosed in WO 2013/036868 which is hereby incorporated by reference.

In a particular embodiment of the invention, —X—Y— is —O—$CR^aR^b$—O—$CR^aR^b$—, such as —O—$CH_2$—O—$CH_2$—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. In such a particular embodiment, $R^a$ can be in particular alkyl such as methyl, $R^b$ hydrogen or methyl, in particular hydrogen. Such LNA nucleosides are also known as COC nucleotides and are disclosed in Mitsuoka et al., Nucleic Acids Research 2009, 37(4), 1225-1238, which is hereby incorporated by reference.

It will be recognized than, unless specified, the LNA nucleosides may be in the beta-D or alpha-L stereoisoform.

Particular examples of LNA nucleosides of the invention are presented in Scheme 1 (wherein B is as defined above).

Scheme 1

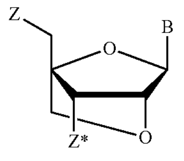
β-D-oxy LNA

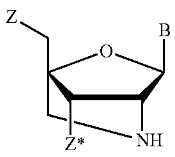
β-D-amino LNA

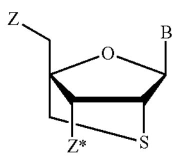
β-D-thio LNA

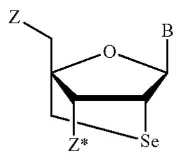
β-D-Se LNA

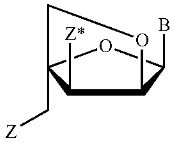
α-L-oxy LNA

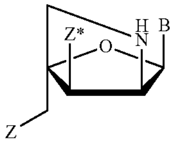
α-L-amino LNA

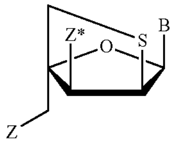
α-L-thio LNA

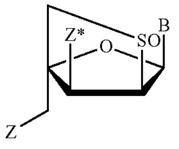

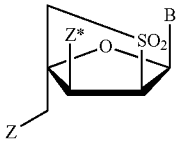

-continued

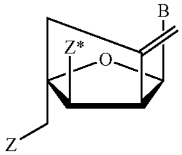

carbocyclic(vinyl)-α-L LNA

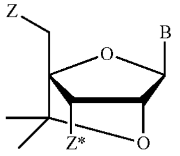

6′-dimethyl-β-D-oxy LNA

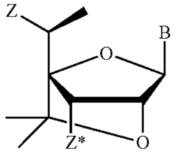

(S)-5′-methyl-6′-di methyl-β-D-oxy LNA

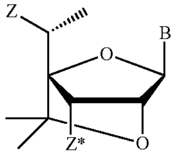

(R)-5′-methyl-6′-di methyl-β-D-oxy LNA

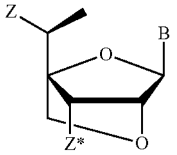

(S)-5′-methyl-β-D-oxy LNA

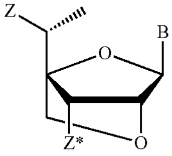

(R)-5′-methyl-β-D-oxy LNA

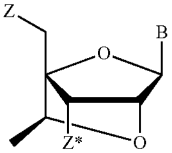

(S)-cET

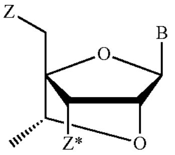

(R)-cET

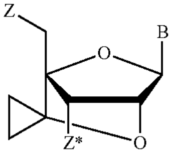

cprop-β-D-oxy LNA

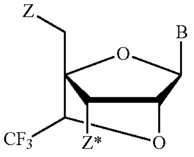

trifluoromethyl-β-D-oxy LNA

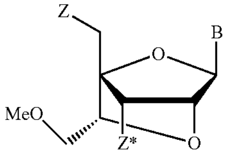

(R)-cMOE

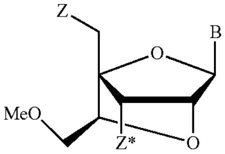

(S)-cMOE

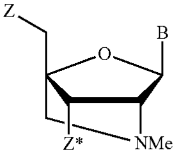

β-D-methylamino LNA

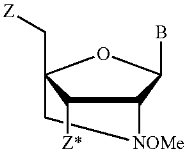

β-D-methoxyamino LNA

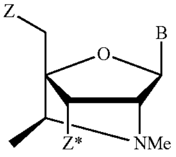

β-D-(S)-cET-methylamino LNA

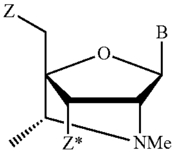

β-D-(R)-cET-methylamino LNA

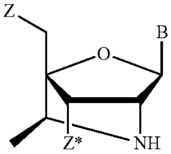

β-D-(S)-cET-amino LNA

-continued

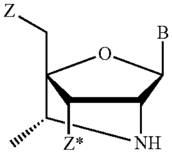

β-D-(R)-cET-amino LNA

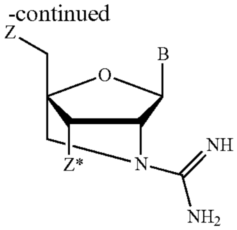

β-D-guanidine LNA

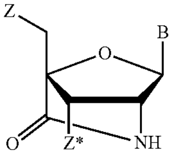

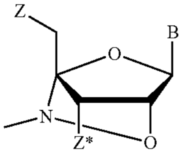

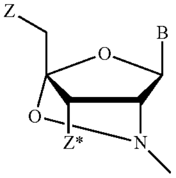

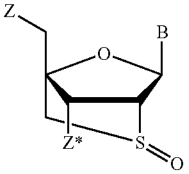

β-D-sulfoxide LNA

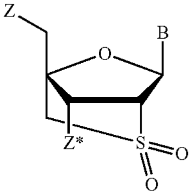

β-D-sulfonyl LNA

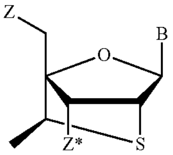

(S)-cET-β-D-thio LNA

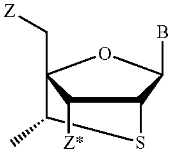

(R)-cET-β-D-thio LNA

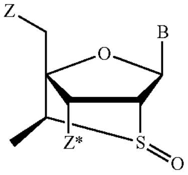

(S)-cET-β-D-sulfoxide LNA

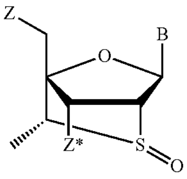

(R)-cET-β-D-sulfoxide LNA

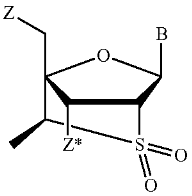

(S)-cET-β-D-sulfonyl LNA

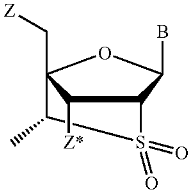

(R)-cET-β-D-sulfonyl LNA

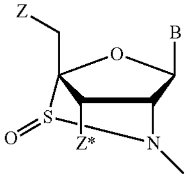

methyl-sulfoxamide-β-D LNA

-continued

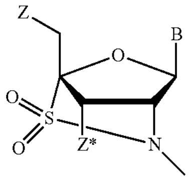

methyl-sulfonamide-β-D LNA

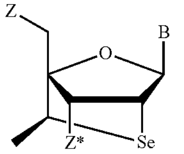

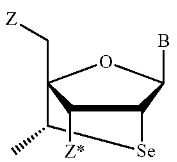

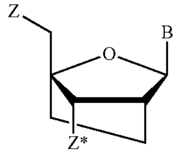

carbocyclic-β-D LNA

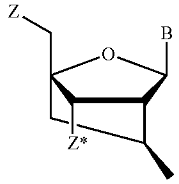

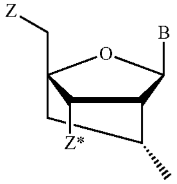

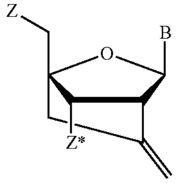

carbocyclic(vinyl)-β-D-Z LNA

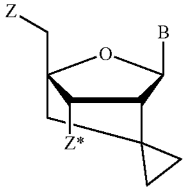

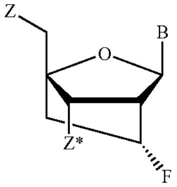

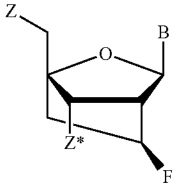

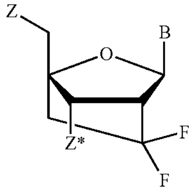

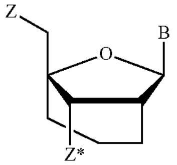

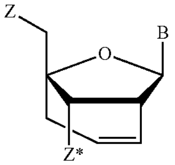

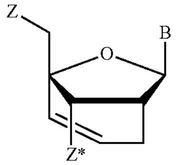

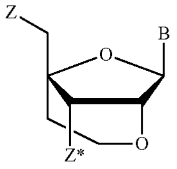

ENA

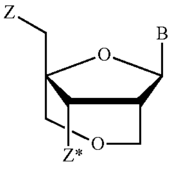

COC

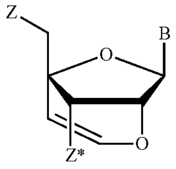

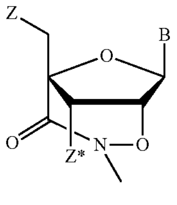

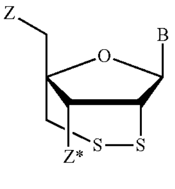

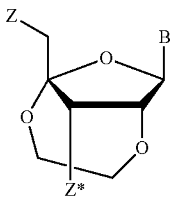

-continued

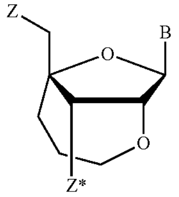

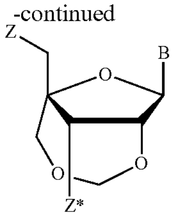

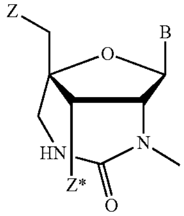

urea-methyl LNA

Particular LNA nucleosides are beta-D-oxy-LNA, 6'-methyl-beta-D-oxy LNA such as (S)-6'-methyl-beta-D-oxy-LNA ((S)-cET) and ENA.

MOE Nucleoside

The term "MOE" stands for "methoxy-ethyl" and refers by means of abbreviation to a nucleoside substituted in 2' position with a methoxy-ethoxy group as represented below.

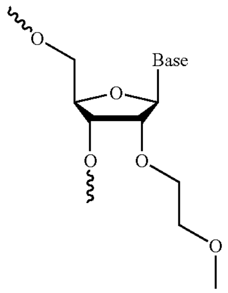

2'-O-MOE

The above nucleoside can thus be named either "MOE" or "2'-O-MOE nucleoside".

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland.

Gapmer

The antisense oligonucleotide of the invention, or contiguous nucleotide sequence thereof may be a gapmer. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides.

By way of example, the gapmer oligonucleotide of the present invention can be represented by the following formulae:

$F_{1-8}$-$G_{5-16}$-$F'_{1-8}$, such as $F_{1-8}$-$G_{7-16}$-$F'_{2-8}$ with the proviso that the overall length of the gapmer regions F-G-F' is at least 12, such as at least 14 nucleotides in length.

Regions F, G and F' are further defined below and can be incorporated into the F-G-F' formula.

Gapmer—Region G

Region G (gap region) of the gapmer is a region of nucleosides which enables the oligonucleotide to recruit RNaseH, such as human RNase H1, typically DNA nucleosides. RNaseH is a cellular enzyme which recognizes the duplex between DNA and RNA, and enzymatically cleaves the RNA molecule. Suitable gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. Cytosine (C) DNA in the gap region may in some instances be methylated, such residues are either annotated as 5-methyl-cytosine ($^{me}$C or with an e instead of a c). Methylation of Cytosine DNA in the gap is advantageous if cg dinucleotides are present in the gap to reduce potential toxicity, the modification does not have significant impact on efficacy of the oligonucleotides.

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue. The modified nucleosides used in such gapmers may be nucleosides which adopt a 2' endo (DNA like) structure when introduced into the gap region, i.e. modifications which allow for RNaseH recruitment). In some embodiments the DNA Gap region (G) described herein may optionally contain 1 to 3 sugar modified nucleosides which adopt a 2' endo (DNA like) structure when introduced into the gap region.

Region G—"Gap-Breaker"

Alternatively, there are numerous reports of the insertion of a modified nucleoside which confers a 3' endo conformation into the gap region of gapmers, whilst retaining some RNaseH activity. Such gapmers with a gap region comprising one or more 3'endo modified nucleosides are referred to as "gap-breaker" or "gap-disrupted" gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleosides at the 5' end of the gap (adjacent to the 3' nucleoside of region F), and a DNA nucleoside at the 3' end of the gap (adjacent to the 5' nucleoside of region F'). Gapmers which comprise a disrupted gap typically retain a region of at least 3 or 4 contiguous DNA nucleosides at either the 5' end or 3' end of the gap region.

Exemplary designs for gap-breaker oligonucleotides include $F_{1-8}$-[$D_{3-4}$-$E_1$-$D_{3-4}$]-$F'_{1-8}$ $F_{1-8}$-[$D_{1-4}$-$E_1$-$D_{3-4}$]-$F'_{1-8}$ $F_{1-8}$-[$D_{3-4}$-$E_1$-$D_{1-4}$]-$F'_{1-8}$ wherein region G is within the brackets [$D_n$-$E_r$-$D_m$], D is a contiguous sequence of DNA nucleosides, E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length.

In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3' most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside.

It should be noted that when the length of region F or F' is one, it is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

Further gapmer designs are disclosed in WO 2004/046160, WO 2007/146511 and WO 2008/113832, hereby incorporated by reference.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: $[LNA]_{1-5}$-[region G]-$[LNA]_{1-5}$, wherein region G is as defined in the Gapmer region G definition.

MOE Gapmers

A MOE gapmers is a gapmer wherein regions F and F' consist of MOE nucleosides. In some embodiments the MOE gapmer is of design $[MOE]_{1-8}$-[Region G]-$[MOE]_{1-8}$, such as $[MOE]_{2-7}$-$[Region\ G]_{5-16}$-$[MOE]_{2-7}$, such as $[MOE]_{3-6}$-[Region G]-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' 25 comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO 2008/049085 and WO 2012/109395, both of which are hereby incorporated by reference.

Alternating Flank Gapmers

Flanking regions may comprise both LNA and DNA nucleoside and are referred to as “alternating flanks” as they comprise an alternating motif of LNA-DNA-LNA nucleosides. Gapmers comprising such alternating flanks are referred to as “alternating flank gapmers”. “Alternative flank gapmers” are thus LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

Alternating flank LNA gapmers are disclosed in WO 2016/127002.

An alternating flank region may comprise up to 3 contiguous DNA nucleosides, such as 1 to 2 or 1 or 2 or 3 contiguous DNA nucleosides.

The alternating flak can be annotated as a series of integers, representing a number of LNA nucleosides (L) followed by a number of DNA nucleosides (D), for example $[L]_{1-3}$-$[D]_{1-4}$-$[L]_{1-3}$ $[L]_{1-2}$-$[D]_{1-2}$-$[L]_{1-2}$-$[D]_{1-2}$-$[L]_{1-2}$ In oligonucleotide designs these will often be represented as numbers such that 2-2-1 represents 5'$[L]_2$-$[D]_2$-[L]3', and 1-1-1-1-1 represents 5'[L]-[D]-[L]-[D]-[L]3'. The length of the flank (region F and F') in oligonucleotides with alternating flanks may independently be 3 to 10 nucleosides, such as 4 to 8, such as 5 to 6 nucleosides, such as 4, 5, 6 or 7 modified nucleosides. In some embodiments only one of the flanks in the gapmer oligonucleotide is alternating while the other is constituted of LNA nucleotides. It may be advantageous to have at least two LNA nucleosides at the 3' end of the 3' flank (F'), to confer additional exonuclease resistance. Some examples of oligonucleotides with alternating flanks are:

$[L]_{1-5}$-$[D]_{1-4}$-$[L]_{1-3}$-$[G]_{5-16}$-$[L]_{2-6}$ $[L]_{1-2}$-$[D]_{1-2}$-$[L]_{1-2}$-$[D]_{1-2}$-$[L]_{1-2}$-$[G]_{5-16}$-$[L]_{1-2}$-$[D]_{1-3}$-$[L]_{2-4}$ $[L]_{1-5}$-$[G]_{5-16}$-[L]-[D]-[L]-[D]-$[L]_2$ with the proviso that the overall length of the gapmer is at least 12, such as at least 14 nucleotides in length.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively it may be used to provide exonucleoase protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO 2014/076195, which include by way of example a phosphodiester linked DNA dinucleotide. The use of biocleavable linkers in poly-oligonucleotide constructs is disclosed in WO 2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

F-G-F'; in particular $F_{1-8}$-$G_{5-16}$-$F'_{2-8}$

D'-F-G-F', in particular $D'_{1-3}$-$F_{1-8}$-$G_{5-16}$-$F'_{2-8}$

F-G-F'-D", in particular $F_{1-8}$-$G_{5-16}$-$F'_{2-8}$-$D''_{1-3}$

D'-F-G-F'-D", in particular $D'_{1-3}$-$F_{1-8}$-$G_{5-16}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Totalmers

In some embodiments, all of the nucleosides of the oligonucleotide, or contiguous nucleotide sequence thereof, are sugar modified nucleosides. Such oligonucleotides are referred to as a totalmers herein.

In some embodiments all of the sugar modified nucleosides of a totalmer comprise the same sugar modification, for example they may all be LNA nucleosides, or may all be 2'O-MOE nucleosides. In some embodiments the sugar modified nucleosides of a totalmer may be independently selected from LNA nucleosides and 2' substituted nucleosides, such as 2' substituted nucleoside selected from the group consisting of 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleosides. In some embodiments the oligonucleotide comprises both LNA nucleosides and 2' substituted nucleosides, such as 2' substituted nucleoside selected from the group consisting of 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleosides. In some embodiments, the oligonucleotide comprises LNA nucleosides and 2'-O-MOE nucleosides. In some embodiments, the oligonucleotide comprises (S)cET LNA nucleosides and 2'-O-MOE nucleosides. In some embodiments, each nucleoside unit of the oligonucleotide is a 2'substituted nucleoside. In some embodiments, each nucleoside unit of the oligonucleotide is a 2'-O-MOE nucleoside.

In some embodiments, all of the nucleosides of the oligonucleotide or contiguous nucleotide sequence thereof are LNA nucleosides, such as beta-D-oxy-LNA nucleosides and/or (S)cET nucleosides. In some embodiments such LNA totalmer oligonucleotides are between 7-12 nucleosides in length (see for example, WO 2009/043353). Such short fully LNA oligonucleotides are particularly effective in inhibiting microRNAs.

Various totalmer compounds are highly effective as therapeutic oligomers, particularly when targeting microRNA (antimiRs) or as splice switching oligomers (SSOs).

In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-OMe RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 7 and 24 nucleotides, such as 7, 9, 10, 11, 12, 13, 14, 15, 16, 17, 18, 19, 20, 21, 22 or 23 nucleotides.

In some embodiments, the contiguous nucleotide sequence of the totolmer comprises of at least 30%, such as at least 40%, such as at least 50%, such as at least 60%, such as at least 70%, such as at least 80%, such as at least 90%, such as 95%, such as 100% LNA units. For full LNA compounds, it is advantageous that they are less than 12 nucleotides in length, such as 7-10.

The remaining units may be selected from the non-LNA nucleotide analogues referred to herein in, such those selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group 2'-OMe RNA unit and 2'-fluoro DNA unit.

Mixmers

The term 'mixmer' refers to oligomers which comprise both DNA nucleosides and sugar modified nucleosides, wherein there are insufficient length of contiguous DNA nucleosides to recruit RNaseH. Suitable mixmers may comprise up to 3 or up to 4 contiguous DNA nucleosides. In some embodiments the mixmers, or contiguous nucleotide sequence thereof, comprise alternating regions of sugar modified nucleosides, and DNA nucleosides. By alternating regions of sugar modified nucleosides which form a RNA like (3'endo) conformation when incorporated into the oligonucleotide, with short regions of DNA nucleosides, non-RNaseH recruiting oligonucleotides may be made. Advantageously, the sugar modified nucleosides are affinity enhancing sugar modified nucleosides.

Oligonucleotide mixmers are often used to provide occupation based modulation of target genes, such as splice modulators or microRNA inhibitors.

In some embodiments the sugar modified nucleosides in the mixmer, or contiguous nucleotide sequence thereof, comprise or are all LNA nucleosides, such as (S)cET or beta-D-oxy LNA nucleosides.

In some embodiments all of the sugar modified nucleosides of a mixmer comprise the same sugar modification, for example they may all be LNA nucleosides, or may all be 2'O-MOE nucleosides. In some embodiments the sugar modified nucleosides of a mixmer may be independently selected from LNA nucleosides and 2' substituted nucleosides, such as 2' substituted nucleoside selected from the group consisting of 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleosides. In some embodiments the oligonucleotide comprises both LNA nucleosides and 2' substituted nucleosides, such as 2' substituted nucleoside selected from the group consisting of 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleosides. In some embodiments, the oligonucleotide comprises LNA nucleosides and 2'-O-MOE nucleosides. In some embodiments, the oligonucleotide comprises (S)cET LNA nucleosides and 2'-O-MOE nucleosides.

In some embodiments the mixmer, or contiguous nucleotide sequence thereof, comprises only LNA and DNA nucleosides, such LNA mixmer oligonucleotides which may for example be between 8-24 nucleosides in length (see for example, WO2007112754, which discloses LNA antmiR inhibitors of microRNAs).

Various mixmer compounds are highly effective as therapeutic oligomers, particularly when targeting microRNA (antimiRs) or as splice switching oligomers (SSOs).

In some embodiments, the mixmer comprises a motif

. . . [L]m[D]n[L]m[D]n[L]m . . . or

. . . [L]m[D]n[L]m[D]n[L]m[D]n[L]m . . . or

. . . [L]m[D]n[L]m[D]n[L]m[D]n[L]m[D]n[L]m . . . or

. . . [L]m[D]n[L]m[D]n[L]m[D]n[L]m[D]n[L]m[D]n[L]m . . .

. . . [L]m[D]n[L]m[D]n[L]m[D]n[L]m[D]n[L]m[D]n[L]m[D]n[L]m . . . or

. . . [L]m[D]n[L]m[D]n[L]m[D]n[L]m[D]n[L]m[D]n[L]m[D]n[L]m[D]n[L]m . . . or

. . . [L]m[D]n[L]m[D]n[L]m[D]n[L]m[D]n[L]m[D]n[L]m[D]n[L]m[D]n[L]m[D]n[L]m . . . or

[L]m[D]n[L]m[D]n[L]m[D]n[L]m[D]n[L]m[D]n[L]m[D]n[L]m[D]n[L]m[D]n[L]m[D]n[L]m . . .

wherein L represents sugar modified nucleoside such as a LNA or 2' substituted nucleoside (e.g. 2'-O-MOE), D represents DNA nucleoside, and wherein each m is independently selected from 1-6, and each n is independently selected from 1, 2, 3 and 4, such as 1-3. In some embodiments each L is a LNA nucleoside. In some embodiments, at least one L is a LNA nucleoside and at least one L is a 2'-O-MOE nucleoside. In some embodiments, each L is independently selected from LNA and 2'-O-MOE nucleoside.

In some embodiments, the mixmer may comprise or consist of a contiguous nucleotide sequence of between 10 and 24 nucleotides, such as 11, 12, 13, 14, 15, 16, 17, 18, 19, 20, 21, 22 or 23 nucleotides.

In some embodiments, the contiguous nucleotide sequence of the mixmer comprises of at least 30%, such as at least 40%, such as at least 50% LNA units.

In some embodiments, the mixmer comprises or consists of a contiguous nucleotide sequence of repeating pattern of nucleotide analogues and naturally occurring nucleotides, or one type of nucleotide analogue and a second type of nucleotide analogue. The repeating pattern, may, for instance be: every second or every third nucleotide is a nucleotide analogue, such as LNA, and the remaining nucleotides are naturally occurring nucleotides, such as DNA, or are a 2' substituted nucleotide analogue such as 2'MOE of 2'fluoro analogues as referred to herein, or, in some embodiments selected form the groups of nucleotide analogues referred to herein. It is recognised that the repeating pattern of nucleotide analogues, such as LNA units, may be combined with nucleotide analogues at fixed positions—e.g. at the 5' or 3' termini.

In some embodiments the first nucleotide of the oligomer, counting from the 3' end, is a nucleotide analogue, such as a LNA nucleotide or a 2'-O-MOE nucleoside.

In some embodiments, which maybe the same or different, the second nucleotide of the oligomer, counting from the 3' end, is a nucleotide analogue, such as a LNA nucleotide or a 2'-O-MOE nucleoside.

In some embodiments, which maybe the same or different, the 5' terminal of the oligomer is a nucleotide analogue, such as a LNA nucleotide or a 2'-O-MOE nucleoside.

In some embodiments, the mixmer comprises at least a region comprising at least two consecutive nucleotide analogue units, such as at least two consecutive LNA units.

In some embodiments, the mixmer comprises at least a region comprising at least three consecutive nucleotide analogue units, such as at least three consecutive LNA units.

Exosomes

Exosomes are natural biological nanovesicles, typically in the range of 30 to 500 nm, that are involved in cell-cell communication via the functionally-active cargo (such as miRNA, mRNA, DNA and proteins).

Exosomes are secreted by all types of cells and are also found abundantly in the body fluids such as: saliva, blood, urine and milk. The major role of exosomes is to carry the information by delivering various effectors or signaling molecules between specific cells (Acta Pol Pharm. 2014 July-August; 71(4):537-43.). Such effectors or signaling molecules can for example be proteins, miRNAs or mRNAs. Exosomes are currently being explored as a delivery vehicle for various drug molecules including RNA therapeutic molecules, to expand the therapeutic and diagnostic applications of such molecules. There are disclosures in the art of exosomes loaded with synthetic molecules such as siRNA, antisense oligonucleotides and small molecules which suggest or show advantages in terms of delivery and efficacy of such molecules compared to the free drug molecules (see for example Andaloussi et al 2013 Advanced Drug Delivery Reviews 65: 391-397, WO2014/168548, WO2016/172598, WO2017/173034 and WO 2018/102397).

Exosomes may be isolated from biological sources, such as milk (milk exosomes), in particular bovine milk is a abundant source for isolating bovine milk exosomes. See for example Manca et al., Scientific Reports (2018) 8:11321.

In some embodiments of the invention, the single stranded oligonucleotide is encapsulated in an exosome (exosome formulation), examples of loading an exosome with a single stranded antisense oligonucleotide are described in EP application No. 18192614.8. In the methods of the invention the antisense oligonucleotide may be administered to the cell or to the subject in the form of an exosome formulation, in particular oral administration of the exosome formulations are envisioned.

In some embodiments, the antisense oligonucleotide may be conjugated, e.g. with a lipophilic conjugate such as cholesterol, which may be covalently attached to the antisense oligonucleotide via a biocleavable linker (e.g. a region of phosphodiester linked DNA nucleotides). Such lipophilic conjugates can facilitate formulation of antisense oligonucleotides into exosomes and may further enhance the delivery to the target cell.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs.

WO 93/07883 and WO 2013/033230 provides suitable conjugate moieties, which are hereby incorporated by reference. Further suitable conjugate moieties are those capable of binding to the asialoglycoprotein receptor (ASGPR). In particular tri-valent N-acetylgalactosamine conjugate moieties are suitable for binding to the ASGPR, see for example WO 2014/076196, WO 2014/207232 and WO 2014/179620 (hereby incorporated by reference). Such conjugates serve to enhance uptake of the oligonucleotide to the liver while reducing its presence in the kidney, thereby increasing the liver/kidney ratio of a conjugated oligonucleotide compared to the unconjugated version of the same oligonucleotide.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Administration

The oligonucleotides or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In some embodiments the oligonucleotide or pharmaceutical compositions of the present invention are administered by a parenteral route including intravenous, intraarterial, subcutaneous, intraperitoneal or intramuscular injection or infusion, intrathecal or intracranial, e.g. intracerebral or intraventricular, intravitreal administration.

In one embodiment the active oligonucleotide or oligonucleotide conjugate is administered intravenously. In another embodiment the active oligonucleotide or oligonucleotide conjugate is administered subcutaneously.

In some embodiments, the oligonucleotide, oligonucleotide conjugate or pharmaceutical composition of the invention is administered at a dose of 0.1-15 mg/kg, such as from 0.2-10 mg/kg, such as from 0.25-5 mg/kg. The administration can be once a week, every 2nd week, every third week or once a month or bi monthly.

The invention also provides for the use of the oligonucleotide or oligonucleotide conjugate of the invention as described for the manufacture of a medicament wherein the medicament is in a dosage form for ophthalmic such as intravitreal injection. In some embodiments, the oligonucleotide for ophthalmic targets is Htra-1.

The invention also provides for the use of the oligonucleotide or oligonucleotide conjugate of the invention as described for the manufacture of a medicament wherein the medicament is in a dosage form for intravenous, subcutaneous, intra-muscular, intracerebral, intracerebroventricular or intrathecal administration (e.g. injection).

Illustrative Advantages

As illustrated herein the achiral phosphorodithioate internucleoside linkage used in the compounds of invention allows for the reduction of the complexity of a non-stereodefined phosphorothioate oligonucleotide, whilst maintaining the activity, efficacy or potency of the oligonucleotide.

Indeed, as illustrated herein, the used in the compounds of invention provides unique benefits in combination with stereodefined phosphorothioates, providing the opportunity to further reduce the complexity of phosphorothioate oligonucleotides, whilst retaining or improving the activity, efficacy or potency of the oligonucleotide.

As illustrated herein the achiral phosphorodithioate internucleoside linkage used in the compounds of invention allows for improvement in cellular uptake in vitro or in vivo.

As illustrated herein the achiral phosphorodithioate internucleoside linkage used in the compounds of invention allows for alteration or improvement in biodistribution in vitro (measured either as tissue or cellula content, or activity/potency in target tissues).

Notably we have seen improvement of tissue uptake, content and/or potency in skeletal muscle, heart, spleen, liver, kidney, fibroblasts, epithelial cells.

In the context of a mixmer oligonucleotides, the inventors have identified incorporating a phosphorodithioate linkages (as shown in IA or IB), between or adjacent to one or more DNA nucleosides, provides improvements, such as enhanced stability and/or improved potency. In the context of gapmer oligonucleotides the inventors has seen that incorporation of phosphorodithioate linkages (as shown in IA or IB) between the nucleosides of the flank region (such as between 2'sugar modified nucleosides) also provides improvements, such as enhanced stability and/or improved potency.

As illustrated herein the achiral phosphorodithioate internucleoside linkage used in the compounds of invention allows for improvement in oligonucleotide stability. The incorportation of the achiral phosphorodithioate internucleoside in the compounds of the invention provides enhanced resistance to serum and cellular exonucleases, particularly 3' exonucleoases, but also 5'exonucleoases, and the remarkable sstability of the compounds of the invention further indicate a resistance to endonucleases for compounds which incorporate the achiral phosphorodithioate linkages. The stabilization of oligonucleotides is of particular importance in reducing or preventing the accumulation of toxic degradation products, and prolonging the duration of action of the antisense oligonucleotide. As illustrated in the examples rat serum stability may be used to assay for improved stability. For evaluation of cellular stability, tissue (e.g. liver) homogenate extract may be used—for example see WO2014076195 which provided such methods). Other assays for measuring oligonucleotide stability include snake venom phosphodiesterase stability assays and S1 nuclease stability).

Reduced toxicity risk of the claimed oligonucleotides is tested in vitro hepatotoxicity assays (e.g. as disclosed in WO 2017/067970) or in vitro nephrotoxicity assays (e.g. as disclosed in WO 2017/216340), or in vitro neurotoxicity assays (e.g. as disclosed in WO2016127000). Alternatively toxicity may be assayed in vivo, for example in mouse or rat.

Enhanced stability can provide benefits to the duration of action of the oligonucleotides of the invention, which is of particular benefit for when the administration route is invasive, e.g. parenteral administration, such as, intravenous, subcutaneous, intra-muscular, intracerebral, intraocular, intracerebroventricular or intrathecal administration.

GENERAL OLIGONUCLEOTIDE EMBODIMENTS

1. An oligonucleotide comprising at least one phosphorodithioate internucleoside linkage of formula (IA) or (IB)

(IA)

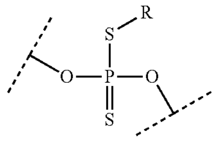

(IB)

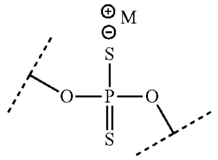

wherein one of the two oxygen atoms is linked to the 3'carbon atom of an adjacent nucleoside (A1) and the other one is linked to the 5'carbon atom of another adjacent nucleoside (A2), wherein at least one of the two nucleosides (A1) and (A2) is a LNA nucleoside and wherein in (IA) R is hydrogen or a phosphate protecting group, and in (IB) M+ is a cation, such as a metal cation, such as an alkali metal cation, such as a Na+ or K+ cation; or M+ is an ammonium cation.

2. An oligonucleotide according to embodiment 1, wherein one of (A1) and (A2) is a LNA nucleoside and the other one is a DNA nucleoside, a RNA nucleoside or a sugar modified nucleoside.
3. An oligonucleotide according to embodiment 1 or 2, wherein one of (A1) and (A2) is a LNA nucleoside and the other one is a DNA nucleoside or a sugar modified nucleoside.
4. An oligonucleotide according to any one of embodiments 1 to 3, wherein one of (A1) and (A2) is a LNA nucleoside and the other one is a DNA nucleoside.
6. An oligonucleotide according to any one of embodiments 1 to 3, wherein one of (A1) and (A2) is a LNA nucleoside and the other one is a sugar modified nucleoside.
7. An oligonucleotide according to any one of embodiments 2 to 6, wherein said sugar modified nucleoside is a 2'-sugar modified nucleoside.
8. An oligonucleotide according to embodiment 7, wherein said 2'-sugar modified nucleoside is 2'-alkoxy-RNA, 2'-alkoxyalkoxy-RNA, 2'-amino-DNA, 2'-fluoro-RNA, 2'-fluoro-ANA or a LNA nucleoside.
9. An oligonucleotide according to embodiment 7 or 8, wherein said 2'-sugar modified nucleoside is a LNA nucleoside.
10. An oligonucleotide according to any one of embodiments 1 to 9, wherein the LNA nucleosides are independently selected from beta-D-oxy LNA, 6'-methyl-beta-D-oxy LNA and ENA.
11. An oligonucleotide according to embodiment 9 or 10, wherein the LNA nucleosides are both beta-D-oxy LNA.
12. An oligonucleotide according to embodiment 7 or 8, wherein said 2'-sugar modified nucleoside is 2'-alkoxy-alkoxy-RNA.
13. An oligonucleotide according to embodiment 10, wherein 2'-alkoxy-RNA is 2'-methoxy-RNA.
14. An oligonucleotide according to any one of embodiments 1 to 12, wherein 2'-alkoxyalkoxy-RNA is 2'-methoxyethoxy-RNA.
15. An oligonucleotide according to any one of embodiment 1 to 14, comprising between 1 and 15, in particular between 1 and 5, more particularly 1, 2, 3, 4 or 5 phosphorodithioate internucleoside linkages of formula (IA) or (IB) as defined in embodiment 1.
16. An oligonucleotide according to any one of embodiments 1 to 15, comprising further internucleoside linkages independently selected from phosphodiester internucleoside linkage, phosphorothioate internucleoside linkage and phosphorodithioate internucleoside linkage of formula (IA) or (IB) as defined in embodiment 1.
17. An oligonucleotide according to embodiment 16, wherein the further internucleoside linkages are independently selected from phosphorothioate internucleoside linkage and phosphorodithioate internucleoside linkage of formula (IA) or (IB) as defined in embodiment 1.
18. An oligonucleotide according to embodiment 16 or 17, wherein the further internucleoside linkages are all phosphorothioate internucleoside linkages.
19. An oligonucleotide according to embodiment 16 to 17, wherein the further internucleoside linkages are all phosphorodithioate internucleoside linkages of formula (IA) or (IB) as defined in embodiment 1.
20. An oligonucleotide according to any one of embodiments 1 to 19, wherein the oligonucleotide is of 7 to 30 nucleotides in length.
21. An oligonucleotide according to any one of embodiments 1 to 20, wherein one or more nucleoside is a nucleobase modified nucleoside.
22. An oligonucleotide according to any one of embodiments 1 to 21, wherein the oligonucleotide is an antisense oligonucleotide, a siRNA, a microRNA mimic or a ribozyme.
23. A pharmaceutically acceptable salt of an oligonucleotide according to any one of embodiments 1 to 22, in particular a sodium or a potassium salt or ammonium salt.
24. A conjugate comprising an oligonucleotide or a pharmaceutically acceptable salt according to any one of embodiments 1 to 23 and at least one conjugate moiety covalently attached to said oligonucleotide or said pharmaceutically acceptable salt, optionally via a linker moiety.
25. A pharmaceutical composition comprising an oligonucleotide, pharmaceutically acceptable salt or conjugate according to any one of embodiments 1 to 24 and a therapeutically inert carrier.

26. An oligonucleotide, pharmaceutically acceptable salt or conjugate according to any one of embodiments 1 to 24 for use as a therapeutically active substance.
27. A process for the manufacture of an oligonucleotide according to any one of embodiments 1 to 24 comprising the following steps:
    (a) Coupling a thiophosphoramidite nucleoside to the terminal 5' oxygen atom of a nucleotide or oligonucleotide to produce a thiophosphite triester intermediate;
    (b) Thiooxidizing the thiophosphite triester intermediate obtained in step a); and
    (c) Optionally further elongating the oligonucleotide.
28. An oligonucleotide manufactured according to a process of embodiment 27.

GAPMER EMBODIMENTS

1. An antisense gapmer oligonucleotide, for inhibition of a target RNA in a cell, wherein the antisense gapmer oligonucleotide comprises at least one phosphorodithioate internucleoside linkage of formula (IA) or (IB)

(IA)

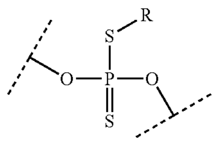

(IB)

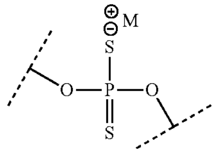

wherein in (IA) R is hydrogen or a phosphate protecting group, and in (IB) M+ is a cation, such as a metal cation, such as an alkali metal cation, such as a Na+ or K+ cation; or M+ is an ammonium cation.
2. The antisense gapmer oligonucleotide according to embodiment 1, wherein the at least one phosphorodithioate internucleoside linkage is of formula (IA), and R is hydrogen; or the at least one phosphorodithioate internucleoside linkage is of formula (IB), and M+ is Na+, K+ or ammonium.
3. A gapmer oligonucleotide according to embodiment 1 or 2, wherein one of the two oxygen atoms of said at least one internucleoside linkage of formula (I) is linked to the 3'carbon atom of an adjacent nucleoside ($A^1$) and the other one is linked to the 5'carbon atom of another nucleoside ($A^2$), wherein at least one of the two nucleosides ($A^1$) and ($A^2$) is a 2'-sugar modified nucleoside.
4. A gapmer oligonucleotide according to any one of embodiments 1-3, wherein one of ($A^1$) and ($A^2$) is a 2'-sugar modified nucleoside and the other one is a DNA nucleoside.
5. A gapmer oligonucleotide according to any one of embodiments 1-3, wherein ($A^1$) and ($A^2$) are both a 2'-modified nucleoside at the same time.
6. A gapmer oligonucleotide according to any one of embodiments 1-3, wherein ($A^1$) and ($A^2$) are both a DNA nucleoside at the same time.
7. A gapmer oligonucleotide according to any one of embodiments 1 to 6, wherein the gapmer oligonucleotide comprises a contiguous nucleotide sequence of formula 5'-F-G-F'-3', wherein G is a region of 5 to 18 nucleosides which is capable of recruiting RNaseH, and said region G is flanked 5' and 3' by flanking regions F and F' respectively, wherein regions F and F' independently comprise or consist of 1 to 7 2'-sugar modified nucleotides, wherein the nucleoside of region F which is adjacent to region G is a 2'-sugar modified nucleoside and wherein the nucleoside of region F' which is adjacent to region G is a 2'-sugar modified nucleoside.
8. A gapmer oligonucleotide according to any one of embodiments 1 to 7, wherein the 2'-sugar modified nucleosides are independently selected from 2'-alkoxy-RNA, 2'-alkoxyalkoxy-RNA, 2'-amino-DNA, 2'-fluoro-RNA, 2'-fluoro-ANA and LNA nucleosides.
9. A gapmer oligonucleotide according to embodiment 8, wherein 2'-alkoxyalkoxy-RNA is a 2'-methoxyethoxy-RNA (2'-O-MOE).
10. A gapmer oligonucleotide according to any one of embodiments 7 to 8, wherein region F and region F' comprise or consist of 2'-methoxyethoxy-RNA nucleotides.
11. A gapmer oligonucleotide according to any one of embodiments 7 to 10, wherein at least one or all of the 2'-sugar modified nucleosides in region F or region F', or in both regions F and F', are LNA nucleosides.
12. A gapmer oligonucleotide according to any one of embodiments 7 to 11, wherein region F or region F', or both regions F and F', comprise at least one LNA nucleoside and at least one DNA nucleoside.
13. A gapmer oligonucleotide according to any one of embodiments 7 to 12, wherein region F or region F', or both region F and F' comprise at least one LNA nucleoside and at least one non-LNA 2'-sugar modified nucleoside, such as at least one 2'-methoxyethoxy-RNA nucleoside.
14. A gapmer oligonucleotide according to any one of embodiments 1 to 13, wherein the gap region comprises 5 to 16, in particular 8 to 16, more particularly 8, 9, 10, 11, 12, 13 or 14 contiguous DNA nucleosides.
15. A gapmer oligonucleotide according to any one of embodiments 1 to 14, wherein region F and region F' are independently 1, 2, 3, 4, 5, 6, 7 or 8 nucleosides in length.
16. A gapmer oligonucleotide according to any one of embodiments 1 to 15, wherein region F and region F' each independently comprise 1, 2, 3 or 4 LNA nucleosides.
17. A gapmer oligonucleotide according to any one of embodiments 8 to 16, wherein the LNA nucleosides are independently selected from beta-D-oxy LNA, 6'-methyl-beta-D-oxy LNA and ENA.
18. A gapmer oligonucleotide according to embodiments 8-18, wherein the LNA nucleosides are beta-D-oxy LNA.
19. A gapmer oligonucleotide according to any one of embodiments 1 to 18, wherein the oligonucleotide, or contiguous nucleotide sequence thereof (F-G-F'), is of 10 to 30 nucleotides in length, in particular 12 to 22, more particularly of 14 to 20 oligonucleotides in length.
20. The gapmer oligonucleotide according to any one of embodiments 1-19, wherein at least one of the flank regions, such as region F and F' comprise a phosphorodithioate linkage of formula (IA) or (IB), as defined in any one of embodiments 1-19.
21. The gapmer oligonucleotide according to any one of embodiments 1-19, wherein both flank regions, such as region F and F' comprise a phosphorodithioate linkage of formula (IA) or (IB), as defined in any one of embodiments 1-19.

22. The gapmer oligonucleotide according to any one of embodiments 1-21, wherein at least one of the flank regions, such as F or F' comprises at least two phosphorodithioate linkage of formula (IA) or (IB), as defined in any one of embodiments 1-19.
23. The gapmer oligonucleotide according to any one of embodiments 1-21, wherein both the flank regions, F and F' comprises at least two phosphorodithioate linkage of formula (IA) or (IB), as defined in any one of embodiments 1-19.
24. The gapmer oligonucleotide according to any one of embodiments 1-23, wherein the one or both of the flank regions each comprise a LNA nucleoside which is has a phosphorodithioate linkage of formula (IA) or (IB) linking the LNA to a 3' nucleoside.
25. The gapmer oligonucleotide according to any one of embodiments 1-24, wherein one or both flank regions each comprise two or more adjacent LNA nucleosides which are linked by phosphorodithioate linkage of formula (IA) or (IB) linking the LNA to a 3' nucleoside.
26. The gapmer oligonucleotide according to any one of embodiments 1-25, wherein one or both flank regions each comprise a MOE nucleoside which is has a phosphorodithioate linkage of formula (IA) or (IB) linking the MOE to a 3' nucleoside.
27. The gapmer oligonucleotide according to any one of embodiments 1-26, wherein one or both flank regions each comprise two or more adjacent MOE nucleosides which are linked by phosphorodithioate linkage of formula (IA) or (IB) linking the MOE to a 3' nucleoside.
28. The gapmer oligonucleotide according to any one of embodiments 1-27, wherein the flank regions, F and F' together comprise 1, 2, 3, 4 or 5 phosphorodithioate internucleoside linkages for formula (IA) or (IB), and wherein optionally, the internucleoside linkage between the 3' most nucleoside of region F and the 5' most nucleoside of region G is also a phosphorodithioate internucleoside linkages for formula (IA) or (IB).
29. A gapmer oligonucleotide according to any one of embodiments 1 to 28, which comprises 1 a phosphorodithioate internucleoside linkage of formula (IA) or (IB) positioned between adjacent nucleosides in region F or region F', between region F and region G or between region G and region F'.
30. The gapmer region according to any on of embodiments 1-29, wherein the gap region comprises 1, 2, 3 or 4 phosphorodithioate internucleoside linkages for formula (IA) or (IB), wherein the remaining internucleoside linkages are phosphorothioate internucleoside linkages.
31. The gapmer according to any one of embodiments 1-30, where in the gap region comprises a region of at least 5 contiguous DNA nucleotides, such as a region of 6-18 DNA contiguous nucleotides, or 8-14 contiguous DNA nucleotides.
32. The gapmer according to any one of embodiments 1-31, which further comprises one or more stereodefined phosphorothioate internucleoside linkages (Sp, S) or (Rp, R)

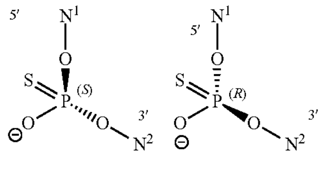

wherein $N^1$ and $N^2$ are nucleosides.

33. The gapmer according to embodiment 32, wherein the gapmer comprises at least one stereodefined internucleoside linkage (Sp, S) or (Rp, R) between two DNA nucleosides, such as between two DNA nucleoside in the gap region.
34. The gapmer oligonucleotide according to embodiment 32 or 33, wherein the gap region comprises 2, 3, 4, 5, 6, 7 or 8 stereodefined phosphorothioate internucleoside linkages, independently selected from Rp and Sp internucleoside linkages.
35. The gapmer oligonucleotide according to any one of embodiments 32-33, wherein region G further comprises at least 2, 3, or 4 internucleoside linkages of formula IB.
34. The gapmer oligonucleotide according to embodiments 32-35, wherein either (i) all remaining internucleoside linkages within region G (i.e. between the nucleoside in region G) are either stereodefined phosphorothioate internucleoside linkages, independently selected from Rp and Sp internucleoside linkages, or (ii) all the internucleoside linkages within region G are either stereodefined phosphorothioate internucleoside linkages, independently selected from Rp and Sp internucleoside linkages.
35. The gapmer oligonucleotide according to any one of embodiments 1-34, wherein all the internucleoside linkages within the flank regions are phosphorodithioate internucleoside linkages of formula (IA) or (IB), wherein optionally the internucleoside linkage between the 3' most nucleoside of region F and the 5' most nucleoside of region G is also a phosphorodithioate internucleoside linkages for formula (IA) or (IB), and the internucleoside linkage between the 3' most nucleoside of region G and the 5' most nucleoside of region F' is a stereodefined phosphorothioate internucleoside linkage.
36. A gapmer oligonucleotide according to any one of embodiments 6 to 35, wherein the internucleoside linkages between the nucleosides of region G are independently selected from phosphorothioate internucleoside linkages and phosphorodithioate internucleoside linkages of formula (I) as defined in embodiment 1.
37. A gapmer oligonucleotide according to any one of embodiments 7 to 36 wherein the internucleoside linkages between the nucleosides of region G comprise 0, 1, 2 or 3 phosphorodithioate internucleoside linkages of formula (I) as defined in embodiment 1, in particular 0 phosphorodithioate internucleoside linkages of formula (I).
38. A gapmer oligonucleotide according to any one of embodiments 1 to 37, wherein the remaining internucleoside linkages are independently selected from the group consisting of phosphorothioate, phosphodiester and phosphorodithioate internucleoside linkages of formula (I) as defined in embodiment 1.
39. A gapmer oligonucleotide according to any one one of embodiments 7 to 38, wherein the internucleoside linkages between the nucleosides of region F and the internucleoside linkages between the nucleosides of region F' are independently selected from phosphorothioate and phosphorodithioate internucleoside linkages of formula (I) as defined in embodiment 1.
40. A gapmer oligonucleotide according to any one of embodiments 7 to 39, wherein each flanking region F and F' independently comprise 1, 2, 3, 4, 5, 6 or 7 phosphorodithioate internucleoside linkages of formula (I) as defined in embodiment 1.
41. A gapmer oligonucleotide according to any one of embodiments 7 to 40, wherein all the internucleoside linkages of flanking regions F and/or F' are phosphorodithioate internucleoside linkages of formula (I) as defined in embodiment 1.

42. A gapmer oligonucleotide according to any one of embodiments 1 to 41, wherein the gapmer oligonucleotide comprises at least one stereodefined internucleoside linkage, such as at least one stereodefined phosphorothioate internucleoside linkage.

43. A gapmer oligonucleotide according to any one of embodiments 1 to 42, wherein the gap region comprises 1, 2, 3, 4 or 5 stereodefined phosphorothioate internucleoside linkages.

44. A gapmer oligonucleotide according to any one of embodiments 1 to 43, wherein all the internucleoside linkages between the nucleosides of the gap region are stereodefined phosphorothioate internucleoside linkages.

45. A gapmer oligonucleotide according to any one one of embodiments 7 to 44, wherein the at least one phosphorodithioate internucleoside linkage of formula (IA) or (IB) is positioned between the nucleosides of region F, or between the nucleosides of region F', or between region F and region G, or between region G and region F', and the remaining internucleoside linkages within region F and F', between region F and region G and between region G and region F', are independently selected from stereodefined phosphorothioate internucleoside linkages, stereorandom internucleoside linkages, phosphorodithioate internucleoside linkage of formula (IA) or (IB) and phosphodiester internucleoside linkages.

46. A gapmer oligonucleotide according to embodiment 45, wherein the remaining internucleoside linkages within region F, within region F' or within both region F and region F' are all phosphorodithioate internucleoside linkages of formula (IA) or (IB).

47. A gapmer oligonucleotide according to any one of embodiments 6 to 33, wherein the internucleoside linkages between the nucleosides of gerion G comprise 0, 1, 2 or 3 phosphorodithioate internucleoside linkages of formula (I) as defined in embodiment 1 and the remaining internucleoside linkages within region G are independently selected from stereodefined phosphorothioate internucleoside linkages, stereorandom internucleoside linkages and phosphodiester internucleoside linkages.

48. The gapmer oligonucleotide according to any one of embodiments 1-47, wherein the 3' terminal nucleoside of the antisense oligonucleotide is a LNA nucleoside or a 2'-O-MOE nucleoside.

49. The gapmer oligonucleotide according to any one of embodiments 1-48, wherein the 5' terminal nucleoside of the antisense oligonucleotide is a LNA nucleoside or a 2'-O-MOE nucleoside.

50. The gapmer oligonucleotide according to any one of embodiments 1-49, wherein the two 3' most terminal nucleosides of the antisense oligonucleotide are independently selected from LNA nucleosides and 2'-O-MOE nucleosides.

51. The gapmer oligonucleotide according to any one of embodiments 1-50, wherein the two 5' most terminal nucleosides of the antisense oligonucleotide are independently selected from LNA nucleosides and 2'-O-MOE nucleosides.

52. The gapmer oligonucleotide according to any one of embodiments 1-51, wherein the three 3' most terminal nucleosides of the antisense oligonucleotide are independently selected from LNA nucleosides and 2'-O-MOE nucleosides.

53. The gapmer oligonucleotide according to any one of embodiments 1-52, wherein the three 5' most terminal nucleosides of the antisense oligonucleotide are independently selected from LNA nucleosides and 2'-O-MOE nucleosides.

54. The gapmer oligonucleotide according to any one of embodiments 1-53, wherein the two 3' most terminal nucleosides of the antisense oligonucleotide are LNA nucleosides.

55. The gamper oligonucleotide according to any one of embodiments 1-54, wherein the two 5' most terminal nucleosides of the antisense oligonucleotide are LNA nucleosides.

56. The gapmer oligonucleotide according to any one of embodiments 1-55, wherein nucleoside ($A^2$) of formula (IA) or (IB) is the 3' terminal nucleoside of the oligonucleotide.

57. The gapmer oligonucleotide according to any one of embodiments 1-56, wherein nucleoside (A') of formula (IA) or (IB) is the 5' terminal nucleoside of the oligonucleotide.

58. The gamper oligonucleotide according to any one of embodiments 7-57, wherein the gapmer oligonucleotide comprises a contiguous nucleotide sequence of formula 5'-D'-F-G-F'-D"-3', wherein F, G and F' are as defined in any one of embodiments 7 to 45 and wherein region D' and D" each independently consist of 0 to 5 nucleotides, in particular 2, 3 or 4 nucleotides, in particular DNA nucleotides such as phosphodiester linked DNA nucleosides [an oligonucleotide which comprises the gapmer oligonucleotide, and a flanking sequence].

59. A gapmer oligonucleotide according to any one of embodiments 1 to 58, wherein the gapmer oligonucleotide is capable of recruiting human RNaseH1.

60. A gapmer oligonucleotide according to any one of embodiments 1 to 59, wherein the gapmer oligonucleotide is for the in vitro or in vivo inhibition of a mammalian, such as a human, mRNA or pre-mRNA target, or a viral target, or a long non coding RNA.

61. A pharmaceutically acceptable salt of a gapmer oligonucleotide according to any one of embodiments 1 to 60, in particular a sodium or a potassium salt.

62. A conjugate comprising a gapmer oligonucleotide or a pharmaceutically acceptable salt according to any one of embodiments 1 to 61 and at least one conjugate moiety covalently attached to said oligonucleotide or said pharmaceutically acceptable salt, optionally via a linker moiety.

63. A pharmaceutical composition comprising a gapmer oligonucleotide, pharmaceutically acceptable salt or conjugate according to any one of embodiments 1 to 62 and a therapeutically inert carrier.

64. A gapmer oligonucleotide, pharmaceutically acceptable salt or conjugate according to any one of embodiments 1 to 63 for use as a therapeutically active substance.

ANTISENSE OLIGONUCLEOTIDE EMBODIMENTS

The invention relates to an oligonucleotide comprising at least one phosphorodithioate internucleoside linkage of formula (IA) or (IB)

(IA)

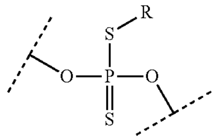

(IB)

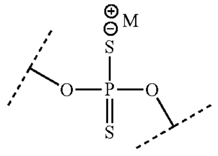

wherein one of the two oxygen atoms is linked to the 3'carbon atom of an adjacent nucleoside (A1) and the other one is linked to the 5'carbon atom of another adjacent nucleoside (A2), and wherein in (IA) R is hydrogen or a phosphate protecting group, and in (IB) M+ is a cation, such as a metal cation, such as an alkali metal cation, such as a Na+ or K+ cation; or M+ is an ammonium cation.

Alternatively stated M is a metal, such as an alkali metal, such as Na or K; or M is $NH_4$.

The oligonucleotide may, for example, be a single stranded antisense oligonucleotide, which is capable of modulating the expression of a target nucleic acid, such as a target microRNA, or is capable of modulating the splicing of a target pre-mRNA. which comprises a contiguous nucleotide sequence. The antisense oligonucleotide of the invention comprises a contiguous nucleotide sequence which is complementary to the target nucleic acid, and is capable of hybridizing to and modulating the expression of the target nucleic acid. In a preferred embodiment, the antisense oligonucleotide, or the contiguous nucleotide sequence thereof, is a mixmer oligonucleotide wherein either (A1) or (A2) is a DNA nucleoside, or both (A1) and (A2) are DNA nucleosides.

In the context of the present invention an antisense oligonucleotide is a single stranded oligonucleotide which is complementary to a nucleic acid target, such as a target RNA, and is capable of modulating (e.g. splice modulating of a pre-mRNA target) or inhibiting the expression of the nucleic acid target (e.g. a mRNA target, a premRNA target, a viral RNA target, or a long non coding RNA target). Depending on the target the length of the oligonucleotide or the length of the region thereof which is complementary to (i.e. antisense—preferably the complementary region is fully complementary to the target) may be 7-30 nucleotides (the region which is referred to as the contiguous nucleotide sequence). For example, LNA nucleotide inhibitors of microRNAs may be as short as 7 contiguous complementary nucleotides (and may be as long as 30 nucleotides), RNaseH recruiting oligonucleotides are typically at least 12 contiguous complementary nucleotides in length, such as 12-26 nucleotides in length. Splice modulating antisense oligonucleotides typically has a contiguous nucleotide region of 10-30 complementary nucleotides.

Splice modulating oligonucleotides, also known as splice-switching oligonucleotides (SSOs) are short, synthetic, antisense, modified nucleic acids that base-pair with a pre-mRNA and disrupt the normal splicing repertoire of the transcript by blocking the RNA-RNA base-pairing or protein-RNA binding interactions that occur between components of the splicing machinery and the pre-mRNA. Splicing of pre-mRNA is required for the proper expression of the vast majority of protein-coding genes, and thus, targeting the process offers a means to manipulate protein production from a gene. Splicing modulation is particularly valuable in cases of disease caused by mutations that lead to disruption of normal splicing or when interfering with the normal splicing process of a gene transcript may be therapeutic. SSOs offer an effective and specific way to target and alter splicing in a therapeutic manner. See Haven's and Hasting NAR (2016) 44, 6549-6563. SSOs may be complementary to an Exon/Intron boundary in the target pre-mRNA or may target splicing enhanced or silencer elements (collectively referred to as cis-acting splice elements) within the pre-mRNA that regulates splicing of the pre-mRNA. Splice modulation may result in exon skipping, or exon inclusion and thereby modulates alternive splicing of a pre-mRNA. SSOs function by non nuclease mediated modulation of the target pre-mRNA, and therefore are not capable of recruiting RNaseH, they are often either fully modified oligonucleotides, i.e. each nucleoside comprises a modified sugar moiety, such as a 2'sugar substituted sugar moiety (for example fully 2'-O-MOE oligonucleotides of e.g. 15-25 nucleotides in length, often 18-22 or 20 nucleotides in length, based on a phosphorothioate back bone), or LNA mixmer oligonucleotides (oligonucleotides 10-30 nucleotides in length which comprises DNA and LNA nucleosides, and optionally other 2' sugar modified nucleosides, such as 2'-O-MOE. Also envisaged are LNA oligonucleotides which do not comprises DNA nucleosides, but comprise of LNA and other 2'sugar modified nucleosides, such as 2'-O-MOE nucleosides. Table 1 of Haven's and Hasting NAR (2016) 44, 6549-6563, hereby incorporated by reference, illustrates a range of SSO targets and the chemistry of the oligonucleotides used which have reported activity in vivo, and is reproduced below in Table A:

TABLE A

| Condition | Target gene | Stage/ Model | SSO | Target (Action) | Route | Ref (see Haven's and Hasting |
|---|---|---|---|---|---|---|
| Block cryptic/Aberrant splicing caused by mutations | | | | | | |
| β-Thalassemia | HBB | mouse | PPMO | intron 2 aberrant 5'ss (correct splicing) | IV | (144) |
| Fukuyama congenital muscular dystrophy | FKTN | mouse | VPMO | exon 10 aberrant 3'ss; alternative 5'ss; ESE (correct splicing) | IM | (145) |

TABLE A-continued

| Condition | Target gene | Stage/ Model | SSO | Target (Action) | Route | Ref (see Haven's and Hasting |
|---|---|---|---|---|---|---|
| Hutchinson-Gilford progeria | LMNA | mouse | VPMO; 2'-MOE/ PS | exon 10 5'ss; exon 11 cryptic 5'ss; exon 11 ESE (block exon 11 splicing) | IV/IP | (146, 147) |
| Leber congenital amaurosis | CEP290 | mouse | 2'-OMe/ PS; AAV | Intron 26 cryptic exon (correct splicing) | IVI | (56) |
| Myotonic dystrophy | CLCN1 | mouse | PMO | exon 7a 3'ss (exon 7a skipping) | IM | (53, 148) |
| Usher syndrome | USH1C | mouse | 2'-MOE/ PS | exon 3 cryptic 5'ss (correct splicing) | IP | (40) |
| X-linked agammaglobulinemia | BTK | mouse | PPMO | pseudoexon 4A ESS (pseudoexon skipping) | IV/SC | (149) |
| Switch alternative splicing | | | | | | |
| Alzheimer's disease | LRP8 | mouse | 2'-MOE/ PS | intron 19 ISS (exon 19 inclusion) | ICV | (42) |
| Autoimmune diabetes susceptibility | CTLA4 | mouse | PPMO | exon 2 3'ss (exon skipping) | IP | (150) |
| Cancer | BCL2L1 | mouse | 2'-MOE/ PS | exon 2 5'ss (alternative 5'ss) | IV/NP | (151) |
| Cancer | ERBB4 | mouse | LNA | exon 26 5'ss (exon skipping) | IP | (152) |
| Cancer | MDM4 | mouse | PMO | exon 6 5'ss (exon skipping) | TTM | (153) |
| Cancer | STAT3 | mouse | VPMO | exon 23 α 3'ss (β 3'ss use) | ITM | (154) |
| Inflammation | IL1RAP | mouse | 2-OMe/ PS; LNA | exon 9 ESE (exon skipping) | IV/NP | (155) |
| Inflammation | TNFRSF1B | mouse | LNA/ PS | exon 7 5'ss (exon skipping) | IP | (156) |
| Neovascularization | FLT1 | mouse | PMO | exon 13 5'ss (alternative pA site) | IVI/ ITM | (157) |
| Neovascularization | KDR | mouse | PMO | exon 13 5'ss (alternative pA site) | IVI/ SCJ | (158) |
| Spinal muscular atrophy | SMN2 | clinical trials | 2'-MOE/ PS | intron 7 ISS (exon 7 inclusion) | IT | (43, 142) |
| Correct open reading frame | | | | | | |
| cardiomyopathy | MYBPC3 | mouse | AAV | Exon 5 and 6 ESEs (exon 5, 6 skipping) | IV | (159) |
| Cardiomyopathy | TTN | mouse | VPMO | exon 326 ESE (exon skipping) | IP | (160) |
| Duchenne muscular dystrophy (DMD) | DMD | clinical trials | 2'-OMe/ PMO | exon 51 ESE (exon skipping) | IV/SC | (46, 98) |
| Nijmegen breakage syndrome | NBN | mouse | VPMO | exon 6/7 ESEs (exon skipping) | IV | (161) |
| Disrupt open reading frame/Protein function | | | | | | |
| Ebola | IL10 | mouse | PPMO | exon 4 3'ss (exon skipping) | IP | (162) |
| Huntington disease | HTT | mouse | 2'-OMe/ PS | exon 12 skipping | IS | (163) |

TABLE A-continued

| Condition | Target gene | Stage/ Model | SSO | Target (Action) | Route | Ref (see Haven's and Hasting |
|---|---|---|---|---|---|---|
| Hypercholesterolemia | APOB | mouse | 2'-OMe/ PS | exon 27 3'ss (exon skipping) | IV | (164) |
| Muscle-Wasting/DMD | MSTN | mouse | PPMO/ VPMO/ 2'-OMe | exon 2 ESE (exon skipping) | IV/ IM/IP | (165, 166) |
| Pompe disease | GYS2 | mouse | PPMO | exon 6 5'ss (exon skipping) | IM/IV | (167) |
| Spinocerebellar ataxia type 3 | ATXN3 | mouse | 2'-OMe/ PS | exon 9, 10 skipping | ICV | (168) |

In some embodiments of the invention, the antisense oligonucleotide is a splice modulating oligonucleotide which is complementary to a pre-mRNA selected from the group consisting of a HBB, FKTN, LMNA, CEP290, CLCN1, USH1C, BTK, LRP8, CTLA4, BCL2L1, ERBB4, MDM4, STAT3, IL1RAP, TNFRSF1B, FLT1, KDR, SMN2, MYBPC3, TTN, DMD, NBN, IL10, HTT, APOB, MSTN, GYS2, and ATXN3. Exemplary diseases which may be treated with the SSOs of the invention, on a target by target basis are provided in Table A.

The following embodiments relate in general to single stranded antisense oligonucleotides of the invention, and splice modulating antisense oligonucleotide (SSOs) in particular:

1. A single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises one or more 2'sugar modified nucleosides, and wherein at least one of the internucleoside linkages present between the nucleosides of the contiguous nucleotide sequence is a phosphorodithioate linkage of formula (IA) or (IB)

(IA')

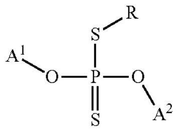

(IB')

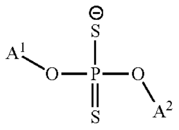

wherein one of the two oxygen atoms is linked to the 3'carbon atom of an adjacent nucleoside ($A^1$) and the other one is linked to the 5'carbon atom of another adjacent nucleoside ($A^2$), and wherein R is hydrogen or a phosphate protecting group.

2. The antisense oligonucleotide according to embodiment 1, wherein at least one of the two nucleosides ($A^1$) and ($A^2$) is a 2' sugar modified nucleoside.
3. The antisense oligonucleotide according to embodiment 1, wherein both nucleosides ($A^1$) and ($A^2$) is a 2' sugar modified nucleoside.
4. The antisense oligonucleotide according to any one of embodiments 1-3, wherein at least one of the two nucleosides ($A^1$) and ($A^2$), or both nucleosides ($A^1$) and ($A^2$) is a DNA nucleoside.
5. The antisense oligonucleotide according to any one of embodiments 1-4, wherein at least one of ($A^1$) and ($A^2$) is a 2'-sugar modified nucleoside or nucleosides are independently selected from 2'-alkoxy-RNA, 2'-alkoxy-alkoxy-RNA, 2'-amino-DNA, 2'-fluoro-RNA, 2'-fluoro-ANA or a LNA nucleoside.
6. The antisense oligonucleotide according to any one of embodiments 1-5, wherein least one of ($A^1$) and ($A^2$) is a LNA nucleoside.
7. The antisense oligonucleotide according to any one of embodiments 1-5, wherein both ($A^1$) and ($A^2$) are LNA nucleosides.
8. The antisense oligonucleotide according to any one of embodiments 1-6, wherein least one of ($A^1$) and ($A^2$) is a 2'-O-methoxyethyl nucleoside.
9. The antisense oligonucleotide according to any one of embodiments 1-5, wherein both of ($A^1$) and ($A^2$) is a 2'-O-methoxyethyl nucleoside.
10. The antisense oligonucleotide according to any one of embodiments 1-8, wherein the LNA nucleosides are selected from the group consisting of beta-D-oxy LNA, 6'-methyl-beta-D-oxy LNA and ENA.
11. The antisense oligonucleotide according to any one of embodiments 1-8, wherein the LNA nucleosides are beta-D-oxy LNA.
12. The antisense oligonucleotide according to any one of embodiments 1-11, wherein the contiguous nucleotide sequence comprises one or more further 2'-sugar modified nucleosides, such as one or more further 2'sugar modified nucleosides selected from the group consisting of 2'-alkoxy-RNA, 2'-alkoxyalkoxy-RNA, 2'-amino-DNA, 2'-fluoro-RNA, 2'-fluoro-ANA or a LNA nucleoside.
13. The antisense oligonucleotide according to any one of embodiments 1-12, wherein the contiguous nucleotide sequence comprises both LNA nucleosides and DNA nucleosides.
14. The antisense oligonucleotide according to any one of embodiments 1-12, wherein the contiguous nucleotide sequence comprises both LNA nucleosides and 2'-O-methoxyethyl nucleosides.
15. The antisense oligonucleotide according to any one of embodiments 1-13, wherein the contiguous nucleotide sequence comprises both LNA nucleosides and 2'fluoro RNA nucleosides.

16. The antisense oligonucleotide according to any one of embodiments 1-13, wherein the contiguous nucleotide sequence comprises either
    (i) only LNA and DNA nucleosides
    (ii) only LNA and 2'-O-methoxyethyl nucleosides
    (iii) only LNA, DNA and 2'-O-methoxyethyl nucleosides
    (iv) only LNA, 2'fluoro RNA and 2'-O-methoxyethyl nucleosides
    (v) only LNA, DNA, 2'fluoro RNA and 2'-O-methoxyethyl nucleosides or only LNA, 2'fluoro RNA and 2'-O-methoxyethyl nucleosides
    (vi) only 2'-O-methoxyethyl nucleosides
17. The antisense oligonucleotide according to any one of embodiments 1-16, wherein the contiguous nucleotide sequence does not comprise a sequence of 4 or more contiguous DNA nucleosides, or does not comprise a sequence of three or more contiguous DNA nucleosides.
18. The antisense oligonucleotide according to any one of embodiments 1-17, wherein the antisense oligonucleotide or the contiguous nucleotide sequence thereof is a mixmer oligonucleotide or a totalmer oligonucleotide.
19. The antisense oligonucleotide according to any one of embodiments 1-18, wherein the antisense oligonucleotide is not capable of recruiting human RNAseH1.
20. The antisense oligonucleotide according to any one of embodiments 1-19, wherein the nucleoside (A2) is the 3' terminal nucleoside of the contiguous nucleotide sequence or of the oligonucleotide.
21. The antisense oligonucleotide according to any one of embodiments 1-20, wherein the nucleoside (A1) is the 5' terminal nucleoside of the contiguous nucleotide sequence or of the oligonucleotide.
22. The antisense oligonucleotide according to any one of embodiments 1-21, which comprises at least two phosphorodithioate internucleoside linkage of formula I, such as 2, 3, 4, 5, or 6 phosphorodithioate internucleoside linkage of formula I.
23. The antisense oligonucleotide according to any one of embodiments 1-22, wherein the internucleoside linkage between the 2 3' most nucleosides of the contiguous nucleotide sequence is a phosphorodithioate internucleoside linkage of formula I, and wherein the internucleoside linkage between the 2 5' most nucleosides of the contiguous nucleotide sequence is a phosphorodithioate internucleoside linkage of formula I.
24. The antisense oligonucleotide according to any one of embodiments 1-23 which further comprises phosphorothioate internucleoside linkages.
25. The antisense oligonucleotide according to any one of embodiments 1-24 which further comprises stereodefined phosphorothioate internucleoside linkages.
26. The antisense oligonucleotide according to any one of embodiments 1-25, wherein the remaining internucleoside linkages are independently selected from the group consisting of phosphorodithioate internucleoside linkages, phosphorothioate internucleoside linkages, and phosphodiester internucleoside linkages.
27. The antisense oligonucleotide according to any one of embodiments 1-26, wherein the remaining internucleoside linkages are phosphorothioate internucleoside linkages.
28. The antisense oligonucleotide according to any one of embodiments 1-27, wherein said contiguous nucleotide sequence is complementary, such as 100% complementary, to a mammalian pre-mRNA, a mammalian mature mRNA target, a viral RNA target, or a mammalian long non coding RNA.
29. The antisense oligonucleotide according to any one of embodiments 28, wherein the RNA target is a human RNA target.
30. The antisense oligonucleotide according to any one of embodiments 1-29, wherein the antisense oligonucleotide modulates the splicing of a mammalian, such as human pre-mRNA target, e.g. is a splice skipping or splice modulating antisense oligonucleotide.
31. The antisense oligonucleotide according to any one of embodiments 1-30, wherein the antisense oligonucleotide is complementary, such as 100% complementary to a intron/exon splice site of a human pre-mRNA, or a splice modulating region of a human pre-mRNA.
32. The antisense oligonucleotide according to any one of embodiments 1-30, wherein the antisense oligonucleotide or contiguous nucleotide sequence thereof is complementary, such as fully complementary to a human pre-mRNA sequence selected from the group consisting of TNFR2, HBB, FKTN, LMNA, CEP290, CLCN1, USH1C, BTK, LRP8, CTLA4, BCL2L1, ERBB4, MDM4, STAT3, IL1RAP, TNFRSF1B, FLT1, KDR, SMN2, MYBPC3, TTN, DMD, NBN, IL10, HTT, APOB, MSTN, GYS2, and ATXN3.
33. The antisense oligonucleotide according to any one of embodiments 1-32, wherein the antisense oligonucleotide consists or comprises of a contiguous nucleotide sequence selected from the group consisting of SSO #1-SSO #25
34. The antisense oligonucleotide according to any one of embodiments 1-33, wherein the cell is a human cell.
35. The antisense oligonucleotide according to any one of embodiments 1-34, wherein the length of the antisense oligonucleotide is 10-30 nucleotides in length.
36. The antisense oligonucleotide according to any one of embodiments 1-34, wherein the length of the antisense oligonucleotide is 12-24 nucleotides in length.
37. The antisense oligonucleotide according to any one of embodiments 1-36, wherein the 3' terminal nucleoside of the antisense oligonucleotide or the antisense oligonucleotide or the contiguous nucleotide sequence thereof is either a LNA nucleoside or a 2-O-methoxyethyl nucleoside.
38. The antisense oligonucleotide according to any one of embodiments 1-27, wherein the 5' terminal nucleoside of the antisense oligonucleotide or the contiguous nucleotide sequence thereof is either a LNA nucleoside or a 2-O-methoxyethyl nucleoside.
39. The antisense oligonucleotide according any one of embodiments 1-38, wherein the 5' terminal nucleoside and the 3' terminal nucleoside of the antisense oligonucleotide or the contiguous nucleotide sequence thereof are both LNA nucleosides.
40. The antisense oligonucleotide according any one of embodiments 1-39, wherein the contiguous nucleotide sequence comprises at least one region of two or three LNA contiguous nucleotides, and/or at least one region of two or three contiguous 2'-O-methoxyethyl contiguous nucleotides.
41. A pharmaceutically acceptable salt of an oligonucleotide according to any one of embodiments 1 to 40, in particular a sodium or a potassium salt or an ammonium salt.
42. A conjugate comprising an oligonucleotide or a pharmaceutically acceptable salt according to any one of embodiments 1 to 41 and at least one conjugate moiety covalently attached to said oligonucleotide or said pharmaceutically acceptable salt, optionally via a linker moiety.

43. A pharmaceutical composition comprising an oligonucleotide, pharmaceutically acceptable salt or conjugate according to any one of embodiments 1 to 42 and a therapeutically inert carrier.
44. An oligonucleotide, pharmaceutically acceptable salt or conjugate according to any one of embodiments 1 to 43 for use as a therapeutically active substance.
45. A method for the modulation of a target RNA in a cell which is expressing said RNA, said method comprising the step of administering an effective amount of the oligonucleotide, pharmaceutically acceptable salt, conjugate or composition according to any one of embodiments 1-44 to the cell.
46. A method for the modulation of a splicing of a target pre-RNA in a cell which is expressing said target pre-mRNA, said method comprising the step of administering an effective amount of the oligonucleotide, pharmaceutically acceptable salt, conjugate or composition according to any one of embodiments 1-44 to the cell.
47. The method according to embodiments 45 or 46 wherein said method is an in vitro method or an in vivo method.
48. Use of an oligonucleotide, pharmaceutical salt, conjugate, or composition of any one of embodiments 1-44, for inhibition of a RNA in a cell, such as in a human cell, wherein said use is in vitro or in vivo.

CERTAIN MIXMER EMBODIMENTS

1. A single stranded antisense oligonucleotide, for modulation of a RNA target in a cell, wherein the antisense oligonucleotide comprises or consists of a contiguous nucleotide sequence of 10-30 nucleotides in length, wherein the contiguous nucleotide sequence comprises alternating regions of 2'sugar modified nucleosides, wherein the maximum length of contiguous DNA nucleoside with the contiguous nucleotide sequence is 3 or 4, and wherein at least one of the internucleoside linkages present between the nucleosides of the contiguous nucleotide sequence is a phosphorodithioate linkage of formula (IA) or (IB)

(IA')

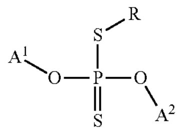

(IB')

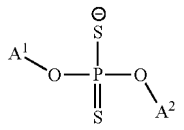

wherein one of the two oxygen atoms is linked to the 3'carbon atom of an adjacent nucleoside ($A^1$) and the other one is linked to the 5'carbon atom of another adjacent nucleoside ($A^2$), and wherein R is hydrogen or a phosphate protecting group.
2. The antisense oligonucleotide according to embodiment 1, wherein at least one of the two nucleosides ($A^1$) and ($A^2$) is a 2' sugar modified nucleoside.
3. The antisense oligonucleotide according to embodiment 1, wherein both nucleosides ($A^1$) and ($A^2$) is a 2' sugar modified nucleoside.
4. The antisense oligonucleotide according to any one of embodiments 1-3, wherein at least one of the two nucleosides ($A^1$) and ($A^2$), or both nucleosides ($A^1$) and ($A^2$) is a DNA nucleoside.
5. The antisense oligonucleotide according to any one of embodiments 1-4, wherein at least one of ($A^1$) and ($A^2$) is a 2'-sugar modified nucleoside or nucleosides are independently selected from 2'-alkoxy-RNA, 2'-alkoxyalkoxy-RNA, 2'-amino-DNA, 2'-fluoro-RNA, 2'-fluoro-ANA or a LNA nucleoside.
6. The antisense oligonucleotide according to any one of embodiments 1-5, wherein least one of ($A^1$) and ($A^2$) is a LNA nucleoside.
7. The antisense oligonucleotide according to any one of embodiments 1-5, wherein both ($A^1$) and ($A^2$) are LNA nucleosides.
8. The antisense oligonucleotide according to any one of embodiments 1-6, wherein least one of ($A^1$) and ($A^2$) is a 2'-O-methoxyethyl nucleoside.
9. The antisense oligonucleotide according to any one of embodiments 1-5, wherein both of ($A^1$) and ($A^2$) is a 2'-O-methoxyethyl nucleoside.
10. The antisense oligonucleotide according to any one of embodiments 1-8, wherein the LNA nucleosides are selected from the group consisting of beta-D-oxy LNA, 6'-methyl-beta-D-oxy LNA and ENA.
11. The antisense oligonucleotide according to any one of embodiments 1-8, wherein the LNA nucleosides are beta-D-oxy LNA.
12. The antisense oligonucleotide according to any one of embodiments 1-11, wherein the contiguous nucleotide sequence comprises one or more further 2'-sugar modified nucleosides, such as one or more further 2'sugar modified nucleosides selected from the group consisting of 2'-alkoxy-RNA, 2'-alkoxyalkoxy-RNA, 2'-amino-DNA, 2'-fluoro-RNA, 2'-fluoro-ANA or a LNA nucleoside.
13. The antisense oligonucleotide according to any one of embodiments 1-12, wherein the contiguous nucleotide sequence comprises both LNA nucleosides and DNA nucleosides.
14. The antisense oligonucleotide according to any one of embodiments 1-12, wherein the contiguous nucleotide sequence comprises both LNA nucleosides and 2'-O-methoxyethyl nucleosides.
15. The antisense oligonucleotide according to any one of embodiments 1-13, wherein the contiguous nucleotide sequence comprises both LNA nucleosides and 2'fluoro RNA nucleosides.
16. The antisense oligonucleotide according to any one of embodiments 1-13, wherein the contiguous nucleotide sequence comprises either
   (i) LNA and DNA nucleosides
   (ii) LNA, DNA and 2'-O-methoxyethyl nucleosides
   (iii) LNA, DNA, 2'fluoro RNA and 2'-O-methoxyethyl nucleosides
17. The antisense oligonucleotide according to any one of embodiments 1-16, wherein the contiguous nucleotide sequence does not comprise a sequence of 3 or more contiguous DNA nucleosides, or does not comprise a sequence of 2 or more contiguous DNA nucleosides.
18. The antisense oligonucleotide according to any one of embodiments 1-17, wherein the antisense oligonucleotide or the contiguous nucleotide sequence thereof is a mixmer oligonucleotide, such as a splice modulating oligonucleotide or a microRNA inhibitor oligonucleotide.

19. The antisense oligonucleotide according to embodiment 18 wherein the miximer consists or comprises the alternating region motif
   [L]m[D]n[L]m[D]n[L]m or
   [L]m[D]n[L]m[D]n[L]m[D]n[L]m or
   [L]m[D]n[L]m[D]n[L]m[D]n[L]m[D]n[L]m or
   [L]m[D]n[L]m[D]n[L]m[D]n[L]m[D]n[L]m[D]n[L]m or
   [L]m[D]n[L]m[D]n[L]m[D]n[L]m[D]n[L]m[D]n[L]m [D]n[L]m or
   [L]m[D]n[L]m[D]n[L]m[D]n[L]m[D]n[L]m[D]n[L]m [D]n[L]m[D]n[L]m or
   [L]m[D]n[L]m[D]n[L]m[D]n[L]m[D]n[L]m[D]n[L]m [D]n[L]m[D]n[L]m[D]n[L]m or
   [L]m[D]n[L]m[D]n[L]m[D]n[L]m[D]n[L]m[D]n[L]m [D]n[L]m[D]n[L]m[D]n[L]m[D]n[L]m
   wherein L represents 2' sugar modified nucleoside, D represents DNA nucleoside, and wherein each m is independently selected from 1-6, and each n is independently selected from 1, 2, 3 and 4, such as 1-3.
20. The antisense oligonucleotides according to embodiment 19, wherein each L nucleoside is independently selected from the group consisting of LNA, 2'-O-MOE or 2'fluoro nucleosides, or each L is independently LNA or 2'-O-MOE.
21. The antisense oligonucleotide according to embodiment 20, wherein each L is LNA.
22. The antisense oligonucleotide according to any one of embodiments 1-21, wherein the antisense oligonucleotide is not capable of recruiting human RNAseH1.
23. The antisense oligonucleotide according to any one of embodiments 1-22, wherein the nucleoside ($A^2$) is the 3' terminal nucleoside of the contiguous nucleotide sequence or of the oligonucleotide.
24. The antisense oligonucleotide according to any one of embodiments 1-23, wherein the nucleoside ($A^1$) is the 5' terminal nucleoside of the contiguous nucleotide sequence or of the oligonucleotide.
25. The antisense oligonucleotide according to any one of embodiments 1-24, which comprises at least two phosphorodithioate internucleoside linkage of formula I, such as 2, 3, 4, 5, or 6 phosphorodithioate internucleoside linkage of formula I.
26. The antisense oligonucleotide according to any one of embodiments 1-25, wherein the contiguous nucleotide sequence comprises two contiguous DNA nucleotides wherein the nucleoside linkage between the two contiguous DNA nucleotides is a phosphorodithioate internucleoside linkage of formula (IA) or (IB), i.e. a P2S linked DNA nucleotide pair.
27. The antisense oligonucleotide according to any one of embodiments 1-26, wherein the contiguous nucleotide sequence comprises more than one P2S linked DNA nucleotide pair.
28. The antisense oligonucleotide according to any one of embodiments 1-26, wherein all the nucleosides linkage between the two contiguous DNA nucleotides present in the contiguous nucleotide sequence are phosphorodithioate internucleoside linkage of formula (IA) or (IB).
29. The antisense oligonucleotide according to any one of embodiments 1-27, wherein at least one internucleoside linkage between a 2'sugar modified nucleoside and a DNA nucleoside are phosphorodithioate internucleoside linkage of formula (IA) or (IB).
30. The antisense oligonucleotide according to any one of embodiments 1-27, wherein more than one internucleoside linkage between a 2'sugar modified nucleoside and a DNA nucleoside are phosphorodithioate internucleoside linkage of formula (IA) or (IB).
31. The antisense oligonucleotide according to any one of embodiments 1-27, wherein all internucleoside linkages between a 2'sugar modified nucleoside and a DNA nucleoside are phosphorodithioate internucleoside linkage of formula (IA) or (IB).
32. The antisense oligonucleotide according to any one of embodiments 1-27, wherein at least one of the internucleoside linkages between a two 2'sugar modified nucleosides is not a phosphorodithioate internucleoside linkage of formula (IA) or (IB), such as is a phosphorothioate internucleoside linkage.
33. The antisense oligonucleotide according to any one of embodiments 1-27, wherein all of the internucleoside linkages between two 2'sugar modified nucleosides are not a phosphorodithioate internucleoside linkage of formula (IA) or (IB), such as are phosphorothioate internucleoside linkages.
34. The antisense oligonucleotide according to any one of embodiments 1-33, wherein the internucleoside linkage between the 2 3' most nucleosides of the contiguous nucleotide sequence is a phosphorodithioate internucleoside linkage of formula I, and wherein the internucleoside linkage between the 2 5' most nucleosides of the contiguous nucleotide sequence is a phosphorodithioate internucleoside linkage of formula I.
35. The antisense oligonucleotide according to any one of embodiments 1-34 which further comprises phosphorothioate internucleoside linkages.
36. The antisense oligonucleotide according to any one of embodiments 1-35 which further comprises stereodefined phosphorothioate internucleoside linkages.
37. The antisense oligonucleotide according to any one of embodiments 1-35, wherein the remaining internucleoside linkages are independently selected from the group consisting of phosphorodithioate internucleoside linkages, phosphorothioate internucleoside linkages, and phosphodiester internucleoside linkages.
38. The antisense oligonucleotide according to any one of embodiments 1-36, wherein the remaining internucleoside linkages are phosphorothioate internucleoside linkages.
39. The antisense oligonucleotide according to any one of embodiments 1-37, wherein said contiguous nucleotide sequence is complementary, such as 100% complementary, to a mammalian such as a human pre-mRNA.
40. The antisense oligonucleotide according to any one of embodiments 1-38, wherein the antisense oligonucleotide modulates the splicing of a mammalian, such as human pre-mRNA target, e.g. is a splice skipping or splice modulating antisense oligonucleotide.
41. The antisense oligonucleotide according to any one of embodiments 1-39, wherein the antisense oligonucleotide is complementary, such as 100% complementary to a intron/exon splice site of a human pre-mRNA, or a splice modulating region of a human pre-mRNA.
42. The antisense oligonucleotide according to any one of embodiments 1-41, wherein the antisense oligonucleotide or contiguous nucleotide sequence thereof is complementary, such as fully complementary to a human pre-mRNA sequence selected from the group consisting of TNFR2, HBB, FKTN, LMNA, CEP290, CLCN1, USH1C, BTK, LRP8, CTLA4, BCL2L1, ERBB4, MDM4, STAT3, IL1RAP, TNFRSF1B, FLT1, KDR, SMN2, MYBPC3, TTN, DMD, NBN, IL10, HTT, APOB, MSTN, GYS2, and ATXN3.

43. The antisense oligonucleotide according to any one of embodiments 1-42, wherein the antisense oligonucleotide consists or comprises of a contiguous nucleotide sequence selected from the group consisting of SSO #1-SSO #25
44. The antisense oligonucleotide according to any one of embodiments 1-43, wherein the cell is a mammalian cell.
45. The antisense oligonucleotide according to any one of embodiments 1-44, wherein the length of the antisense oligonucleotide is 10-30 nucleotides in length.
46. The antisense oligonucleotide according to any one of embodiments 1-44, wherein the length of the antisense oligonucleotide is 12-24 nucleotides in length.
47. The antisense oligonucleotide according to any one of embodiments 1-46, wherein the 3' terminal nucleoside of the antisense oligonucleotide or the antisense oligonucleotide or the contiguous nucleotide sequence thereof is either a LNA nucleoside or a 2-O-methoxyethyl nucleoside.
48. The antisense oligonucleotide according to any one of embodiments 1-47, wherein the 5' terminal nucleoside of the antisense oligonucleotide or the contiguous nucleotide sequence thereof is either a LNA nucleoside or a 2-O-methoxyethyl nucleoside.
49. The antisense oligonucleotide according any one of embodiments 1-48, wherein the 5' terminal nucleoside and the 3' terminal nucleoside of the antisense oligonucleotide or the contiguous nucleotide sequence thereof are both LNA nucleosides.
50. The antisense oligonucleotide according any one of embodiments 1-49, wherein the contiguous nucleotide sequence comprises at least one region of two or three LNA contiguous nucleotides, and/or at least one region of two or three contiguous 2'-O-methoxyethyl contiguous nucleotides.
51. A pharmaceutically acceptable salt of an oligonucleotide according to any one of embodiments 1 to 50, in particular a sodium or a potassium salt or an ammonium salt.
52. A conjugate comprising an oligonucleotide or a pharmaceutically acceptable salt according to any one of embodiments 1 to 51 and at least one conjugate moiety covalently attached to said oligonucleotide or said pharmaceutically acceptable salt, optionally via a linker moiety.
53. A pharmaceutical composition comprising an oligonucleotide, pharmaceutically acceptable salt or conjugate according to any one of embodiments 1 to 52 and a therapeutically inert carrier.
54. An oligonucleotide, pharmaceutically acceptable salt or conjugate according to any one of embodiments 1 to 53 for use as a therapeutically active substance.
55. A method for the modulation of a target RNA in a cell which is expressing said RNA, said method comprising the step of administering an effective amount of the oligonucleotide, pharmaceutically acceptable salt, conjugate or composition according to any one of embodiments 1-54 to the cell.
56. A method for the modulation of a splicing of a target pre-RNA in a cell which is expressing said target pre-mRNA, said method comprising the step of administering an effective amount of the oligonucleotide, pharmaceutically acceptable salt, conjugate or composition according to any one of embodiments 1-54 to the cell.
57. The method according to embodiments 55 or 56 wherein said method is an in vitro method or an in vivo method.
58. Use of an oligonucleotide, pharmaceutical salt, conjugate, or composition of any one of embodiments 1-54, for inhibition of a RNA in a cell, such as in a mammalian cell, wherein said use is in vitro or in vivo.

CERTAIN EMBODIMENTS RELATING TO 3' END PROTECTION

1. A single stranded antisense oligonucleotide comprising at least one phosphorodithioate internucleoside linkage of formula (IA) or (IB)

(IA)

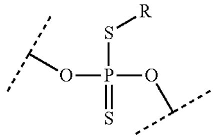

(IB)

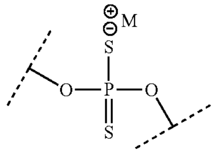

wherein one of the two oxygen atoms is linked to the 3'carbon atom of an adjacent nucleoside ($A^1$) and the other one is linked to the 5'carbon atom of another adjacent nucleoside ($A^2$), and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein at least one of the two nucleosides ($A^1$) and ($A^2$) is a 2' sugar modified nucleoside, such as a LNA nucleoside or a 2'-O-MOE nucleoside, and wherein R is hydrogen or a phosphate protecting group, wherein $A^2$ is the 3' terminal nucleoside of the oligonucleotide.
2. The single stranded antisense according to embodiment 1, wherein ($A^2$) is a LNA nucleoside, or both ($A^1$) and ($A^2$) are LNA nucleosides.
3. The single stranded antisense according to embodiment 1, wherein ($A^2$) is a LNA nucleoside and ($A^1$) is a sugar modified nucleotide.
4. The single stranded antisense according to embodiment 1, wherein ($A^2$) is a LNA nucleoside and ($A^1$) is DNA nucleotide.
5. The single stranded antisense according to embodiment 1, wherein ($A^1$) is a LNA nucleoside and ($A^2$) is a sugar modified nucleotide.
6. The single stranded antisense according to embodiment 1, wherein ($A^1$) is a LNA nucleoside and ($A^2$) is a DNA nucleotide.
7. The single stranded antisense according to any one of embodiments 3 or 5, wherein said sugar modified nucleoside is a 2'-sugar modified nucleoside.
8. The single stranded antisense according to embodiment 7, wherein said 2'-sugar modified nucleoside is 2'-alkoxy-RNA, 2'-alkoxyalkoxy-RNA, 2'-amino-DNA, 2'-fluoro-RNA, 2'-fluoro-ANA or a LNA nucleoside.
9. The single stranded antisense according to embodiment 7 or 8, wherein said 2'-sugar modified nucleoside is a 2'-O-methoxyethyl nucleoside.
10. The single stranded antisense according to any one of embodiments 1-9, wherein the LNA nucleoside or nucleotides are in the beta-D configuration.

11. The single stranded antisense according to any one of embodiments 1 to 10, wherein the LNA nucleosides are independently selected from beta-D-oxy LNA, 6'-methyl-beta-D-oxy LNA and ENA.
12. The single stranded antisense according to any one of embodiment 1 to 11, wherein LNA is beta-D-oxy LNA.
13. The single stranded antisense according to any one of embodiments 1-12, wherein the single stranded antisense consists or comprises of 7-30 contiguous nucleotides which are complementary to a target nucleic acid, such as a target nucleic acid selected from the group consisting of a pre-mRNA, and mRNA, a microRNA, a viral RNA, and a long non coding RNA [referred to as the contiguous nucleotide sequence of an antisense single stranded antisense].
14. The single stranded antisense according to any one of embodiments 1 to 13, wherein the contiguous nucleotide sequence comprises a gapmer region of formula 5'-F-G-F'-3', wherein G is a region of 5 to 18 nucleosides which is capable of recruiting RnaseH, and said region G is flanked 5' and 3' by flanking regions F and F' respectively, wherein regions F and F' independently comprise or consist of 1 to 7 2'-sugar modified nucleotides, wherein the nucleoside of region F which is adjacent to region G is a 2'-sugar modified nucleoside and wherein the nucleoside of region F' which is adjacent to region G is a 2'-sugar modified nucleoside.
14. The single stranded antisense according to any one of embodiments 1 to 13, wherein the contiguous nucleotide sequence is a mixmer oligonucleotide, wherein the mixmer oligonucleotide comprises both LNA nucleosides and DNA nucleoside, and optionally 2'sugar modified nucleosides [such as those according to embodiments 8-9], wherein the single stranded antisense does not comprise a region of 4 or more contiguous DNA nucleosides.
15. The single stranded antisense according to any one of embodiments 1 to 13, wherein the contiguous nucleotide sequence only comprises sugar modified nucleosides.
16. The oligonucleotide according to embodiment 14 or 15, wherein the oligonucleotide is a splice modulating oligonucleotide [capable of modulating the splicing of a pre-mRNA splice event].
17. The oligonucleotide according to embodiment 14 or 15, wherein the oligonucleotide is complementary to a microRNA, such as is a microRNA inhibitor.
18. An oligonucleotide according to any one of embodiments 1 to 17, comprising further internucleoside linkages independently selected from phosphodiester internucleoside linkage, phosphorothioate internucleoside linkage and phosphorodithioate internucleoside linkages; or wherein the further internucleoside linkages within the oligonucleotide or within the contiguous nucleotide sequence thereof, are independently selected from phosphorothioate internucleoside linkage and phosphorodithioate internucleoside linkages.
18. An oligonucleotide according to any one of embodiments 1-18, wherein the further internucleoside linkages of the oligonucleotide, or contiguous nucleotide sequence thereof, are all phosphorothioate internucleoside linkages.
19. The oligonucleotide according to any one of embodiments 1-18, wherein the oligonucleotide comprises a 5' region position 5' to the contiguous nucleotide sequence, wherein the 5' nucleoside region comprises at least one phosphodiester linkage.
20. The oligonucleotide according to embodiment 19, wherein the 5' region comprises 1-5 phosphodiester linked DNA nucleosides, and optionally may link the oligonucleotide or contiguous nucleotide sequence thereof to a conjugate moiety.
21. The oligonucleotide according to any one of embodiments 1 to 20, wherein one or more nucleoside is a nucleobase modified nucleoside.
22. The oligonucleotide according to any one of embodiments 1 to 21, wherein one or more nucleoside is 5-methyl cytosine, such as a LNA 5-methyl cytosine or a DNA 5-methyl cytosine.
23. A pharmaceutically acceptable salt of an oligonucleotide according to any one of embodiments 1 to 22, in particular a sodium or a potassium salt or ammonium salt.
24. A conjugate comprising an oligonucleotide or a pharmaceutically acceptable salt according to any one of embodiments 1 to 23 and at least one conjugate moiety covalently attached to said oligonucleotide or said pharmaceutically acceptable salt, optionally via a linker moiety.
25. A pharmaceutical composition comprising an oligonucleotide, pharmaceutically acceptable salt or conjugate according to any one of embodiments 1 to 24 and a therapeutically inert carrier.
26. An oligonucleotide, pharmaceutically acceptable salt or conjugate according to any one of embodiments 1 to 25 for use as a therapeutically active substance.
27. The oligonucleotide, pharmaceutically acceptable salt or conjugate according to any one of embodiments 1 to 24 for use in therapy, for administration to a subject via parenteral administration, such as, intravenous, subcutaneous, intra-muscular, intracerebral, intracerebroventricular or intrathecal administration.

EMBODIMENTS RELATING TO OLIGONUCLEOTIDES WITH ACHIRAL PHOSPHORODITHIOATE AND STEREODEFINED PHOSPHOROTHIOATE LINKAGES

1. A single stranded antisense oligonucleotide comprising at least one phosphorodithioate internucleoside linkage of formula (IA) or (IB)

(IA')

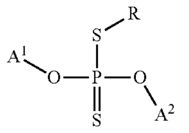

(IB')

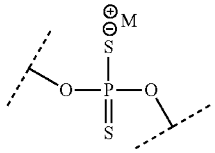

wherein one of the two oxygen atoms is linked to the 3'carbon atom of an adjacent nucleoside (A1) and the other one is linked to the 5'carbon atom of another adjacent nucleoside (A2), and wherein in (IA) R is hydrogen or a phosphate protecting group, and in (IB) M+ is a cation, such as a metal cation, such as an alkali metal cation, such as a Na+ or K+ cation; or M+ is an ammonium cation, and wherein the single stranded oligonucleotide further comprises at least one stereodefined phosphorothioate internucleoside linkage, (Sp, S) or (Rp, R)

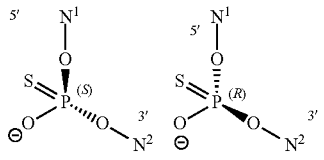

wherein $N^1$ and $N^2$ are nucleosides. (Note: In some non limiting embodiments $N^1$ and/or $N^2$ are DNA nucleotides).

2. The single stranded antisense oligonucleotide according to embodiment 1, wherein A2 is the 3' terminal nucleoside of the oligonucleotide.
3. The single stranded antisense oligonucleotide according to embodiment 1, wherein A1 is the 5' terminal nucleoside of the oligonucleotide.
4. The single stranded antisense oligonucleotide according to anyone of embodiments 1-3, wherein said single stranded oligonucleotide comprises 1, 2, 3, 4, 5, or 6 internucleoside linkages of formula IB.
5. The single stranded antisense oligonucleotide according to anyone of embodiments 1-4, wherein both the 5' most internucleoside linkage of the antisense oligonucleotide, and the 3' most internucleoside linkage of the antisense oligonucleotide are internucleoside linkages of formula IB.
6. The single stranded antisense oligonucleotide according to any one of embodiments 1-5, wherein in at least one of the internucleoside linkages of formula IB, at least one of the two nucleosides (A1) and (A2) is a 2' sugar modified nucleoside, such as a 2' sugar modified nucleoside selected from the group consisting of 2'-alkoxy-RNA, 2'-alkoxyalkoxy-RNA, 2'-amino-DNA, 2'-fluoro-RNA, 2'-fluoro-ANA and a LNA nucleoside.
7. The single stranded antisense oligonucleotide according to any one of embodiments 1-6, wherein in at least one of the internucleoside linkages of formula IB, at least one of the two nucleosides (A1) and (A2) is a LNA nucleoside.
8. The single stranded antisense oligonucleotide according to any one of embodiments 1-6, wherein in at least one of the internucleoside linkages of formula IB, at least one of the two nucleosides (A1) and (A2) is a 2'-O-MOE nucleoside.
9. The single stranded antisense oligonucleotide according to any one of embodiments 1-8, wherein the 3' terminal nucleoside of the antisense oligonucleotide is a LNA nucleoside or a 2'-O-MOE nucleoside.
10. The single stranded antisense oligonucleotide according to any one of embodiments 1-9, wherein the 5' terminal nucleoside of the antisense oligonucleotide is a LNA nucleoside or a 2'-O-MOE nucleoside.
11. The single stranded antisense oligonucleotide according to any one or embodiments 1-10, wherein the two 3' most terminal nucleosides of the antisense oligonucleotide are independently selected from LNA nucleosides and 2'-O-MOE nucleosides.
12. The single stranded antisense oligonucleotide according to any one or embodiments 1-11, wherein the two 5' most terminal nucleosides of the antisense oligonucleotide are independently selected from LNA nucleosides and 2'-O-MOE nucleosides.
13. The single stranded antisense oligonucleotide according to any one or embodiments 1-12, wherein the three 3' most terminal nucleosides of the antisense oligonucleotide are independently selected from LNA nucleosides and 2'-O-MOE nucleosides.
14. The single stranded antisense oligonucleotide according to any one or embodiments 1-13, wherein the three 5' most terminal nucleosides of the antisense oligonucleotide are independently selected from LNA nucleosides and 2'-O-MOE nucleosides.
15. The single stranded antisense oligonucleotide according to any one or embodiments 1-14, wherein the two 3' most terminal nucleosides of the antisense oligonucleotide are LNA nucleosides.
16. The single stranded oligonucleotide according to any one or embodiments 1-15, wherein the two 5' most terminal nucleosides of the antisense oligonucleotide are LNA nucleosides.
17. The single stranded antisense oligonucleotide according to any one of embodiments 1-16, wherein the antisense oligonucleotide further comprises a region of 2-16 DNA nucleotides, wherein the internucleoside linkages between the DNA nucleotides are stereodefined phosphorothioate internucleoside linkages.
18. The single stranded antisense oligonucleotide according to any one of embodiments 1 to 17, wherein the LNA nucleosides are independently selected from beta-D-oxy LNA, 6'-methyl-beta-D-oxy LNA and ENA.
19. The single stranded antisense oligonucleotide according to any one of embodiments 1 to 17, wherein the LNA nucleosides are beta-D-oxy LNA
20. The single stranded antisense oligonucleotide according to any one of embodiments 1-19, wherein the oligonucleotide consists or comprises of 7-30 contiguous nucleotides which are complementary to, such as fully complementary to a target nucleic acid, such as a target nucleic acid selected from the group consisting of a pre-mRNA, and mRNA, a microRNA, a viral RNA, and a long non coding RNA [the antisense oligonucleotide].
21. The single stranded antisense oligonucleotide according to any one of embodiments 1-20, wherein the single stranded oligonucleotide is capable of modulating the RNA target.
22. The single stranded antisense oligonucleotide according to any one of embodiments 1-20, wherein the single stranded antisense oligonucleotide is capable of inhibiting the RNA target, such as via RNAse H1 recruitment.
23. The single stranded antisense oligonucleotide according to any one of embodiments 1 to 22, wherein the contiguous nucleotide sequence of the oligonucleotide comprises a gapmer region of formula 5'-F-G-F'-3', wherein G is a region of 5 to 18 nucleosides which is capable of recruiting RNaseH1, and said region G is flanked 5' and 3' by flanking regions F and F' respectively, wherein regions F and F' independently comprise or consist of 1 to 7 2'-sugar modified nucleotides, wherein the nucleoside of region F which is adjacent to region G is a 2'-sugar modified nucleoside and wherein the nucleoside of region F' which is adjacent to region G is a 2'-sugar modified nucleoside.
24. The single stranded antisense oligonucleotide according to embodiment 23, regions F or region F' comprise an internucleoside linkage of formula IB, according to any one of embodiments 1-19.
25. The single stranded antisense oligonucleotide according to embodiment 24, wherein both of regions F and F' comprise an internucleoside linkage of formula IB, according to any one of embodiments 1-19.
26. The single stranded antisense oligonucleotide according to embodiment 23-25, wherein all the internucleoside linkages within regions F and/or F' are internucleoside linkage of formula IB, according to any one of embodiments 1-19.

27. The single stranded antisense oligonucleotide according to embodiments 23-26, wherein regions F and F' both comprise or consist of LNA nucleosides.

28. The single stranded antisense oligonucleotide according to embodiments 23-27, wherein regions F and F' both comprise or consist of MOE nucleosides.

29. The single stranded antisense oligonucleotide according to embodiments 23-28, wherein regions F comprises LNA nucleoside(s) and F' comprise or consist of MOE nucleosides.

30. The single stranded antisense oligonucleotide according to embodiments 23-29, wherein region G further comprises at least one internucleoside linkage of formula IB positioned between the 3' most nucleoside of region F and the 5' most nucleoside of region G.

31. The single stranded antisense oligonucleotide according to embodiments 23-30, wherein region G comprises at least one stereodefined phosphorothioate linkage positioned between two DNA nucleosides.

32. The single stranded antisense oligonucleotide according to embodiments 23-31, wherein region G comprises at least one internucleoside linkage of formula IB positioned between two DNA nucleosides.

33. The single stranded antisense oligonucleotide according to embodiments 23-32, wherein region G further comprises at least 2, 3, or 4 internucleoside linkages of formula IB.

34. The single stranded antisense oligonucleotide according to embodiments 23-31, wherein all the remaining internucleoside linkages within region G are stereodefined phosphorothioate internucleoside linkages, independently selected from Rp and Sp internucleoside linkages.

35. The single stranded antisense oligonucleotide according to embodiments 23-31, wherein all the internucleoside linkages within region G are stereodefined phosphorothioate internucleoside linkages, independently selected from Rp and Sp internucleoside linkages, optionally other than the internucleoside linkage between the 3' most nucleoside of region F and the 5' most nucleoside of region G.

36. The single stranded antisense oligonucleotide according to any one of embodiments 1 to 22, wherein the antisense oligonucleotide comprises less than 4 contiguous DNA nucleotides.

37. The single stranded antisense oligonucleotide according to any one of embodiments 1 to 22 or 36, wherein the antisense oligonucleotide is a mixmer or a totalmer oligonucleotide.

38. The single stranded oligonucleotide according to embodiment 37 wherein the mixmer oligonucleotide comprises both LNA nucleosides and DNA nucleosides, and optionally 2'sugar modified nucleosides (e.g. see the list in embodiment 6), such as 2'-O-MOE nucleoside(s).

39. The single stranded antisense oligonucleotide according to any one of embodiments 1 to 38 wherein the antisense oligonucleotide comprises a region of 3 or more contiguous MOE nucleosides, and optionally wherein all the nucleosides of the oligonucleotide are 2'MOE nucleosides.

40. The single stranded antisense oligonucleotide according to any one of embodiments 1-39, wherein the target is a mRNA or a pre-mRNA target.

41. The single stranded antisense oligonucleotide according to any one of embodiments 1-40, wherein the oligonucleotide targets a pre-mRNA splice site or a region of the pre-mRNA which regulates the splicing event at a pre-mRNA splice site.

42. The single stranded antisense oligonucleotide according to any one of embodiments 1-41, which is a splice modulating oligonucleotide capable of modulating the splicing of a pre-mRNA target.

43. The single stranded antisense oligonucleotide according to any one of embodiments 1-42, wherein the target is a microRNA.

44. The single stranded antisense oligonucleotide according to any one of embodiments 1-42, wherein the antisense oligonucleotide is 10-20 nucleotides in length, such as 12-24 nucleotides in length.

45. The single stranded antisense oligonucleotide according to embodiment 43, wherein the length of the antisense oligonucleotide is 7-30, such as 8-12 or 12 to 23 nucleotides in length.

46. An single stranded antisense oligonucleotide comprising the antisense oligonucleotide according to any one of embodiments 1-45, wherein the oligonucleotide further comprises a 5' region position 5' to the contiguous nucleotide sequence, wherein the 5' nucleoside region comprises at least one phosphodiester linkage.

47. The single stranded antisense oligonucleotide according to embodiment 46, wherein the 5' region comprises 1-5 phosphodiester linked DNA nucleosides, and optionally may link the oligonucleotide or contiguous nucleotide sequence thereof to a conjugate moiety.

48. The single stranded antisense oligonucleotide according to any one of embodiments 1 to 47, wherein one or more nucleoside is a nucleobase modified nucleoside.

49. The single stranded antisense oligonucleotide according to any one of embodiments 1 to 48, wherein one or more nucleoside is 5-methyl cytosine, such as a LNA 5-methyl cytosine or a DNA 5-methyl cytosine.

50. A pharmaceutically acceptable salt of a single stranded antisense oligonucleotide according to any one of embodiments 1 to 49, in particular a sodium or a potassium salt or ammonium salt.

51. A conjugate comprising a single stranded antisense oligonucleotide, or a pharmaceutically acceptable salt according to any one of embodiments 1 to 49 and at least one conjugate moiety covalently attached to said oligonucleotide or said pharmaceutically acceptable salt, optionally via a linker moiety.

52. A pharmaceutical composition comprising a single stranded antisense oligonucleotide, pharmaceutically acceptable salt or conjugate according to any one of embodiments 1 to 51 and a therapeutically inert carrier.

53. A single stranded antisense oligonucleotide, pharmaceutically acceptable salt or conjugate according to any one of embodiments 1 to 52 for use as a therapeutically active substance.

54. The single stranded antisense oligonucleotide, pharmaceutically acceptable salt or conjugate according to any one of embodiments 1 to 53 for use in therapy, for administration to a subject via parenteral administration, such as, intravenous, subcutaneous, intra-muscular, intracerebral, intracerebroventricular or intrathecal administration.

55. The in vitro use of a single stranded antisense oligonucleotide, salt, or composition according to any one of the preceding embodiments for use in the inhibition of a target RNA in a cell, wherein the single stranded antisense oligonucleotide is complementary to, such as fully complementary to the target RNA.

56. An in vivo or in vitro method for the inhibition of a target RNA in a cell which is expressing said target RNA, said method comprising administering an effective amount of the antisense oligonucleotide, salt, conjugate or composition according to any one of the preceding embodiments to the cell, so as to inhibit the target RNA.
57. The in vitro or in vivo use of a single stranded antisense oligonucleotide, salt, or composition according to any one of the preceding embodiments for use in the modulating the splicing of a target pre-mRNA in a cell.
58. An in vivo or in vitro method for modulating the splicing of a target pre-RNA in a cell which is expressing said target pre-RNA, said method comprising administering an effective amount of the antisense oligonucleotide, salt, conjugate or composition according to any one of the preceding embodiments to the cell, so as to modulate the splicing of the target RNA.

Htra-1 Targeting Antisense Oligonucelotides of the Invention

In some embodiments, the antisense oligonucleotide of the invention is complementary to the mRNA or pre-mRNA encoding the human high temperature requirement A1 Serine protease (Htra1)—see WO 2018/002105 for example. Inhibition of Htra1 expression using the antisense oligonucleotides of the invention which target Htra1 mRNa or premRNA are beneficial for a treating a range of medical disorders, such as macular degeneration, e.g. age-related macular degeneration (geographic atrophy). Human Htra1 pre-mRNA and mRNA target sequences are available as follows:

| Species | Chr. | Strand | Genomic coordinates Start | End | Assembly | NCBI reference sequence* accession number for mRNA |
|---|---|---|---|---|---|---|
| Human | 10 | fwd | 122461525 | 122514908 | GRCh38.p2 release 107 | NM_002775.4 |

Compounds of the invention which target Htra-1 are listed as Htra1 #1-38 in the examples.

1. An antisense oligonucleotide of the invention which is 10-30 nucleotides in length, wherein said antisense oligonucleotide targets the human HTRA1 mRNA or pre-mRNA, wherein said antisense oligonucleotide comprises a contiguous nucleotide region of 10-22 nucleotides which are at least 90% such as 100% complementarity to SEQ ID NO 1 or 2 of WO 2018/002105, which are disclosed in the sequence listing as SEQ ID NO 9 and 10, wherein said antisense oligonucleotide comprises at least one phosphorodithioate internucleoside linkage of formula IA or formula IB.
2. The antisense oligonucleotide according to embodiment 1 or 2, wherein the contiguous nucleotide region is identical to a sequence present in a sequence selected from the group consisting of

```
SEQ ID NO 11, 12, 13, 14, 15, 16, 17 and 18:
SEQ ID NO 11:
CAAATATTTACCTGGTTG

SEQ ID NO 12:
TTTACCTGGTTGTTGG
```

-continued

```
SEQ ID NO 13:
CCAAATATTTACCTGGTT

SEQ ID NO 14:
CCAAATATTTACCTGGTTGT

SEQ ID NO 15:
ATATTTACCTGGTTGTTG

SEQ ID NO 16:
TATTTACCTGGTTGTT

SEQ ID NO 17:
ATATTTACCTGGTTGT

SEQ ID NO 18:
ATATTTACCTGGTTGTT
```

3. The antisense oligonucleotide according to any one of embodiments 1-3, wherein the contiguous nucleotide region comprises the sequence

```
SEQ ID NO 19:
TTTACCTGGTT
```

4. The antisense oligonucleotide according to any one of embodiments 1-4, wherein the contiguous nucleotide region of the oligonucleotide consists or comprises of a sequence selected from any one of SEQ ID NO 11, 12, 13, 14, 15, 16, 17 and 18.
5. The antisense oligonucleotide according to any one of embodiments 1-5 wherein the contiguous nucleotide region of the oligonucleotide comprises one or more 2' sugar modified nucleosides such as one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
6. The antisense oligonucleotide according to any one of embodiments 1-5, where the contiguous nucleotide region of the oligonucleotide comprises at least one modified internucleoside linkage, such as one or more phosphorothioate internucleoside linkages, or such as all the internucleoside linkages within the contiguous nucleotide region are phosphorothioate internucleoside linkages.
7. The antisense oligonucleotide according to any one of embodiments 1-6, wherein the oligonucleotide or contiguous nucleotide sequence thereof is or comprises a gapmer such as a gapmer of formula 5'-F-G-F'-3', where region F and F' independently comprise 1-7 sugar modified nucleosides and G is a region 6-16 nucleosides which is capable of recruiting RNaseH, wherein the nucleosides of regions F and F' which are adjacent to region G are sugar modified nucleosides.
8. The antisense oligonucleotide according to embodiment 7, wherein at least one of or both of region F and F' each comprise at least one LNA nucleoside.

9. The antisense oligonucleotide according to any one of embodiments 1-8, selected from the group selected from: Htra1 #1-38, wherein a capital letter represents beta-D-oxy LNA nucleoside unit, a lower case letter represents a DNA nucleoside unit, subscript s represents a phosphorothioate internucleoside linkage, wherein all LNA cytosines are 5-methyl cytosine, P represents a phosphorodithioate internucleoside linkage of formula IB, S represents a Sp stereodefined phosphorothioate internucleoside linkage, R represents a Rp stereodefined phosphorothioate internucleoside linkage, and X represents a stereorandom phosphorothioate linkage.
10. The antisense oligonucleotide according to any one of the previous embodiments in the form a salt, such as a sodium salt, a potassium salt or an ammonium salt (e.g. a pharmaceutically acceptable salt).
11. A conjugate comprising the oligonucleotide according to any one of embodiments 1-10, and at least one conjugate moiety covalently attached to said oligonucleotide, or salt thereof.
12. A pharmaceutical composition comprising the oligonucleotide of embodiment 1-10 or the conjugate of embodiment 11 and a pharmaceutically acceptable diluent, solvent, carrier, salt and/or adjuvant.
13. An in vivo or in vitro method for modulating HTRA1 expression in a target cell which is expressing HTRA1, said method comprising administering an oligonucleotide of any one of embodiments 1-10 or the conjugate according to embodiment 11 or the pharmaceutical composition of embodiment 12 in an effective amount to said cell.
14. A method for treating or preventing a disease comprising administering a therapeutically or prophylactically effective amount of an oligonucleotide of any one of embodiments 1-10 or the conjugate according to embodiment 11 or the pharmaceutical composition of embodiment 12 to a subject suffering from or susceptible to the disease.
15. The oligonucleotide of any one of embodiments 1-10 or the conjugate according to embodiment 11 or the pharmaceutical composition of embodiment 12 for use in medicine.
16. The oligonucleotide of any one of embodiments 1-10 or the conjugate according to embodiment 11 or the pharmaceutical composition of embodiment 12 for use in the treatment or prevention of a disease is selected from the group consisting of macular degeneration (such as wetAMD, dryAMD, geographic atrophy, intermediate dAMD, diabetic retinopathy), Parkinson's disease, Alzhiemer's disease, Duchenne muscular dystrophy, arthritis, such as osteoarthritis, and familial ischemic cerebral small-vessel disease.
17. Use of the oligonucleotide of embodiment 1-10 or the conjugate according to embodiment 11 or the pharmaceutical composition of embodiment 12, for the preparation of a medicament for treatment or prevention of a disease is selected from the group consisting of macular degeneration (such as wetAMD, dryAMD, geographic atrophy, intermediate dAMD, diabetic retinopathy), Parkinson's disease, Alzhiemer's disease, Duchenne muscular dystrophy, arthritis, such as osteoarthritis, and familial ischemic cerebral small-vessel disease.
18. The oligonucleotide, conjugate, salt or composition or use according to any one of the preceding embodiments, for use in the treatment of geographic atrophy.

FURTHER EMBODIMENTS OF THE INVENTION

The invention thus relates in particular to:

An oligonucleotide according to the invention wherein the oligonucleotide is an antisense oligonucleotide capable of modulating the expression of a target RNA in a cell expressing said target RNA;

An oligonucleotide according to the invention wherein the oligonucleotide is an antisense oligonucleotide capable of inhibiting the expression of a target RNA in a cell expressing said target RNA;

An oligonucleotide according to the invention wherein one of ($A^1$) and ($A^2$) is a LNA nucleoside and the other one is a DNA nucleoside, a RNA nucleoside or a sugar modified nucleoside;

An oligonucleotide according to the invention wherein one of ($A^1$) and ($A^2$) is a LNA nucleoside and the other one is a DNA nucleoside or a sugar modified nucleoside;

An oligonucleotide according to the invention wherein one of ($A^1$) and ($A^2$) is a LNA nucleoside and the other one is a DNA nucleoside;

An oligonucleotide according to the invention wherein one of ($A^1$) and ($A^2$) is a LNA nucleoside and the other one is a sugar modified nucleoside;

An oligonucleotide according to the invention wherein said sugar modified nucleoside is a 2'-sugar modified nucleoside;

An oligonucleotide according to the invention wherein said 2'-sugar modified nucleoside is 2'-alkoxy-RNA, 2'-alkoxyalkoxy-RNA, 2'-amino-DNA, 2'-fluoro-RNA, 2'-fluoro-ANA or a LNA nucleoside;

An oligonucleotide according to the invention wherein said 2'-sugar modified nucleoside is a LNA nucleoside;

An oligonucleotide according to the invention wherein the LNA nucleosides are independently selected from beta-D-oxy LNA, 6'-methyl-beta-D-oxy LNA and ENA; An oligonucleotide according to the invention wherein the LNA nucleosides are both beta-D-oxy LNA;

An oligonucleotide according to the invention wherein said 2'-sugar modified nucleoside is 2'-alkoxyalkoxy-RNA;

An oligonucleotide according to the invention wherein 2'-alkoxy-RNA is 2'-methoxy-RNA;

An oligonucleotide according to the invention wherein 2'-alkoxyalkoxy-RNA is 2'-methoxyethoxy-RNA;

An oligonucleotide according to the invention comprising between 1 and 15, in particular between 1 and 5, more particularly 1, 2, 3, 4 or 5 phosphorodithioate internucleoside linkages of formula (I) as defined above;

An oligonucleotide according to the invention comprising further internucleoside linkages independently selected from phosphodiester internucleoside linkage, phosphorothioate internucleoside linkage and phosphorodithioate internucleoside linkage of formula (I) as defined above;

An oligonucleotide according to the invention wherein the further internucleoside linkages are independently selected from phosphorothioate internucleoside linkage and phosphorodithioate internucleoside linkage of formula (I) as defined above.

An oligonucleotide according to the invention wherein the further internucleoside linkages are all phosphorothioate internucleoside linkages; An oligonucleotide according to the invention wherein the further internucleoside linkages are all phosphorodithioate internucleoside linkages of formula (I) as defined above;

An oligonucleotide according to the invention wherein the oligonucleotide is a gapmer, in particular a LNA gapmer, a mixed wing gapmer, an alternating flank gapmer, a splice switching oligomer, a mixmer or a totalmer;

An oligonucleotide according to the invention which is a gapmer and wherein the at least one phosphorodithioate internucleoside linkage of formula (I) is comprised in the gap region and/or in one or more flanking region of the gapmer;

An oligonucleotide according to the invention where the contiguous nucleotide sequence, such as the gapmer region F-G-F', is flanked by flanking region D' or D" or D' and D", comprising one or more DNA nucleosides connected to the rest of the oligonucleotide through phosphodiester internucleoside linkages;

An oligonucleotide according to the invention which is a gapmer wherein one or both, particularly one, of the flanking regions F and F', are further flanked by phosphodiester linked DNA nucleosides, in particular 1 to 5 phosphodiester linked DNA nucleosides (region D' and D");

An oligonucleotide according to the invention wherein the oligonucleotide is of 7 to 30 nucleotides in length.

When the oligonucleotide of the invention is a gapmer, it is advantageously of 12 to 26 nucleotides in length. 16 nucleotides is a particularly advantageous gapmer oligonucleotide length.

When the oligonucleotide is a full LNA oligonucleotide, it is advantageously of 7 to 10 nucleotides in length.

When the oligonucleotide is a mixmer oligonucleotide, it is advantageously of 8 to 30 nucleotides in length.

The invention relates in particular to:

An oligonucleotide according to the invention wherein one or more nucleoside is a nucleobase modified nucleoside;

An oligonucleotide according to the invention wherein the oligonucleotide is an antisense oligonucleotide, a siRNA, a microRNA mimic or a ribozyme;

A pharmaceutically acceptable salt of an oligonucleotide according to the invention, in particular a sodium or a potassium salt;

A conjugate comprising an oligonucleotide or a pharmaceutically acceptable salt according to the invention and at least one conjugate moiety covalently attached to said oligonucleotide or said pharmaceutically acceptable salt, optionally via a linker moiety;

A pharmaceutical composition comprising an oligonucleotide, pharmaceutically acceptable salt or conjugate according to the invention and a therapeutically inert carrier;

An oligonucleotide, pharmaceutically acceptable salt or conjugate according to the invention for use as a therapeutically active substance; and The use of an oligonucleotide, pharmaceutically acceptable salt or conjugate according to the invention as a medicament;

In some embodiments, the oligonucleotide of the invention has a higher activity in modulating its target nucleic acid, as compared to the corresponding fully phosphorothioate linked-oligonucleotide. In some embodiments the invention provides for oligonucleotides with enhanced activity, enhanced potency, enhanced specific activity or enhanced cellular uptake. In some embodiments the invention provides for oligonucleotides which have an altered duration of action in vitro or in vivo, such as a prolonged duration of action in vitro or in vivo. In some embodiments the higher activity in modulating the target nucleic acid is determined in vitro or in vivo in a cell which is expressing the target nucleic acid.

In some embodiments the oligonucleotide of the invention has altered pharmacological properties, such as reduced toxicity, for example reduced nephrotoxicity, reduced hepatotoxicity or reduced immune stimulation. Hepatotoxicity may be determined, for example in vivo, or by using the in vitro assays disclosed in WO 2017/067970, hereby incorporated by reference. Nephrotoxicity may be determined, for example in vitro, or by using the assays disclosed in PCT/EP2017/064770, hereby incorporated by reference. In some embodiments the oligonucleotide of the invention comprises a 5' CG 3' dinucleotide, such as a DNA 5' CG 3' dinucleotide, wherein the internucleoside linkage between C and G is a phosphorodithioate internucleoside linkage of formula (I) as defined above.

In some embodiments, the oligonucleotide of the invention has improved nuclease resistance such as improved biostability in blood serum. In some embodiments, the 3' terminal nucleoside of the oligonucleotide of the invention has an A or G base, such as a 3' terminal LNA-A or LNA-G nucleoside. Suitably, the internucleoside linkage between the two 3' most nucleosides of the oligonucleotide may be a phosphorodithioate internucleoside linkage according to formula (I) as defined above.

In some embodiments the oligonucleotide of the invention has enhanced bioavailability. In some embodiments the oligonucleotide of the invention has a greater blood exposure, such as a longer retention time in blood.

The non-bridging phosphorodithioate modification is introduced into oligonucleotides by means of solid phase synthesis using the phosphoramidite method. Syntheses are performed using controlled pore glass (CPG) equipped with a universal linker as the support. On such a solid support an oligonucleotide is typically built up in a 3' to 5' direction by means of sequential cycles consisting of coupling of 5'O-DMT protected nucleoside phosphoramidite building blocks followed by (thio)oxidation, capping and deprotection of the DMT group. Introduction of non-bridging phosphorodithioates is achieved using appropriate thiophosphoramidite building blocks followed by thiooxidation of the primary intermediate.

While the corresponding DNA thiophosphoramidites are commercially available, the respective LNA building blocks have not been described before. They can be prepared from the 5'-O-DMT-protected nucleoside 3'-alcohols e.g. by the reaction with mono-benzoyl protected ethanedithiol and tripyrrolidin-1-ylphosphane.

The oligonucleotide according to the invention can thus for example be manufactured according to Scheme 2, wherein $R^1$, $R^{2a}$, $R^{2b}$, $R^{4a}$, $R^{4b}$, $R^5$, $R^x$, $R^y$ and V are as defined below.

Scheme 2

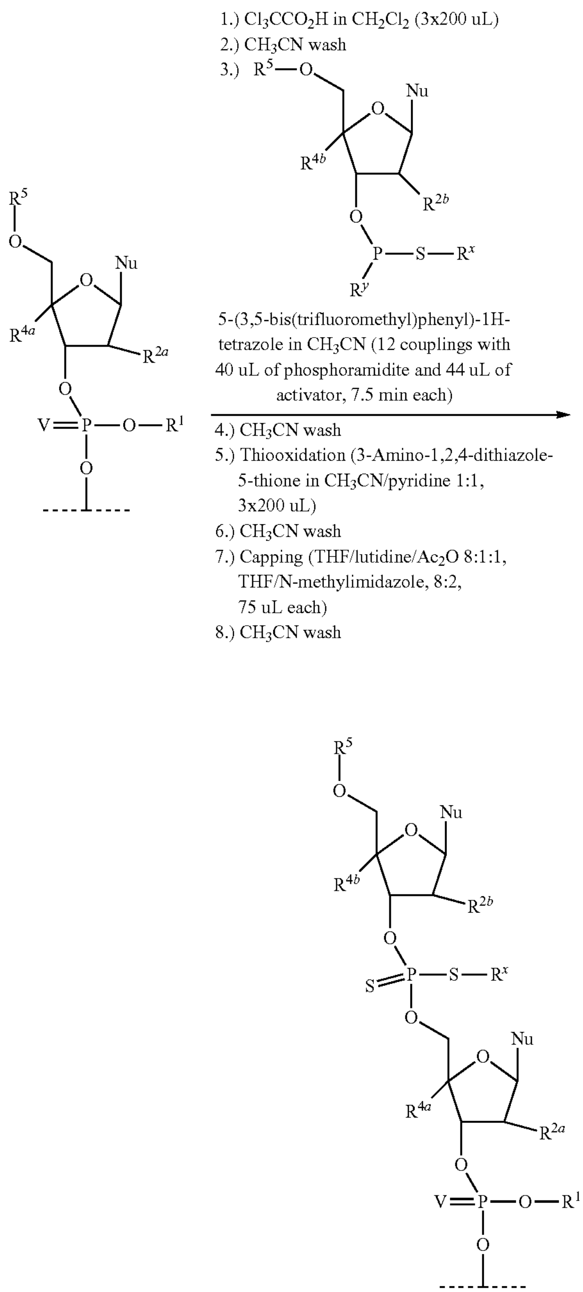

The invention thus also relates to a process for the manufacture of an oligonucleotide according to the invention comprising the following steps:

(a) Coupling a thiophosphoramidite nucleoside to the terminal 5' oxygen atom of a nucleotide or oligonucleotide to produce a thiophosphite triester intermediate;

(b) Thiooxidizing the thiophosphite triester intermediate obtained in step (a); and (c) Optionally further elongating the oligonucleotide.

The invention relates in particular to a process for the manufacture of an oligonucleotide according to the invention comprising the following steps:

(a1) Coupling a compound of formula (A)

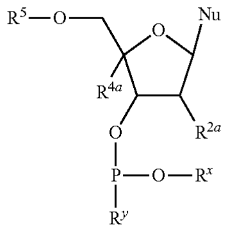

(A)

to the 5' oxygen atom of a nucleotide or oligonucleotide of formula (B)

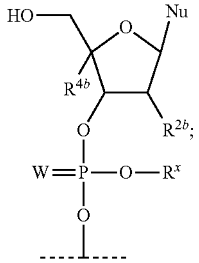

(B)

(b1) Thiooxidizing the thiophosphite triester intermediate obtained in step (a1); and (c1) Optionally further elongating the oligonucleotide; wherein $R^{2a}$ and $R^{4a}$ together form —X—Y— as defined above; or $R^{4a}$ is hydrogen and $R^{2a}$ is selected from alkoxy, in particular methoxy, halogen, in particular fluoro, alkoxyalkoxy, in particular methoxyethoxy, alkenyloxy, in particular allyloxy and aminoalkoxy, in particular aminoethyloxy;

$R^{2b}$ and $R^{4b}$ together form —X—Y— as defined above; or $R^{2b}$ and $R^{4b}$ are both hydrogen at the same time; or $R^{4b}$ is hydrogen and $R^{2b}$ is selected from alkoxy, in particular methoxy, halogen, in particular fluoro, alkoxyalkoxy, in particular methoxyethoxy, alkenyloxy, in particular allyloxy and aminoalkoxy, in particular aminoethyloxy;

V is oxygen or sulfur; and wherein $R^5$, $R^x$, $R^y$ and Nu are as defined below.

The invention relates in particular to a process for the manufacture of an oligonucleotide according to the invention comprising the following steps:

(a2) Coupling a compound of formula (II)

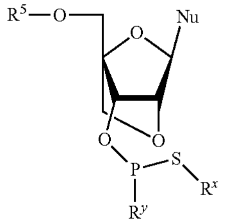

(A1)

to the 5' oxygen atom of a nucleotide or oligonucleotide of formula (IV)

(B1)

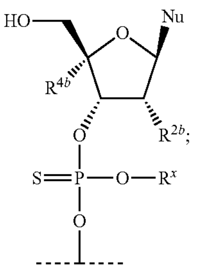

(b2) Thiooxidizing the thiophosphite triester intermediate obtained in step (a2); and (c2) Optionally further elongating the oligonucleotide; wherein $R^{2b}$ and $R^{4b}$ together form —X—Y— as defined above; or $R^{2b}$ and $R^{4b}$ are both hydrogen at the same time; or $R^{4b}$ is hydrogen and $R^{2b}$ is selected from alkoxy, in particular methoxy, halogen, in particular fluoro, alkoxyalkoxy, in particular methoxyethoxy, alkenyloxy, in particular allyloxy and aminoalkoxy, in particular aminoethyloxy; and wherein $R^5$, $R^x$, $R^y$ and Nu are as defined below.

The invention also relates to an oligonucleotide manufactured according to a process of the invention.

The invention further relates to:

A gapmer oligonucleotide comprising at least one phosphorodithioate internucleoside linkage of formula (I)

(I)

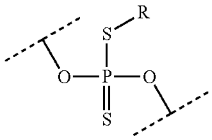

wherein R is hydrogen or a phosphate protecting group;

A gapmer oligonucleotide as defined above wherein the oligonucleotide is an antisense oligonucleotide capable of modulating the expression of a target RNA in a cell expressing said target RNA;

A gapmer oligonucleotide as defined above wherein the oligonucleotide is an antisense oligonucleotide capable of inhibiting the expression of a target RNA in a cell expressing said target RNA;

A gapmer oligonucleotide as defined above capable of recruiting RNAseH, such as human RNaseH1;

A gapmer oligonucleotide according to the invention wherein one of the two oxygen atoms of said at least one internucleoside linkage of formula (I) is linked to the 3'carbon atom of an adjacent nucleoside ($A^1$) and the other one is linked to the 5'carbon atom of another nucleoside ($A^2$), wherein at least one of the two nucleosides ($A^1$) and ($A^2$) is a 2'-sugar modified nucleoside;

A gapmer oligonucleotide according to the invention wherein one of ($A^1$) and ($A^2$) is a 2'-sugar modified nucleoside and the other one is a DNA nucleoside;

A gapmer oligonucleotide according to the invention wherein ($A^1$) and ($A^2$) are both a 2'-modified nucleoside at the same time;

A gapmer oligonucleotide according to the invention wherein ($A^1$) and ($A^2$) are both a DNA nucleoside at the same time;

A gapmer oligonucleotide according to the invention wherein the gapmer oligonucleotide comprises a contiguous nucleotide sequence of formula 5'-F-G-F'-3', wherein G is a region of 5 to 18 nucleosides which is capable of recruiting RnaseH, and said region G is flanked 5' and 3' by flanking regions F and F' respectively, wherein regions F and F' independently comprise or consist of 1 to 7 2'-sugar modified nucleotides, wherein the nucleoside of region F which is adjacent to region G is a 2'-sugar modified nucleoside and wherein the nucleoside of region F' which is adjacent to region G is a 2'-sugar modified nucleoside;

A gapmer oligonucleotide according to the invention wherein the 2'-sugar modified nucleosides are independently selected from 2'-alkoxy-RNA, 2'-alkoxyalkoxy-RNA, 2'-amino-DNA, 2'-fluoro-RNA, 2'-fluoro-ANA and LNA nucleosides;

A gapmer oligonucleotide according to the invention wherein 2'-alkoxyalkoxy-RNA is a 2'-methoxyethoxy-RNA (2'-O-MOE);

A gapmer oligonucleotide according to the invention wherein region F and region F' comprise or consist of 2'-methoxyethoxy-RNA nucleotides;

A gapmer oligonucleotide according to the invention, wherein both regions F and F' consist of 2'-methoxyethoxy-RNA nucleotides, such as a gapmer comprising the F-G-F' of formula $[MOE]_{3-8}[DNA]_{8-16}[MOE]_{3-8}$, for example $[MOE]_5[DNA]_{10}[MOE]_5$—i.e. where region F and F' consist of five 2'-methoxyethoxy-RNA nucleotides each, and region G consists of 10 DNA nucleotides;

A gapmer oligonucleotide according to the invention wherein at least one or all of the 2'-sugar modified nucleosides in region F or region F', or in both regions F and F', are LNA nucleosides;

A gapmer oligonucleotide according to the invention wherein region F or region F', or both regions F and F', comprise at least one LNA nucleoside and at least one DNA nucleoside;

A gapmer oligonucleotide according to the invention wherein region F or region F', or both region F and F' comprise at least one LNA nucleoside and at least one non-LNA 2'-sugar modified nucleoside, such as at least one 2'-methoxyethoxy-RNA nucleoside;

A gapmer oligonucleotide according to the invention wherein the gap region comprises 5 to 16, in particular 8 to 16, more particularly 8, 9, 10, 11, 12, 13 or 14 contiguous DNA nucleosides;

A gapmer oligonucleotide according to the invention wherein region F and region F' are independently 1, 2, 3, 4, 5, 6, 7 or 8 nucleosides in length;

A gapmer oligonucleotide according to the invention wherein region F and region F' each independently comprise 1, 2, 3 or 4 LNA nucleosides;

A gapmer oligonucleotide according to the invention wherein the LNA nucleosides are independently selected from beta-D-oxy LNA, 6'-methyl-beta-D-oxy LNA and ENA;

A gapmer oligonucleotide according to the invention wherein the LNA nucleosides are beta-D-oxy LNA;

A gapmer oligonucleotide according to the invention wherein the oligonucleotide, or contiguous nucleotide sequence thereof (F-G-F'), is of 10 to 30 nucleotides in length, in particular 12 to 22, more particularly of 14 to 20 oligonucleotides in length; A gapmer oligonucleotide according to the invention wherein the gapmer oligonucleotide comprises a contiguous nucleotide sequence of formula 5'-D'-F-G-F'-D''-3', wherein F, G and F' are as defined in any one of claims 4 to 17 and wherein region D' and D'' each independently consist of 0 to 5 nucleotides, in particular 2, 3 or 4 nucleotides, in particular DNA nucleotides such as phosphodiester linked DNA nucleosides;

A gapmer oligonucleotide according to the invention wherein the gapmer oligonucleotide is capable of recruiting human RNaseH1;

A gapmer oligonucleotide according to the invention wherein said at least one phosphorodithioate internucleoside linkage of formula (I) as defined above is positioned between adjacent nucleosides in region F or region F', between region F and region G or between region G and region F';

A gapmer oligonucleotide according to the invention which further comprises phosphorothioate internucleoside linkages;

A gapmer oligonucleotide according to the invention wherein the internucleoside linkages between the nucleosides of region G are independently selected from phosphorothioate internucleoside linkages and phosphorodithioate internucleoside linkages of formula (I) as defined above;

A gapmer oligonucleotide according to the invention wherein the internucleoside linkages between the nucleosides of region G comprise 0, 1, 2 or 3 phosphorodithioate internucleoside linkages of formula (I) as defined above;

A gapmer oligonucleotide according to the invention wherein the remaining internucleoside linkages are independently selected from the group consisting of phosphorothioate, phosphodiester and phosphorodithioate internucleoside linkages of formula (I) as defined above;

A gapmer oligonucleotide according to the invention wherein the internucleoside linkages between the nucleosides of region F and the internucleoside linkages between the nucleosides of region F' are independently selected from phosphorothioate and phosphorodithioate internucleoside linkages of formula (I) as defined above;

A gapmer oligonucleotide according to the invention wherein each flanking region F and F' independently comprise 1, 2, 3, 4, 5, 6 or 7 phosphorodithioate internucleoside linkages of formula (I) as defined above;

A gapmer oligonucleotide according to the invention wherein the flanking regions F and F' together or individually comprise 1, 2, 3, 4, 5 or 6 phosphorodithioate internucleoside linkages of formula (I) as defined above, or all the internucleoside linkages in region F and/or region F' are phosphordithioate internucleoside linkages of formula (I) as defined above;

A gapmer oligonucleotide according to the invention wherein the flanking regions F and F' together comprise 1, 2, 3 or 4 phosphorodithioate internucleoside linkages of formula (I) as defined above;

A gapmer oligonucleotide according to the invention wherein flanking regions F and F' each comprise 2 phosphorodithioate internucleoside linkages of formula (I) as defined above;

A gapmer oligonucleotide according to the invention wherein all the internucleoside linkages of flanking regions F and/or F' are phosphordithioate internucleoside linkages of formula (I) as defined above;

A gapmer oligonucleotide according to the invention wherein the gapmer oligonucleotide comprises at least one stereodefined internucleoside linkage, such as at least one stereodefined phosphorothioate internucleoside linkage;

A gapmer oligonucleotide according to the invention wherein the gap region comprises 1, 2, 3, 4 or 5 stereodefined phosphorothioate internucleoside linkages;

A gapmer oligonucleotide according to the invention wherein all the internucleoside linkages between the nucleosides of the gap region are stereodefined phosphorothioate internucleoside linkages;

A gapmer oligonucleotide according to the invention wherein the at least one phosphorodithioate internucleoside linkage of formula (I) as defined above is positioned between the nucleosides of region F, or between the nucleosides of region F', or between region F and region G, or between region G and region F', and the remaining internucleoside linkages within region F and F', between region F and region G and between region G and region F', are independently selected from stereodefined phosphorothioate internucleoside linkages, stereorandom internucleoside linkages, phosphorodithioate internucleoside linkage of formula (I) and phosphodiester internucleoside linkages;

A gapmer oligonucleotide according to the invention wherein the at least one phosphorodithioate internucleoside linkage of formula (I) as defined above is positioned between at least two adjacent nucleosides of region F, or between the two adjacent nucleosides of region F', or between region F and region G, or between region G and region F', and the remaining internucleoside linkages between the nucleotides of region F and F' are independently selected from phosphorothioate internucleoside linkages, phosphorodithioate internucleoside linkage of formula (I) and phosphodiester internucleoside linkages. The phosphorothioate internucleoside linkages of region F and F' may be either stereorandom or stereodefined, or may be independently selected from stereorandom and stereodefined;

A gapmer oligonucleotide according to the invention wherein the at least one phosphorodithioate internucleoside linkage of formula (I) as defined above is positioned between at least two adjacent nucleosides of region F, or between at least two adjacent nucleosides of region F', or between region F and region G, or between region G and region F', and the remaining internucleoside linkages between the nucleotides of region F and F' are independently selected from phosphorothioate internucleoside linkages, and phosphorodithioate internucleoside linkages of formula (I). The phosphorothioate internucleoside linkages of region F and F' may be either stereorandom or stereodefined, or may be independently selected from stereorandom and stereodefined;

A gapmer oligonucleotide according to the invention wherein the at least one phosphorodithioate internucleoside linkage of formula (I) as defined above is positioned between at least two adjacent nucleosides of region F, or between at least two adjacent nucleosides of region F', or between region F and region G, or between region G and region F', and the remaining internucleoside linkages between the nucleotides of region F and F', between region F and region G and between region G and region F', are independently selected from phosphorothioate internucleoside linkages and phosphorodithioate internucleoside linkage of formula (I); The phosphorothioate internucleoside linkages of region F and F' may be either stereorandom or stereodefined, or may be independently selected from stereorandom and stereodefined;

A gapmer oligonucleotide according to the invention wherein the at least one phosphorodithioate internucleoside linkage of formula (I) as defined above is positioned between at least two adjacent nucleosides of region F, or between at least two adjacent nucleosides of region F', or between region F and region G, or between region G and region F', and the remaining internucleoside linkages between the nucleotides of region F and F' and between region F and region G and between region G and region F', are independently selected from stereodefined phosphorothioate internucleoside linkages and phosphorodithioate internucleoside linkage of formula (I);

A gapmer oligonucleotide according to the invention wherein the at least one phosphorodithioate internucleoside linkage of formula (I) as defined above is positioned between at least two adjacent nucleosides of region F, or between at least two adjacent nucleosides of region F', or between region F and region G, or between region G and region F', and the remaining internucleoside linkages within region F and F', between region F and region G and between region G and region F', are phosphorothioate internucleoside linkages, which may be all stereorandom phosphorothioate internucleoside linkages, all stereodefined phosphorothioate internucleoside linkages, or may be independently selected from stereorandom and stereodefined phosphorothioate internucleoside linkages;

A gapmer oligonucleotide according to the invention wherein the remaining internucleoside linkages within region F, within region F' or within both region F and region F' are all phosphorodithioate internucleoside linkages of formula (I) as defined above;

A gapmer oligonucleotide according to the invention wherein the internucleoside linkages between the nucleosides of region G comprise 0, 1, 2 or 3 phosphorodithioate internucleoside linkages of formula (I) as defined above and the remaining internucleoside linkages within region G are independently selected from stereodefined phosphorothioate internucleoside linkages and stereorandom phosphorothioate internucleoside linkages;

A gapmer oligonucleotide according to the invention wherein the internucleoside linkages between the nucleosides of region G comprise 0, 1, 2 or 3 phosphorodithioate internucleoside linkages of formula (I) as defined above and at least one of the remaining internucleoside linkages within region G, or all of the remaining internucleoside linkages within region G are stereodefined phosphorothioate internucleoside linkages;

A gapmer oligonucleotide according to the invention wherein the internucleoside linkages between the nucleosides of region G comprise 0, 1, 2 or 3 phosphorodithioate internucleoside linkages of formula (I) as defined above and the remaining internucleoside linkages within region G are phosphorothioate internucleoside linkages, such as stereorandom phosphorothioate internucleoside linkages;

A gapmer oligonucleotide according to the invention wherein at least one of region F or F' comprise the at least one phosphorodithioate internucleoside linkages of formula (I) as defined above and all the internucleoside linkages within region G are phosphorothioate internucleoside linkages, such as stereorandom phosphorothioate internucleoside linkages;

A gapmer oligonucleotide according to the invention wherein at least one of region F or F' comprise the at least one phosphorodithioate internucleoside linkages of formula (I) as defined above and all the internucleoside linkages within region G are phosphorothioate internucleoside linkages, wherein at least one of the phosphorothioate internucleoside linkages within region G is a stereodefined phosphorothioate internucleoside linkage;

A gapmer oligonucleotide according to the invention wherein at least one of region F or F' comprise the at least one phosphorodithioate internucleoside linkages of formula (I) as defined above and all the internucleoside linkages within region G are stereodefined phosphorothioate internucleoside linkages;

A gapmer oligonucleotide according to the invention wherein the internucleoside linkage between region F and G, or the internucleoside linkage between region G and F', or both the internucleoside linkages between region F and G and between region G and F', are phosphorodithioate internucleoside linkages of formula (I) as defined above, and wherein, in the event that only one of the internucleoside linkages between region F and G and between region G and F' is a phosphorodithioate internucleoside linkages of formula (I) as defined above, the other internucleoside linkage between region F and G or between region G and F' is a phosphorothioate internucleoside linkage;

A gapmer oligonucleotide according to the invention wherein at least one of region F or F' comprise the at least one phosphorodithioate internucleoside linkage of formula (I) as defined above, wherein the internucleoside linkage between region F and G, or the internucleoside linkage between region G and F', or both the internucleoside linkages between region F and G and between region G and F', are phosphorodithioate internucleoside linkages of formula (I) as defined above and wherein in the event that only one of the internucleoside linkages between region F and G and between region G and F' is a phosphorodithioate internucleoside linkages of formula (I) as defined above, the other internucleoside linkage between region F and G or between region G and F' is a phosphorothioate internucleoside linkage;

A gapmer oligonucleotide according to the invention wherein the internucleoside linkages between the nucleosides of region G comprise 0, 1, 2 or 3 phosphorodithioate internucleoside linkages of formula (I) as defined above and the remaining internucleoside linkages within region G are phosphorothioate internucleoside linkages, wherein the internucleoside linkage between region F and G, or the internucleoside linkage between region G and F', or both the internucleoside linkages between region F and G and between region G and F', are phosphorodithioate internucleoside linkages of formula (I) as defined above and wherein in the event that only one of the internucleoside linkages between region F and G and between region G and F' is a phosphorodithioate internucleoside linkages of formula (I) as defined above, the other internucleoside linkage between region F and G or between region G and F' is a phosphorothioate internucleoside linkage;

A gapmer oligonucleotide according to the invention wherein at least one of region F or F' comprise the at least one phosphorodithioate internucleoside linkages of formula (I) as defined above, wherein the internucleoside linkages between the nucleosides of region G comprise 0, 1, 2 or 3 phosphorodithioate internucleoside linkages of formula (I) as defined above and the remaining internucleoside linkages within region G are phosphorothioate internucleoside linkages, wherein the internucleoside linkage between region F and G, or the internucleoside linkage between region G and F', or both the internucleoside linkages between region F and G and between region G and F', are phosphorodithioate internucleoside linkages of formula (I) as defined above, and wherein, in the event that only one of the internucleoside linkages between region F and G and between region G and F' is a phosphorodithioate internucleoside linkage of formula (I) as defined above, the other internucleoside linkage between region F and G or between region G and F' is a phosphorothioate internucleoside linkage;

A gapmer oligonucleotide according to the invention wherein region F or region F' comprise at least one phosphorodithioate internucleoside linkages of formula (I) as defined above, or wherein the internucleoside linkage between region F and region G, or between region G and region F' comprise at least one phosphorodithioate internucleoside linkage of formula (I) as defined above, region G comprises 1, 2 or 3 phosphorodithioate internucleoside linkages of formula (I) as defined above, and the remaining internucleoside linkages within region G are phosphorothioate internucleoside linkages;

A gapmer oligonucleotide according to the invention wherein region F or region F' comprise at least one phosphorodithioate internucleoside linkages of formula (I) as defined above, or wherein the internucleoside linkage between region F and region G, or between region G and region F' comprise at least one phosphorodithioate internucleoside linkages of formula (I) as defined above, all of the internucleoside linkage within region G are phosphorothioate internucleoside linkages and wherein at least one of the phosphorothioate internucleoside linkages within region G is a stereodefined phosphorothioate internucleoside linkage;

A gapmer oligonucleotide according to the invention wherein region F or region F' comprise at least one phosphorodithioate internucleoside linkages of formula (I) as defined above, or wherein the internucleoside linkage between region F and region G, or between region G and region F' comprise at least one phosphorodithioate internucleoside linkages of formula (I) as defined above, all of the internucleoside linkages within region G are phosphorothioate internucleoside linkages and wherein all of the phosphorothioate internucleoside linkages within region G are stereodefined phosphorothioate internucleoside linkages;

A gapmer oligonucleotide according to the invention wherein other than the at least one phosphorodithioate internucleoside linkages of formula (I) as defined above, all the remaining internucleoside linkages within the gapmer region F-G-F' are phosphorothioate internucleoside linkages; A gapmer oligonucleotide according to the invention wherein at least one of region F or F' comprise the at least one phosphorodithioate internucleoside linkages of formula (I) as defined above and all the internucleoside linkages within region G are stereodefined phosphorothioate internucleoside linkages;

A gapmer oligonucleotide according to the invention wherein other than the at least one phosphorodithioate internucleoside linkages of formula (I) all the remaining internucleoside linkages within the gapmer region F-G-F' are stereodefined phosphorothioate internucleoside linkages;

A gapmer oligonucleotide according to the invention which is LNA gapmer, a mixed wing gapmer, an alternating flank gapmer or a gap-breaker gapmer.

A pharmaceutically acceptable salt of a gapmer oligonucleotide according to the invention, in particular a sodium or a potassium salt;

A conjugate comprising a gapmer oligonucleotide or a pharmaceutically acceptable salt according to the invention and at least one conjugate moiety covalently attached to said oligonucleotide or said pharmaceutically acceptable salt, optionally via a linker moiety, in particular via a a biocleavable linker, particularly via 2 to 4 phosphodiester linked DNA nucleosides (e.g. region D' or D");

A pharmaceutical composition comprising a gapmer oligonucleotide, pharmaceutically acceptable salt or conjugate according to the invention and a therapeutically inert carrier;

A gapmer oligonucleotide, pharmaceutically acceptable salt or conjugate according to the invention for use as a therapeutically active substance;

The use of a gapmer oligonucleotide, pharmaceutically acceptable salt or conjugate as a medicament;

A method of modulating the expression of a target RNA in a cell comprising administering an oligonucleotide or gapmer oligonucleotide according to the invention to a cell expressing said target RNA so as to modulate the expression of said target RNA;

A method of inhibiting the expression of target RNA in a cell comprising administering an oligonucleotide or gapmer oligonucleotide according to the invention to a cell expressing said target RNA so as to inhibit the expression of said target RNA; and An in vitro method of modulating or inhibiting a target RNA in a cell comprising administering an oligonucleotide or gapmer oligonucleotide according to the invention to a cell expressing said target RNA, so as to modulate or inhibit said target RNA in said cell.

The target RNA can, for example be a mammalian mRNA, such as a pre-mRNA or mature mRNA, a human mRNA, a viral RNA or a non-coding RNA, such as a microRNA or a long non coding RNA.

In some embodiments, modulation is splice modulation of a pre-mRNA resulting in an altered splicing pattern of the target pre-mRNA.

In some embodiments, the modulation is inhibition which may occur via target degradation (e.g. via recruitment of RNaseH, such as RNaseH1 or RISC), or the inhibition may occur via an occupancy mediate mechanism which inhibits the normal biological function of the target RNA (e.g. mixmer or totalmer inhibition of microRNAs or long non coding RNAs).

The human mRNA can be a mature RNA or a pre-mRNA.

The invention also further relates to a compound of formula (II)

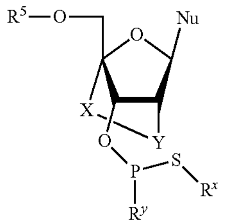

(II)

wherein

X is oxygen, sulfur, $—CR^aR^b—$, $—C(R^a)═C(R^b)—$, $—C(═CR^aR^b)—$, $—C(R^a)═N—$, $—Si(R^a)_2—$, $—SO_2—$, $—NR^a—$; $—O—NR^a—$, $—NR^a—O—$, —C(=J)-, Se, $—O—NR^a—$, $—NR^a—CR^aR^b—$, $—N(R^a)—O—$ or $—O—CR^aR^b—$;

Y is oxygen, sulfur, $—(CR^aR^b)_n—$, $—CR^aR^b—O—CR^aR^b—$, $—C(R^a)═C(R^b)—$, $—C(R^a)═N—$, $—Si(R^a)_2—$, $—SO_2—$, $—NR^a—$, —C(=J)-, Se, $—O—NR^a—$, $—NR^a—CR^aR^b—$, $—N(R^a)—O—$ or $—O—CR^aR^b—$;

with the proviso that —X—Y— is not —O—O—, $Si(R^a)_2—Si(R^a)_2—$, $—SO_2—SO_2—$, $—C(R^a)═C(R^b)—C(R^a)═C(R^b)$, $—C(R^a)═N—C(R^a)═N—$, $—C(R^a)═N—C(R^a)═C(R^b)$, $—C(R^a)═C(R^b)—C(R^a)═N—$ or $—Se—Se—$;

J is oxygen, sulfur, $═CH_2$ or $═N(R^a)$;

$R^a$ and $R^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, $—OC(═X^a)R^c$, $—OC(═X^a)NR^cR^d$ and $—NR^eC(═X^a)NR^cR^d$;

or two geminal $R^a$ and $R^b$ together form optionally substituted methylene;

or two geminal $R^a$ and $R^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocylyl, aryl and heteroaryl;

$X^a$ is oxygen, sulfur or $—NR^c$;

$R^c$, $R^d$ and $R^e$ are independently selected from hydrogen and alkyl;

n is 1, 2 or 3.

$R^5$ is a hydroxyl protecting group;

$R^x$ is phenyl, nitrophenyl, phenylalkyl, halophenylalkyl, cyanoalkyl, phenylcarbonylsulfanylalkyl, halophenylcarbonylsulfanylalkyl alkylcarbonylsulfanylalkyl or alkylcarbonylcarbonylsulfanylalkyl;

$R^y$ is dialkylamino or pyrrolidinyl; and

Nu is a nucleobase or a protected nucleobase.

The invention further relates to:

A compound of formula (II) wherein —X—Y— is $—CH_2—O—$, $—CH(CH_3)—O—$ or $—CH_2CH_2—O—$;

The invention further provides a compound of formula (IIb)

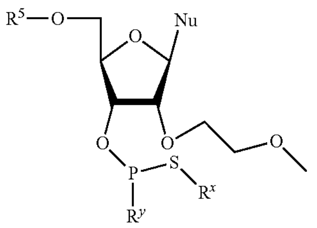

(IIb)

wherein $R^5$ is a hydroxyl protecting group, $R^x$ is phenyl, nitrophenyl, phenylalkyl, halophenylalkyl, cyanoalkyl, phenylcarbonylsulfanylalkyl, halophenylcarbonylsulfanylalkyl alkylcarbonylsulfanylalkyl or alkylcarbonylcarbonylsulfanylalkyl;

$R^y$ is dialkylamino or pyrrolidinyl; and

Nu is a nucleobase or a protected nucleobase;

A compound of formula (II) which is of formula (III) or (IV)

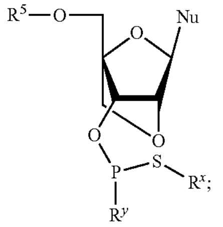

(III)

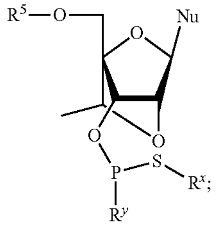

(IV)

wherein $R^5$, $R^x$, $R^y$ and Nu are as above;

A compound of formula (II), (IIb), (III) or (IV) wherein R is phenyl, nitrophenyl, phenylmethyl, dichlorophenylmethyl, cyanoethyl, methylcarbonylsulfanylethyl, ethylcarbonylsulfanylethyl, isopropylcarbonylsulfanylethyl, tert.-butylcarbonylsulfanylethyl, methylcarbonylcarbonylsulfanylethyl or difluorophenylcarbonylsulfanylethyl;

A compound of formula (II), (IIb), (III) or (IV) wherein R is phenyl, 4-nitrophenyl, 2,4-dichlorophenylmethyl, cyanoethyl, methylcarbonylsulfanylethyl, ethylcarbonylsulfanylethyl, isopropylcarbonylsulfanyethyl, tert.-butylcarbonylsulfanylethyl, methylcarbonylcarbonylsulfanylethyl or 2,4-difluorophenylcarbonylsulfanylethyl;

A compound of formula (II), (IIb), (III) or (IV) wherein $R^x$ is phenylcarbonylsulfanylalkyl;

A compound of formula (II), (IIb), (III) or (IV) wherein $R^x$ is phenylcarbonylsulfanylethyl;

A compound of formula (II), (IIb), (III) or (IV) wherein $R^y$ is diisopropylamino or pyrrolidinyl;

A compound of formula (II), (IIb), (III) or (IV) wherein $R^y$ is pyrrolidinyl;

A compound of formula (II) which is of formula (V)

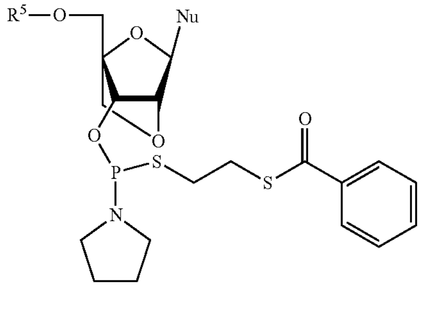

(V)

wherein $R^5$ and Nu are as defined above;

A compound of formula (IIb) which is of formula (Vb)

(Vb)

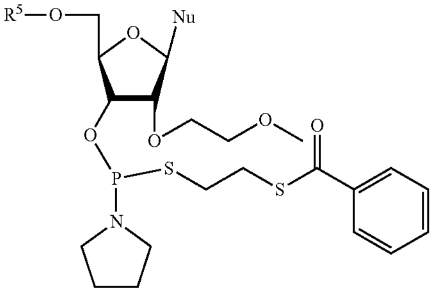

wherein $R^5$ and Nu are as defined above;

A compound of formula (II), (IIb), (III), (IV) or (V) or (Vb) wherein Nu is thymine, protected thymine, adenosine, protected adenosine, cytosine, protected cytosine, 5-methylcytosine, protected 5-methylcytosine, guanine, protected guanine, uracyl or protected uracyl;

A compound of formula (IIb) wherein Nu is thymine, protected thymine, adenosine, protected adenosine, cytosine, protected cytosine, 5-methylcytosine, protected 5-methylcytosine, guanine, protected guanine, uracyl or protected uracyl;

A compound of formula (Vb) wherein Nu is thymine, protected thymine, adenosine, protected adenosine, cytosine, protected cytosine, 5-methylcytosine, protected 5-methylcytosine, guanine, protected guanine, uracyl or protected uracyl;

A compound of formula (II) selected from

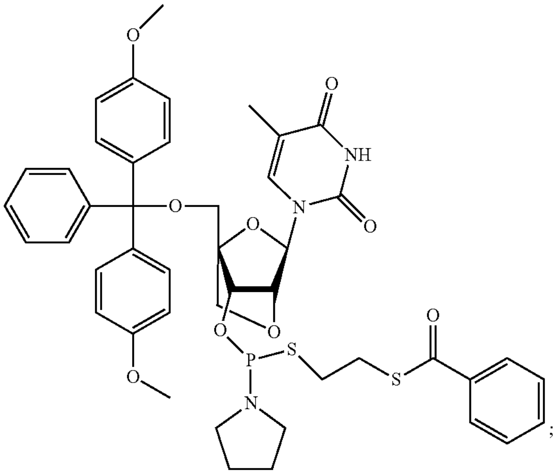

;

-continued

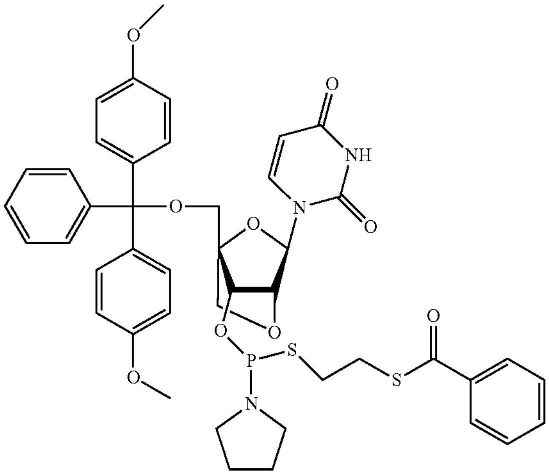

;

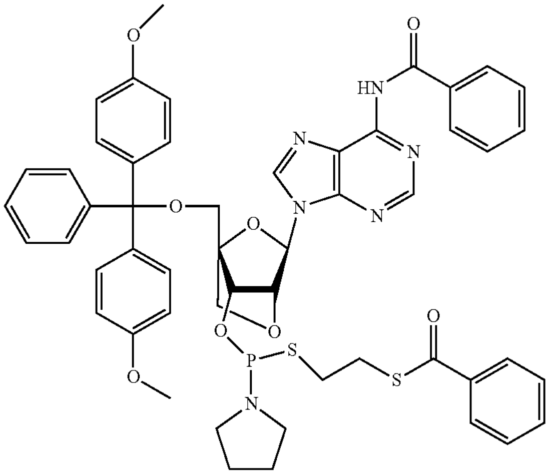

;

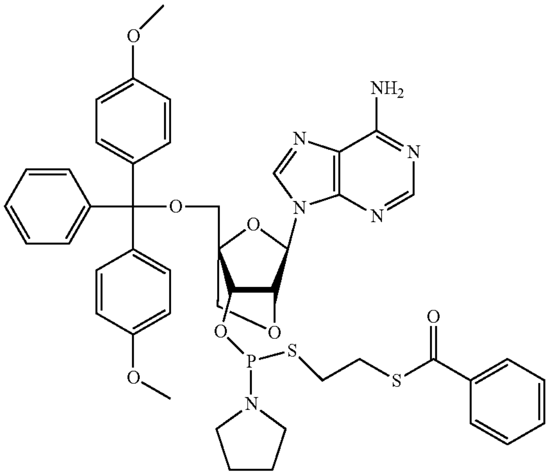

;

-continued
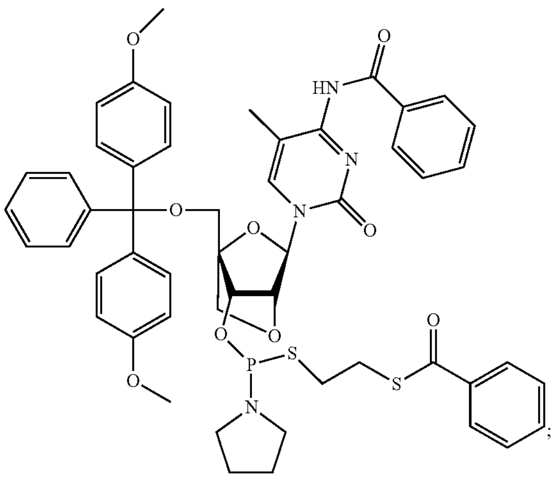
;
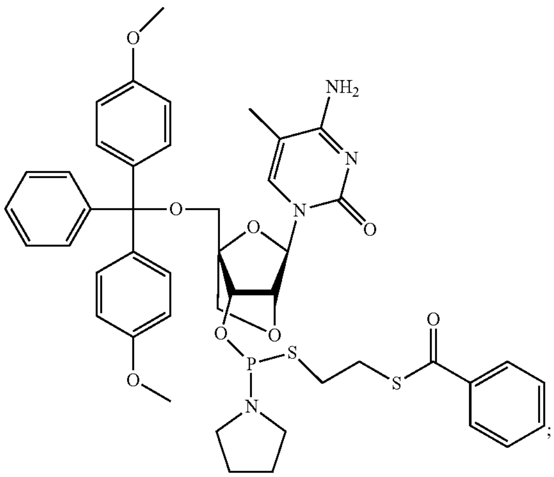
;
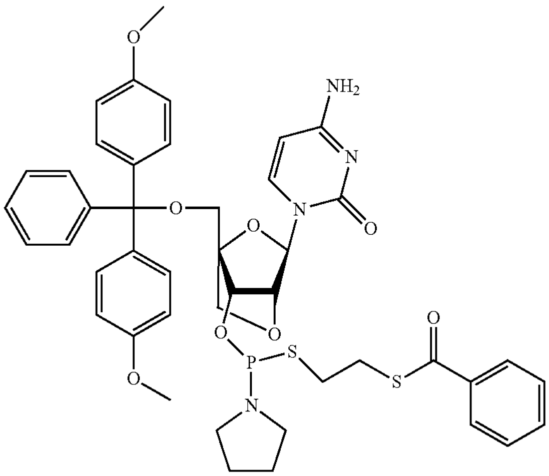
;
-continued
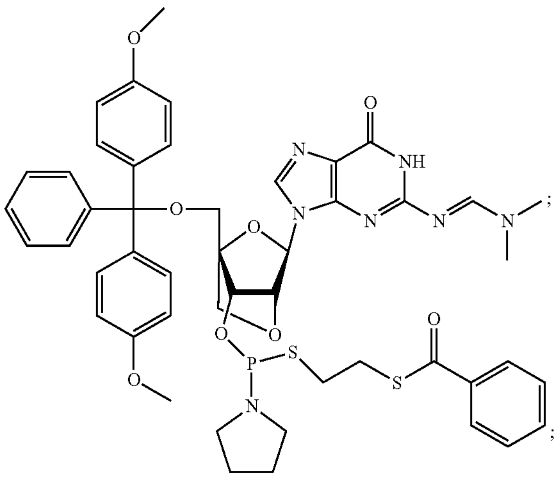
;
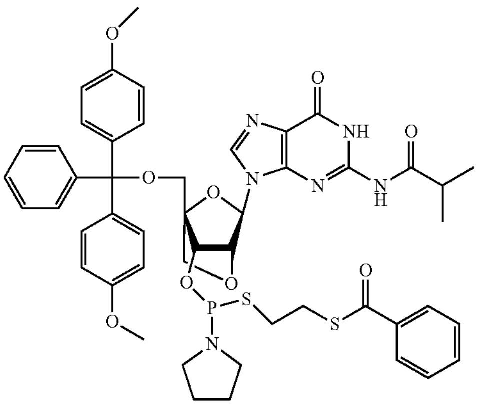
; and
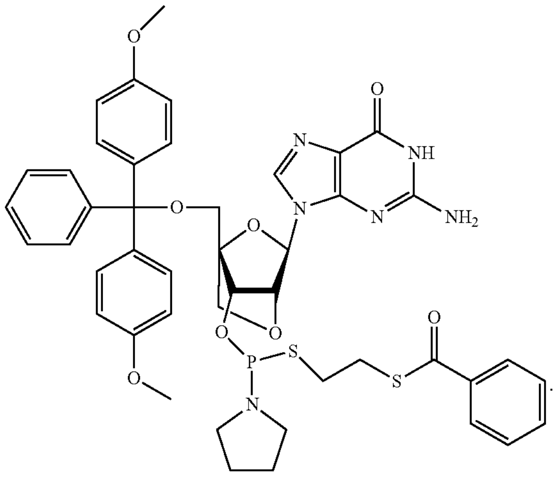
.

A compound of formula (IIb) selected from
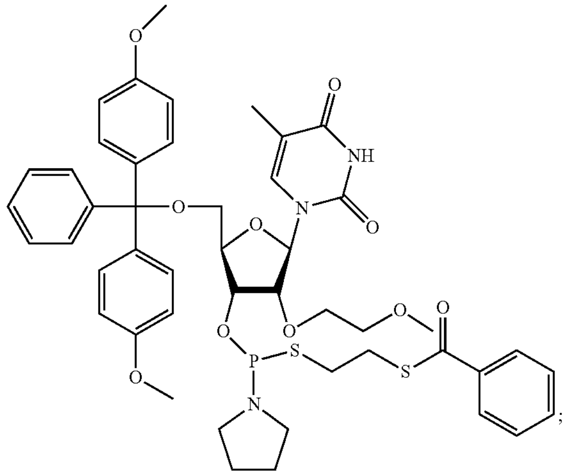
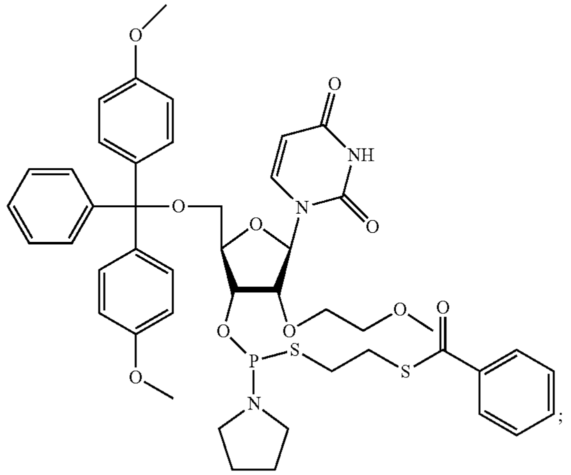
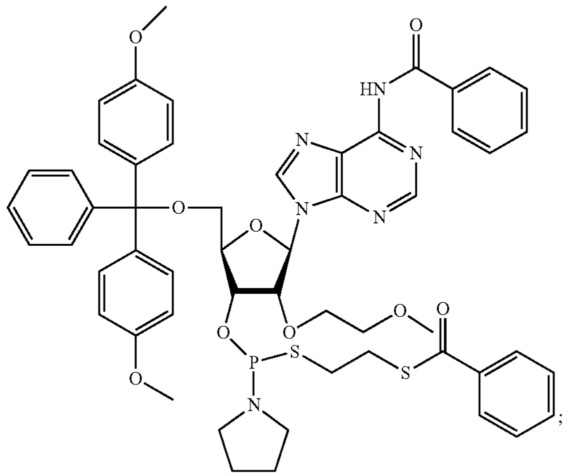
-continued
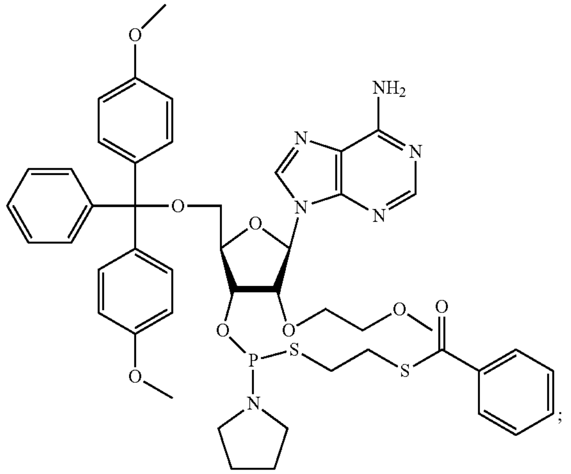
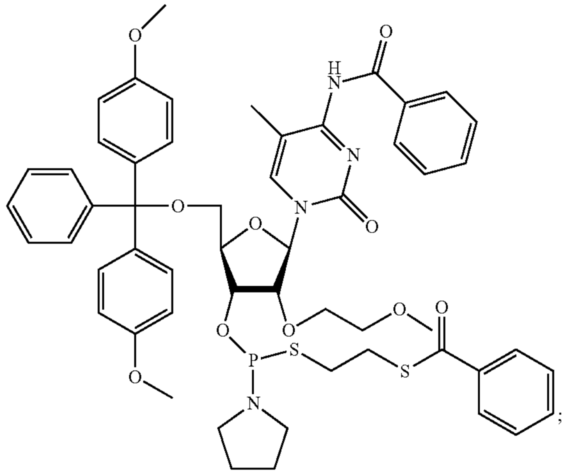
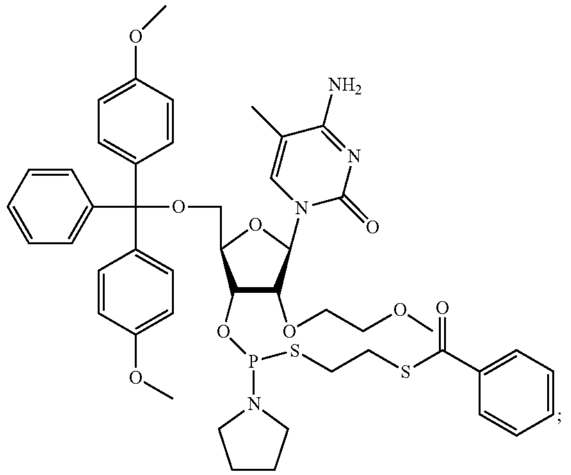

-continued
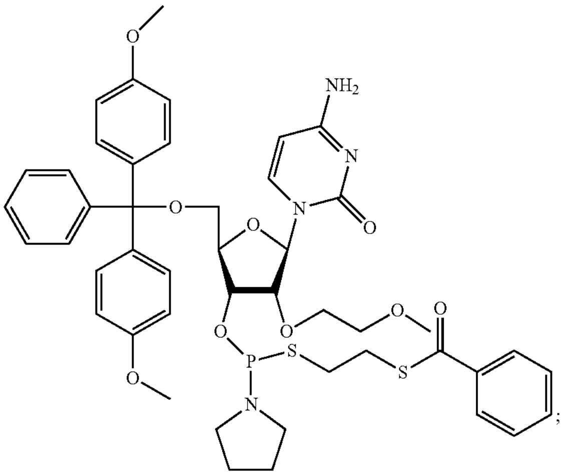
;
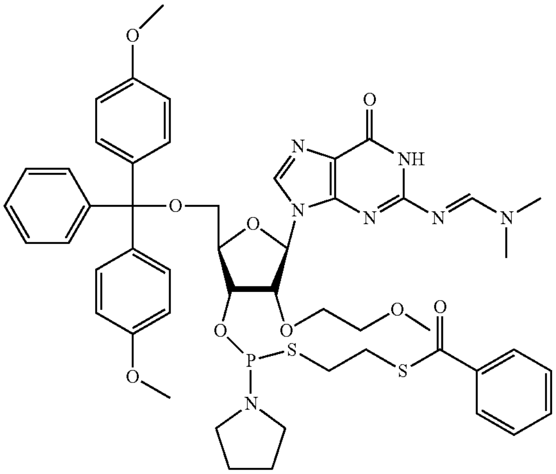
;
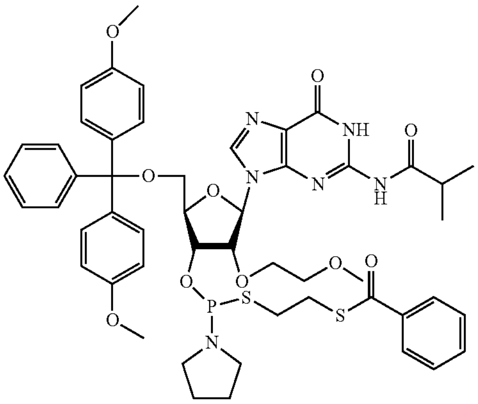
; and
-continued
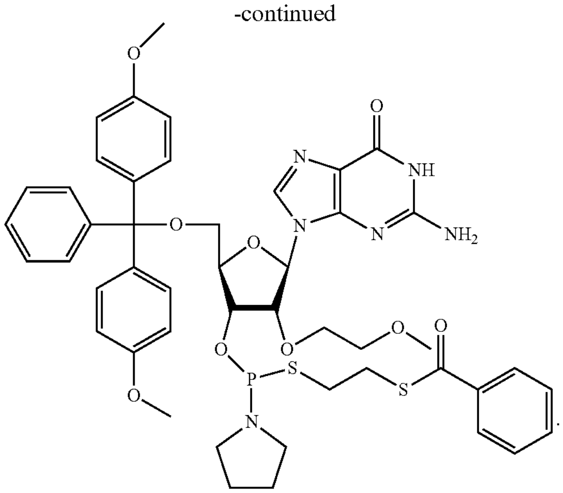
.
The presence of impurities in the compound of formula (II) and (IIb) results in byproducts during the manufacture of oligonucleotides and hampers the success of the synthesis. Furthermore, in the presence of impurities, the compound of formula (II) or (IIb) is unstable on storage.
The compounds of formula (X1), (X2), X(11) and (X21)
(X1)
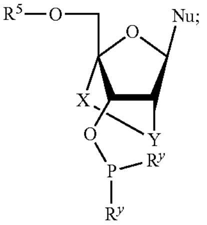
(X2)
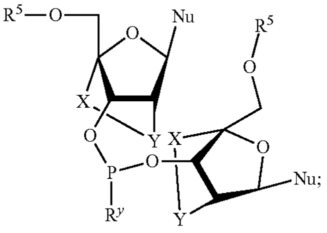
(X11)
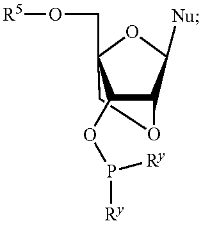
(X21)
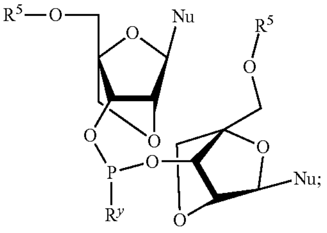

are, among others, examples of such impurities.

There was thus the need for a compound of formula (II) or (IIb) in a sufficiently pure form for storage and oligonucleotide manufacture purposes.

The invention thus also relates to a compound of formula (II) (IIb) having a purity of at least 98%, particularly of 99%, more particularly of 100%.

The invention thus relates in particular to a compound of formula (II) comprising less than 1%, particularly 0%, of the compound of formula (X1) and/or of the compound of (X2) as impurities.

The invention further relates to a process for the manufacture of a compound of formula (II) as defined above comprising the reaction of a 5'-protected LNA nucleoside with a phosphine and a mono-protected dithiol in the presence of an acidic coupling agent and a silylation agent.

The invention further relates to a process for the manufacture of a compound of formula (IIb) as defined above comprising the reaction of a 5'-protected MOE nucleoside with a phosphine and a mono-protected dithiol in the presence of an acidic coupling agent and a silylation agent.

The invention relates to a process for the manufacture of a compound of formula (II) comprising the reaction of a compound of formula (C)

(C)

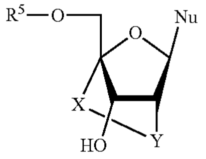

with a compound of formula $P(R^y)_3$ and a compound of formula $HSR^x$ in the presence of an acidic coupling agent and a silylation agent, wherein X, Y, $R^5$, Nu, $R^x$ and $R^y$ are as defined above.

The invention further relates to a process for the manufacture of a compound of formula (II) comprising the reaction of a compound of formula (C1)

(C1)

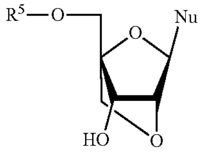

with a compound of formula $P(R^y)_3$ and a compound of formula $HSR^x$ in the presence of an acidic coupling agent and a silylation agent, wherein $R^5$, Nu, $R^x$ and $R^y$ are as defined above.

The invention also relates to a process for the manufacture of a compound of formula (IIb) comprising the reaction of a compound of formula (Cb)

(Cb)

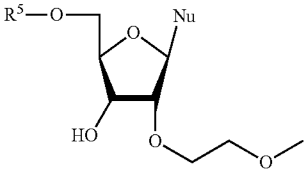

with a compound of formula $P(R^y)_3$ and a compound of formula $HSR^x$ in the presence of an acidic coupling agent and a silylation agent, wherein $R^5$, Nu, $R^x$ and $R^y$ are as defined above.

Examples of acidic coupling agents, also known as acidic activator, are azole based activators like tetrazole, 5-nitrophenyl-1H-tetrazole (NPT), 5-ethylthio-1H-tetrazole (ETT), 5-benzylthio-1H-tetrazole (BTT), 5-methylthio-1H-tetrazole (MTT), 5-mercapto-tetrazoles (MCT), 5-(3,5-bis(trifluoromethyl)phenyl)-1H-tetrazole and 4,5-dicyanoimidazole (DCI), or acidic salts like pyridinium hydrochloride, imidazoliuim triflate, benzimidazolium triflate, 5-nitrobenzimidazolium triflate, or weak acids such as 2,4-dinitrobenzoic acid or 2,4-dinitrophenol. Tetrazole is a particular acidic coupling agents.

Examples of silylation agents, also known as hydroxyl group quenchers, are bis(dimethylamino)dimethylsilane, N,O-bis(trimethylsilyl)acetamide (BSA), N,O-bis(trimethylsilyl)carbamate (BSC), N,N-bis(trimethylsilyl)methylamine, N,O-bis(trimethylsilyl)trifluoroacetamide (BSTFA), N,N'-bis(trimethylsilyl)urea (BSU), bromotrimethylsilane (TMBS), N-tert-butyldimethylsilyl-N-methyltrifluoroacetamide (MTBSTFA), chlorodimethyl(pentafluorophenyl)silane, chlorotriethylsilane (TESCI), chlorotrimethylsilane (TMCS), 1,3-dimethyl-1,1,3,3-tetraphenyldisilazane (TPDMDS), N,N-dimethyltrimethylsilylamine (TMSDMA), hexamethyldisilazane (HMDS), hexamethyldisiloxane (HMDSO), N-methyl-N-trimethylsilylacetamide (MSA), N-methyl-N-trimethylsilylheptafluorobutyramide (MSHFA), N-methyl-N-(trimethylsilyl)trifluoroacetamide (MSTFA), 1,1,3,3-tetramethyl-1,3-diphenyldisilazane (DPTMDS), 4-(trimethylsiloxy)-3-penten-2-one (TMS acac), 1-(trimethylsilyl)imidazole (TMSI) or trimethylsilyl methallylsulfinate (SILMAS-TMS). 1-(Trimethylsilyl)imidazole is a particular silylation agent.

The invention further relates to a process for the manufacture of a compound of formula (II), (IIb) or (III) wherein the crude compound of formula (II) or (IIb) is purified by preparative HPLC.

The invention further relates to a process for the manufacture of a compound of formula (II), (IIb) or (III) wherein the crude compound of formula (II), (IIb) or (III) is purified by preparative HPLC and eluted with a gradient of acetonitrile versus ammonium hydroxyde in water.

The ammonium hydroxyde content in water is in particular at least around 0.05% v/v, in particular between around 0.05% and 1% v/v, more particularly between around 0.05% and 0.5% v/v, more particularly around 0.05% v/v.

The gradient of acetonitrile is in particular between 0% and 25% to between 75% and 100% acetonitrile, in particular within 20 min to 120 min, more particularly between 10% and 20% to between 75% and 90% acetonitrile, in particular within 25 min to 60 min, more particularly around 25% to 75% acetonitrile, in particular within 30 min.

The invention also relates to the use of a compound of formula (II), (IIb) or (III) in the manufacture of an oligonucleotide, in particular of an oligonucleotide or a gapmer oligonucleotide according to the invention.

The invention will now be illustrated by the following examples which have no limiting character.

EXAMPLES

Example 1: Monomer Synthesis

1.1: S-(2-sulfanylethyl) benzenecarbothioate

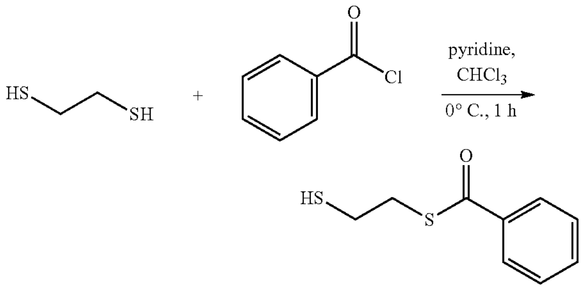

To a solution of 1,2-ethanedithiol (133.57 mL, 1592 mmol, 1 eq) and pyridine (64.4 mL, 796 mmol, 0.5 eq) in chloroform (200 mL) was added benzoyl chloride (92.4 mL, 796 mmol, 0.5 eq) in chloroform (200 mL) dropwise for 1 hr, and the reaction was stirred at 0° C. for 1 hr. The mixture was washed with water (300 mL) and brine (300 mL). The organic phase was dried over $Na_2SO_4$ and concentrated to a yellow oil. The oil was distilled (135~145° C.) to afford S-(2-sulfanylethyl) benzenecarbothioate (40 g, 202 mmol, 13% yield) as a colorless oil. $^1H$ NMR (400 MHz, $CDCl_3$) δ 7.97 (d, J=7.34 Hz, 2H), 7.53-7.64 (m, 1H), 7.47 (t, J=7.58 Hz, 2H), 3.31 (t, J=7.34 Hz, 2H), 2.77-2.86 (m, 2H), 1.70 (t, J=8.56 Hz, 1H).

1.2: S-[2-[[(1R,3R,4R,7S)-1-[[bis(4-methoxyphenyl)-phenyl-methoxy]methyl]-3-(5-methyl-2,4-dioxo-pyrimidin-1-yl)-2,5-dioxabicyclo[2.2.1]heptan-7-yl]oxy-pyrrolidin-1-yl-phosphanyl]sulfanylethyl] benzenecarbothioate

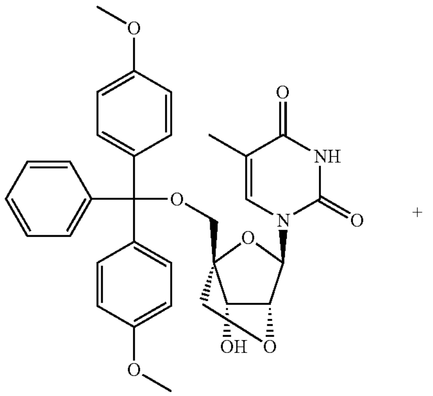

-continued

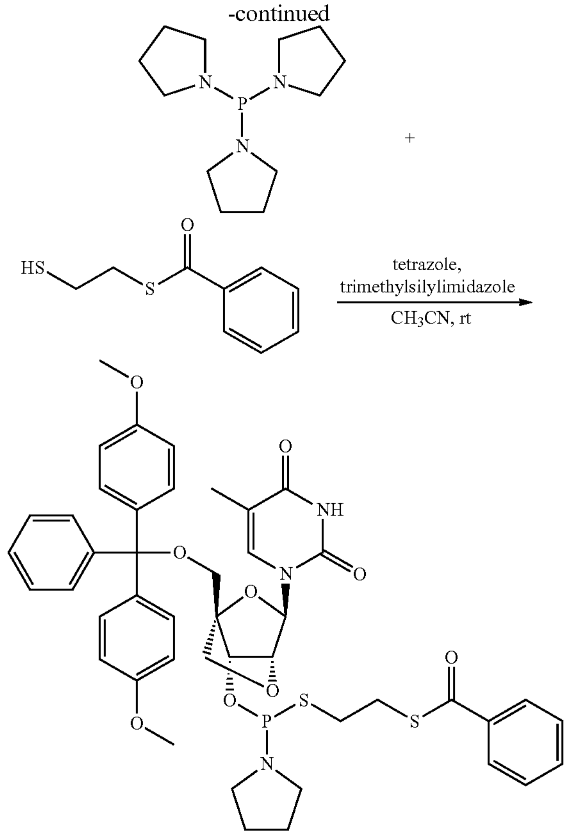

1-[(1R,4R,6R,7S)-4-[[bis(4-methoxyphenyl)-phenyl-methoxy]methyl]-7-hydroxy-2,5-dioxabicyclo[2.2.1]heptan-6-yl]-5-methyl-pyrimidine-2,4-dione (2.29 g, 4.00 mmol, 1.0 eq) was dissolved in 60 mL of anhydrous dichloromethane to which a spatula of 3 Å molecular sieves was added. Tripyrrolidin-1-ylphosphane (960 mg, 3.98 mmol, 0.99 eq) was added via syringe followed by seven 0.1 mmol aliquots of tetrazole (7*0.4 mL of a 0.5 M solution in anhydrous acetonitrile stored over 3 Å molecular sieves) at 2 min intervals. N-trimethylsilylimidazole (56.0 mg, 0.400 mmol, 0.1 eq) was then added to the reaction. After 5 min, tetrazole (21.6 mL of a 0.5 M solution in anhydrous acetonitrile) was added, immediately followed by the addition of S-(2-sulfanylethyl) benzenecarbothioate (1.04 g, 5.24 mmol, 1.31 eq). The reaction was allowed to proceed for 120 sec. Four identical batches of the reaction were united and quenched by pouring the solution into 600 mL of dichloromethane containing 40 mL of triethylamine. The mixture was immediately washed with saturated sodium bicarbonate (800 mL) followed by 10% sodium carbonate (2*800 mL) and brine (800 mL). The organic layer was dried over $Na_2SO_4$. After 10-15 min the drying agent was removed by filtration. Triethylamine (40 mL) was added to the solution which was concentrated using a rotary evaporator to a syrup. The syrup was dissolved in toluene (200 mL) and triethylamine (40 mL), and this solution was pipetted into 4500 mL of vigorously stirred heptane to precipitate the fluffy white product. After most of the heptane was decanted, the white precipitate was collected by filtration through a medium sintered glass funnel and subsequently dried under vacuum to give a white solid. The solid was purified by prep-HPLC (Phenomenex Gemini C18, 250×50 mm, 10 mm column, 0.05% ammonium hydroxide in water/$CH_3CN$), and freeze-dried to afford 4.58 g of target compound as a white solid.

$^{31}$P NMR (162 MHz, $CD_3CN$) δ 167.6, 164.2. $^{1}$H NMR (400 MHz, $CD_3CN$) δ 9.16 (br s, 1H), 7.93 (t, J=7.41 Hz, 2H), 7.60-7.71 (m, 1H), 7.45-7.57 (m, 4H), 7.24-7.45 (m, 7H), 6.90 (d, J=8.93 Hz, 4H), 5.53-5.63 (m, 1H), 4.41-4.64 (m, 2H), 3.74-3.88 (m, 8H), 3.39-3.63 (m, 2H), 3.03-3.32 (m, 5H), 2.77-2.94 (m, 2H), 1.66-1.84 (m, 4H), 1.54-1.66 (m, 3H).

1.3: S-[2-[[(1R,3R,4R,7S)-3-(6-benzamidopurin-9-yl)-1-[[bis(4-methoxyphenyl)-phenyl-methoxy]methyl]-2,5-dioxabicyclo[2.2.1]heptan-7-yl]oxy-pyrrolidin-1-yl-phosphanyl]sulfanylethyl] benzenecarbothioate

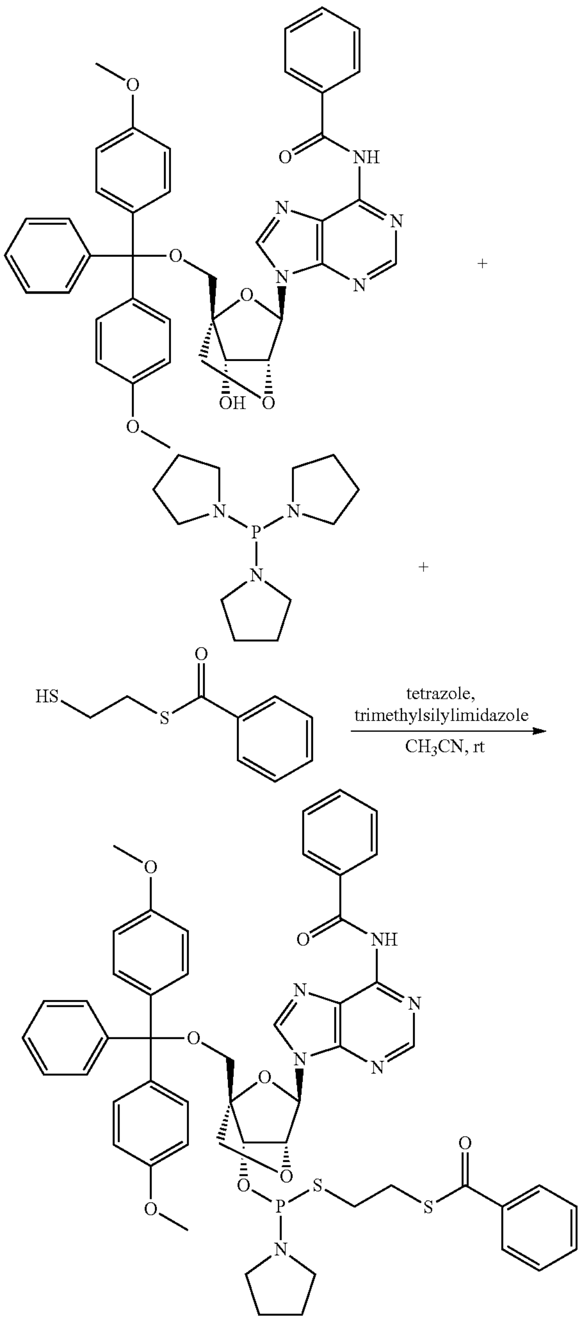

N-[9-[(1R,4R,6R,7S)-4-[[bis(4-methoxyphenyl)-phenyl-methoxy]methyl]-7-hydroxy-2,5-dioxabicyclo[2.2.1]heptan-6-yl]purin-6-yl]benzamide (2.74 g, 4.00 mmol, 1.0 eq) was dissolved in 60 mL of anhydrous dichloromethane to which a spatula of 3 Å molecular sieves was added. Tripyrrolidin-1-ylphosphane (960 mg, 3.98 mmol, 0.99 eq) was added via syringe followed by seven 0.1 mmol aliquots of tetrazole (7*0.4 mL of a 0.5 M solution in anhydrous acetonitrile stored over 3 Å molecular sieves) at 2 min intervals. 1-(trimethylsilyl)-1H-imidazole (56.0 mg, 0.400 mmol, 0.1 eq) was then added to the reaction. After 5 min, tetrazole (21.6 mL of a 0.5 M solution in anhydrous acetonitrile) was added, immediately followed by the addition of S-(2-sulfanylethyl) benzenecarbothioate (1.04 g, 5.24 mmol, 1.31 eq). The reaction was allowed to proceed for 120 s.

Four identical batches of the reaction were united and quenched by pouring the solution into 600 mL of dichloromethane containing 40 mL of triethylamine. The mixture was immediately washed with saturated sodium bicarbonate (800 mL) followed by 10% sodium carbonate (2*800 mL) and brine (800 mL). The organic layer was dried over $Na_2SO_4$. After 10-15 min the drying agent was removed by filtration. Triethylamine (10 mL) was added to the solution which was concentrated using a rotary evaporator to a syrup. The syrup was dissolved in toluene (100 mL) and triethylamine (20 mL), and this solution was pipetted into 4500 mL of vigorously stirred heptane to precipitate the fluffy white product. After most of the heptane was decanted, the white precipitate was collected by filtration through a medium sintered glass funnel and subsequently dried under vacuum to give a white solid. The solid was purified by prep-HPLC (Phenomenex Gemini C18, 250×50 mm, 10 mm column, 0.05% ammonium hydroxide in water/$CH_3CN$), and freeze-dried to afford 5.26 g of target compound as a white solid. $^{31}$P NMR (162 MHz, $CD_3CN$) δ 165.6, 164.7. $^{1}$H NMR (400 MHz, $CD_3CN$) δ 8.56 (d, J=10.76 Hz, 1H), 8.24 (d, J=10.27 Hz, 1H), 7.82-7.93 (m, 2H), 7.71-7.80 (m, 2H), 6.92-7.54 (m, 14H), 6.68-6.83 (m, 4H), 6.03 (d, J=6.48 Hz, 1H), 4.70-4.90 (m, 2H), 3.81-3.98 (m, 2H), 3.59-3.68 (m, 7H), 3.25-3.47 (m, 2H), 2.81-3.02 (m, 6H), 2.56-2.81 (m, 2H), 1.44-1.72 (m, 4H).

1.4: S-[2-[[(1R,3R,4R,7S)-3-(4-benzamido-5-methyl-2-oxo-pyrimidin-1-yl)-1-[[bis(4-methoxyphenyl)-phenyl-methoxy]methyl]-2,5-dioxabicyclo[2.2.1]heptan-7-yl]oxy-pyrrolidin-1-yl-phosphanyl]sulfanylethyl]benzenecarbothioate

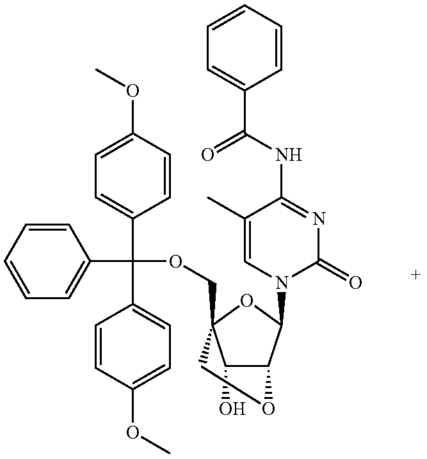

-continued

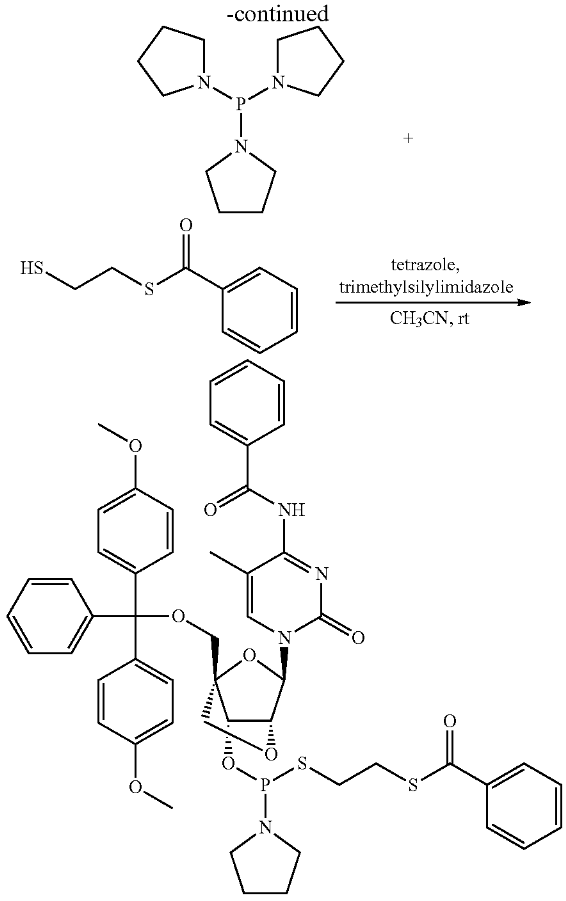

N-[1-[(1R,4R,6R,7S)-4-[[bis(4-methoxyphenyl)-phenyl-methoxy]methyl]-7-hydroxy-2,5-dioxabicyclo[2.2.1]heptan-6-yl]-5-methyl-2-oxo-pyrimidin-4-yl]benzamide (2.70 g, 4.00 mmol, 1.0 eq) was dissolved in 60 mL of anhydrous dichloromethane to which a spatula of 3 Å molecular sieves was added. Tripyrrolidin-1-ylphosphane (965 mg, 4.00 mmol, 1.0 eq) was added via syringe followed by seven 0.1 mmol aliquots of tetrazole (7*0.4 mL of a 0.5 M solution in anhydrous acetonitrile stored over 3 Å molecular sieves) at 2 min intervals. 1-(trimethylsilyl)-1H-imidazole (56.0 mg, 0.400 mmol, 0.1 eq) was then added to the reaction. After 5 min, tetrazole (21.6 mL of a 0.5 M solution in anhydrous acetonitrile) was added, immediately followed by the addition of S-(2-sulfanylethyl) benzenecarbothioate (1.04 g, 5.24 mmol, 1.31 eq). The reaction was allowed to proceed for 120 sec. Four identical batches of the reaction were quenched and united by pouring the solution into 600 mL of dichloromethane containing 40 mL of triethylamine. The mixture was immediately washed with saturated sodium bicarbonate (800 mL) followed by 10% sodium carbonate (2*800 mL) and brine (800 mL). The organic layer was dried over $Na_2SO_4$. After 10-15 min the drying agent was removed by filtration. Triethylamine (40 mL) was added to the solution which was concentrated using a rotary evaporator to a syrup. The syrup was dissolved in toluene (100 mL) and triethylamine (30 mL), and this solution was pipetted into 4500 mL of vigorously stirred heptane to precipitate the fluffy white product. After most of the heptane was decanted, the white precipitate was collected by filtration through a medium sintered glass funnel and subsequently dried under vacuum to give a white solid. The solid was purified by prep-HPLC (Phenomenex Gemini C18, 250×50 mm, 10 mm column, 0.05% ammonium hydroxide in water/$CH_3CN$) and freeze-dried to afford 2.05 g of target compound as a white solid. $^{31}P$ NMR (162 MHz, $CD_3CN$) δ 171.2, 167.4. $^1H$ NMR (400 MHz, $CD_3CN$) δ 8.18-8.32 (m, 2H), 7.81-7.93 (m, 3H), 7.35-7.60 (m, 14H), 7.17-7.35 (m, 2H), 6.93 (d, J=8.93 Hz, 4H), 5.65 (d, J=15.04 Hz, 1H), 4.56-4.72 (m, 2H), 3.69-3.90 (m, 8H), 3.45-3.61 (m, 2H), 3.03-3.26 (m, 6H), 2.76-3.02 (m, 2H), 1.65-1.93 (m, 7H).

1.5: S-[2-[[(1R,3R,4R,7S)-1-[[bis(4-methoxyphenyl)-phenyl-methoxy]methyl]-3-[2-[(E)-dimethylaminomethyleneamino]-6-oxo-1H-purin-9-yl]-2,5-dioxabicyclo[2.2.1]heptan-7-yl]oxy-pyrrolidin-1-yl-phosphanyl]sulfanylethyl]benzenecarbothioate

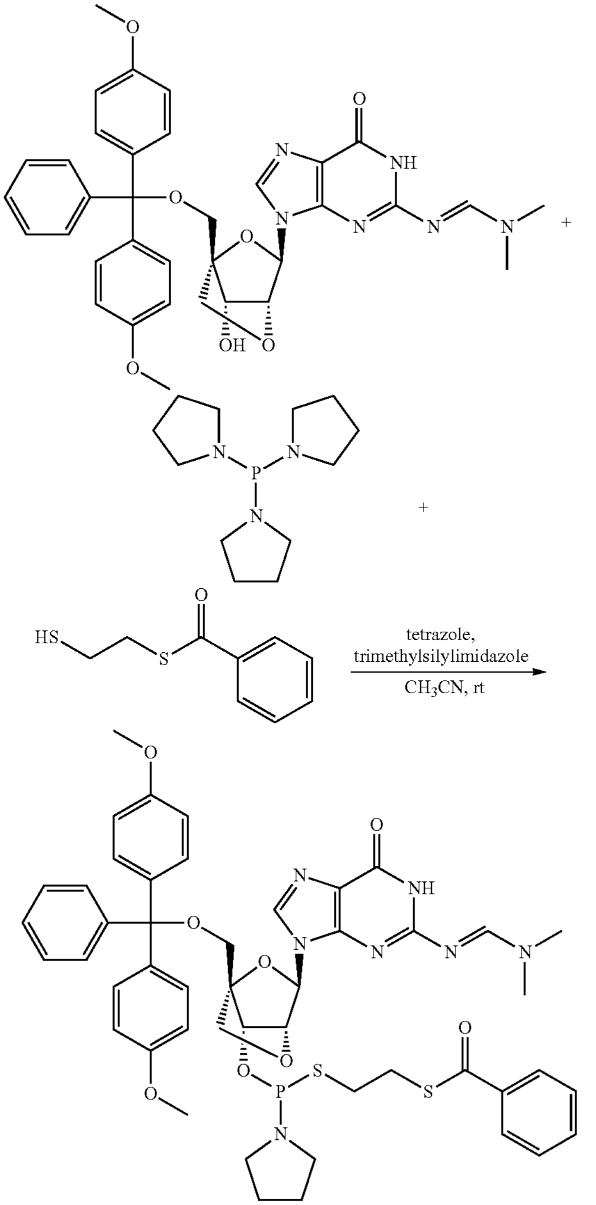

N'-[9-[(1R,4R,6R,7S)-4-[[bis(4-methoxyphenyl)-phenyl-methoxy]methyl]-7-hydroxy-2,5-dioxabicyclo[2.2.1]heptan-6-yl]-6-oxo-1H-purin-2-yl]-N,N-dimethyl-formamidine (2.62 mg, 4.00 mmol, 1.0 eq) was dissolved in 200 mL of anhydrous dichloromethane to which a spatula of 3 Å molecular sieves was added. Tripyrrolidin-1-ylphosphane (965 mg, 4.00 mmol, 1.0 eq) was added via syringe followed by seven 0.1 mmol aliquots of tetrazole (7*0.4 mL of a 0.5 M solution in anhydrous acetonitrile stored over 3 Å molecular sieves) at 2 min intervals. 1-(trimethylsilyl)-1H-imidazole (56.0 mg, 0.400 mmol, 0.1 eq) was then added to the reaction. After 5 min, tetrazole (21.6 mL of a 0.5 M solution in anhydrous acetonitrile) was added, immediately followed by the addition of S-(2-sulfanylethyl) benzenecarbothioate (1.04 g, 5.24 mmol, 1.31 eq). The reaction was allowed to proceed for 180 s.

Four identical batches were combined and quenched by pouring the solutions into 600 mL of dichloromethane containing 40 mL of triethylamine. The mixture was immediately washed with saturated sodium bicarbonate (800 mL) followed by 10% sodium carbonate (2*800 mL) and brine (800 mL). The organic layer was dried over $Na_2SO_4$. After 10-15 min the drying agent was removed by filtration. Triethylamine (40 mL) was added to the solution which was concentrated using a rotary evaporator to a syrup. The syrup was dissolved in toluene (100 mL) and triethylamine (30 mL), and this solution was pipetted into 4500 mL of vigorously stirred heptane to precipitate the fluffy white product. After most of the heptane was decanted, the white precipitate was collected by filtration through a medium sintered glass funnel and subsequently dried under vacuum to give a white solid. The solid was purified by prep-HPLC (Phenomenex Gemini C18, 250×50 mm, 10 mm column, 0.05% ammonium hydroxide in water/$CH_3CN$) and freeze-dried to afford 3.82 g of target compound as a yellow solid. $^{31}P$ NMR (162 MHz, $CD_3CN$) δ 167.1, 162.2. $^1H$ NMR (400 MHz, $CD_3CN$) δ 9.36 (br s, 1H), 8.63 (d, J=16.51 Hz, 1H), 7.78-8.00 (m, 3H), 7.66 (t, J=7.62 Hz, 1H), 7.42-7.57 (m, 4H), 7.24-7.40 (m, 7H), 6.89 (d, J=8.68 Hz, 4H), 5.92-5.98 (m, 1H), 4.72-4.97 (m, 2H), 3.86-4.05 (m, 2H), 3.78 (2s, 6H), 3.27-3.70 (m, 3H), 2.87-3.20 (m, 12H), 2.67-2.82 (m, 2H), 1.54-1.79 (m, 4H).

Example 2: Oligonucleotide Synthesis

Oligonucleotides were synthesized using a MerMade 12 automated DNA synthesizer by Bioautomation. Syntheses were conducted on a 1 μmol scale using a controlled pore glass support (500 Å) bearing a universal linker.

In standard cycle procedures for the coupling of DNA and LNA phosphoramidites DMT deprotection was performed with 3% (w/v) trichloroacetic acid in $CH_2Cl_2$ in three applications of 200 μL for 30 sec. The respective phosphoramidites were coupled three times with 100 μL of 0.1 M solutions in acetonitrile (or acetonitrile/$CH_2Cl_2$ 1:1 for the LNA-$^{Me}$C building block) and 110 μL of a 0.1 M solution of 5-(3,5-bis(trifluoromethylphenyl))-1H-tetrazole in acetonitrile as an activator and a coupling time of 180 sec. For thiooxidation a 0.1 M solution of 3-amino-1,2,4-dithiazole-5-thione in acetonitrile/pyridine 1:1 was used (3×190 μL, 55 sec). Capping was performed using THF/lutidine/$Ac_2O$ 8:1:1 (CapA, 75 μmol) and THF/N-methylimidazole 8:2 (CapB, 75 μmol) for 55 sec.

Synthesis cycles for the introduction of thiophosphoramidites included DMT deprotection using 3% (w/v) trichloroacetic acid in in $CH_2Cl_2$ in three applications of 200 μL for 30 sec. Commercially available DNA thiophosphoramidites or freshly prepared LNA thiophosphoramidites were coupled three times with 100 μL of 0.15 M solutions in 10% (v/v) $CH_2Cl_2$ in acetonitrile and 110 μL of a 0.1 M solution of 5-(3,5-bis(trifluoromethylphenyl))-1H-tetrazole in acetonitrile as an activator and a coupling time of 600 sec each. Thiooxidation was performed using a 0.1 M solution of 3-amino-1,2,4-dithiazole-5-thione in acetonitrile/pyridine in three applications for 55 sec. Capping was performed using THF/lutidine/$Ac_2O$ 8:1:1 (CapA, 75 μmol) and THF/N-methylimidazole 8:2 (CapB, 75 μmol) for 55 sec.

Upon completion of the automated synthesis, removal of the nucleobase protecting groups and cleavage from the solid support is carried out using an ammonia (32%):ethanol (3:1, v:v) mixture containing 20 mM DTT at 55° C. for 15-16 h.

Crude DMT-on oligonucleotides were purified either using a solid phase extraction cartridge and repurification with ion exchange chromatography or by RP-HPLC purification using a C18 column followed by DMT removal with 80% aqueous acetic acid and ethanol precipitation.

In the following examples we have used the following thio linkage chemistries

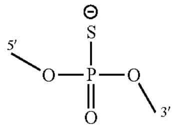

Phosphorothiate

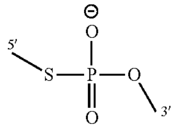

5′S Phosphoromonothiate

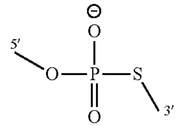

3′S phosphoromonothiate

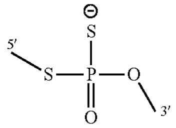

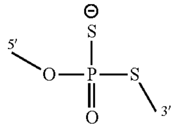

Chiral phosphorodithioates

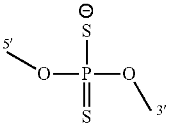

achiral phosphorodithioates

In the following examples, unless otherwise indicated, the achiral phosphorodithioate linkages (also referred to as P2S) are non-bridging dithioates (as illustrated in formula (IA) or (IB)), and are labelled as *. The compounds used in the example include compounds with the following sequence of nucleobases:

SEQ ID NO 1:
GCATTGGTATTCA

SEQ ID NO 2:
TCTCCCAGCGTGCGCCAT

SEQ ID NO 3:
GAGTTACTTGCCAACT

SEQ ID NO 4:
TATTTACCTGGTTGTT

-continued

SEQ ID NO 5:

CAATCAGTCCTAG

The following molecules have been prepared following the above procedure.

| Compound ID No. | Compound (SEQ ID NO) | Calculated mass | Found mass |
|---|---|---|---|
| #1 | G$^m$Ca*ttggtatT$^m$CA | 4341.6 | 4341.6 |
| #2 | G$^m$Cat*tggtatT$^m$CA | 4341.6 | 4341.6 |
| #3 | G$^m$Catt*ggtatT$^m$CA | 4341.6 | 4341.6 |
| #4 | G$^m$Cattg*gtatT$^m$CA | 4341.6 | 4341.6 |
| #5 | G$^m$Cattgg*tatT$^m$CA | 4341.6 | 4341.6 |
| #6 | G$^m$Cattggt*atT$^m$CA | 4341.6 | 4341.6 |
| #7 | G$^m$Cattggta*tT$^m$CA | 4341.6 | 4341.6 |
| #8 | G$^m$Cattggtat*T$^m$CA | 4341.6 | 4341.6 |
| #9 | G$^m$Cat*t*ggtatT$^m$CA | 4357.6 | 4356.8 |
| #10 | G$^m$Cattggt*at*T$^m$CA | 4357.6 | 4356.8 |
| #11 | G$^m$Cat*tggt*atT$^m$CA | 4357.6 | 4357.2 |
| #12 | G$^m$Catt*ggtat*T$^m$CA | 4357.6 | 4356.8 |
| #13 | G$^m$Cat*tggtat*T$^m$CA | 4357.6 | 4356.9 |
| #14 | G$^m$Cat*t*ggtat*T$^m$CA | 4373.7 | 4373.5 |
| #15 | G$^m$Catt*ggt*at*T$^m$CA | 4373.7 | 4373.1 |
| #16 | G$^m$Cat*t*ggt*atT$^m$CA | 4373.7 | 4373.0 |
| #17 | G$^m$Cat*t*ggt*at*T$^m$CA | 4389.8 | 4389.1 |
| #18 | G$^m$Ca*ttg*gta*tT$^m$CA | 4373.7 | 4373.0 |
| #19 | G$^m$Ca*tt*gg*ta*tT$^m$CA | 4389.8 | 4389.0 |
| #20 | G$^m$Ca*ttggta*tT$^m$CA | 4357.6 | 4356.9 |
| #21 | G$^m$Ca*ttggtat*T$^m$CA | 4357.6 | 4357.1 |
| #22 | G$^m$Cat*tggta*tT$^m$CA | 4357.6 | 4356.9 |
| #23 | G$^m$Cattg*gt*atT$^m$CA | 4357.6 | 4357.6 |
| #24 | G$^m$Cattg*g*t*atT$^m$CA | 4373.7 | 4373.7 |
| #25 | G$^m$Cattg*g*t*at*T$^m$CA | 4389.8 | 4389.8 |
| #26 | G$^m$Cattg*g*t*a*t*T$^m$CA | 4405.8 | 4405.8 |
| #27 | G$^m$CattggtatT$^m$C*A | 4341.6 | 4342.0 |
| #28 | G*$^m$CattggtatT$^m$CA | 4341.6 | 4342.5 |
| #29 | G*$^m$CattggtatT$^m$C*A | 4357.6 | 4359.0 |
| #30 | G*$^m$CattggtatT*$^m$C*A | 4373.7 | 4368.5 |
| #31 | G*$^m$C*attggtatT$^m$C*A | 4373.7 | 4369.2 |
| #32 | G*$^m$C*attggtatT*$^m$C*A | 4389.8 | 4390.6 |

*Dithioate modification between adjacent nucleotides
A, G, $^m$C, T represent LNA nucleotides
a, g, c, t represent DNA nucleotides
all other linkages were prepared as phosphorothioates

Example 3: In Vitro Efficacy and Cellular Uptake Experiments

Primary rat Hepatocytes were plated in 96-well plates and treated in Williams Medium E containing 10% FCS without antibiotics. Cells were treated with LNA solutions in the indicated concentrations in full cell culture medium. After an incubation time of 24 and 72 hrs, respectively, the cells were washed 3 times with PBS containing $Ca^{2+}$ and $Mg^{2+}$ and lysed with 165 uL PureLink Pro lysis buffer. Total RNA was isolated using the PureLink PRO 96 RNA Kit from Thermo Fisher according to the manufacturers instructions and RT-qPCR was performed using the LightCycler Multiplex RNA Virus Master (Roche) with Primer Probe Sets for RnApoB (Invitrogen). The obtained data was normalized to Ribogreen.

Intracellular concentrations of the LNA oligonucleotides were determined using an hybridization based ELISA assay for a variety of compounds. All data points were performed in triplicates and data is given as the average thereof.

The results are shown in FIGS. 1 to 4.

Example 4: Thermal Melting (Tm) of Oligonucleotides Containing a Phophorodithioate Internucleoside Linkage Hybridized to RNA and DNA The following oligonucleotides have been prepared. Phosphorothoiate linkages are designated by the S subscript; Phosphorodithioate linkages according to the invention are designated by the PS2 subscript.

| Compound | |
|---|---|
| 1 | 5'-$G_S$ $^mC_S$ $a_S$ $t_S$ $t_S$ $g_S$ $g_S$ $t_S$ $a_S$ $t_S$ $T_S$ $^mC_{PS2}$ A -3' |
| 2 | 5'-$G_{PS2}$ $^m$CS $a_S$ $t_S$ $t_S$ $g_S$ $g_S$ $t_S$ $a_S$ $t_S$ $T_S$ $^mC_S$ A -3' |
| 3 | 5'-$G_{PS2}$ $^m$CS $a_S$ $t_S$ $t_S$ $g_S$ $g_S$ $t_S$ $a_S$ $t_S$ $T_S$ $^mC_{PS2}$ A -3' |
| 4 | 5'-$G_{PS2}$ $^m$CS $a_S$ $t_S$ $t_S$ $g_S$ $g_S$ $t_S$ $a_S$ $t_S$ $T_{PS2}$ $^mC_{PS2}$ A -3' |
| 5 | 5'-$G_{PS2}$ $^mC_{PS2}$ $a_S$ $t_S$ $t_S$ $g_S$ $g_S$ $t_S$ $a_S$ $t_S$ $T_S$ $^mC_{PS2}$ A -3' |
| 6 | 5'-$G_{PS2}$ $^mC_{PS2}$ $a_S$ $t_S$ $t_S$ $g_S$ $g_S$ $t_S$ $a_S$ $t_S$ $T_{PS2}$ $^mC_{PS2}$ A -3' |
| Control DNA | 5'-$G_S$ $^mC_S$ $a_S$ $t_S$ $t_S$ $g_S$ $g_S$ $t_S$ $a_S$ $t_S$ $T_S$ $^mC_S$ A -3' |
| Control SEQ ID NO 2 | 5'-$t_S$ $c_S$ $t_S$ $c_S$ $c_S$ $c_S$ $a_S$ $g_S$ $c_S$ $g_S$ $t_S$ $g_S$ $c_S$ $g_S$ $c_S$ $c_S$ $a_S$ t -3' |

Compounds 1-6 have the sequence motif SEQ ID NO 1.

The thermal melting (Tm) of compounds 1-6 hybridized to RNA and DNA was measured according to the following procedure.

A solution of equimolar amount of RNA or DNA and LNA oligonucleotide (1.5 μM) in buffer (100 mM NaCl, 0.1 mM EDTA, 10 mM $Na_2HPO_4$, pH 7) was heated to 90° C. for 1 min and then allowed to cool to room temperature. The UV absorbance at 260 nm was recorded using a Cary Series UV-Vis spectrophotometer (heating rate 1° C. per minute; reading rate one per min). The absorbance was plotted against temperature and the Tm values were calculated by taking the first derivative of each curve.

Figure 1:
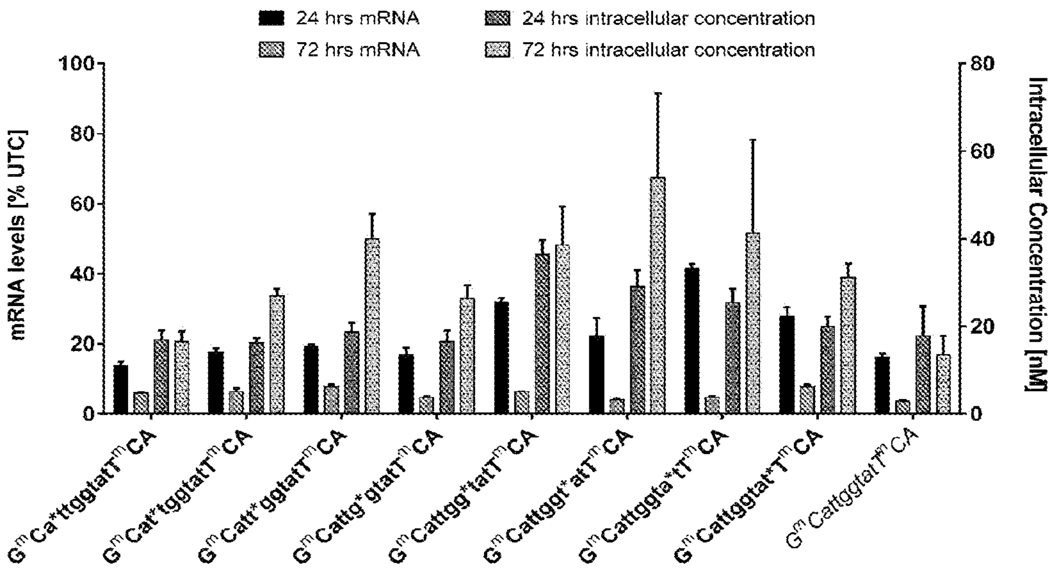
FIGS. 1-4 show the target mRNA levels in primary rat hepatocytes after 24 and 74 hours of administration of oligonucleotides according to the invention.
Figure 2:
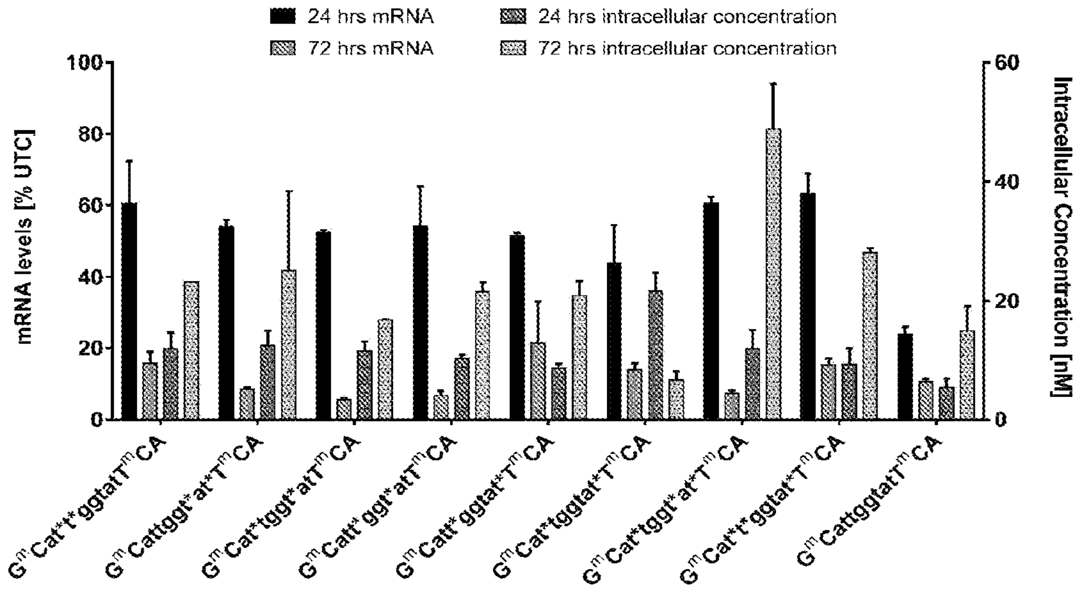
Figure 3:
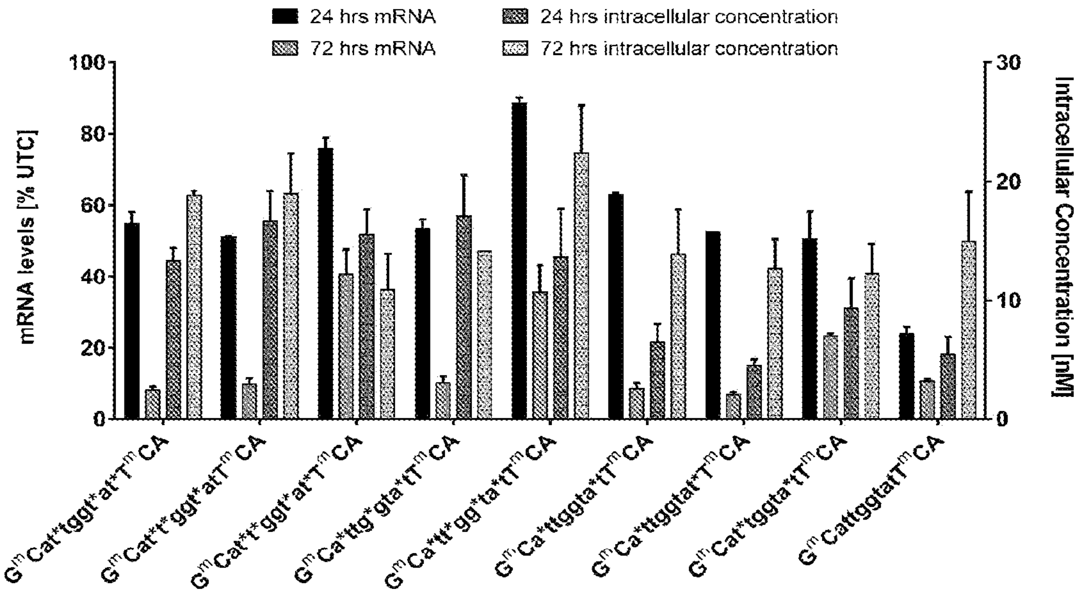
Figure 4:
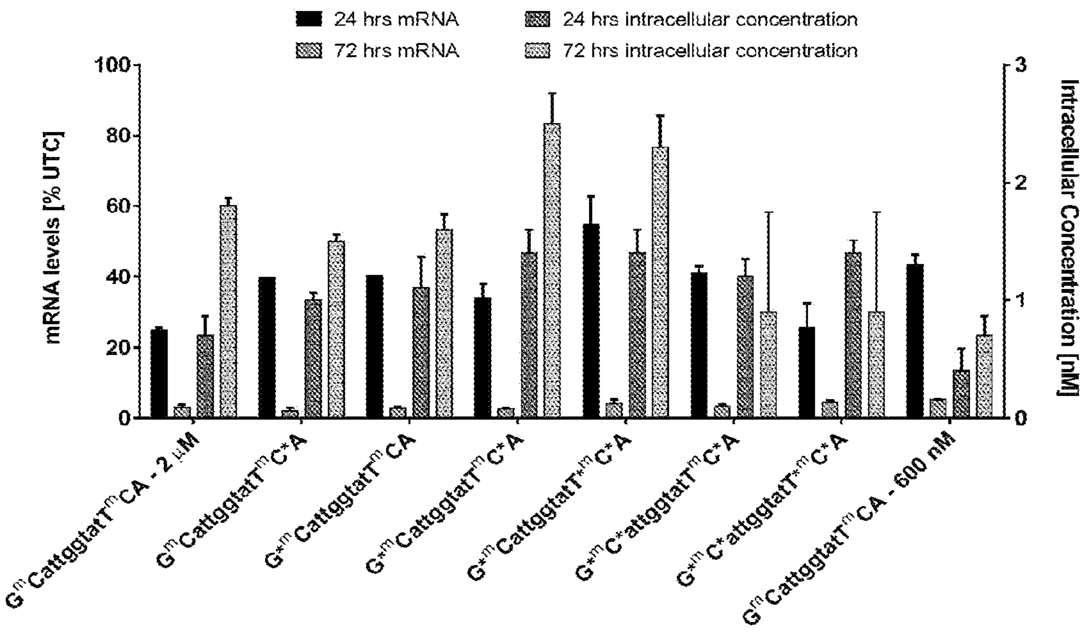
Figure 5:
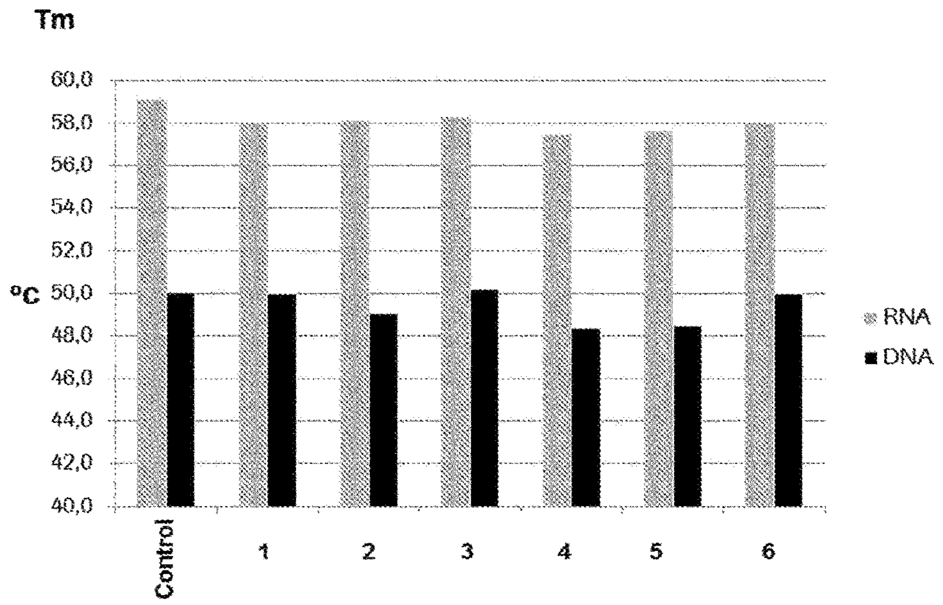
FIG. 5 shows the thermal melting (Tm) of oligonuicleotides containing a phophorodithioate internucleoside linkage according to the invention hybridized to RNA and DNA.

The results are summarized in the Table below and in FIG. 5.

| | RNA | | | DNA | | |
|---|---|---|---|---|---|---|
| | Td | Ta | ΔTm | Td | Ta | ΔTm |
| Control | 59.1 | 57.7 | 1.5 | 50.1 | 47.7 | 2.4 |
| 1 | 58.0 | 54.8 | 3.2 | 50.0 | 46.9 | 3.1 |
| 2 | 58.1 | 55.7 | 2.5 | 49.1 | 46.7 | 2.4 |
| 3 | 58.3 | 55.5 | 2.8 | 50.2 | 47.6 | 2.6 |
| 4 | 57.5 | 54.4 | 3.1 | 48.4 | 46.5 | 1.8 |
| 5 | 57.6 | 56.3 | 1.3 | 48.5 | 47.4 | 1.1 |
| 6 | 58.0 | 55.8 | 2.2 | 50.0 | 46.9 | 3.1 |

Td: Temperature of dissociation (denaturation);
Ta: Temperature of association (renaturation)

The compounds according to the invention retain the high affinity for RNA and DNA of the control.

Example 5: Serum Stability of Oligonucleotides Containing a Phophorodithioate Internucleoside Linkage Stability of oligonucleotides 1-6 in serum from male Sprague-Dawling rats was measured according to the following procedure.

A 25 μM oligonucleotide solution in rat serum mixed with Nuclease buffer (30 mM sodium acetate, 1 mM zinc sulfate, 300 mM NaCl, pH 4.6) 3:1 were incubated at 37° C. for 0, 5, 25, 52 or 74 hours. Samples 2 μL were injected for UPLC-MS analysis on a Water Acquity UPLC equipped with a Water Acquity BEH Cis, 1.7 μm column. The analogue peak areas measured at 260 nm compensated with the extention constants of the different degradation lengths were used to establish the % of uncleaved oligonucleotide.

UPLC eluents: A: 2.5% MeOH, 0.2 M HEP, 16.3 mM TEA B: 60% MeOH, 0.2 M HEP, 16.3 mM TEA

| TIME MIN. | FLOW ML/ MIN | % A BUFFER | % B BUFFER |
|---|---|---|---|
| 0 | 0.5 | 90 | 10 |
| 0.5 | 0.5 | 90 | 10 |
| 5 | 0.5 | 70 | 30 |
| 6 | 0.5 | 70 | 30 |
| 7 | 0.5 | 0 | 100 |
| 8 | 0.5 | 0 | 100 |
| 9 | 0.5 | 90 | 10 |
| 14.9 | 0.5 | 90 | 10 |
| 15 | 0.5 | 90 | 10 |

Figure 6:
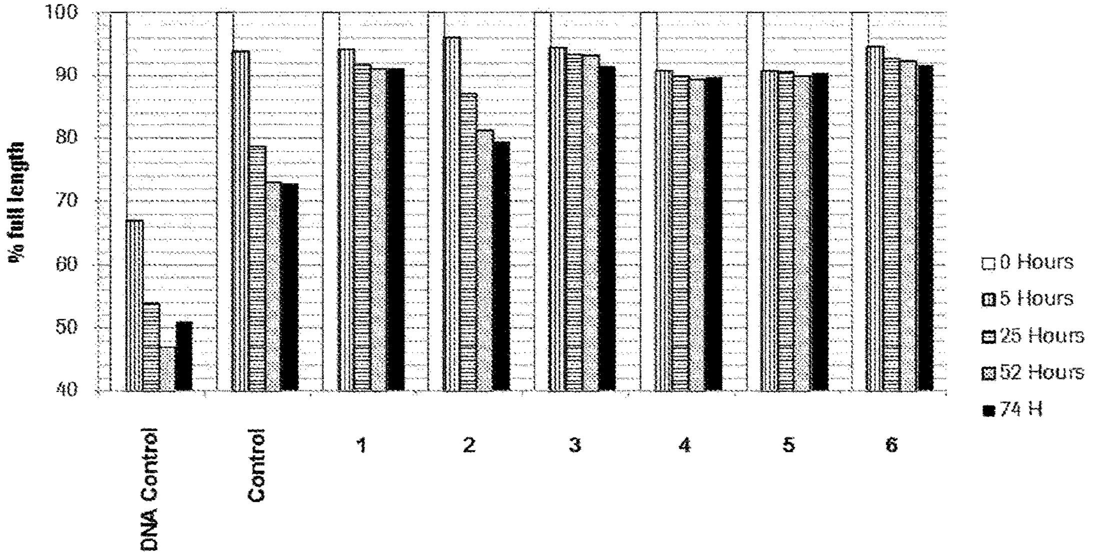
FIG. 6 shows the stability of oligonucleotides containing a phosphorodithioate internucleoside linkage according to the invention in rat serum.

The results are summarized in FIG. 6.

The compounds having at least one phosphorodithioate internucleoside linkage according to the invention have a superior nuclease resistance than the compounds having only phosphorothioate internucleoside linkages.

The initial oligonucleotide degradation seen after 5 hours in compounds 1-6 was found to be caused by the presence of a monothioate impurity.

Example 7: Dithioate Modified Gapmers: Exploring the Dithioates in the Gap Region of LNA Gapmers Compounds Tested

| single modification in the gap | |
|---|---|
| #1 | GCa*ttggtatTCA |
| #2 | GCat*tggtatTCA |
| #3 | GCatt*ggtatTCA |
| #4 | GCattg*gtatTCA |
| #5 | GCattgg*tatTCA |
| #6 | GCattggt*atTCA |
| #7 | GCattggta*tTCA |
| #8 | GCattggtat*TCA |
| **cumulation in gap region** | |
| #9 | GCattg*gt*atTCA |
| #10 | GCattg*g*t*atTCA |
| #11 | GCattg*g*t*at*TCA |
| #12 | GCattg*g*t*a*t*TCA |
| Ref. | GCattggtatTCA |
| **dithioate in LNA flanks** | |
| #13 | GC*attggtatTCA |
| #14 | GCattggtatT*CA |
| #15 | GCattggtatTC*A |
| #16 | GC*attggtatT*C*A |

Compounds #1-#16 and Ref. have the sequence motif shown in SEQ ID NO 1.
Upper case letter: beta-D-oxy LNA nucleoside; lower case letter DNA nucleoside;
*= achiral phosphorodithioate modified linkages; all other linkages phosphorothioate Experimental: The above compounds targeting ApoB mRNA, were tested in primary rat hepatocytes using gymnotic uptake, with incubation for 72 hrs with a compound concentration of 2 μM. The target mRNA levels were then measured using RT-PCR. Results are shown in FIG. 7.

The results shown in FIG. 7 illustrate that both single and multiple achiral phosphorodithioates are accommodated in the gap and flank regions. The use of more than 3 or 4 achiral phosphorodithioates in the gap may tend to reduce potency as compared to the use of multiple achiral phosphorodithioates in the flank region.

Example 8: Positional Dependency on Activity—Design Optimisation

Compounds Tested

| 2 modifications | |
|---|---|
| #1 | GCat*t*ggtatTCA |
| #2 | GCattggt*at*TCA |
| #3 | GCat*tggt*atTCA |

-continued

| | |
|---|---|
| #4 | GCatt*ggt*atTCA |
| #5 | GCatt*ggtat*TCA |
| #6 | GCat*tggtat*TCA |
| #7 | GCa*ttggta*tTCA |
| #8 | GCa*ttggtat*TCA |
| #9 | GCat*tggta*tTCA |
| | 3 modifications |
| #10 | GCat*tggt*at*TCA |
| #11 | GCat*t*ggtat*TCA |
| #12 | GCatt*ggta*t*TCA |
| #13 | GCat*t*ggt*atTCA |
| #14 | GCa*ttg*gta*tTCA |
| Ref. | GCattggtatTCA |
| | 4 modifications |
| #15 | GCat*t*ggt*at*TCA |
| #16 | GCa*tt*gg*ta*tTCA |

Compounds #1-#16 and Ref. have the sequence motif shown in SEQ ID NO 1.
Upper case letter: beta-D-oxy LNA nucleoside; lower case letter DNA nucleoside;
*= achiral phosphorodithioate modified linkages; all other linkages phosphorothioate Experimental: The above compounds targeting ApoB mRNA, were tested in primary rat hepatocytes using gymnotic uptake, with incubation for 72 hrs with a compound concentration of 2 μM. The target mRNA levels were then measured using RT-PCR. Results are shown in FIG. 8.

Example 9: Cellular Uptake of Achiral Phosphorodithioate Gapmers

Compounds Tested

| single modification in the gap | |
|---|---|
| #1 | GCa*ttggtatTCA |
| #2 | GCat*tggtatTCA |
| #3 | GCatt*ggtatTCA |
| #4 | GCattg*gtatTCA |
| Ref. | GCattggtatTCA |
| #5 | GCattgg*tatTCA |
| #6 | GCattggt*atTCA |
| #7 | GCattggta*tTCA |
| #8 | GCattggtat*TCA |

Compounds #1-#16 and Ref. have the sequence motif shown in SEQ ID NO 1.
Upper case letter: beta-D-oxy LNA nucleoside; lower case letter DNA nucleoside;
*= achiral phosphorodithioate modified linkages; all other linkages phosphorothioate Experimental: The above compounds targeting ApoB mRNA, were tested in primary rat hepatocytes using gymnotic uptake, with incubation for 72 hrs with a compound concentration of 2 μM. Oligonucleotide content was determined using a hybridization based ELISA assay. The results are shown in FIGS. 9A and 9B.

Without exception, the inclusion of an achiral phosphorodithioate provided enhanced cellular uptake. There was however a diversity in the uptake improvement depending upon the position of the achiral phosphorodithioate linkage.

Example 10: Increasing the Achiral Phosphorodithioate Load in the Flank Region of a Gapmer Compounds Tested (Sequence Motif=SEQ ID NO 1)

| modifications in the flanks | | |
|---|---|---|
| | | IC50 [nM] |
| ● | GCattggtatTC*A | 7.3 |
| ■ | G*CattggtatTCA | 10.4 |
| ▲ | G*CattggtatTC*A | 6.8 |
| Ref. | GCattggtatTCA | 33.3 |
| ▼ | G*CattggtatT*C*A | 9.2 |
| ◆ | G*C*attggtatTC*A | 8.9 |
| O\| | G*C*attggtatT*C*A | 4.9 |

Upper case letter: beta-D-oxy LNA nucleoside; lower case letter DNA nucleoside;
*= achiral phosphorodithioate modified linkages; all other linkages phosphorothioate Experimental: The above compounds targeting ApoB mRNA, were tested in primary rat hepatocytes using gymnotic uptake, with incubation for 72 hrs with a compound concentration of 2 μM. The target mRNA levels were then measured using RT-PCR. The results are shown in FIGS. 10A and 10B.

The introduction of achiral phosphorodithioate modifications in the flank regions of gapmers provided without exception a pronounced increase in potency, with a reduction in IC50 of 3-7×. Interestingly, an increase in the number of chiral phosphorodithioate modifications in the flanks results in a lower IC50.

Example 11: Effect of Achiral Phosphorodithioate Linkages in Different Cell Types, In Vitro Compounds Tested (Sequence Motif=SEQ ID NO 3)

| modification in the flanks | |
|---|---|
| #1 | GAGttacttgccaAC*T |
| #2 | G*AGttacttgccaACT |
| #3 | G*AGttacttgccaAC*T |
| #4 | G*AGttacttgccaA*C*T |
| Ref | GAGttacttgccaACT |
| #5 | G*A*GttacttgccaAC*T |

-continued

| modification in the flanks | |
|---|---|
| #6 | G*A*GttacttgccaA*C*T |
| #7 | G*A*G*ttacttgccaA*C*T |

Upper case letter: beta-D-oxy LNA nucleoside; lower case letter DNA nucleoside;
*= achiral phosphorodithioate modified linkages; all other linkages phosphorothioate The above compounds which target Malat-1 were tested in three in vitro cell systems: human primary skeletal muscles, human primary bronchial epithelial cells and mouse fibroblasts (LTK cells) using gymnotic uptake for 72 hours, at a range of concentrations to determine the compound potency (IC50).

Concentration range for LTK cells: 50 μM, ½% log dilution, 8 concentrations.

RNA levels of Malat1 were quantified using qPCR (Normalised to GAPDH level) and IC50 values were determined.

The IC50 results are shown in FIG. 11. The introduction of achiral phosphorodithioate provided a reliable enhanced potency in skeletal muscle cells, and in general gave an improved potency into mouse fibroblasts. The effect in human bronchial epithelial cells was more compound specific, however in some compounds (#5) were markedly more potent than the reference compound.

Example 12: In Vitro Rat Serum Stability of 5' and 3' End Protected LNA Oligonucleotides Compounds Tested (Sequence Motif=SEQ ID NO 1)

| | |
|---|---|
| #1 | PS/DNA oligonucleotide |
| #2 | GCattggtatTCA |
| #3 | G*CattggtatTCA |
| #4 | GCattggtatTC*A |
| #5 | G*CattggtatTC*A |
| #6 | G*CattggtatT*C*A |
| #7 | G*C*attggtatTC*A |
| #8 | G*C*attggtatT*C*A |

Upper case letter: beta-D-oxy LNA nucleoside; lower case letter DNA nucleoside;
*= achiral phosphorodithioate modified linkages; all other linkages phosphorothioate Experimental—see example 5.

The results are shown in FIG. 12. We have identified that the 3' end of LNA phosphorothioate oligonucleotides are more susceptible to serum nucleases than previously thought and this appears to be related to the chirality of the phosphorothioate linkage(s) at the 3' end of the oligonucleotide—as illustrated by the rapid cleavage of 50% of the parent oligonucleotide #1. The 5' end protection with an achiral phosphorodithioate provided an improved protection. The 3' end protection with an achiral phosphorodithioate provided complete protection to rat serum exonucleases—the slight reduction seen for compound #4-#8 was correlated to a monothioate impurity.

The 5' and/or 3' end protection of antisense oligonucleotides with the achiral phosphorothioate linkages is therefore considered to provide a solution to a major instability problem with stereorandom and stereodefined phosphorothioates.

Example 13: In Vivo Assessment of Gapmers with Achiral Phosphorodithioate Linkages in the Flanks Compounds Tested (Sequence Motif=SEQ ID NO 1)

| | |
|---|---|
| #1 | GCattggtatTC*A |
| #2 | G*CattggtatTCA |
| #3 | G*CattggtatTC*A |
| #4 | G*CattggtatT*C*A |
| #5 | G*C*attggtatTC*A |
| #6 | G*C*attggtatT*C*A |
| #7 | G*C***attggtat**T*C*A |
| #8 | GCat*tggt*at*TCA |
| #9 | **GCa**t* **tgg**t* **a**t* **TC**A |
| Ref. | GCattggtatTCA |

Upper case letter: beta-D-oxy LNA nucleoside; lower case letter DNA nucleoside;
*= achiral phosphorodithioate modified linkages; all other linkages phosphorothioate. Note the underlined bold nucleosides are linked at the 3'position by stereodefined phosphorothioate internucleoside linkages. Compound #7 has a stereodefined motif in the gap region of SSRSSRSR (S = Sp, R = Rp). The backbone motif of compound 9 = RRSPRSSPSPSS, wherein S = Sp, R = Rp, and P = achiral PS2 linkage (*).

Experimental: The above compounds targeting ApoB were administered to female C57BL/6JBom mice, using al mg/kg single iv dose, and were sacrificed on day 7, n=5. The mRNA reduction in the liver was measured using RT-PCR and the results are shown in FIG. 13.

The results show that in general the introduction of the achiral phosphorodithioate internucleoside linkages provides an improved potency, notably all the compounds with achiral phosphorodithioate linkages in the flank regions show improved potency. As illustrated in the in vitro experiment, the use of multiple phosphorodithioate linkages in the agap region (#8) was accommodated without a notable loss of potency. Of particular interest is the combined effect of gapmer designs with stereodefined phosphorothioate linkages in the gap region, with achiral phosphorodithioate linkages in the flanks, illustrating a synergy in combining these linkages technologies with an antisense oligonucleotide.

Example 14: In Vivo Tissue Content in Liver of Gapmers with Achiral Phosphorodithioates with Modified Flanks and Gap Region Compounds and experimental—see example 13. The results of the tissue content (determined by hybridisation based ELISA to measure content in liver and kidney samples from the sacrificed animals) is shown in FIGS. 14A & B. Note that there was an experimental error for compound #1—see FIG. 14B data.

Results: FIG. 14A. All the antisense oligonucleotides which contained the achiral phosphorodithioate linkages had a higher tissue uptake/content as compared to the reference compound. FIG. 14B shows that the introduction of the achiral phosphorodithioate linkage enhanced the biodistribution (as determined by the liver/kidney ratio) of all the compounds tested.

Example 15: Metabolite Analysis from In Vivo Experiment

Compounds and experimental—see example 13. Metabolite analysis was performed using the methods disclosed in C. Husser et al., Anal. Chem. 2017, 89, 6821.

The results are shown in FIGS. 15A and 15B. The phosphorodithioate modification efficiently prevents 3'-exonucleolytic degradation in vivo. There remains some endonuclease cleavage (note compounds #1-6 tested all have DNA phosphorothioate gap regions so this was expected). Given the remarkable exonuclease protection it is considered that the use of achiral phosphorodithioate linkages within antisense oligonucleotides may be used to prevent or limit endonuclease cleavage. The enhanced nuclease resistance of achiral phosphorodithioates is expected to provide notable pharmacological benefits, such as enhanced activity and prolonged duration of action, and possibly avoidance of toxic degradation products.

Example 16: In Vivo—Long Term Liver Activity (ApoB)

Compounds Tested (Sequence Motif=SEQ ID NO 1):

| Ref. | GCattggtatTCA |
|---|---|
| #1 | G*C*attggtatT*C*A |
| #2 | **GCattggtatTCA** |
| #3 | G*C***attggtat**T*C*A |

Upper case letter: beta-D-oxy LNA nucleoside; lower case letter DNA nucleoside;
*= achiral phosphorodithioate modified linkages; all other linkages phosphorothioate. Note the underlined bold nucleosides are linked at the 3' position by stereodefined phosphorothioate internucleoside linkages. Compound #3 has a stereodefined motif in the gap region of SSRSSRSR (S = Sp, R =Rp). The backbone motif of compound #2 = RRSSRSSRSRSS, wherein S = Sp, R = Rp, and P = achiral PS2 linkage (*).

Experimental: As in example 13, however sacrifice was performed at day 7 or 21.

The results are shown in FIG. 16. Compared to the phosphorothioate reference compound, the introduction of the achiral phosphorodithioate provided a prolonged duration of action in the liver and this was correlated with a higher tissue content at 21 days. Notably, the combination of phosphorodithioate linked flank regions with stereodefined phosphorothioate linkages in the gap region provided further benefit with regards to prolonged potency and duration of action, again emphasising the remarkable synergy in combining achiral phosphorodithioate internucleoside linkages with stereodefined phosphorothioate linkages in antisense oligonucleotides.

Example 17: In Vivo Study Using Malat-1 Targeting Achiral Phosphorodithioates Modified Gapmers Compounds Tested (Sequence Motif=SEQ ID NO 3)

| Ref | GAGttacttgccaACT |
|---|---|
| Increasing P2S load in flanks | |
| #1 | G*AGttacttgccaACT |
| #2 | GAGttacttgccaAC*T |
| #3 | G*AGttacttgccaAC*T |

-continued

| Ref | GAGttacttgccaACT |
|---|---|
| #4 | G*AGttacttgccaA*C*T |
| #5 | G*A*GttacttgccaAC*T |
| #6 | G*A*GttacttgccaA*C*T |
| #7 | G*A*G*ttacttgccaA*C*T |

Upper case letter: beta-D-oxy LNA nucleoside; lower case letter DNA nucleoside;
*= achiral phosphorodithioate modified linkages; all other linkages phosphorothioate.

Experimental:

In vitro: Mouse LTK cells were used to determined the in vitro concentration dose response curve—measuring the MALAT-1 mRNA inhibition.

In vivo: Mice (C57/BL6) were administered 15 mg/kg dose subcutaneously of the oligonucleotide in three doses on day 1, 2 and 3 (n=5). The mice were sacrificed on day 8, and MALAT-1 RNA reduction and tissue content was measured for liver, heart, kidney, spleen and lung. The parent compounds was administered in two doses 3*15 mg/kg and 3*30 mg/kg.

Results: The in vitro results are shown in FIG. 17—compounds with 1, 2, 3 and 4 achiral phosphorodithioates in the flanks were found to be highly potent in vitro. The compound #7 with 5 achiral phosphorodithioates in the flanks was found to have a lower potency than those with 1-4 achiral phosphorodithioates in the flanks. The most potent compounds #1, #2 and #6 were selected for the in vivo study. The in vivo results are shown in FIG. 17B (heart)—which illustrates that the achiral phosphorodithioate compounds were about twice as potent in knocking down MALAT-1 in the heart as the reference compound. Notably the use of the achiral phosphorodithioate internucleoside linkage between the two 3' terminal nucleosides of the antisense oligonucleotides provided a marked improvement over the equivalent 5' end protected oligonucleotide.

FIG. 17C shows the results of the tissue content analysis from the in vivo study. All three oligonucleotide containing the achiral phosphorodithioate internucleoside linkages had higher tissue content in liver. The di-thioates results in similar or higher content in heart and liver, and lower content in kidney, again illustrating superiority over PS-modified antisense oligonucleotides. Notably the tissue content in heart was only higher for compound 1, indicating that the enhanced in vivo potency may not be a consequence of the tissue content, but a higher specific activity.

Example 18: Achiral Monophosphothioate Modifications Tested do not Provide the Portable Benefits Seen with Achiral Phosphorodithioate Linkages Compounds Tested (Sequence Motif=SEQ ID NO 1)

| | |
|---|---|
| #1 | GCa■ttggtatTCA |
| #2 | GCat■tggtatTCA |
| #3 | GCatt■ggtatTCA |
| #4 | GCattg■gtatTCA |
| #5 | GCattgg■tatTCA |

-continued

| | |
|---|---|
| #6 | GCattggt■atTCA |
| #7 | GCattggta■tTCA |
| #8 | GCattggtat■TCA |
| Ref. | GCattggtatTCA |
| #9 | GC†attggtatTCA |
| #10 | GCa†ttggtatTCA |
| #11 | GCat†tggtatTCA |
| #12 | GCatt†ggtatTCA |
| #13 | GCattg†gtatTCA |
| #14 | GCattgg†tatTCA |
| #15 | GCattggt†atTCA |
| #16 | GCattggta†tTCA |

Upper case letter: beta-D-oxy LNA nucleoside; lower case letter DNA nucleoside;
■= 3'-S phosphorothioate linkage, all other linkages are phosphorothioate.† = 5'-S phosphorothioate linkage, all other linkages are phosphorothioate.

In this study we synthesised a series of 3' or 5'S modified phosphorothioates oligonucleotide gapmers targeting ApoB—the positioning of the sulfur in the backbone linkages results in an achiral internucleoside linkage. For synthesis methods see WO2018/019799.

The compounds were tested in vitro as previously described—e.g. see example 8.

The results are shown in FIG. 18A: The results show that in general the achiral monophosphorothioates were detremental to potency of the compounds, although in some instances the compounds retained potency. This appears to correlate with the cellular content (FIG. 18B).

Example 19: Chiral Phosphorodithioate Modifications can Provide Benefits to Antisense Oligonucleotide Gapmers Compounds Tested (Sequence Motif=SEQ ID NO 1)

| | |
|---|---|
| #1 | GCa◆ttggtatTCA |
| #2 | GCat◆tggtatTCA |
| #3 | GCatt◆ggtatTCA |
| #4 | GCattg◆gtatTCA |
| #5 | GCattgg◆tatTCA |
| #6 | GCattggt◆atTCA |
| #7 | GCattggta◆tTCA |
| #8 | GCattggtat◆TCA |
| Ref. | GCattggtatTCA |

Upper case letter: beta-D-oxy LNA nucleoside; lower case letter DNA nucleoside;
◆= chiral phosphorodithioate linkage, all other linkages are phosphorothioate.

In this study we synthesised a series of stereorandom chiral phosphorodithioates oligonucleotide gapmers targeting ApoB—the positioning of the sulfur in the backbone linkages results in an chiral internucleoside linkage.

The compounds were tested in vitro as previously described—e.g. see example 8.

The results are shown in FIG. 19A: The results show that in some positions the chiral phosphorodithioate compounds were as potent as the reference compound, indicating the chiral phosphorodithioate was not incompatible with antisense functionality—however the benefit was compound specific (i.e. does not appear portable). A similar picture is seen with regards to cellular uptake (FIG. 19B), although there does not appear to be a correlation between antisense activity and cellular uptake.

Example 20: In Vivo Study Using Htra-1 Targeting Achiral Phosphorodithioates Modified Gapmers Compounds Tested All compounds have the sequence: TATttacctggtTGTT (SEQ ID NO 4), wherein capital letters are beta-D-oxy LNA nucleosides, lowercase letters are DNA nucleosides. In the following table, the backbone motif represents the pattern of backbone modifications for each internucleoside linkage starting at the linkage between the 5' dinucleotide, and finishing with the internucleoside linkage between the 3' dinucleotide (left to right). X=stereorandom phosphorothioate internucleoside linkage, P=achiral phosphorodithioate (*), S=Sp stereodefined phosphorothioate internucleoside linkage, R=Rp stereodefined phosphorothioate internucleoside linkage.

| | | |
|---|---|---|
| Htra1#Parent | TATttacctggtTGTT | XXXXXXXXXXXXXXX |
| Htra1#1 | TATttacctggtTGTT | XXXPXXXXXXXXXXX |
| Htra1#2 | TATttacctggtTGTT | XXXXPXXXXXXXXXX |
| Htra1#3 | TATttacctggtTGTT | XXXXXPXXXXXXXXX |
| Htra1#4 | TATttacctggtTGTT | XXXXXXPXXXXXXXX |
| Htra1#5 | TATttacctggtTGTT | XXXXXXXPXXXXXXX |
| Htra1#6 | TATttacctggtTGTT | XXXXXXXXPXXXXXX |
| Htra1#7 | TATttacctggtTGTT | XXXXXXXXXPXXXXX |
| Htra1#8 | TATttacctggtTGTT | XXXXXXXXXXPXXXX |
| Htra1#9 | TATttacctggtTGTT | XXXXXXXXXXXPXXX |
| Htra1#10 | TATttacctggtTGTT | XXXXPPPPXXXXXXX |
| Htra1#11 | TATttacctggtTGTT | XXXXXXPPPPXXXXX |
| Htra1#12 | TATttacctggtTGTT | XXXXXXXXPPPPXXX |
| Htra1#13 | TATttacctggtTGTT | PSRRRSSSRRRRRRP |
| Htra1#14 | TATttacctggtTGTT | PSRRRSSSRRRRPXP |
| Htra1#15 | TATttacctggtTGTT | PRRRRSSSSRRRRSP |
| Htra1#16 | TATttacctggtTGTT | PRRRRSSSSRRRRSS |
| Htra1#17 | TATttacctggtTGTT | RRRRRSSSSRRRRSP |
| Htra1#18 | TATttacctggtTGTT | PXPRRSSSSRRRPXP |
| Htra1#19 | TATttacctggtTGTT | PXXRRSSSSRRRXXP |
| Htra1#20 | TATttacctggtTGTT | PXXXXXXXXXXXXXX |
| Htra1#21 | TATttacctggtTGTT | XXPXXXXXXXXXXXX |
| Htra1#22 | TATttacctggtTGTT | XXXXXXXXXXXXPXX |

-continued

| | | |
|---|---|---|
| Htra1#23 | TATttacctggtTGTT | XXXXXXXXXXXXXXP |
| Htra1#24 | TATttacctggtTGTT | PXXXXXXXXXXXXXP |
| Htra1#25 | TATttacctggtTGTT | PXPXXXXXXXXXPXP |
| Htra1#26 | TATttacctggtTGTT | XPXXXXXXXXXXXXX |
| Htra1#27 | TATttacctggtTGTT | PPPXXXXXXXXXPXP |
| Htra1#28 | TATttacctggtTGTT | PXXXXXXXXXXXXPP |
| Htra1#29 | TATttacctggtTGTT | PPXXXXXXXXXXXXP |
| Htra1#30 | TATttacctggtTGTT | PPXXXXXXXXXXXPP |
| Htra1#31 | TATttacctggtTGTT | PPXXXXXXXXXXPPP |
| Htra1#32 | TATttacctggtTGTT | PPPXXXXXXXXXXPP |
| Htra1#33 | TATttacctggtTGTT | PPPXXXXXXXXXPPP |
| Htra1#34 | TATttacctggtTGTT | PSPRRSSSSRRRPRP |
| Htra1#35 | TATttacctggtTGTT | PSPRRSSSSRRRPSP |
| Htra1#36 | TATttacctggtTGTT | PRPRRSSSSRRRPSP |
| Htra1#37 | TATttacctggtTGTT | PRPRRSSSSRRRPRP |
| Htra1#38 | TATttacctggtTGTT | PPPPRRSSSSRRRPPP |

Experimental:

Human glioblastoma U251 cell line was purchased from ECACC and maintained as recommended by the supplier in a humidified incubator at 37° C. with 5% $CO_2$. For assays, 15000 U251 cells/well were seeded in a96 multi well plate in starvation media (media recommended by the supplier with the exception of 1% FBS instead of 10%). Cells were incubated for 24 hours before addition of oligonucleotides dissolved in PBS. Concentration of oligonucleotides: 5, 1 and 0.2 µM. 4 days after addition of oligonucleotides, the cells were harvested. RNA was extracted using the PureLink Pro 96 RNA Purification kit (Ambion, according to the manufacturer's instructions). cDNA was then synthesized using M-MLT Reverse Transcriptase, random decamers RETROscript, RNase inhibitor (Ambion, according the manufacturer's instruction) with 100 mM dNTP set PCR Grade (Invitrogen) and DNase/RNase free Water (Gibco). For gene expressions analysis, qPCR was performed using TagMan Fast Advanced Master Mix (2×) (Ambion) in a doublex setup. Following TaqMan primer assays were used for qPCR: HTRA1, Hs01016151_ml (FAM-MGB) and house keeping gene, TBP, Hs4326322E (VIC-MGB) from Life Technologies. EC50 determinations were performed in Graph Pad Prism6. The relative HTRA1 mRNA expression level in the table is shown as % of control (PBS-treated cells).

Results:

| | mRNA level remaining at varions doses | | | | Potency EC50 | Max Efficacy mRNA level |
|---|---|---|---|---|---|---|
| | 5 µM | 1 µM | 0.2 µM | 1 µM | [µM] | [% of ctrl] |
| Htra1 # Parent | 18 | 38 | 116 | 58 | 1.16 | 5.9 |
| Htra1 #1 | 34 | | | | | |
| Htra1 #2 | 50 | | | | | |
| Htra1 #3 | 28 | | | | | |
| Htra1 #4 | 44 | | | | | |
| Htra1 #5 | 39 | | | | | |
| Htra1 #6 | 47 | | | | | |
| Htra1 #7 | 41 | | | | | |
| Htra1 #8 | 44 | | | | | |
| Htra1 #9 | 47 | | | | | |
| Htra1 #10 | 36 | | | | | |
| Htra1 #11 | 53 | | | | | |
| Htra1 #12 | 36 | | | | | |
| Htra1 #13 | 11 | 57 | 97 | | | |
| Htra1 #14 | 3 | 18 | 83 | | | |
| Htra1 #15 | 3 | 18 | 85 | | | |
| Htra1 #16 | 4 | 24 | 85 | | | |
| Htra1 #17 | 3 | 19 | 108 | | | |
| Htra1 #18 | 2 | 10 | 76 | | 0.15 | 4.0 |
| Htra1 #19 | 4 | 35 | 90 | | 0.44 | 3.7 |
| Htra1 #20 | 25 | 87 | 96 | 57 | | |
| Htra1 #21 | 22 | 73 | 78 | | | |
| Htra1 #22 | 24 | | 100 | | | |
| Htra1 #23 | 20 | 50 | 117 | 53 | 0.91 | 9.0 |
| Htra1 #24 | 5 | 51 | 136 | 44 | | |
| Htra1 #25 | 3 | 27 | 69 | | | |
| Htra1 #26 | 27 | 72 | 93 | | | |
| Htra1 #27 | 7 | 30 | 99 | | 0.35 | 4.7 |
| Htra1 #28 | | | | 67 | | |
| Htra1 #29 | | | | 55 | | |
| Htra1 #30 | | | | 56 | | |
| Htra1 #31 | | | | 54 | | |
| Htra1 #32 | | | | 61 | | |
| Htra1 #33 | | | | 54 | | |
| Htra1 #34 | | | | 54 | 0.78 | 5.1 |
| Htra1 #35 | | | | 20 | 0.17 | 3.6 |
| Htra1 #36 | | | | 15 | 0.13 | 3.1 |
| Htra1 #37 | | | | 42 | 0.69 | 3.9 |
| Htra1 #38 | | | | 24 | 0.23 | 4.2 |

Example 21: A PS2 Walk on a LNA Mixmer Targeting TNFRSF1B Exon 7 Skipping

We have previously identified that the skipping of TNFRSF1B exon 7 using a mixmer (13'mer) SSO #26—is highly effective in targeting the 3' splice site of intron 6-exon 7 of TNFRSF1B (see WO2008131807& WO2007058894 for background information).

This experiment was established to determine whether the presence of phosphorodithioate linkages of formula (IA) or (IB) (PS2) can be useful in further enhancing the splice modulation activity of splice switching oligonucleotides. To determine the effect, we introduced phosphorodithioates linkages of formula (IA) or (IB) in different positions of the parent oligonucleotide SSO #26 and synthesized the following compounds (Table below).

Compounds tested: Dithioate modified oligonucleotides of the parent oligonucleotide (SSO #26). Phosphorodithioate internucleoside linkages of formula ((IA) or (IB)) were introduced in positions marked with a *, all other internucleoside linkages are phosphorothioate internucleoside linkages (stereorandom), capital letters represent beta-D-oxy LNA nucleosides, and LNA Care 5-methyl-cytosine, lower case letters represent DNA nucleosides.

| Compounds (Sequence motif = SEQ ID NO 5) | |
|---|---|
| SSO#1 | CAaT*cAG*tcCtA*G |
| SSO#2 | CAaTcAG*tcCtA*G |
| SSO#3 | C*AaTcAGtcC*tAG |
| SSO#4 | C*AaTcAGtcCtAG |
| SSO#5 | CA*aTcAGtcCtAG |
| SSO#6 | CAa*TcAGtcCtAG |
| SSO#7 | CAaT*cAGtcCtAG |
| SSO#8 | CAaTc*AGtcCtAG |
| SSO#9 | CAaTcA*GtcCtAG |
| SSO#10 | CAaTcAG*tcCtAG |
| SSO#11 | CAaTcAGt*cCtAG |
| SSO#12 | CAaTcAGtc*CtAG |
| SSO#13 | CAaTcAGtcC*tAG |
| SSO#14 | CAaTcAGtcCt*AG |
| SSO#15 | CAaTcAGtcCtA*G |
| SSO#16 | C*A*aT*cA*G*tcC*tA*G |
| SSO#17 | C*AaT*cAG*tcC*tA*G |
| SSO#18 | C*A*aTc*A*GtcCt*A*G |
| SSO#19 | C*A*aTcAG*t*cCt*A*G |
| SSO#20 | C*A*a*T*cA*G*t*cCtAG |
| SSO#21 | CAaTcA*G*t*cCt*A*G |
| SSO#22 | CAa*Tc*AGt*c*Ct*AG |
| SSO#23 | CAa*Tc*AGt*cCt*AG |
| SSO#24 | CAa*TcAGt*c*Ct*AG |
| SSO#25 | CAa*Tc*AGtc*CtAG |
| SSO#26 | CAaTcAGtcCtAG |

Experimental:

Oligonucleotide uptake and exon skipping in Colo 205 cells (human colorectal adenocarcinoma) was analyzed by gymnotic uptake at two different concentrations (5 μM and 25 μM). Cells were seeded in 96 well plates (25,000 cells per well) and the oligonucleotide added. Three days after addition of oligonucleotides, total RNA was isolated from 96 well plates using Qiagen setup. The percentage of splice-switching was analyzed by droplet digital PCR (BioRad) with a FAM-labelled probe spanning the exon 6-8 junction (exon 7 skipping) and the total amount of TNFRSF1B (wild type and exon 7 skipped) was analyzed with a HEX-labelled probe and primers from IDT spanning exon 2-3. The presence of a phosphorodithioate linkage has an effect on the ability of an oligonucleotide to introduce exon skipping (FIG. 20). At 5 μM, the most potent PS2 oligonucleotide increases the exon skipping by more than two fold, where the parent (SSO #26) shows approximately 10% exon skipping, SSO #25 shows more than 20% exon 7 skipping. At 25 μM, the most potent oligonucleotide reaches more than 60% exon skipping (SSO #7), again more than 2 fold better than the parent. Oligonucleotide SSO #22, in which all DNA nucleotides have a dithioate modification (PS2) instead of the phosphorothioate modification (PS) shows increased activity, compared to the parent, and is the third most potent oligonucleotide at 5 μM, and second most potent splice switching oligonucleotide at 25 μM (FIG. 20). Exchanging all linkages between LNA nucleosides with a PS2 linkage (SSO #16) however reduced the potency in splice switching compared to the parent oligonucleotide (FIG. 20). Furthermore, it is clear that introducing a PS2 at certain positions, may not be beneficial for the exon skipping activity and at 5 μM, SSO #1, SSO #9, SSO #11, SSO #12 and SSO #14 do not show significant splice switching activity at the lower concentration, but all were effective at the higher concentration (FIG. 20). This examples illustrate that the PS2 linkage is compatible with splice modulating oligonucleotides and further emphasizes a clear benefit in introducing PS2 linkages adjacent to DNA nucleosides, or between adjacent DNA nucleosides, within the mixmer oligonucleotide, such as LNA mixmers—these designs were notably more effective in modulating splicing.

Materials and Methods

Assay to detect TNFRSF1B exon 7 skipping by droplet digital PCR

```
Forward sequence:
                                          (SEQ ID NO 6)
CAACTCCAGAACCCAGCACT

Reverse sequence:
                                          (SEQ ID NO 7)
CTTATCGGCAGGCAAGTGAG

Probe Sequence:
                                          (SEQ ID NO 8)
GCACAAGGGCTTCTCAACTGGAAGAG

Fluorophore: FAM
```

Assay to detect total amount of TNFRSF1B

IDT assay Hs.PT.58.40638488 spanning exon 2-3

Example 22: The Stability of Mixmer Oligos Containing Phosphorodithioates Modifications Three dithioate modified oligonucleotides of the parent (SSO #26) were selected for stability assay using S1 nuclease (table 2). The selected oligonucleotides were incubated at 37° C. at 25 μM for either 30 min or 2 h in 100 μL reaction buffer containing 1× S1 Nuclease buffer, and 10U of S1 nuclease according to manufacturer's instruction (Invitrogen, Catalogue no. 18001-016). The S nuclease reaction was stopped by adding 2 μL of 500 mM EDTA solution to the 100 μL reaction mixture. 2.5 μL of the reaction mixture was diluted in Novex™ TBE-Urea 2× sample buffer (LC6876 Invitrogen) and loaded onto Novex™ 15% TBE-Urea gels (EC6885BOX, Invitrogen). The gels were run for approximately 1 hour at 180 V, afterwards gel images were acquired with SYBR gold staining (S11494, Invitrogen) and the ChemiDoc™ Touch Imaging System (BIO-RAD).

The stability of the PS2 containing oligonucleotides was tested with 30 and 120 minutes incubation of the S1 nuclease. The position of the PS2 linkage is influencing the stability, and the presence of a PS2 3' to a DNA nucleotide (SSO #14) has the greatest impact (FIG. 21). After 30 minutes of incubation with S nuclease, the parent oligonucleotide is almost degraded, whereas the PS2 modified oligos shows a strong band representing the 13'mer. In addition, SSO #14 shows stronger bands representing degradation products indicating a stabilization of the remaining oligo, even after the initial cleavage by S1 nuclease (FIG. 21, lane 5+9).

These data illustrate that the presence of a phosphorodithioates when introduced into oligonucleotides, such as mixmer oligonucleotides, provides protection against endonuclease activity—and surprisingly this is achieved whilst maintaining efficacy of the oligonucelotides, indeed as shown in the present experiments, the splice modulating activity may be notably improved. It is considered that PS2 linkages adjacent to DNA nucleosides, or between DNA nucleosides, in a mixmer oligonucelotides, herein illustrated by mixmers comprising LNA and DNA nucleosides enhances endonuclease stability. For use in antisense oligonucleotides, such as mixmers (SSOs or antimiRs for example), it is therefore considered that using PS2 linkages between contiguous DNA nucleosides is beneficial. Such benefits can also be provided by using a 5' or 3' PS2 linkage adjacent to a DNA nucleoside which is flanked 5' or 3' (respectively) by a 2'sugar modified nucleoside, such as LNA or MOE.

The invention therefore further provides improved antisense oligonucelotides for use in occupation based mechanisms, such as in splice modulating or for microRNA inhibition.

The invention claimed is:

1. A compound of formula (II)

(II)

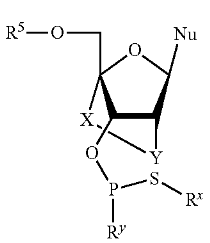

wherein

X is oxygen, sulfur, —$CR^aR^b$—, —$C(R^a)$=$C(R^b)$—, —C(=$CR^aR^b$)—, —$C(R^a)$=N—, —$Si(R^a)_2$—, —$SO_2$—, —$NR^a$—; —O—$NR^a$—, —$NR^a$—O—, —C(=J)-, Se, —O—$NR^a$—, —$NR^a$—$CR^aR^b$—, —$N(R^a)$—O— or —O—$CR^aR^b$—;

Y is oxygen, sulfur, —$(CR^aR^b)_n$—, —$CR^aR^b$—O—$CR^aR^b$—, —$C(R^a)$=$C(R^b)$—, —$C(R^a)$=N—, —$Si(R^a)_2$—, —$SO_2$—, —$NR^a$—, —C(=J)-, Se, —O—$NR^a$—, —$NR^a$—$CR^aR^b$—, —$N(R^a)$—O— or —O—$CR^aR^b$—;

with the proviso that —X—Y— is not —O—O—, $Si(R^a)_2$—$Si(R^a)_2$—, —$SO_2$—$SO_2$—, —$C(R^a)$=$C(R^b)$—$C(R^a)$=$C(R^b)$, —$C(R^a)$=N—$C(R^a)$=N—, —$C(R^a)$=N—$C(R^a)$=$C(R^b)$, —$C(R^a)$=$C(R^b)$—$C(R^a)$=N— or —Se—Se—;

J is oxygen, sulfur, =$CH_2$ or =$N(R^a)$;

$R^a$ and $R^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, —OC(=$X^a$)$R^c$, —OC(=$X^a$)$NR^cR^d$ and —$NR^e$C(=$X^a$)$NR^cR^d$;

or two geminal $R^a$ and $R^b$ together form optionally substituted methylene;

or two geminal $R^a$ and $R^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocylyl, aryl and heteroaryl;

$X^a$ is oxygen, sulfur or —$NR^c$;

$R^c$, $R^d$ and $R^e$ are independently selected from hydrogen and alkyl; and n is 1, 2 or 3;

$R^5$ is a hydroxyl protecting group;

$R^x$ is phenyl, nitrophenyl, phenylalkyl, halophenylalkyl, cyanoalkyl, phenylcarbonylsulfanylalkyl, halophenylcarbonylsulfanylalkyl alkylcarbonylsulfanylalkyl or alkylcarbonylcarbonylsulfanylalkyl;

$R^y$ is dialkylamino or pyrrolidinyl; and

Nu is a nucleobase or a protected nucleobase.

2. A compound according to claim 1, wherein —X—Y— is —$CH_2$—O—, —$CH(CH_3)$—O— or —$CH_2CH_2$—O—.

3. A compound according to claim 1 of formula (III) or (IV)

(III)

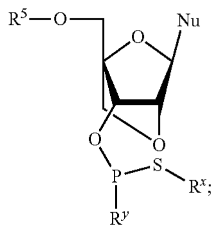

(IV)

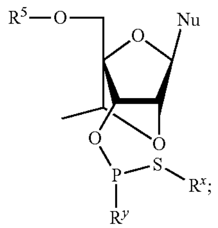

wherein $R^5$, $R^x$, $R^y$ and Nu are as defined in claim 1.

4. A compound of formula (IIb)

(IIb)

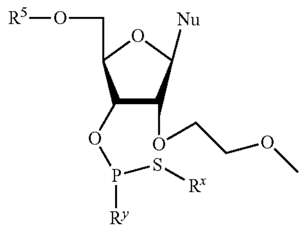

wherein $R^5$ is a hydroxyl protecting group, $R^x$ is phenyl, nitrophenyl, phenylalkyl, halophenylalkyl, cyanoalkyl, phenylcarbonylsulfanylalkyl, halophenylcarbonylsulfanylalkyl alkylcarbonylsulfanylalkyl or alkylcarbonylcarbonylsulfanylalkyl;

$R^y$ is dialkylamino or pyrrolidinyl; and

Nu is a nucleobase or a protected nucleobase.

5. A compound according to claim 1, wherein $R^x$ is phenyl, nitrophenyl, phenylmethyl, dichlorophenylmethyl, cyanoethyl, methylcarbonylsulfanylethyl, ethylcarbonylsulfanylethyl, isopropylcarbonylsulfanylethyl, tert. -butylcarbonylsulfanylethyl, methylcarbonylcarbonylsulfanylethyl or difluorophenylcarbonylsulfanylethyl.

6. A compound according to claim 1, wherein $R^x$ is phenylcarbonylsulfanylalkyl.

7. A compound according to claim 1, wherein $R^x$ is phenylcarbonylsulfanylethyl.

8. A compound according to claim 1, wherein $R^y$ is diisopropylamino or pyrrolidinyl.

9. A compound according to claim 1, wherein $R^y$ is pyrrolidinyl.

10. A compound according to claim 1 of formula (V)

(V)

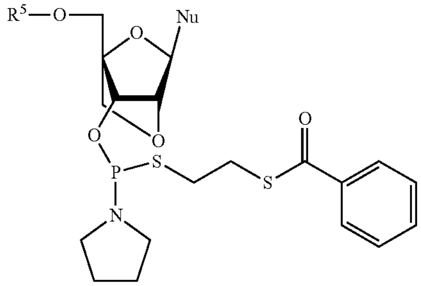

wherein $R^5$ and Nu are as defined in claim 1.

11. A compound according to claim 4 of formula (Vb)

(Vb)

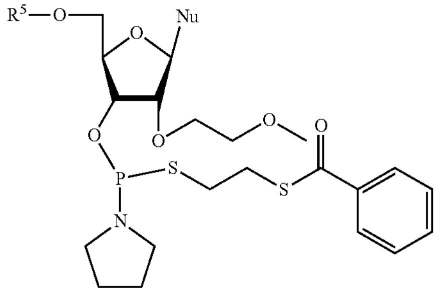

wherein $R^5$ and Nu are as defined in claim 4.

12. A compound according to claim 1, wherein Nu is thymine, protected thymine, adenosine, protected adenosine, cytosine, protected cytosine, 5-methylcytosine, protected 5-methylcytosine, guanine, protected guanine, uracyl or protected uracyl.

13. A compound according to claim 1 selected from

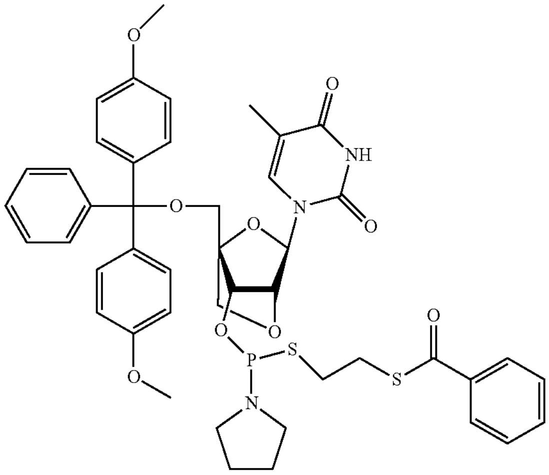
;

-continued
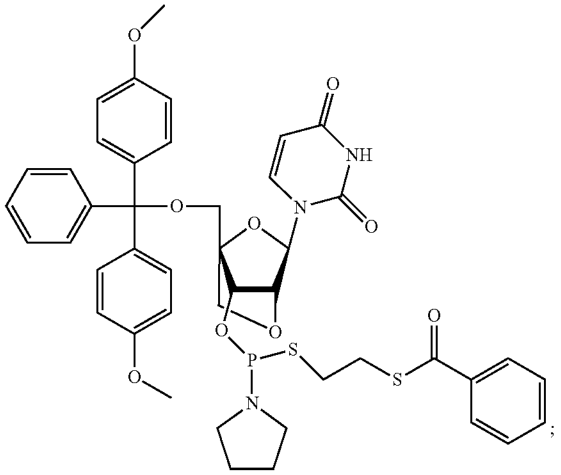
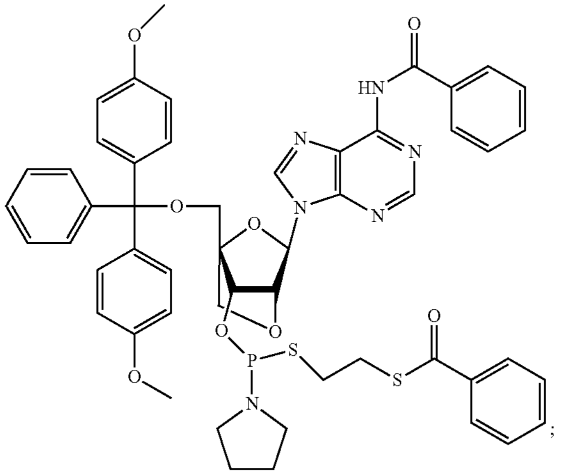
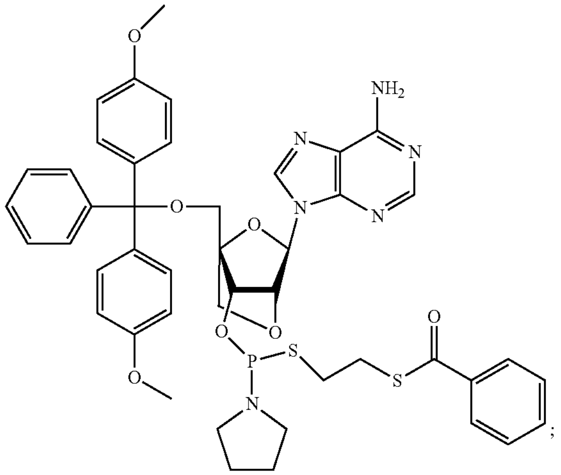
-continued
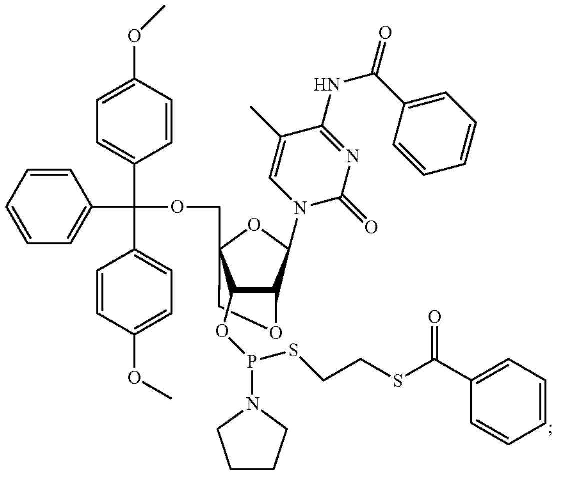
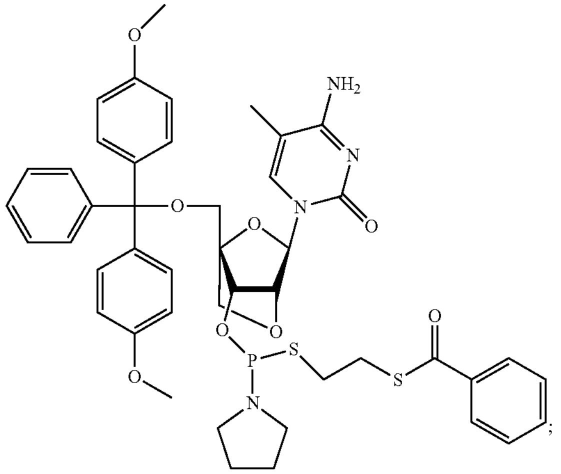
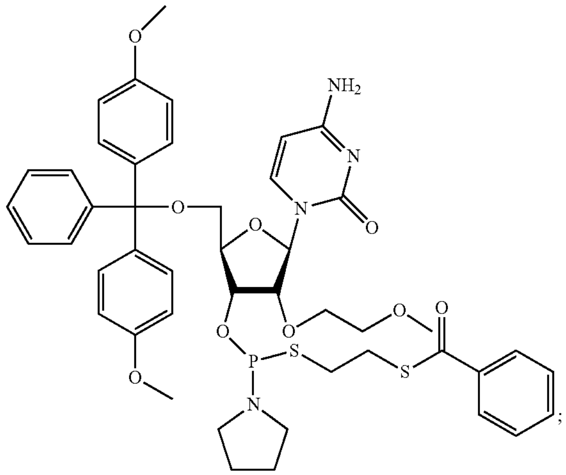

-continued
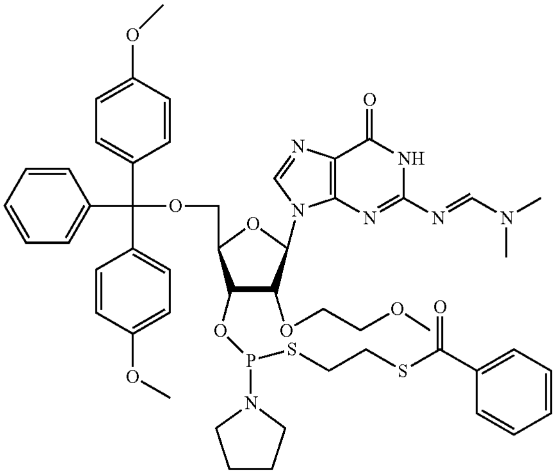
;
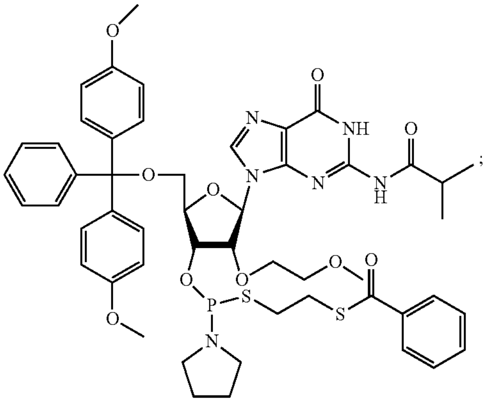
; and
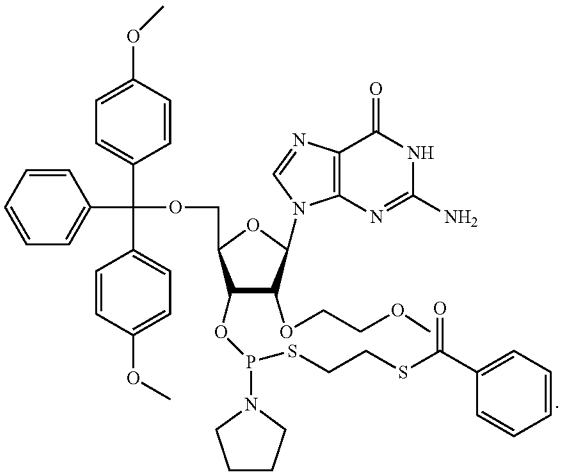
.
14. A compound according to claim 4 selected from
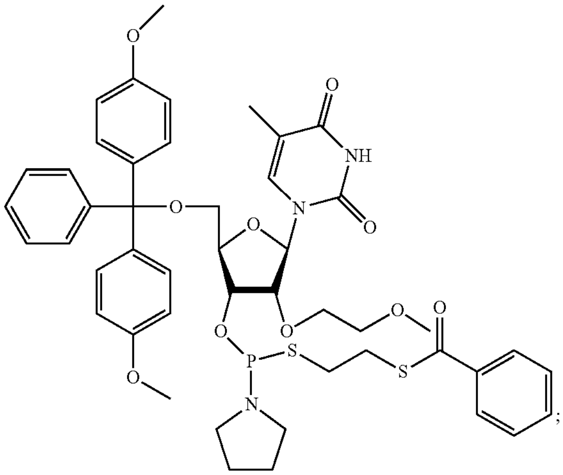
;
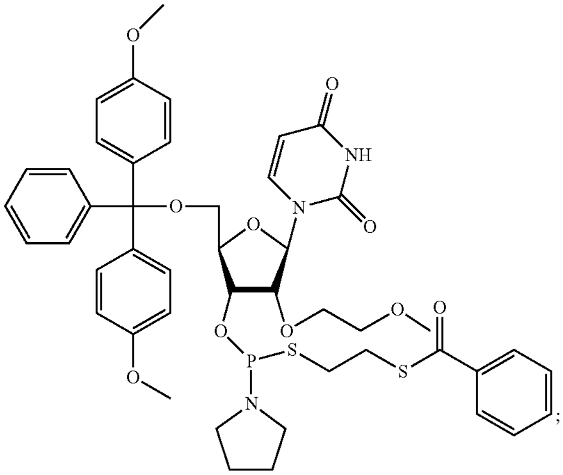
;
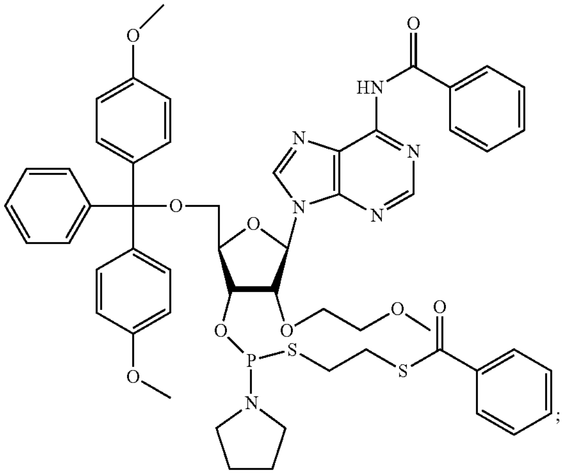
;

-continued
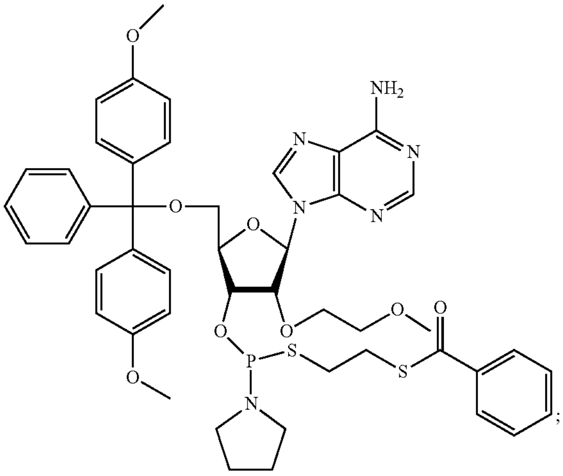
;
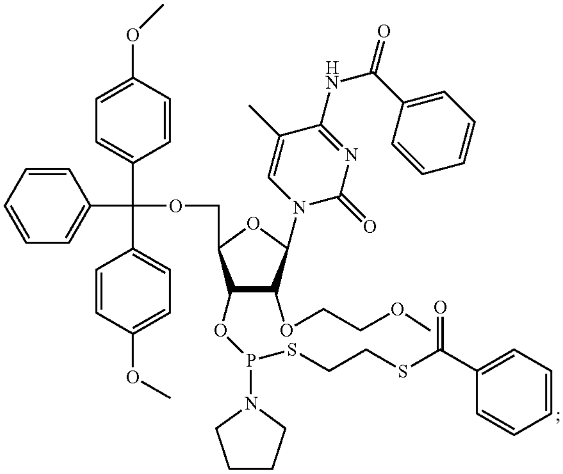
;
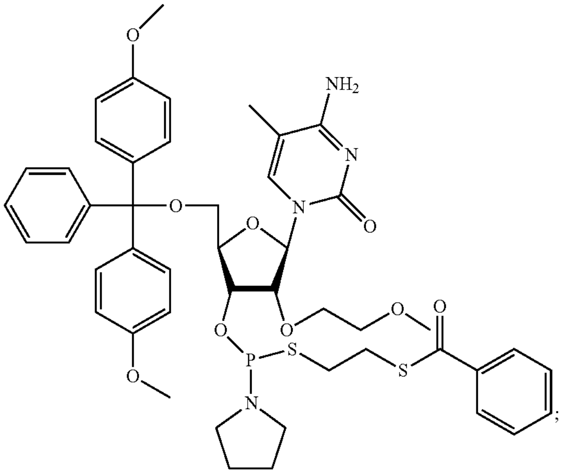
;
-continued
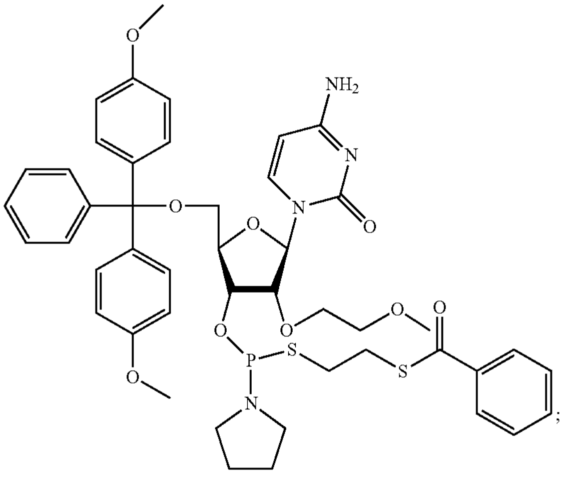
;
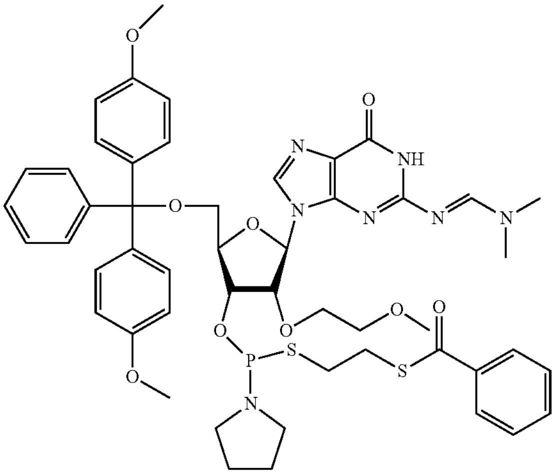
;
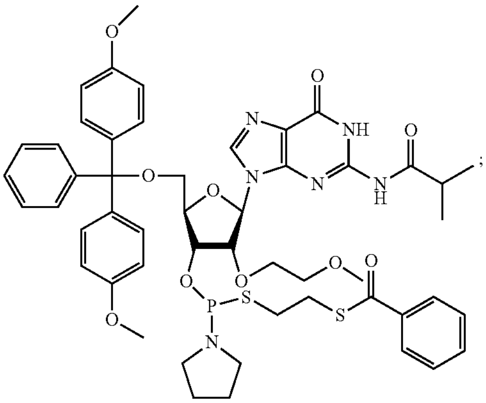
; and -continued

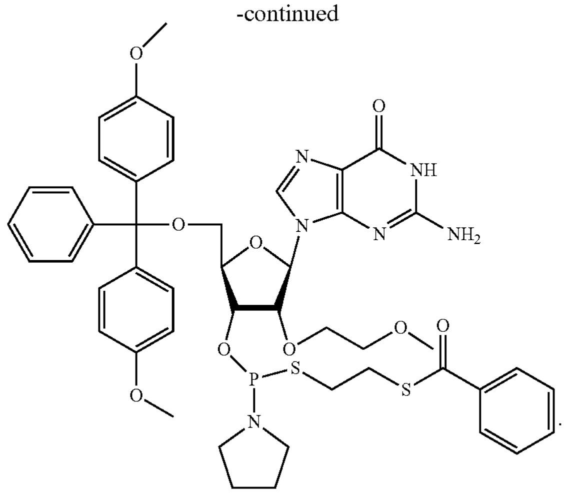

15. A process for the manufacture of a compound of formula (II) according to claim 1, comprising reacting a 5'-protected LNA or MOE nucleoside with a phosphine and a mono-protected dithiol in the presence of an acidic coupling agent and a silylation agent to form a product, wherein either the product is the compound of formula (II) or the process further comprises manufacturing the compound of formula (II) from the product.

16. A process according to claim 15 comprising the reaction of a compound of formula (C)

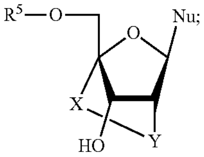

(C)

with a compound of formula $P(R^y)_3$ and a compound of formula $HSR^x$ in the presence of an acidic coupling agent and a silylation agent, wherein X, Y, $R^5$, Nu, $R^x$ and $R^y$ are as defined in claim 1.

17. A process according to claim 15, comprising the reaction of a compound of formula (C1)

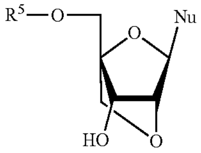

(C1)

with a compound of formula $P(R^y)_3$ and a compound of formula $HSR^x$ in the presence of an acidic coupling agent and a silylation agent, wherein $R^5$, Nu, $R^x$ and $R^y$ are as defined in claim 1.

18. A process according to claim 15, wherein the crude compound of formula (II) is purified by preparative HPLC.

19. A process according to claim 18, wherein the crude compound of formula (II) is eluted with a gradient of acetonitrile versus ammonium hydroxide in water.

20. A method of using a compound according to claim 1 in the manufacture of an oligonucleotide, comprising providing the compound according to claim 1; and using the compound to manufacture the oligonucleotide, wherein the manufacturing comprises forming at least one phosphorodithioate internucleoside linkage between the compound and another nucleotide of the oligonucleotide.

* * * * *

SEQUENCE LISTING

```
<160> NUMBER OF SEQ ID NOS: 19

<210> SEQ ID NO 1
<211> LENGTH: 13
<212> TYPE: DNA
<213> ORGANISM: Artificial
<220> FEATURE:
<223> OTHER INFORMATION: Oligonucleotide motif

<400> SEQUENCE: 1

gcattggtat tca                                                    13


<210> SEQ ID NO 2
<211> LENGTH: 18
<212> TYPE: DNA
<213> ORGANISM: artificial
<220> FEATURE:
<223> OTHER INFORMATION: Oligonucleotide motif

<400> SEQUENCE: 2

tctcccagcg tgcgccat                                               18


<210> SEQ ID NO 3
<211> LENGTH: 16
<212> TYPE: DNA
<213> ORGANISM: artificial
<220> FEATURE:
<223> OTHER INFORMATION: Oligonucleotide motif

<400> SEQUENCE: 3

gagttacttg ccaact                                                 16


<210> SEQ ID NO 4
<211> LENGTH: 16
<212> TYPE: DNA
<213> ORGANISM: artificial
<220> FEATURE:
<223> OTHER INFORMATION: TATTTACCTGGTTGTT

<400> SEQUENCE: 4

tatttacctg gttgtt                                                 16


<210> SEQ ID NO 5
<211> LENGTH: 13
<212> TYPE: DNA
<213> ORGANISM: artificial
<220> FEATURE:
<223> OTHER INFORMATION: Oligonucleotide motif

<400> SEQUENCE: 5

caatcagtcc tag                                                    13
```

<210> SEQ ID NO 6
<211> LENGTH: 20
<212> TYPE: DNA
<213> ORGANISM: artificial
<220> FEATURE:
<223> OTHER INFORMATION: Primer sequence

<400> SEQUENCE: 6
caactccaga acccagcact 20

<210> SEQ ID NO 7
<211> LENGTH: 20
<212> TYPE: DNA
<213> ORGANISM: artificial
<220> FEATURE:
<223> OTHER INFORMATION: Primer sequence

<400> SEQUENCE: 7
cttatcggca ggcaagtgag 20

<210> SEQ ID NO 8
<211> LENGTH: 26
<212> TYPE: DNA
<213> ORGANISM: artificial
<220> FEATURE:
<223> OTHER INFORMATION: Primer sequence

<400> SEQUENCE: 8
gcacaagggc ttctcaactg gaagag 26

<210> SEQ ID NO 9
<211> LENGTH: 2138
<212> TYPE: DNA
<213> ORGANISM: homo sapiens

<400> SEQUENCE: 9
caatgggctg ggccgcgcgg ccgcgcgcac tcgcacccgc tgcccccgag gccctcctgc 60
actctccccg gcgccgctct ccggccctcg ccctgtccgc cgccaccgcc gccgccgcca 120
gagtcgccat gcagatcccg cgcgccgctc ttctcccgct gctgctgctg ctgctggcgg 180
cgcccgcctc ggcgcagctg tcccgggccg gccgctcggc gcctttggcc gccgggtgcc 240
cagaccgctg cgagccggcg cgctgcccgc cgcagccgga gcactgcgag ggcggccggg 300
cccgggacgc gtgcggctgc tgcgaggtgt gcggcgcgcc cgagggcgcc gcgtgcggcc 360
tgcaggaggg cccgtgcggc gaggggctgc agtgcgtggt gcccttcggg gtgccagcct 420
cggccacggt gcggcggcgc gcgcaggccg gcctctgtgt gtgcgccagc agcgagccgg 480
tgtgcggcag cgacgccaac acctacgcca acctgtgcca gctgcgcgcc gccagccgcc 540
gctccgagag gctgcaccgg ccgccggtca tcgtcctgca gcgcggagcc tgcggccaag 600
ggcaggaaga tcccaacagt ttgcgccata aatataactt tatcgcggac gtggtggaga 660
agatcgcccc tgccgtggtt catatcgaat tgtttcgcaa gcttccgttt tctaaacgag 720
aggtgccggt ggctagtggg tctgggttta ttgtgtcgga agatggactg atcgtgacaa 780
atgcccacgt ggtgaccaac aagcaccggg tcaaagttga gctgaagaac ggtgccactt 840
acgaagccaa aatcaaggat gtggatgaga aagcagacat cgcactcatc aaaattgacc 900
accagggcaa gctgcctgtc ctgctgcttg gccgctcctc agagctgcgg ccgggagagt 960
tcgtggtcgc catcggaagc ccgttttccc ttcaaaacac agtcaccacc gggatcgtga 1020
gcaccaccca gcgaggcggc aaagagctgg ggctccgcaa ctcagacatg gactacatcc 1080

-continued agaccgacgc catcatcaac tatggaaact cgggaggccc gttagtaaac ctggacggtg 1140
aagtgattgg aattaacact ttgaaagtga cagctggaat ctcctttgca atcccatctg 1200
ataagattaa aaagttcctc acggagtccc atgaccgaca ggccaaagga aaagccatca 1260
ccaagaagaa gtatattggt atccgaatga tgtcactcac gtccagcaaa gccaaagagc 1320
tgaaggaccg gcaccgggac ttcccagacg tgatctcagg agcgtatata attgaagtaa 1380
ttcctgatac cccagcagaa gctggtggtc tcaaggaaaa cgacgtcata atcagcatca 1440
atggacagtc cgtggtctcc gccaatgatg tcagcgacgt cattaaaagg gaaagcaccc 1500
tgaacatggt ggtccgcagg ggtaatgaag atatcatgat cacagtgatt cccgaagaaa 1560
ttgacccata ggcagaggca tgagctggac ttcatgtttc cctcaaagac tctcccgtgg 1620
atgacggatg aggactctgg gctgctggaa taggacactc aagacttttg actgccattt 1680
tgtttgttca gtggagactc cctggccaac agaatccttc ttgatagttt gcaggcaaaa 1740
caaatgtaat gttgcagatc cgcaggcaga agctctgccc ttctgtatcc tatgtatgca 1800
gtgtgctttt tcttgccagc ttgggccatt cttgcttaga cagtcagcat ttgtctcctc 1860
ctttaactga gtcatcatct tagtccaact aatgcagtcg atacaatgcg tagatagaag 1920
aagccccacg ggagccagga tgggactggt cgtgtttgtg cttttctcca agtcagcacc 1980
caaaggtcaa tgcacagaga ccccgggtgg gtgagcgctg gcttctcaaa cggccgaagt 2040
tgcctctttt aggaatctct ttggaattgg gagcacgatg actctgagtt tgagctatta 2100
aagtacttct tacacattgc aaaaaaaaaa aaaaaaaa 2138

<210> SEQ ID NO 10
<211> LENGTH: 53384
<212> TYPE: DNA
<213> ORGANISM: homo sapiens

<400> SEQUENCE: 10
caatgggctg ggccgcgcgg ccgcgcgcac tcgcacccgc tgcccccgag gccctcctgc 60
actctccccg gcgccgctct ccggccctcg ccctgtccgc cgccaccgcc gccgccgcca 120
gagtcgccat gcagatcccg cgcgccgctc ttctcccgct gctgctgctg ctgctggcgg 180
cgcccgcctc ggcgcagctg tcccgggccg gccgctcggc gcctttggcc gccgggtgcc 240
cagaccgctg cgagccggcg cgctgcccgc cgcagccgga gcactgcgag ggcggccggg 300
cccgggacgc gtgcggctgc tgcgaggtgt gcggcgcgcc cgagggcgcc gcgtgcggcc 360
tgcaggaggg cccgtgcggc gaggggctgc agtgcgtggt gcccttcggg gtgccagcct 420
cggccacggt gcggcggcgc gcgcaggccg gcctctgtgt gtgcgccagc agcgagccgg 480
tgtgcggcag cgacgccaac acctacgcca acctgtgcca gctgcgcgcc gccagccgcc 540
gctccgagag gctgcaccgg ccgccggtca tcgtcctgca gcgcggagcc tgcggccaag 600
gtactccgcc gcgctcctgg gcagctcccc actctctcca tcccagctcg gacctgcttc 660
tgcgggactg gtgggcaggt tgaggggcag cgaagcgttg tggggtggcc agggcaactc 720
tcggggacag gcaggtgggc cccggggtgg cggatttccg cgggctgcct cggaaccgag 780
cttcgcgccc agcccggggc cggttctgcg cccagacgat gccagtacgc ccggcctgca 840
ctctggggct cgagacgccg ggcgaccggc catggagtgc cctgagggca accacacagc 900
gcggggaccc caggacaaat aagaggaatg ggggcataaa ggaaggagag aagttcagga 960
ctgggaattg gcgcctcgca gagcggcttc aggaccacaa gaagtcattt cggttgcttt 1020

-continued

```
ttcttctatt tacgtcctcc gtccccttta aaattcactg ctttgatcac gggaccgctc   1080
agtgaaaact gtatgtaact cttttggaaa ggaacagtgt ttgccggccc gccccggagt   1140
ttctccaaaa agtctacccc gagcagggaa cggtttggca ccgctctcgt ttcggcggcg   1200
ttgctgcctg tcttgctttc ctcgttttga gccagcccta caaaaatgaa agtggctcct   1260
tttgaataag ctgaatcggg ctttggatca cgaaatctgc agaggcggag aagggaccgg   1320
gttagtgatg aggaagaagt ctacccctct gttcctacag ccgcacacag gacctgttct   1380
ggcaggggag acggtggtga tgggggaagg agtggaatgg agcaatgtct aactctctcg   1440
cgggaccttc cggagagatg ctcctcatct tcaggcagag gccatgtgga aaaataatat   1500
cgagttcagc agcggccagc cccgcgttgt aggaaccaga cagcggggct tggcagtgcg   1560
cttgggcgca gccgtgccgc tgctgccgga ccccagtgct gcctcctcaa cacgggcagt   1620
gccaggagag gggcataggg gagcacagtg cagagggact ggtctagagt ttactttata   1680
ggaatatggt tcggtgtgac caactagggc ttagcatagt ttggcttacg tggacgggaa   1740
gatgccagag ccgaactggg tgaaattcga gattgcgtat ttcaccaaca caggagcaca   1800
gccctcggga aactcagcct agtcaggcag tagagagttg tcccggagag aagtgatcct   1860
gcagactcga gaaggggcat gatgatagca cacgtctgtt gagcacccag tctgtgtgcc   1920
gggtgtgtta cctctgtgac ctcatttggt caaacgagga ggcagttgct cctctctctc   1980
tcttttttt tcttaagaga cagggtctcc ctctgtcgcc catgctggag tgtagtggtg   2040
tgatcatggc tcactgcagc ctccgacccc tgggctcaat gattctcctg cttcagcctc   2100
ccaagtggct gggactacag gcggatgcca ccacacccag cttctcattc ccgttttaca   2160
gatagcggag ctaaggttga aaaacttgcc caaggtcatt cagctggaat ttaaacccag   2220
acagcctcat tcagaggagt cagcccagca cttaactcca agggtgtggg agaggggtca   2280
ggtgctgtaa atttcctggt gggctggacg tgcatccccc tcagagctgg gaacagcata   2340
cacaaagcct aagacttgtt tggaggtgaa tagatcagtg tggctgggga acgttttggg   2400
agggcagcag gagtgagcca ggctggtggc ccagagtccc agggctgaag aggctggctg   2460
tgccccgtgc cctgtgcgca gatgttcttg aactggagca actcaaagcc tagtgtagtg   2520
tagggctgac ctagcagtgg agtgcggaat gcatccaggg tggagagttt agactactgc   2580
aataatctgg gtgtgaggcg acaacattga aaaagcatgt ttttgtccaa aacaagccag   2640
ctgttactgg tctcgctgtt tgtggtctca tcgcacgggg tcctgagttg ctggcaccat   2700
gcgagccgcc taatttattg ctagtgaggc aagttgctta acaagttttg gagttggctg   2760
agtccctgtg tggaggaaaa caggtccccc attggccatc gggctcacag cgggcccccg   2820
gtgtaccagt gaggggacag ccacagaggg ataagcatgg tggctttgaa aggagggaga   2880
gacagagtgg gtacaatgct tttcttatcc ctccctcctt cttttgcaaa tatttattga   2940
gctctgtagg gtgtctgaca ccgtttgcat gtttgtctgt ctggcacatc ggaggtactt   3000
ggtacgagtg gattagtgaa tgaataaatg aatgaatgaa gacaaacggg aggtgcttgc   3060
gatacacagc cattctgttt ttccttagtg gaaggcactg ctttgctgcg ccccctctct   3120
ggatctcaca ctccaccctt gacttttcgg aggtgtttcc gaggacaggc gcctgggagc   3180
cagcagactt cattcagtcc aagccaggct ccaggactca acagctggtg cccacgggca   3240
ggtcacttga cgtcactgtt aaatgaggtg aattggctgc ctgctctggc tggaagattg   3300
gcgggagagt cactttagct gccatggaca tgagcctttt ctaggggtgc cacttgacta   3360
gaggcctgga gttggagcaa gtcatacacg gatctggaga cagagctctc gaggcaggag   3420
```

-continued cgggtgctgc gatttcaaat attataaggt ggctttgtct ggggcagagc atgccagggg 3480
atgagaggta gaaatgtcat cagatcaggg gtccccaggg aggtgactag cactttgggt 3540
cacagtagat ctttggatag aggaacatgt caccattcaa aggaaagcac tttcatctgt 3600
aagctgttta ttgaatagac ctcagagaac atctctgctc accgctctgg aaatgaaggc 3660
aaatcatcta tttcagaagt caatgcactg gcagggtttg gatgggaaag tatacaattc 3720
agctagagaa caaagatctg tcatctccag ctgtactggt cagatgatta caaaaaagaa 3780
aggaattgaa atactaatag ggtactaata atgagggcta acatatatgt tgtgcttatt 3840
ctatgccggg tgcatactaa ttcatttgat cctccggaca gtcctatgag tgagtgctgt 3900
agtcttccct gggttacagc tgggcagcta agtcacagag aagtaccttg ctcaggactg 3960
gtggtcccac acaactggat ggagagcctc gttcataacc accatgctgt gctgttgaca 4020
gagcaacaga gattttaaac caaccccagc taagccccag ctaatagctg aaataaacag 4080
ggctccagat ggctgtggct tagagatgga acaggacaga tcacagcctt cactctgcag 4140
gctcaggagc ctgaagacaa ggttgcctcc agttgccgtc agtgcagccc tcactaaaga 4200
aaagcaaaaa gagccgaggg actgtaggaa ggctgtttcc aagccagaga tccagacaaa 4260
ctgctcttga agagagaaag cccttccaga ttcccccatg tcccaaaaga ccagccggga 4320
ttccggacct ctgctaaaac atggacaaga agccaggaac gagacctgaa acagacttcc 4380
caaacagcag aagcctcatc catttctcct gctagtacat cctccaggaa agcccaccct 4440
actccatgca gcagcccaga caagcttgga ggtctgcaag ctgcaggggt gcccagaaac 4500
tccacccctg gaggttttta ggatcgcctg ctcctggtct caccccagag cctctaaagg 4560
cagaggctgt atgtacatac ctggtgaaga accaagggct tagatggttg ctttacttct 4620
tggagccctg gaatgtttgt aaaatttact tttttttttg agacagtgtc tcgttctgtc 4680
gcctacgctg gagtgcagtg gcgcgatctc ggctcactgc aagctccacc tcccgggttc 4740
atgccattct cctgccttag cctccagagt agctgggact acaggcaccc gccaccacgc 4800
ccagctaatt tttttgtatt ttttggtaga gacggggttt caccgtgtta gccaggatgg 4860
tctccatctc ctgaccttgt gatccgcccg ctttggcctc ccaaagtgct gggattacag 4920
gagtgagcca ctgcacccgt gccaaaatgt actttattta ggtgactctt tcgtgggaac 4980
ctcaaacaag caatcattgc tagctgagtg ctgaccctgt actgagctct ggggagacag 5040
ggttgaataa aacaaagtca ctgcccacag gtaacttata ttcaatacaa tgggggaaaa 5100
tacaatcact gcttccctgg ggttgtattt ttccattgtt aaagtgggca gtttgctcga 5160
gagtcatttt cactattggc aattcaaata caccttttgt cagttaaaaa acaagtgtgc 5220
cagggacctg agcttcatct tagggcaggg tgggtggaaa catttgtgag tctccagctt 5280
ttagtcacct gaaacttgga aacttggagg tcttttgagc agtttatgag tctctgcctg 5340
ctctggtcgg ctgccttctt ttattgctct gttggttttg ctaaagagtt aaaatattaa 5400
ggcttcataa aattaggaag ttaacaagct caaaaaccaa gtgtttgagt tacttcattc 5460
cactgagaga gctgtaaatg ggttgcattg gaacttaaaa taactgcatt gagtaagtga 5520
tggtggcggg caccatgagc taactgtggt cagaagcctg atggcctccg ctttggggct 5580
ggattctccg tttggagctg tgtgatcctg gatgagtttc atgccttgga ttcagaaatc 5640
agactttcca tgagcttata tttcaagtga ataaatagct ctggtcaggc ttaatttgaa 5700
gaagaagtaa gcttggcagt gggtgagggt tccttggaag gccaactggg gcggaggggc 5760
tgagggcaag cggctctggc ccttcctggg gtgttacctg accaggtaac agctccctcg 5820
acctctcgga gcctcggcag tgaggggatt gggccagttg atctctgagg ctccttttaa 5880
ctagaatggt ctgggatttt tctaagaaaa caagtctttg aggaggttgt ggtcacctca 5940
ttcctaattt aaagcctggg gaggcttcct tatgagctac ttctttttcc taaattattg 6000
atggttaaag ccaaggctgg catcgaatag atgtgatcca tcttgagcct ggttgctttg 6060
tgtttcagct ttgtactggc tgctgaagtc cccgggagac cacaggggtg acatgttcat 6120
ctccaagaga tgagcttcca cgagactcat accccttgct ccttccctgg ggctccaagg 6180
cctttgggtc atctgaagtg agataccctt gtgtcatttc atcttttcct tctccacctt 6240
ctctgccgtt aaaaaaaaaa gaagaaagag aaaaatccta ttaatagaga aaccgagaag 6300
tgtagccatt ctgaatgtgt ttccaaaagg ctcctggaag tggcatggaa gttacagtga 6360
ttcagcacta cttggtgacg tgtgcctaga accacagggg gacattagcc aggacaacac 6420
gcctcaggac agaagtaagt ggctgcgaag aggcatgtcc atcactgccg gaaagatgca 6480
gagttcagtt tttggagtca gtgctgagag ttccatttct aaattcattc agagcattta 6540
tttaacacct actgtgtgct cagaagtgta tcaggtatgg ggactcagag gtaagggctg 6600 gtggccccctg atctcaaggt actcgtggta gatagtatga tgctcagctt aagggctggg 6660
cttctgaagt cggattgcca ttttctggat gtgtggtgtt tcttgggtga cttcatctct 6720
aagtctcagt ttccccatca gtaagataag agaagtaata gcagatacat acgtagctct 6780
tagggcattg cagaatggaa ggacctcctt atatgaaacg caaagcactg tgcctgatgc 6840
attgctagaa ctcaggcaat attagcgtgt tgtcattgtc atcatcatca tcatcatcat 6900
catcatcatc atcatcatct tcaaggcact gacaaaggag tcagctgtgt gggaggagtg 6960
ctgggacact cttgtctccc tggggatgag gtgggtgggt gggttaggaa atcttcacag 7020
agaaggaggg tgatgtgaga cttctgtccg ggagctgact cggaatttgc catctaatat 7080
gttggaaaag gttctctggg cagaggtatc caaagtcact ttgcctgtca ccctttgagg 7140
tcccagttgt tgcctatatc atgtgaccag tgtgtggctt ctcttgaatt aagagctgca 7200
tgtctggact gcctgggatt ttacagatgt catctcgtta actctccctg gagcttgtga 7260
cacccaggag atggcagttt atagaagccc tggcaccttc ttgaatgatg cttggtttgg 7320
tttctatgca ctgggaattc ctcacaagga aagatttgtc acatcttaag gaaggaaaaa 7380
aaggcaaatt tgggagtcca tggataccct attattttag attccaggac aaattgtcga 7440
ataagcacgt ttcataaaaa caatcctccg cagcatcccg tgacagcagc tggtccctcg 7500
ccacaggata attatgtctc cttgtgcaca caaaagtctc cgagggcata ttgttgtggc 7560
tggagtttct gataatttcc aaattgaaca acctcagtcc taatgagtca gaggcttgtg 7620
caatattttc aaacctcagg aacatctttt tcattagttg tgcaataaag atggtaggcc 7680
tatctctgtg atgagctgtt ttttttctc aaagtttgat gagattcgcc gtagaattcc 7740
ttctcacata gtcttgggca agattttacc cgatcttcca acacatgagt catctcatat 7800
cctgtgacta agaagagctg tctctttggt gccagttttc taagtgcagt caccacttga 7860
tggagacgga tggacacagt tgggattgcc caggcagatg ggcaatcttg ccagctagac 7920
ataggggagg gaagcctcaa tgttcagcgg tcacatctgc ttttctgtgg cacagagtga 7980
gctatacagg aatattgtat tctccaggac agttagggca gtgggaaatg tcatcaaaca 8040
gaacagtgac ccaaagagcc actgccactg ggtgctctgt gggagctggg cactgtgctc 8100
attgtgttat gggccttgct ttgttcttac cttgtagcca cccagagagg cagggcatta 8160

```
tccttgcttc ctagctgagg ccacagaaga ggctcctaga ggttagctgt aacttgtcca   8220
aggccagcca gtgcaaggag gcagagccag gatttgagcc catgtctgtt tcactcccaa   8280
actattcttc agatttcttt aagtcaagtg ttatttagaa atgttttgtt tattcatcaa   8340
atatttggtg ggtgtttcca gctatctttc tgttattaat ttctagttta attctattgt   8400
gggctgagaa tatattttgt atgatttcta ttctattacg tttgttaggg tgtattttct   8460
ggtctagaat gtggtctgtc ttggtgagtg ttccctgtgt gcttgagagg aatgtgtgtt   8520
ctgtcattgt tgaatggagt gttctataaa tgtcacttag gtctagtgga ttgatagtgc   8580
ggttcaggtc aactgtatcc ttcctgattt tctgcctact gatctatcaa ttcctgaaag   8640
agaagtgttg acgtctcctg agtctattct gaaacactga attgcggtct ccatgatgaa   8700
ccactagagt tagaaaacct gggtcctagc cccatttggg cctttgggat gactcccttc   8760
tgcctcagtt tcctcatcta caacaggggg acaatgatgc tgcctaggag acatcagcag   8820
gatactgtga aagtccagtg gcataagggg tatggaggag cttcgtcaac tcctaaagct   8880
tcagtgctag gaatcctaaa gcattgaaat ccaaagatat aaggaatatg aaggagtttt   8940
gtcaattcct aatgcttcag tgctaggaat cctaaagcat taaagtccaa tgatataagg   9000
aatatgaagg agctttgtca actcctaaag cttcaatgct aggaatccta aagcattgaa   9060
gtccagtgat ataaggaata tgaaggagtt ttatcaactc ccaatgcttc agtgctagga   9120
atcctaaagc actgaagtcc aatgatacaa ggaatatgaa ggagctttgt caactcctaa   9180
agcttcagtg ctttaggagt cctaaagcat tgaagctgta agagattagg acctctagtt   9240
ggcaattcca gactcttcca ggactcctga tagagccaac accaagaata gtgaagccag   9300
aaggatggaa atagtaaaat gcctcctggg tgtcaaagca tgggtctcct ctgggcatgt   9360
tctcttgtcc tactgagaca tgatagctct tggccaaagt gactgaactt gaccctctgt   9420
ttcaggaagg ccaaatgcag ggttcactac catcatgtcc aagggcagat gcgttggtcc   9480
agaacatcag catcccaatc attataccaa gcaaacagcc gtctctgcct gcaccgtgga   9540
gagcacacgc tcctcctggg gtggcctgca tcctgtgttc ttctcaggcc gactttctgt   9600
ttaatgtttg ctggtcagga aatggcctga gctgaggttc ttcagatccc agtctgacct   9660
ttctccacca gcatttgtgg ctctgaaaaa tatagcccag tgtggtttag ccccactgga   9720
tgaaacccag taggaaaagt ctgataatag cagaagacgc acaggaggaa gagtgaggat   9780
ttgagagcat ctgggaagga ccatgtgcct ggatatcgtt ctgtctgtgg gattctgtga   9840
cacttgtcat ttacagtctg ttcccatgga attctcatca ttggccaaac atatagtcct   9900
tctgtcctct gaaaaatatc attctgctcc gacctttcac acccatctct gaccacatca   9960
actccctgtt tgcatgcatc ttgtggatga aggacaccac tttacctgta aagacactgg  10020
tggcttccca aagccaccaa ctgacttgta gagaagacag aatcccagag tatgaaacct  10080
gagggtgaag ggtcctggca ggtcctagag ctcaaccctt cacttcacag gtggggaaac  10140
tgagggagcc aatgggaaca tgactctcac aagctgcaca gctcatctgt aggggccagt  10200
gtggagtctg tttgtcctga gacccagggc tgagcctttg agccctccgc atctcagccg  10260
catcctcctg ttggagcagt taggtgtttg ggagaggcca cggtccatgc tcatggtttt  10320
cctgtaaggc tggagaaaca ggccttgttc ccttagtctc tctaatcaaa atgaggttgc  10380
agaaaaccct tctccctact tctccctaaa ataatttcct tgggttagaa gatgactaaa  10440
agactattca tccgatgact gatgtctccc ttcaagagtt ataagcacat ataaatgcct  10500
```

ttgaatggta attataataa ttttgctgaa gggaaaatat cagtataaat atcatggtgg 10560
acacatggaa tgaggactga gatgctttca tgtcttttca gctgtggtta gattttcttt 10620
aagcagaata tacaagtttt tcctctccta gcataaggac tctttttttt tgtatctttt 10680
ctctctactt tttagacatg atggaaaatg catttataca tttgatgaca tattgtacta 10740
tctcagttgt ttaaaattat aaatgtaatt taatcatatg aaaaattaag aaaagaagat 10800
tcatatttca ccatcatctc cccagaaata tcatttcttt attactatta ttattattat 10860
tattattatt attattatta ttattatttt gagacagggt cttgctccat cacccaggct 10920
ggagtaaggg gcacgatctt gactccctgc aacctccacc tcccaggttc aagcagttct 10980
catgcctcag cctcctcagt agctgggatt acaggcctgc accaccacac ccagctacct 11040
tttatatttt taagtagaga cagtttcgcc atgttggcca gactggtctc gaactcctgg 11100
cctcaagtga ttggcctgct tcagcctccc aaagtgtggg gattacaggc atgagctacc 11160
atgcctggcc taattccatc atttctgtcc caagtgttgc caccgtttgg ttaactgttc 11220
ccctgttcac atccatttgg gccaaggttg caatgttaaa caatcctgag atggacattt 11280
tcatgtttat ggctatttct gtatctaggg tcattctctt aggagaggta ctaaggagta 11340
caaaaactgg gaagaaggat atggaatttt tatggatctg gtataaattg ccaaattatt 11400
ttccagaagg gttgtagcca tatttgttgc catcagctct agaatttcaa cctcgtaagt 11460
cactgaaaga aattctccca aaatcaatcc ttcaggaata atggaagaag atggtgccaa 11520
accccagcca ttctgctcac tgttagattc ctttttggt cttacaggtt acttttattc 11580
tcaggttgat ggctcttaga gttgagcaat gtttggggta gaataacgag cacttttaaa 11640
acttggttct acctggggag ggggtgagtt gtgatcacag acagtctcac ctgggagggg 11700
cttgggtgtt tgtcggcttg tccttctaac actcgtgtct caggcgagca gcctgggacc 11760
agtgaggtga cctgaaggct ggaggtcaca agctaagagg cgacagagaa cccaggtctc 11820
aggaagccca gcccagagct cgctgcactg agcctctcgg atgccagctc tgtccaggat 11880
gcgggaggag gccagactga tttggtctgt tttgaaaagt gatgaaaata tttattcaaa 11940
tgttttgtac tcataggcag aagtataaca ggagctgcat atacaaaatt attttctagt 12000
agtcacatta aaaaagtaaa aagaaagaac acgattattt ttctttttaa aacagcttta 12060
ttgagagata atttacatac tataaaattt accccttttaa agtgtacaat ttgctgttct 12120
tatatattca caatcatgca cgtatcacta ccagctccag gacactttca tcaccgtaaa 12180
aagaaacccc gtatccatta gtagccaccc catacttctc ctctgcccag ccctaggaaa 12240
ccaccggttc attttctatt tctatgaatt tgcttattct ggacatttca tataaatgga 12300
atcaaagaat acgtaacggg cttctgtctc ttagcataat gttttcaagg ttgtccacat 12360
tgtagcatgg atcattattt cattccattt tatgattaaa aatatgcctt ttaagggata 12420
cagggagacc agacgtctat tttatctccc ctccctgatg gggaatccta atttcagcct 12480
ggaaagtcac tgcgaaagtc taaactgcag aggtgatact gtttccactg gaagaaactg 12540
tagcacctga ctcaggaagc cagcattaaa accaagaata ttctatatgg atggggatta 12600
cgcactgaaa ggaaaacatg aggaaatgca cttttcagat ttattagatc atagaacttt 12660
tttggagctg gaaaggatgt cggaaaccgt ctagcctacc ccctcatctt accactgagg 12720
taactgaggc ccaggaaggg gaagtggctt gttttgggtc cgggaccact cttcatttct 12780
tatttgagcc aaagcttcct tctggcgtct gtctctgttt cacaagttcc cctcgcatgg 12840
gggctgggta ctgcttggaa gaactggctt cttccttgat acaggggctc gttcaccatc 12900
acctccctcc ctcacgtctc ttctgcctct ctgcagcctc aggccctcct cctgcaccag 12960
gggggcagac tcaacccggg tgggcactgc ctcccagtcc gtggccagag gctggagggc 13020
tagggagact gaacagcccc ggcagctcca gacataacaa cctatgttga ggagtcaggg 13080
caggaagcga acccagctga gaaatctgcg aaggtcagga ccagagccag acgcttatca 13140
agagcaaagt taatggtttt tgtgaaccga gcagtcagct gtttccccga agataataat 13200
agacacatca tgttgggcat tcaggaggca tctgaaaaaa aaaatgtgca gtggaattga 13260
ttggaagctt ttccctaatg cataaaatag gccagaaaag actatcaaat gtaacagcac 13320
cgatcaaacc caatagatca agcaaggact gaaaaacaca attttttttt tctttgccag 13380
tgagtctgaa aagtgatttt caatgacagg cgcctttaaa catagacaac ataaacaaca 13440
acatagttgt tctggaagag gcatcttttc ccagtaaagc caaagatgca gatctaggct 13500
gtgcttgtga ctgacagcac agtgaggggt tcacagccag ctggccaggt gccccccgaa 13560
agcacatttc gaatctactc tatttgagag agactgcctt agccttgttt gggtaagtct 13620
tcctccttca cttcacctgc cacagacttt tccaggcacc atctgctgca gtcttggccc 13680
agcccctgca acagttactg ctcaaggcac ccgggacatg caggacgggg gagcagcctg 13740
aggtctggcg tccggcgagc ttttcccact tggagccgtc tgggagactg tcccggaaag 13800
agaggggctg ccaacacttg gaagtgccaa tgtgtgctgc aagtcgaggc caggctcccg 13860
gctcccccgc ctcttcctcc ttgattcatt aaaaggaaag aaagaggcca cacgaaactc 13920
tcctgaattt catttctttg tttctatgca aaagacagag cgtggtcatt catcattcaa 13980
attttagcct tttaaacaa ataataattc ctgcttgtga attcagtgta ttttaacaag 14040
agtaggtctg agggccgttg gccgtgtctt tccttagatt tgcagacagc ggccctgatg 14100
gtgcataggg tttcaggttt cctttagacc tcagctggct gcctgggcca ccacttagca 14160
atgccattgt ccttcctgtg cattttcttt gcagaattcg aggaaatcca gtcgcacagg 14220
cccctctgtg cccatgtccc cggcgccctg gaatgtgcag taccagcagc agcgattaga 14280
atgggggtct ggtttcccgg aatgtgcaag gtctggcttc tgtttctgct gcctccatgc 14340
cccagaccag tgctgggccg ggctctgggc tggagccgtg gctgacaagt ttccttggaa 14400
tttaatggag cgggccagac agcatgcagc cactcaaact gaaaacctgg gaaagaaatg 14460
agtgttgtgg ggcagctttg ctgcattcac tgggtcatat atgcttcttt ttcttttcct 14520
caggcaaccc ctcttgcaga caggaggccc cctccccttt cgcttcatgc ctcactggcc 14580
attaggaacc ttttaaaact gatttctctc ctgaccctca gagagaacat agtccaagtt 14640
ccctggagga ggaggaagcg ctctgtgttt ctctgcagtt cacggctcag ttaaatgcag 14700
cctacgtgct gtctttcccc actcctctgc ctgctcccgt tgtgcttctc atgatcattc 14760
tcaaattcag cgagaaacct cacaaaggga gcttttctta gggaagagtc atccttggcc 14820
tcccgaatgt ggaccagccc ctctccccag ctgcacagca tcaggttagt taaccacctg 14880
cctccatctg ggtcctgtct ggacaggcct actcacacct gctgcaggca tccaacttgc 14940
cctcaggtgc ctgtggctcg tccagagggg tggagcccac attccagtcc tgacaggtaa 15000
agttcagtgg cggggaccct gcatttagtg taaagatcaa tattccaggt cctctcttcc 15060
tgccacccag cgactggccg tttgcaggca ctcggtccca gttgtcctgg gcctgcagcc 15120
cttgcattct ctctgctttg tctctgctat tgcacccctg ccccatcaga aatgcaggtg 15180
ggggggcctt ccgctgggac agtgagagac tgggtagtaa ggggagcgct agagggatgg 15240

-continued ttgcgcttgc atccagccct gactgcattc gctctccccc gcctctctgt gaaggtgctg 15300
agctgtgagt ggaaccaagt ggatgagagt ggccttgggc acctgccgat aaatttcccg 15360
gtgtgtcttc tcctcctggg agtcccatct ggatttgggt ctggatttat ttattcagca 15420
agtagcctct ttatagttac tttttttttt tttttttttt tgagatggag tttcactttg 15480
tcacccaggc tggagtgcac tggcgcaatc ttggctcact gcaagctccg ccttccaggt 15540
tcacgccatt ctcctgcctc agcctcccga gtagctggga ccacaggtgc ctgccaccat 15600
gcctggctaa tttttgtat ttttagtaga gactgggttt cactgtgtta gccaggacgg 15660
tctcgatctc ctgacctcat gatctgccca ccttggcctc ccaaagcgct gggattacag 15720
gtgtgagcca ccatgcccgg cctgtagtta cttttaattt agccatgctc ggggctgaag 15780
gggatgccaa agaaatataa gatgagcccc tcagacggct aaagatgaag atgaggcctc 15840
cagtatgtac ctcccacata caccccagga aattctgggt gtcactggat tctggacctc 15900
ccaaaagctg ctggcacctg gaggatgggg ccccgaggct ggacctcact cctgctgggt 15960
tgctggactg ggaaagtact gatggcagct gaggagtgtg tcccagactt cactgagcca 16020
ttcccaaaga ttattccaag ttctcctgac actgcactgg aggcctgctg tgctggcctt 16080
ctttatttac agtttctgac tggtgtctag cagccctgcc agagagagcg gcagtgtgtc 16140
tgcaggcgac caggagaaat gtctcaggct ttagagcagg actttgagca catagctgtg 16200
ggggcccagc aggctgtctc ctgcacggtt acttctcctt gtcctttcat ggtcgagagg 16260
ttgctgcctg gcccttcaag tgaggatggg acatgctatc cattggcctt aatttccaac 16320
ctctgcatga tgcattttat gctcctgcct ttgaaagaac ttttattttc ttgtcattta 16380
tgcccagacc ccacatggca gaaggaaggg aggctgggac aggggaggcg gataagctgc 16440
cgctgacaga cctgcccagt ttcttagctc atcccggcct ccatcctggt gagcagacac 16500
tggcccaatc cagccatatt tttggctgag tttctgtctt cacatctcat ccttaaccct 16560
gaatcctggc catagttggt actgggttgt attcttattt gtaatcttta aagtaggaat 16620
acctttgctg gtatttaaag tggaagaaat caggtgaaga atcacaagtg atttgcaaac 16680
tggaagagac attagaatgt aaatgtgagg aagcgtcagc atgaggggct tgcctgggct 16740
gcacagcttg ccttggctgg agtatgcact gttctggcat tgcagagagg atgggtacct 16800
tgcctccctg caggtggggg actgtatcag cccccgcaga ctgctcctgg gctcctgagt 16860
ttgacagatt tttttttttt ttttttgaga cggactctca ctctgttgcc caggctggag 16920
tgcagtggtg cgatctcggc tcactgcaag ctccacctcc tgggttcacg ccattctcct 16980
gcctcagcct cccgagtagc tgggactaca ggcgcctgcc accacgcctg gctaattttt 17040
tgtattttta gtagagacag ggtttcaccg tgttagccag gatggtctcg atttcctgac 17100
ctcatgatct gcctgccttg gcctcccaaa gtgctgggat tacaggcttg agccactcgc 17160
ccggctgagt ttgaccagat taaggcagca tctccagtgg cacctgagca gctcctgaga 17220
tgcttttctg tgctaaatct ggatttgggg tattaaatca aatgaatttg aaatgcaggc 17280
acagctggcc ccatgggcat ggacctgtgc agtcacacct tgccccgtgt tcagaagggt 17340
gctgtgcctg ttttaatgct ctgctgttgc tctcttgaga ttcttaataa tttttgaaca 17400
aagggcccca catactcatt ttgtactggg tactgcatat tatgtagcta gtcttgaatc 17460
taggacagtg cattaaaatg ccattgattg gatcaatctg ctcttgcaac tgatttgaat 17520
tttgggaaca tgctgtttcc tgtgaataaa ggaggattca tttcttttcc ctcgaataca 17580
ctgcgttctg ttttccaaat tagctctacg tatcaactca gctgagaaat tggaagcggg 17640
gattgttctg gctggaaggg aaggttagat tgttaatcct gcatcctggc cctgatctca 17700
ccgagtgtga agcatgttcc cacaatggtg tgggctgcgg ggggctggag gctggctgag 17760
aaggtgggga ccaaggaggg aggctagcct gggagccaga cagatggggt taggctcttg 17820
cttttgccac tcgccagctc tgaggcttag ggcaacatga tttaattctc tgatccttgt 17880
ttttttcatc tttctgtaga ctggtgatga gatgcaccct gcaggcttgc aggcttgcag 17940
gagtaattaa aggtaatatt tgtgcctatt attgggcttg acatatagta gatgctctac 18000
aataaataga tcctattatt cttattgata atattatttt attgctaaca ttgaaggttg 18060
ggtgggattt gactagctgg aggcgaggag aatgagatca tccaggccgg aaggaaaaga 18120
gacatgaatg caggggatg gggtggagca ctttggaggt gtggggagag gtctgcaggg 18180
tgggagttgt gcattaagga gtcgtgggga gagtggagga atcagtgcca catggtgaat 18240
gagaggggat cgtgggcccg aggagatggc gatggctgcg gggatcctgc aggaagttta 18300
tgtgccccaa agtggcatta tcagttaggg ggagacactg aagacagagg tgaggcctgc 18360
ctgaattagc gtagagtggg attcttggaa gcttcagaag cttgagaaga gccacttgga 18420
ggtgttgaaa tgcacctggg agggacgtgg ggacccagct ctgggctgag agctgggaga 18480
cggaaacgca ggtgaccttg gccttgaaga tggggcatga tatttagtgc tttatgtgca 18540
atctcaccta ggactcccaa gccctttgga gtaggtgata ttagctccgt gttacagaaa 18600
gggagactga ggctgaagca gggacattca tgatctgaag tcacacagct gtacggggca 18660
gaagtgggca tggaggcatt aacttagagc cgaaaggtgt gacctttctt agtgtggctg 18720
gccccacggg gaacgtgtgt gggttggagt acaacttggt gttcctaccc atcccagatg 18780
ctctgcgttt gtgaacccca gttgccacat cagggcgggc gagggcagga agctctgcag 18840
ggagaaggga caagggacag agccaagaac aggggcagtg ccccagggtc ctgcaggggc 18900
aatgaagggg gttggcacac ctgggttagt tgctggccag tgtggggaga gagctggcct 18960
gggagtctaa tgggaatgcc agggaaagct gccttggtcc cctaaagtga agccccccatg 19020
ctggccatgg agtgttggtg attgagggtc cctgctagtt gtctggccga ggcagcatgt 19080
cctataggca tagctctggt gtcctgctgg cgtggcgtga gtgcccctca tgctgggagc 19140
cagccctgtg ctctggaggg aggtggtggg aggacaaggg acagtgggac ctgccacctg 19200
agcaggaatt ggcaccttct cccactggca ggtccaggtt ttatggaatc tgaaacttgt 19260
acaattcagt ataccctctt caagaaaaac acccctcaaa attatgaata taacattagg 19320
tatgaaacta ttattgatat agattgaaaa aagaaaatgc ccaaaatgac aaacttcaga 19380
aaatagacaa atactgcaaa catcacaaaa tcagaaaaat aagattaaaa aaagctaact 19440
gctgaacact ccgtcatctt gaaaatgccc ctctctcctc ctctattttt tggctgtgaa 19500
ctctttgctc accttttcat gtgacaatgc ttttgtaata tttcctacag agaaaataga 19560
ataatttatt attactttta ttgtttttgg attattatta tgatcaattc aatatttttc 19620
tgctacccac acactcactg tcttctgtcc aacctctggc ctgcaccagg ggaaccagca 19680
gtttcccctg ccatagggtg tccctggaga ccacacatat agcaggatag atatagcaat 19740
ttaactagac acagaaggga cttcaaagcc acaaatatat ctcatttaac ctgaacaaaa 19800
tgattatcca gttttacttt tcccttagcc tcttccccca aatgctggca gccaccctga 19860
tgggatagat gtgtgacaga gggcaagaga ccgtggcccc aaccagctgc agcttcactc 19920
tttcatttct gtatactctc tacaagctgt gatgatagca ctttgctagg gcccctcaca 19980

-continued

```
gggcagatgg agggctccac gctgaagctt tgtggatgtt tgctgtctat ccacctctgc  20040
tccttgtgcc tatgcaggga ttcaggccca accactgcag agagcccaag agcatcaggc  20100
agaggttccc aaactgtcat gattggtggc acctttagta gttgatacgg tttggttgtg  20160
tcctcaccca aatctcatct tgaattccca catgttgtgg gagggacccg gttggtggta  20220
attgaatcat gggggcagat ctttcccgca ctgttctcat gatagtgaat aagtctccca  20280
agatctgttg gctttataaa ggggagtttc cctgcacaag ctctctctct gactgctgcc  20340
atccatgtaa gacatgacat gctcctcctt gcctccccacc atgattgtga ggcttcccca  20400
gccacgtgga actggaagtc caataaaacc tccttctttt gtaaatcacc cagtctcagg  20460
tatgtcttta tcagcagtgt gaaaatggac taatacagta gtgcagtcat tttttcatgg  20520
tccccagtaa ggccaaaaaa tacccaacag ttccatttat caattagtgg aggccaaaca  20580
atttgataag tatttgtgtc cctataacac agtggtcatt aaaaaaagac attttaattt  20640
cattattcaa taagcatgat tacttatgaa tgggatatgt gcacctgttg ggtgtcacat  20700
gacctttcaa atcttggagt cagattggac accaccatgc ccatttccag ttcaactctg  20760
atttttgtgt ggtacatgct ttttatcaca gtgactgcca gaaatccaac ttcatatgga  20820
atcatgaaaa gggatgtagt gtgatctgat ttcaaaacta tgatcaatct agagctagtt  20880
tacaaggtgt ctaacagtga tcaagtatca ctgtatttcc ctagaaaacc tgaaatatcg  20940
atgaattttc tgtggcactc tggggtccct tggggcacac tatgggaacc atgggattag  21000
gaccataagg atatgatttt ggcttcttcc tgcctcagat ctaatcttta cctggcattt  21060
ttgccttaaa gatgaaagaa gcatacattt tgatgtattt aaagcacata ttcggccagg  21120
tgcggtggct cacacctgta gtcccagcac tttgggtggc tgaggcaggc agatcacaag  21180
gttggaagtt tgagaccagc ctgaccaaca tggtgaaacc ccatctctac taaaaataca  21240
aaaaatagct gggtgtggtg gcatgtgcct gtaatcccag ctactcagga ggctgaggca  21300
ggagaatcac ttgaacccag gaggcagagg ttgcagtgaa ccaagattgc accactgcac  21360
tccagcctgg gctacagagc aagactctgt ctcaaaaaaa aaaaaaaaaa aaaaaaagca  21420
catattcatt ttgtgcttat tcttttgaga gaaacacaga taaaagccta tcctttaatt  21480
catactcccc atactgtgat tttcattttt actgcaacaa attttgttca gtgtgataat  21540
gaatgtcaaa cacttaatgc cttgctcttt tcagtaacat gacatattgg agaataatga  21600
ctgaagctta tctacactgc ctacgtctgt tttcttccac cttgaaagaa gttgttgaaa  21660
gtaattaaga agtattatgt gtaaaactcc agggatgatg tgcttcaagg aagcaacatt  21720
tatgaagttg tgtgcttgac tagtagttta taaagaggaa agacgaatca tttattgtct  21780
tgggattgaa tcttggcaat ttttaaacta taaagttaca ggaaatgttg gctgctctta  21840
atgggccatt tgttgtgtta aaaatcagta atgagaaata tttactaggt aagtggaaag  21900
atccatctct ataaattgtt gtaacttacc attttacaaa tcttagttac tcagtttttc  21960
tgcttaaaaa tgaaatcatg tagcactgta taagtcattc agttttttat tttggagaat  22020
tactctggat tgtctaggct ctgtgctctc cacatatatt tttgaaatag tttgtgaatt  22080
tctacaaaaa ctcctgctca gaattttcac tgagagtatg cttaatctat gggttaattt  22140
gtgagaaatt gatagcttaa caatagtgaa tcttctgatc tacaagtgtg gtatttctct  22200
ccatttattt aggtcttctt tattttgata gcgttttgta gctttcaatg tacagatctt  22260
gcaaatatct tgttaaatat ttccctaatt acttgatatt tatttttgat gctgttatag  22320
ttatatttta aaaattttga ttccaattgt tgctaataca tagaaatgaa attatttatt  22380
```

gacctcttat cctgtgacat tgataaacgc agtcatatat tcgtagattt ctagaatttt 22440
tctatataga ctatcatata tatcatctgc aaataaagac ggttttacat tttcctttcc 22500
aatctctatg ccttttgttt ctttctcatg cctcattgtg tggtccatta ctgaacggca 22560
gccagttcca gctttctgtt caattaagga gcaggtaaaa tggccaggcc ttgacctttc 22620
agggggcttc ccgtcctcat tgccttctgc tgcctcagtt ctggcttaac agaacagtgt 22680
ggggaggagg catggtcctt acctactagg gcgttacttg gccttcttca ggttggttgc 22740
ttcgtcaggt ttaagagctc acctgggctg cagttcaggc taggttatct gctgacctgg 22800
ccctgtctcc cttctgtagt gtctgtgggg tacccttgta agctagggag aagagacaca 22860
cgtgaaggcc agaaaaaaca gcctgccaca cagcttccct ggatcatacc ttcgcagtga 22920
catgacgacg tcgttaggag gcgccgaggt ggctgagtgg gtctccagac acctcccttt 22980
acctctctgc tgtgccactg atgtgtgact tgcttacacc tatgcagagc tgccactgag 23040
cagcactgtg gccagtcctt tggattttct tctttctaaa ttgtatgccg tggcttgatc 23100
aagcatttca tatacagtag atcatgaaat cagcatagaa aacacattga ggtaggtggt 23160
gttaccacat tttatggatg agaggctaac acttggagga gtcaggtaac atgtccaagg 23220
ccacacagct agtgagtacc ctgctgaggg tcacactctg gtccatctga ggccagagcc 23280
tgtgccagcc ttctcctcat gctgatagac gaggaaacag aaagaaggag cagtggacgc 23340
ccccaccctc tgtcccctga accccttgga gagtaggcag tggcagagcc agcctgggcc 23400
catctatggg aattctccat cgggattgac tcctctggaa ggaagacagt tgacccacag 23460
ttgagatcac agcagatggg ccagccaggg tgtctgtaga ccatcaggca gtggccactc 23520
catgtagttt aatggacaag cccttttaat ggaacaggaa tctaacactg aaccaagctg 23580
cttttagaca cacttttatt cctcactctg aaatggcgtt tggacaagcc aaatatttct 23640
tcttctttca gttgacattt tgtccatctt tgaactgtta gttgatgctt cttctgttta 23700
gttattcctg ttctattttc ctgttgccac tagtccaccc agggatggta agaatggaag 23760
tcaatggttg ctttttcatc tgagatgcac cacgaaggct tgtcagtcag ccttgtcata 23820
tggtctgtgc tcccactgct ccttctttct gtttcctcat ctgcagaatt tggagagtcc 23880
tggacctgat ctcaaatttc acatgttatt tatcttcctg cagcacgctg gggagaggaa 23940
gagacaggga catagaaggt tggagctgga acagacttca catctcattc cagaggcatt 24000
tggtccatct tacagatgag gaaatggagg ctgctcagtg gactgaggct ggaactgggc 24060
cttccagtgg ccaggccaga tcctccttga tctcccttgt tgctttcctg gtgggaagac 24120
cctggaacca ctttatgtga ctgtgtgaga agggaactgc ctctcatttt acccagcaaa 24180
atccaccttc aatccatctt catttttgcc cctggtgtgg gcaaattctc ccatacctaa 24240
ttcaggaagc cagaaagagg aagtgagtta atgatcctta gtgggaaggc gctggtaatg 24300
gtccttcttg tgagagtttc tgaaacacca cgctgtctct gtgttctggc ctggctggag 24360
ttaaacctct tcttggcctt tccccaggaa gctggtctga ggaagcccag atgcgtttgt 24420
ttacagctgt ctggtgacat tcgccaggct ctgttttcag aaggaacatt tccattccct 24480
tatttacacc tcccattgga gtgctcgggg ggacacacca attatttgca actacctgga 24540
aacctaggag ggtagcagat ctgtaggagg ccagtgttga agtgagaagc tgtagatctg 24600
gtgacactgt gggcttggga gggcttgccc agatctgtta cttatactct ctattaagaa 24660
acttcagtgt ccatggagaa gttatttaaa gtctgcgagc ctcagtttcc ccatatataa 24720
tatgggaagg atacctgatt ttcctattcc acatgaaggt agaaaaaatt aaattaaggc 24780
agccaatgaa agggttttga aagcaaaaat aataatatga tactgttctg aatttgttaa 24840
attattcttc caagtagttg cagatctttt tctgtacctt agaaaaaaac catgctatgt 24900
aaaaggagat gattccaatc tttaaataaa gcaactcaga ggtcaggggc taggacagaa 24960
aacggccctt tgttcacaga agcgctctca cttccaagaa agcaagcgtg ggagaggcag 25020
gtggtcctcc cgatgtccct gtgccccatg gtgtcaagct gggttactat ggcccttcgt 25080
gacccagtgc agcagggatg tgggaaccag tgggtgtgaa gctgtgacgg gtcacaagag 25140
ggctgggacg tctcacagct tttacttata gcctagagcc tggggaaggg ttgccactct 25200
agtgatgaga gaggcgtgtg tgtgtgtgtg tgtatgcgtc tgtatgtatg tgtgcatttg 25260
catgtatata tgtgtgactg tatgtatgtg cacatctgtg agtatatgaa tgtgtgtgga 25320
agtgtgtata ggtgtttatg tgacagtttg tgtgtaaatg tgggtgtatg tgtgggtgtg 25380
tttatgcatg tacatctgtg ggtgtgtatg catagtgtgt atgtgtgagt ttgtgtgtgt 25440
gtgtgcattt gcatctctgt gtatatatgc atgtgtgtta ggggcaggca cacaggcctg 25500
ttggtaaatg agacacaaaa tacctacaaa atacaaaatg tgagacagga aatacaagcc 25560
ccagttactc atttttcagt gcaacagaca taagattacc atgtgaaatt gctatgaaag 25620
tttccgaaag cttcctgtca attcgtagtg agcagctagc agaggagtgc gggtccctgg 25680
agcctgcttg tgcaacgctg agctagtcca agggggaaga atggggtgca tggctctcag 25740
ctgcagacca gcctggaacc tctccagcct gctttagcag agacttgtta agaggtagca 25800
gcaggtggca agattaggag ccggagtagt aggctaaggc tgcacttcca gggacacact 25860
gcctctgcca ccacccgtgc cacgaaaatg ggagcccagg accctgaatc tctagcagtc 25920
cgtttctgaa tcagttacct tgggtatgtg cctctggttg atggaaacta acttgtagcc 25980
ctgctgggtg agagcctcac atcgggacat gtgacagctt tgttgaaagt agctttggaa 26040
acgcccacca cgtggggcca ctcactgtaa tataaacggt catgcatcac tgagcaacag 26100
ggatacgttc tgagaaatgc gtcgttaggc gatttcatca ctgtgggaat gttacagagt 26160
gtgcctacgc aaacctagat ggcagagccc actccacacc taggccagat ggcagagcct 26220
gttgtttcta ggatgcacgc ccgtacagta ggttactgta ctgaatactg taggcagttg 26280
taacaatggt gagtatttgt gtattcaaac atagaaaagg tatagtaaaa acaatggtgt 26340
tatggtccgc ggctggctga aacgttatgt ggtgcatgac tgtaggtata aagcattaca 26400
gttgtttgat ttttctcttt ttctcaccca cagtcttaag gcacctctta tgccttttgt 26460
ctgggatgtc ccgggcaggg ttggaacgtg tggttaaggc atggcggaaa ctgctttggg 26520
gacagacgat ggcctcagct tgccttgggg tgtcagtggg aaagatagga gctgcccctt 26580
tgccttcgtg tttcttcgta ataatctcag atgtacccgt ctggtgggcc tctcctagaa 26640
aaagccccgg tgctctttgc tcctgcggtg tttctcagga gggttgttgc ttctttgtaa 26700
tggtggggac tcagggaagg gacgcaggca gagggtgatg ccacatcaaa aagggaccct 26760
tggctgggtg tggtggctta cgcctgtaat cctagcactt tgggaggccg aggcaggtgg 26820
atcacctgag gtcaggagtt cgagaccagc ctggccaacg tggtgaaacc cggtccctag 26880
taaaaataca aaaatacaaa ggtggtgggt gcctgtaatc ccagttactc agtaggctga 26940
ggcagaagaa tcgcttgaac cggagaggtg gaggttgtga tgagccaaga ttgcgccatt 27000
gcactccagc ctgggtgaca gagtgcgact ccatctaaaa ataaactgaa aaaaaacaaa 27060
aaacaaactt gggccatcag cttcttggaa aggctggtgt gaggttgaag catttgctgg 27120

-continued

```
tgcctctgct caacgttttt gtggtgaacc tgagcaaaga ggttatcatt agtggatttt  27180
actgccttac ctgggtgggc actcccttgg gaggtggatg gacatttgca gctgagccca  27240
ggtgggggaa ttgcgctcac tccgccttca gaattccaaa ggctgggcat gcatcttggc  27300
ttcctctaac ccatgtcttt ctctaggtgg ccacagcaga gtgtcattaa gtatctattc  27360
tttgcttttg ttctcagggc aggaagatcc caacagtttg cgccataaat ataactttat  27420
cgcggacgtg gtggagaaga tcgcccctgc cgtggttcat atcgaattgt ttcgcaagta  27480
aagagagcct tccttttcc tataacctcc gaagctttca ccgccactag caaaacatga  27540
gagctatttt tgagatacat taaagtgtca aagtgtcact gaatatcttc ctacttaaga  27600
taagtgtgtc tcccttagaa cattttccct attcgactat ataaatctac attcttgacc  27660
cttctgaatg tttaaagaac ctcgggctct gaagagattc tctaagaata ttttgtaagt  27720
ggaagttttt gatgcatgca aaaaattggc aggatgttta gtgtttaaat gctaagcccg  27780
atatataaag gagcgatggc taggtgtgtg tggctgttgc acaacccatt aatcaatgcg  27840
ttgaagcgtt cattttaagg tgctacaggc ttaagtgtgt actcctttgg attttaggct  27900
tccgttttct aaacgagagg tgccggtggc tagtgggtct gggtttattg tgtcggaaga  27960
tggactgatc gtgacaaatg cccacgtggt gaccaacaag caccgggtca aagttgagct  28020
gaagaacggt gccacttacg aagccaaaat caaggatgtg gatgagaaag cagacatcgc  28080
actcatcaaa attgaccacc aggtaagggt gttctcgcct gcagaggtga gttctcagat  28140
gccccggaac acccttggca aaggcaccag agctctctga ttgcagctga ttctcggggg  28200
gcactgaagc cagtctgagc cagtcacagg agggccttga ggagatgctg agtatggcct  28260
gggggtgtgg gagaggaagg ggctcaggaa aacttctgta aggagccaga taaaagtttt  28320
taaaataatg ttttaaatgt ttgtcaaaga aagcaataga tttgtaaaga aattagtagg  28380
taagtagtga aaattgattc tccttcccat tcccaatcct gtggcaactc ttgttacaga  28440
ttttatttat cctccacaga tacatcatgc gttcacaatg aacatagaat ttactgggtt  28500
ttagactgag ccatccttaa cttgtcaaca gttactttga aaacaaacca gctctcccaa  28560
attggggttt tgcggggtta tgagatgtgt ttcaaaagaa tgtttcgtac tttaaacatc  28620
ttggaaaact tgaattaaaa cagagctaat ggatttcttc tttccagacc ttctcagagc  28680
ttttagtatg ctagtgtgca cgtggcttgc ctacaaaagg gtgttgactg aactatttgc  28740
ccaaattata atcatttgag tatacagctt tttgtggggg caggcagaac tgagacatac  28800
caaaatcagt ttgggaaatg ctgtatttga aaatgctttc tatttaaata ttctctttgc  28860
aatcattttt gctctgttga tttgcttagc aaagtcttca tgtctgggac aatatccatt  28920
tcttactgac tcatcaaaaa cccccactcg acacgtcgat gagagaggtt ttgtttgctg  28980
tgtggcatgt tcagtgaaag cgtggtttcc agtttcttca catccttata attttctaga  29040
cttcagatgg agggaacaat cagaggaggc tggaatcctg cctctgacca aggaaaagac  29100
cagaggctga gccaggtggg gtctcttgtc cagccctctg cttgcctcgc tttacctggg  29160
tgtgggctga gtaattccag acaagcgtgg aattaatctg gctgtttgtg ctgttcagtg  29220
gcacgctggt tacacctcct tctggaaaca actctgcgtg tgctgtttgg gtggtaggat  29280
tccgggtctc cttctccgtc tttttataac atcaagttgc tgcccagctc aggctccttt  29340
acggccagtc ttcagaaaac caccagctaa cacatttact accctccttc cccgatgttc  29400
ctgtagcttc tctatggctg ggtggccagg catggccgaa gaggctctgg gtagatatag  29460
```

-continued

```
gctctgtgcc cggtgtgtgt aactggcctt gagtgaggct gcagttgtgt gttatttcta  29520
ttaggtcact gtggaatttc tagcgacaac taatctttca aagtgtgttt attggtcaca  29580
ggattattgg gccagcctct gccttcattc tttttcacct aatctgcata atagctgtgt  29640
tatccccatt ttagagaaga agaaacaggg gctcagagaa gtctagtaac ctgtgtgagg  29700
ccacacagca aacacctcat gaccctgccc tcctaaggca gcccatggct actgctggag  29760
ggatagaggc cggccccgtg gtttgatggg acagcttgac cttaaacagc ccatgggaag  29820
gcgggtgcat ctggtttagg aacaggctgc tagaaaggta tccaggatgt ggtagtctca  29880
ccggaaggag ccagtcagaa tagcacagcc tgtggccacg cgtgggacct gttcagcctc  29940
atggagcttt gggaggcagc cagcagcagg gcatgggctg tgtgcaggcg aggcgctggc  30000
ctggacgccg cccccactgc gtaacttcgt gtttggaatg cgtgggcaca taccgtgcgg  30060
ctgcttctgg ccgggggata ttcttttcca attttgagcc aaggtggaga ctgtctcctc  30120
gtgccatccc tggcatgtcc tggcaagacg tgaacgatct caatagacga gctttgcaga  30180
gtgtgtctga cctgactcct gctgtcttgg gagtttagct cttcagccag cagcatgctg  30240
tttgacatgt gtttcaagcc ccccaagaaa gggtgcttga aatttaaaat tgaactgatg  30300
tggcttttca aaatggaatt ggaaatgaaa ggatattaaa ttgcagacac ccacacaaaa  30360
gactggtttc cactgactaa actgcttttt tttgctgata gtagttgaaa gtagggagag  30420
taacagcatc tcttccagct ttttctcttt tgttcccttg ttttgatgat gggttatttc  30480
gggggaagct ctggctggcc ttgctttgtg tcatcttagg gataacaaag aggatgaaag  30540
agatcaggaa aaccgagaag gcagaacaga accagcagaa actgtgcttg aggaatgaaa  30600
atcacctaca cggctccttg tcatatgaga ctgtggccca gcctcctgca aagccattta  30660
agagtaaccc agtgaagctg gtgagactgc ctgccgcgtc cgtgggccca gtgactaact  30720
cggtggctta tcatctgggc ccagctcctc ccctggcatc ctgatttcac ttggaggggc  30780
ccccgttgtc cttcataaac atgtttattt cattttattt ttatgttttg agacagagtt  30840
ttactgttgc ccaggctgga gtgcagtggc gccatctccg ctcactgcaa cctccacctc  30900
caggactcaa gtgattctcc tgcctcagcc tcctgagtgg ctgggactac aggcgtgcac  30960
caccatgcct ggctactttt tgtattttta gtagagaccg ggttttgcca tgttggccag  31020
gctggtctca aactcctgac ctcaggtgat ccacctgcct cagcctccca aagtgctggg  31080
attacaggtg tgagccattg cgcgtggctg taaacgtgat attcttgaga ctttcagtga  31140
aataagaatt gccacggaca tctgtggtca ttgtccactt gccactcacc taccccccttt  31200
tctggcagca acagccggca tttcacatgt ccatcatcgg acagcgtagg tgggaccatc  31260
agtcatggtg tcctaccctc tgtggccaag gagtggacac aggacccagt tagggcaagc  31320
agaggctccc cttggaatcg caaagtgaag ctggatgcca cccacagaga ctaacatggt  31380
gaagctgctg tagcccctgc tgttgagccc ccagcactgc ctgagttctt gcactttgtg  31440
agtccagttt aatatctgct tttcctccca ttcttggagc tcccctcaca tctccagtgg  31500
cttgaagttg ccagagatgt ttctgggctt gtgaccaaat gactcctttt ctgcttctca  31560
ctgctgagca gacacatgtg cgctcacttt gcctgctgag tcttgggacc cggaagagct  31620
tttgggagac aatcacggac cagccccctc ttgcctgccc tgctgtctcc ctccaagcag  31680
gaggtgagaa ggtgtccacc tgcagccccg gccaggcatc cctttctgtg cttctgccca  31740
aatctgaaat tcccctctcc ttgggaccca cgactggggc cagcctgcct ggggagggaa  31800
tcccagctgc agaaagtcgg gacagtgtgc gtgtaaacat gttaatagaa agcagctttg  31860
```

agggcagact agttcagctt cagttacaaa ctctttccaa atgcgtttaa catgagccac 31920
tggctgtgcg cagcatatgt caagctttca tccaatggtg gcattttgtc cctgcggggt 31980
ttttttttcc tgagcagttt ggggcagggg tggggacagg gagagagaaa agtaaaaaga 32040
gagcagtttg gtttcttcag gctggagtac aaggcagagg taatgggatg tattgaagaa 32100
ggtaggaggg aaagttactt tagctacagc tatttgtcca gctgtgctga ttaagaaact 32160
tggagaaaag catctttgga atcatgtcct tcccatctta tatacagcct ttgcagattt 32220
cctgctgttc tgagagagat ctgaactcct taccaggacc ttgagggccc cacctgattg 32280
ggcacccctc actctctctg cccctcctcc ccttcccctc ctcccctcct ttctccaccc 32340
ccacctgctc tgctcagaca ccccttcctt ggttgcttcc cacaggccag ggctgtcccc 32400
tggggccttg gctgttcccc tcccaggagc gcccctctcc agctcctcat gcagccaacc 32460
ttcctgtcct tcaggcctct gattaaattc tgccttagac atctctcccc accccgctgt 32520
gtgaggtagc gccccatgcc ccagtcccct caactccact gcctcacttt ggggacacat 32580
caccccaggg acaactgcat tccactcttg gtttttccct cctcgtctat ttatcacaat 32640
ttagagtcgc ctcactcatt tgtcaaatga agttcatctc tgcagctgga ctgcggggtt 32700
gggggcacat ccggctgtcg gtcctcaggt aggaggtgct tggcaacctt gttcagagta 32760
ggacgttcac agctgtctgc cccggaggaa gcaagggcac ccgccacatg gatggaattg 32820
aggggaaggc acccggggct cctgcatcga gcttccctcc tatattcaat gaggaaatga 32880
ccctgcagaa ggctggctgc agatgcccct gcctcccggc tttgcctgct tggagtttga 32940
tggacacgtg gtcctgtcag ggctacagca ggtctatggt ctttggtaac ggaaagcgct 33000
ggtgaaacag tgagctttcc cgtgggtgct tttccctgac gccaacaacc aggtaaatat 33060
ttggaaacgg ccttgttgag gcttgtgagg tggttttcct ccctcccctg taggcctgcg 33120
ccaccccccc aaccccacgg ccacctttgg gccagatggc acccacagac ctgtttgaag 33180
tggccacaga gggagccctc tgggcgctgg ggccgctgtg tttgcagagg gtcctcttac 33240
tgctgagctg gctggtgcag tgagaaggaa ggccgacacc cctgatcctc atcaagttca 33300
gacgggggtc actgcgggtg aggggcctgg ggccttttac atgtcccggg agctgctgag 33360
caggccactc ttctccaggc caccagaact tggccctgcg catggtgaat cttccctgag 33420
tcagctgagt gagggggttc aggcagcccc ccgggacatg gcagtggcgg ggagtggact 33480
ggggtggtgc ttgccatgac tcacgccggt tctcctcagg caaccggatg gtcagatgcg 33540
ctgactcagt ggcctgagct cgtccaaaag cgaatcagag aacacagggc ctgggctcac 33600
ccgctgccct cttctggagt catctgtcac tcatcctcat gaaggaagcg cctgggagcc 33660
tggaatgcac atcgcactgc cccagctccc ctcttgtttc tgtgtttttc cattttggat 33720
tctttccccc aacgccttct gtactgggca ttttgtggtc tcttcttttt ctccgagaac 33780
tctgagggct accattgcat ttgctaatga tgccacagac ggtgttgacg ttatgaggct 33840
tctattactg tattgatttt taccattttt agggggacgg gaatcaatat ttcatgaggg 33900
aatgtgaagc cagacagtga agtagaagct ggcttttatt ttgtgccagg ctttgtccag 33960
aggcgggtgg ggacgtggct cctaagctct tgattgcagc tccttctggc ttgggaaacg 34020
tttcagttcc ccaaactctc agaactggat cccctgtgtg ttctctggcc cggattcaag 34080
aacttagttg attgtcaagg aaattctttg gctatatttt tctcttaata tggtaatgcc 34140
tttttcact ctggcactct cttttcaggg aattggatta agactattat ttatgggtct 34200

-continued

```
gacaaagcag ttcccaagtt gttgggactg gatttgttta ggaatgtctc ctgtcctctt  34260
cattgagggg ggaatacaaa ttgcttccat ttgacagttt atcaagtgtg tgacagagta  34320
tcagagtcca gggttggcca actacagcca gtagtccaaa gctggccctc tgttgttgta  34380
aataaagttt tattgggaca tggtcatgct cacttattta ggtagagtgt atggctgcat  34440
tcagtctaca ccagcagagt taaatagttg tgatgaagac cacgtggccc gtgaagccaa  34500
aaatatttgc ttcctggccc tttacaggaa aaaaattccc agccccagtg gcaggcaatt  34560
aacaccttgt cctcgaggag ctgaaagtgg ctggaggcag gaatgcttat aagaaccaag  34620
cgaggtgaag cactaggtgg ccgcggcgag caggaagaga agctgatttt gtttgccctt  34680
tcgtttgcca gagattgtgg gttctttttt tttttttttt tttttttttt tttttgcaga  34740
gatgaagctt tgatcttgtc acaatagcag agggaggcct tatttttgtc tatttctctg  34800
tgacattggt agaaaggact ttgtcagaat tccaagctat ttggcaatta tccaattttg  34860
agatcctaat ggatctttcg aggtctagtt tgttcattct tttagtgatt ccttgttaat  34920
tccctgattt tataaatgtg tgttgaacat ctgtcttggc caaatacttc ttaggtgctg  34980
aggatgcagc aatagtgggc aaagccatgg ggcttaagat ctagtgtggg aaatgggtga  35040
tgtaaagtaa atatggcgat aagtacagtg cacgaagcaa acaagtgaag ggtagaaggg  35100
tatcaggctg caaagacagc agatagtgta ggcagggaat cttatctgag ggggtgacat  35160
ctaagctgag atggaaagga cagtgagagc cagccaagga aacaagttgg gtgacaagag  35220
ttgcaggtgg agttgcttaa tttcccactt ctgctcagcc tgcagatcct ggatcttgga  35280
ctaattgcaa actgtcattt cctcgtgagt ttattagaac cctccagaac aagtttctgg  35340
ttagctagtt tctctgtgtg ttgtctcatt tcttgttggt tctggttctt tggggttcct  35400
actcatactc tggaaagctc cagtgtctta agtagtcagt ctcccaagag tctgaaagca  35460
caaagattca caatgatacg atcacctctc aatcatagca gcattgatgc agttccgtag  35520
ctggtttcct aaagccatcc agatctcttt ctgtggcaag agagaaataa gaccttctgg  35580
tgaattgagg actaattatc ctaataaaca tgcgaattaa cagttccttt ggttaaacaa  35640
agcaccagaa tctgataatg ggaacatgtg actcatggta tttccttctt tgctttatct  35700
accaggcagc tcacagaaac cactggcctt ccctgtgttc ccattttatg tcataaatat  35760
atatttaatt aacttattat aaaaggccct ttgttcattg accatatcaa attattctta  35820
tatagaagag gttatacatg ttttaaacat tttaaaataa atctgaaaag aatgctacat  35880
cctgggcaac ttccctgcat ttggggctca aagaagctct atgtggttat gggtaatgag  35940
gagccagagt gccttcaggg cagttcagca gatgctgaaa ggctgctgtg tgctgttcgc  36000
tgggcccacc aaatagagta ggactgagcc cctgtccacc atgacagccg ggagatacaa  36060
gctgttccct ttgcctccct gagccctgag ctttatagcc tatagacagc tgaaaagcag  36120
gctgcatccg ttacccagtc agttacccag acccaaatgc caggccttgg ctaaccccag  36180
ttattaccta attttaatat cccaatggat gttttaagac ctggctggtt cattctttca  36240
tttatttact tattcattga ttttgtaaat atttctggag catctgccat ggccacatgc  36300
tgttgtagca gcatcagcca ctctgaagtt ggtggatgaa aggggatgca tcaaaggcgc  36360
tgatgtatgg aggagacgca agttagactt gaccaagaca atattattcc tcctctggat  36420
gccccgaata tatacagtca ttagctgtcg ggcccccatg tggcactgtt gacattttgt  36480
ggtttaaaca ctgaagagta agggaatatt ggaaatggca aacatctgat atagtgtaaa  36540
ggagactaaa tattttgatg gtgttcataa acaccgagga ggaaagtctt ttcatttttt  36600
```

-continued tcatttgtgt gctctctctt tctctgtttt tgcacactgt cctctgttct ccttctcctt 36660
ctctttttcc ttttttctcc cttcatctcc ccatttatct gatctctccc acctgaaccc 36720
cttctaccct gctgccctcc tgtccattct accttctcta ctcccctccc tagacagtag 36780
taatcacatg tcagttggag aaacatgatg gcaacttggt cacaccgttc ttctcagtct 36840
gtatatgtcg gtgatctcag tgcccatctg gcagatcctt cctgccctgg ctcttctgct 36900
cactgcgacc acccttgact ttgtgatcac tgataacctt caccttctct aatctaaatc 36960
ccaagcttct cactcttggt ccaccacctc ccagccttgt ccgttctgaa ccctgaacgg 37020
aagctgaatg gaaccctgaa cggaagggtt ctgaagctgt tcagaaccct gaatggaagc 37080
tgaaatatca atgggccatt gcttttcaca gtcctctgtg aaagattact ggccaagcca 37140
gcatctggag aattcctggt ccaccacctc cctgtctgga gaagctggaa cagccagctg 37200
catgagcatg tgacccgtgt actcacaggc cctgtgccct gagctcgctg ttttaatttt 37260
atctttgaat ttgtattttt gtgaataaag ccctatgagc taatggagca tgctcaggga 37320
acttggggct ttagctcagg ctggattcct cctgctgcct ccccagtccc tggtcccctg 37380
agaactccag ccccatctga ccttcccttc cctgtctcta tgcaggggtc attgctaccc 37440
tctatccctg gaaaggatgt aggcacaggg cagttctagg ttccagcttg ggcaccgctt 37500
aacatcttgg tggtgcaggg atcaggctga tgataccgtg gttgttctgt gggctactgg 37560
gcagggtcaa gccactccca ccctgatcca ggtacctaat gcacccgaca cagaagcggc 37620
agtgtccttg ggtcatcca ttatccatgt gttggaggag tgggacccta gggaagatgc 37680
ttggctcgac ttccccaccc ctagccaggg cacaatcaga ggtccagggg ctggtgggca 37740
caatgccaag tcgtgaggcc tccagtgtct gcgctcactg tcccataaat aaccacagta 37800
ataactagca aatcaaaaac attgtgatag gtcgagagag acagcatgtg gaagaaagga 37860
aaaagctttc tattttagta cctttaacag tgctttctgt atgctttatg aacaaggagc 37920
ctgcattttt attttgcact gggctctgct aattttgtag ctggtcctgc cccctagtag 37980
ctcaagtcag caaatctttg gttcatctga gtccacagtc cgctgacccg ccctttttca 38040
cagttcctcc cctgcccatg tgctcacttc cctccttacc cagcttggcg cactccctca 38100
agcaagtctt tggatgctga catcccccgt aaacaaccct tctgcggcct ggtttgattt 38160
tccttaggag acatgcaagt tctatagcac tgtttcttgc tgggtatgga ggatgtgcta 38220
ttttgtccat tgcatatttt ttaaagaaaa tgaaaggtta gcataactgt ttccagaagg 38280
cacattgaat cactcagttg agtcccagcc agttgctgca atgttagcct ttgaagcaaa 38340
cttgaaccaa cacaggacca gcctagaagt cccagcctcc agaaatgatg cagtggattc 38400
tgcagattca gcaacaacaa tatttttgta actcaagagc acttagtaat tttcaaagga 38460
gagaaagaag taattgactt ggcttattag gttgaaaaag agttgccaac tttttctttg 38520
gttttgatgt tattggtttt tttttatttt tcttttctcc aagcttcagg gaatgagatt 38580
gaatgagcac tcaagtgcta ctaggcagaa ccctgaatgg aaggaagctg aaataccgat 38640
gggtcattgc ttttcacagt cctctatgaa agattactgg ccaagccagc atctggagaa 38700
ttctaggaac gccccctcct cttgcagcag tataagtttg cggggatcat ctgaccccat 38760
tggggagttg tatgaaaaag gggatttatt ggggaccctg ttgcctgttt ggatcttact 38820
tacatttaac tattgtctgc taatggattt tttggaaagc aaccaggttt tccgtaaaga 38880
atagctaatt gtcagagctg agatgaccat tggagatcac tgggctcaac tccctaattt 38940

-continued

```
tagaggtgct aaaaccgcaa tccagagaag ctaatcaagt ggttcaaggt tgtagactga  39000
gttcatatag gaccaagacc cagcccagat gtcctactgt ctgggacagt gttctctcag  39060
catacgtgga gcctgagggg gtaatgtgtg tgcgtgtgtg tgcatgtatg catatacaca  39120
taggtgtttt gcctaagttt tcacttctgc cccaccttgg ttgatcttgg agaatgagcc  39180
tgaggcgcgc tgtcaacctg gggcctcat tcagcacagg cccaactttt ctgccctggg  39240
ggagttccag cagttatggt tcatctgtgg ttcagttatg gaactcacac cacacatagt  39300
gcccccaaaa ccgaggctgc gtgcacagac ctcccctccc ttcccgtggt gggcccctgc  39360
ttgggttctt cctaaacttc ccctttgccc tgctctgtgt tataccctct ctggtcccct  39420
gtccctgtgg agtgatccgg ggcacaaggg cagctgtttc cccgctgacc tctgtgtgcc  39480
ctgagcatct gggaggtggg gagcaggctg gtgagaagaa cacctggagt ggaggttggg  39540
gtcagggagg gtcccagtcc cggtaccacc cccacctgct gtgggacctg cagtcccctc  39600
atcagcagaa cggctatgaa gccatcctgc ccatccacag ggtggtgggt cgtgaaggct  39660
gcatacctgg cagagcggga gaagctctgg gaagatgccg gacacgcgcc gtgggagtga  39720
tttccctgcc ttgcccagat tctgctccca tcacctgaac ctgcctgtca ccaccatgga  39780
actgctgtga ccattgcttt ccttttaagc agattagcag acatctcctg ctccaccctg  39840
ccaaacaaac aaacaaacaa gcaaacaaac aaacaaaaat gtgcatgagg gagtatggac  39900
ttgtagagtc ttttctaaac attgttaggt gcttgtattg ggatcctctc ttaaaatgaa  39960
ccatattccc caggctttgg atgacactca tggttgccca ccctccaact tccttccctg  40020
ctggcagagc cctgggtttg ttttagttcc aaccctgacc ccaccgcatt cctgactcag  40080
gcaaattcgc agggtccaat gcagtcaggg gagccacgtt ccctcctcca acgagtgctg  40140
aggtcgctgc ttgattggat actgccgatg acctacgagg aggagggtgc cagggcgctt  40200
ttgggacttt gcttttctgg agagatgctt ccacagcatg gtcatggaca cagtcacgtc  40260
ttgatgtgat gtctggaatg gtggtggccg tcttgtggct gtgagaacag gctgaggttg  40320
attggatgga gggaaggaag gagccttgtt cttgatgctg tctgtgagcc tttgagttat  40380
cagcctggta ccacccagcc cttggacaga tatctactct acatactcca tttggagttt  40440
tttttttttt tttttttttt tttttttttt gtcacttgca gttgaaaaca ccctaattga  40500
tacacacaaa ctatttttag tgctggtctg tgtttggccc ttatggaaga ctctgggctg  40560
agctgcccat ggtgagggag gtggactttg tgttttctta ctgctctgtg tcctggtggc  40620
ttgtttgtgt ctctgcccat gagacaaaag ccgagagggc aagggcagat tttcttaatc  40680
atatgttccc tgcaccaagc tcataggaga cactcactga atggttgttg agagagttct  40740
ctttcacgga ggcaatgttt tgtgaaacga tgctgcttgt tgttgtctgt tggttgtaat  40800
atgcatgaac actaagagcc atctttaatc atgctgtggg ccgcctcttc caaggtgtta  40860
gcattactcc cactacctgg tcagcatcct gcctatggct aggactttgc aatttacata  40920
gatatggtgg ggagacctgg agcccatggc caggactctg acaccctcac tggatctgtt  40980
tctacatcta cctggatggc cgtctaggac attagaggat ttgtgtcttc ctaaagtccc  41040
tctgttgaga gacttctggc tctgttaaga ggacactatt tagcattgtg agtccctgca  41100
ggctgggggc cagtgggcgt ttttcttcta gatgcccccct ctcttcttct ggcctcccag  41160
gcttcctgct cctgagattg tgagaactgg cctgtgctgg gctcactgca gaaagactgt  41220
cgtccccaaa ggttttgcac caaacttgag ctacaagatc ttttaggggg acctgagatc  41280
tccgcctggg ctctatgaga gcaggcatgg gttgtttttg ccccgtcact gcagtcatgc  41340
```

ccacacttgc atttcttttt ccccccagca gtgtgaggat ctggcatgag gagtgggact 41400
cgcgtgccct ctttcttctc ctcttccctc tggccttttc atccgtcagt gggggacaga 41460
tgtttgccct gtttacttct aggcttactg tggggctcca gggagatggt gaagtggcca 41520
aggagaggag ctgccacctt caagacggcc tgtggccggt gccgctttaa agggagactc 41580
agaggtgctt tgctgtgggt ggcgcgggaa ccagcctggg gacagcagtg cagaggcctt 41640
ggactcagag tgcgtgggcc ccgcggggct tcacggcgcc tgtggctgtg cacttccagc 41700
catatctgtg ctgcatctct tccacattcc cccatggagc tgatgtctag acagctatgg 41760
aattaaatgc tcaattaccg agtaggaatt tggccagcag aggtatagct gctgagtaga 41820
cagactcgag gtgaggctca cggctgagaa caggccccat ctggctttgg aatgagctga 41880
ggtgccccgat gctcctgcag ccagtggctc ctgtggggag ctggggccgt gacccccaaa 41940
aggcagcttg acctcatgga ccaccataaa tctggcctgg tcaacatctc tgccagacat 42000
cattcccttg caaagatttc tgcctgtgat tggaattctg gatgaacatg tactgggcgt 42060
gtgggtctga cagctgggaa gcttgttctc ttgtttagcc aggctgccca tcatctgtaa 42120
gcctcagtat ccacatcttt aaaatggggg gaaaatatag ctcaactcct aatggtgcca 42180
tgagaatact ttgtcacctg ccaggcaaaa gcttattcct ttcacagaaa tccagggttt 42240
acaatgtgag acccctcccc actccgccgc atgtgtctgc ttgctttttt ctgtcttagg 42300
gttgcccttc atgagctagg aaatgtctga gtggatgaaa acctaaacga gatgatcact 42360
ggtggtgccc attggtgcag cctttgccta aatggctact tacgtagcca catttcctcg 42420
tctgtgttca ggtgaggact ggttcctggg cagactgcct gggtttgcat cacgggtgtc 42480
catcttgtcg aagcccatgt ggtcacccaa gtgtgactga gccaggcttg cccacggggt 42540
gctctgggcc ccattttcgg cagcaggcag cgtcccctgg aggcctggcc ctccccggga 42600
gcatggggag tagcgcctat gggcaagcag cctgcagcct ccatccctgc ctgggggctc 42660
ccccgcccca gcctcacagc ttctccaaaa gtgtttgtct ccttgccgca tcctctaggc 42720
ctgagctcag acggtggaaa agaagagctg gaaggagagt tgcctttcag tctctctgcc 42780
ttctgaggtc tcctgagaca tagagcctgg gcctgcctcc ctttctagga ggcgccaagg 42840
ggtggtaaga ataggggatg agtgagatgt gaattaggat ccccacagca agccctgcct 42900
cgtaactttc tgatgggttt tcaatgtgtg gtgaagcaga cgcctgctgg gccccccttcc 42960
tgagttgagt ttgacctcct gcctcctgtc tatctccttg ggcagccagg ccaccccgct 43020
ccattaacct gtgccacccc atccctttac ctgtcgcaag cccagccctg aaggcctcaa 43080
aggcctggtc ttccagccag tccagggcct gaagggatgg cagtgtccct ggtggacctc 43140
ccctggtgtg gcctagtgca catcccagcc ctgcctcctg ccccgcctgc acgccatgag 43200
tgctgaagtc atgcctggca ggggctgctg gcccaggccc agagtaaaca cactgcgctg 43260
agctcgctgg tgtgctgctg gatgctgatg agcttgagga gtgtgggaag tgagcatggg 43320
gctgagtaga gatgcggcag gcctgcacct ccccgcagct gccctgcatg ctccagcctc 43380
aggcagccac acagggaaag ggtcacccac tgtcagggca gacctttacc atggctgggt 43440
gacacgggct ggctgtggaa aggtgtttgg tggttcccgc tgttggattt gcacaggccc 43500
agatgctcac agcaaaacca acacctagat ggtgcttaca ggagccagcg ggtattcaaa 43560
gagctgttca gatcttaagt tgcttcattc tcacagtgga ccattgaggt agctgtacgt 43620
tagtcccatt ttccagatga gaaaactgag gacctgagtg gtcataagct caggccctca 43680

-continued tctaaatcac gcagcctggc cccaggtgtg tgctcttgac catggacagt gctctcctgg 43740
tcctcttggt atctgtgatc tgagggacct tcctcctcct cagtctcgta tagtcagttt 43800
taggtcttgg actctgtctt catatccctt tctcccttcg tgagctttct cacccagcac 43860
cttccttatt tggtgtgtgt tgggggatat ttgtggtgtg gcgtggcact gtgtagtgga 43920
tgagagagtc tgtttttccg atcccagtcc caggtttcaa accctgctct gtctcgagtc 43980
acccagaatc ttggaccctc agtttcctca tctgttaaat gggcatggtg gtcaccccac 44040
ctcatcagct agtgtctgct ccatccctgg tggaggagat gactcaagta acccctgggt 44100
tccacctgcc ccaccccact ggtcccctgg ctctttcttt gttgagatag acgaatgtga 44160
ggctctggag ttgcagttcc cacgagggct ggggtggctg tctgatttct gggcctggtc 44220
catgttgttc agggcagctg ctcgttctaa gtgaataaag gctgaaggaa ctcgggaggt 44280
ctgctcggct ccgaggaagg cagagaggga aagggccccg atgccttccc tgatagagct 44340
agggaggccc ttctgtggtt ccccccagct ccttggcctg ggtgaccctg gagctggctt 44400
ctgttccatt ttgttgtgca gagttgtttg agactcctgg ctttgcctgg cctttgtggg 44460
acgctggaga tcagggcttc tggagttggc caattagcct gcccagacca ggaagcacag 44520
gtggctgaca gagggccgtt tcaggagagg agagacagcc tacctattcg gtcttgctgt 44580
ccccatgctc catccctgcc cctgaccagt gtggccctgt actcagcata ggcgtgcacc 44640
tgagtcagta cagttccctg cccgcagagc accccaaata ttccaggcct caggacggat 44700
gtgcacatga tgagtcgggg caggtttcac tgcctgtagc ttgggatcct tccctggggc 44760
ttggttctct agggccatcc ccagcagtct caccccaaac cctaaattca tgttgtcttc 44820
ctctgtctct tggcctcaag gtttcagagt gagtctgtgc tgatagcttc aagatgtgat 44880
gagaccccga cttggcctcc agttacctcc ccacggtttc cttggtgtgt gtgtggcttc 44940
agtgttcact ggctcccgca cggcttgcaa tgtgtggatt acgggtggga gggaaatcca 45000
gtcctgcccg cagcaaaggg atgttagttg tgagctcagt tccccaccgg gcctggtgtt 45060
tccaaatagc ccgtcactgt ccctgcttgg ttttccatga tatctgtgcc tttacctatt 45120
tggttaaatt aaaccaactc agcaacgcca gccattgtgg tttcagggca agctgcctgt 45180
cctgctgctt ggccgctcct cagagctgcg gccgggagag ttcgtggtcg ccatcggaag 45240
cccgttttcc cttcaaaaca cagtcaccac cgggatcgtg agcaccaccc agcgaggcgg 45300
caaagagctg gggctccgca actcagacat ggactacatc cagaccgacg ccatcatcaa 45360
cgtgagcctc tgtccctctg cgggtgggga ttggggcaga gttttgccag ggggagagga 45420
gtcagcatag gtcttagccc ctgactttgt tgtagtctgc gtgaagggat ggaactagac 45480
caagccatgt ggattctagt gccagcagca tggcaggggt cacatggcgg ggacggtgac 45540
accggagcag gtggacagcc agcctcctcc caggaggaag aagttgtatt gggtgcttta 45600
gggtgattgc agttggcttc tgggcttcag agagaaaatc tccctgttta cggcacctct 45660
aaaactttct gaaaattgtt aaggtcattt ttttccggca aaatattagg ttaatgggaa 45720
tgaatctcag agaagaatcg tgccccccac tctaggcacc gtgctcagga aacgaccagg 45780
cagggacata gattgaacca tgttatgaca cgatttgtaa ccttttcatt tctgtttaat 45840
tgcagtatgg aaactcggga ggcccgttag taaacctggt aaggtctttt aaacctatgt 45900
taggtcattt gtttttatct atgtatacgc tgttttttgt ttgtttgttt gttgtttgtt 45960
tgtttttgag gcagggggtc ttttcaaaca taaggttgcc aaagtgtatt ataaattcct 46020
ttaaaatggc tctgtaaatg tactgcgtgc ttgcaaatga ccctacggat cttttctgga 46080

-continued

```
aagagtaagg caggccggag gtgagggttg gaaatgttat gccagagaac acacttgtgt  46140
ctcagagtta caggtaaaca ccgtgaaatt cagggccaat gcaggagtaa ggtgaaggtc  46200
actaaaaatg ctggccagtc accgaaagca cctcctccaa attaaatctc ctgggctgct  46260
gaaggagctg gctgggctca tacacatttt ctcttggcca ggaatcctcc cttaaggcct  46320
ggctggaatg aggaggagtt acccacccac aaagatatca cttaagtctt cccttaaata  46380
cttgagcaga aaaagtgaag ccttagaaca cagaccagca gagctagagg gcagctctgg  46440
ggccatttat agagggcagc tctggggcca tttatagagg gcagctctgg ggccatttat  46500
aggggctgtc tttagcaagg cccagtgtga tggcacctcc tagatggtgc cttggcatca  46560
ggtactgaca tctcagcact cctgggaagt gtgcacttgg cagctttctc ttcccagcag  46620
aggggcagct gtgctcccag ctctgtcctc tgcctccccg cgcagcactt ggggatggag  46680
tggagatggc tttgctggta atgaagcatg acagccctaa gctctagggt tgtttccccc  46740
tgaagtcagc agagtcatct taagatcatt agacatggga gaagcaggaa ggtgtgggca  46800
gccacctaaa ggagtttgag cctttggaaa cgtattcctt gtgaaacagg agcaaatcat  46860
atcgtgcatt ttgaaactat ctgtgcttac cgtgaggtga gcacccagtg ccgacctgga  46920
gtatgtgcga ttcttccaca gctgcgcgtg gctcgcgctg cctgggtgtc ctgatgcctc  46980
tctccctgct gccacgggga tcccctcctt gcatctcccc acttcgatct ctgaaatagc  47040
tcagggactt ctttcaggca tattctctct gggtgtgtac ctgccggtaa agcttcacga  47100
ttcagtaagc cgtgtccttc ttgcttttca ggacggtgaa gtgattggaa ttaacacttt  47160
gaaagtgaca gctggaatct cctttgcaat cccatctgat aagattaaaa agttcctcac  47220
ggagtcccat gaccgacagg ccaaaggtag gcaaggccca cacagccctg gggactccgg  47280
agatggggcc tgaagctcag ctgccctttg ggacttgggg aagggaaaag cggcagcccc  47340
taggactagc caagccgtct ctgatccaga agtgaacggg aatgcacatt actaaatccc  47400
tcgcagaagg tcacagacat ttcaccattt ttgtcctctg atcatggcaa tgtcacttga  47460
gtcagtctaa tatgtaccag gcatgatcct aggtgacttg tgtacattat ttcactttct  47520
ttatgtatgt cacttaattc ttttgcccta tcagttagga attactagtc ccattttgct  47580
gatgagaaaa cggttcaggg agatcattct gcaaacgttt attgccccat ctgctctaag  47640
tcaagcaggg agcttggcag tggacagctc aactggggcc tggggctcaa caggggcctt  47700
tgccggtgtg acttttatgt tctgttgggg gatgggaagg ctgacagtaa ataatcaaac  47760
acataagata ctattagtgc tcccaagaaa acggatcagg gtggccgtca agggagcgac  47820
tggaggggca gctggtggag atggtgtggc caggaaatgc cttccaagct gaggtctgag  47880
tgaggaggaa ccagcgggca gggatgtggg gggaacactc cagaaggaaa gacagaggac  47940
tcagcatagt tgagtgagca caaggcccct gaagtggcct gagggccgga gcacagtgac  48000
agcatggagt tccccggggt ggaaagaggc caaggccggg cgagcaggct cacagcaggc  48060
cgtggtgagg gacctgggtt gcatcctaac gacatttaag aacagggaag tttatgatct  48120
gattgatgtc actgaaagga cactctgatg gctgcgggga gtctgctgga ggggttgctg  48180
gaagttgggg accggttaag gggctctccc agccatctgg atgagacatg ctggggtctc  48240
agacaagggt ggtggcagtg gaggtgggac agaggggtca cattccagat atatatgggg  48300
ggtagagcaa gcttggggaa gggccagctg tcaggatgag gccatgagga attaagggtc  48360
atgcccaggt acctgaccat taattgaaac aatgggactt tcccaaggtc ccccagaggg  48420
```

-continued

```
gaggggtcca gaccaggatt tgagccgcaa cctcagtgta cccttctgtg gcccttcctg  48480
caacctgggg gattgggccc ccggcccctg gtgtccccag caccccccacc aactgggctg  48540
accttctgct gtccctttgt tgtctcacca ggaaaagcca tcaccaagaa gaagtatatt  48600
ggtatccgaa tgatgtcact cacgtccagg tgggtaaaca ggatgcgtgt ctgtgtctta  48660
aattttaata aacctgaact tcagaaggtg ctcacgggca cccctgaaag agaaacctta  48720
tgctgcctta agacgtctca gtttctgctt ataatgaagt agcatcggga aagaggacag  48780
gtcattagcc ttggcccctt tgtttggttt taacctgtgt tttgcattc tgagctggtt  48840
ttcttcactg gcagcaggcc ctccggtgta gaaggttctg ccctcctctt tgaaggcagg  48900
cctgaacagt gtgtgcgtgg tggggctgtt gattcactct ggctcacgtc ttccttaccc  48960
cacattctgt tgaaacccac attccaggag ggccccaagc cctcccgca gctctaggca  49020
ctctgctttc gttgctctgc agctcgtggg ccgcggctcc aggaatgcca gggcaggtcc  49080
agcgcaggga agtgaatgac tgatgtgctt gttttccccg agctggtgga attgcggcct  49140
gtggttggca ggctcatggc atcctggtgt tctaaactgg atgaaaaatt ctggtgtaat  49200
ctcatgagtc ctggtagtag actcacctgg catggctaaa actgtcagag gtaaagtagg  49260
taaagactag aatatagtaa cagatagatt aatgtgttca ttactatgat gaattaatga  49320
ttcactcact gtgaaagtat taatatattt tgatacatgt tatgaatggt ggtccctttc  49380
ttagcactcc agaagatgga gccatttgtc aaggttaaag tgtcccctca gttgtttgcc  49440
tttggaacta cgaggtgtag ggaaagatgg taagcccttg gtgcccagct tcctgggttc  49500
ctgtccctgc tctgatatgt cctgccttgt gaccttggga acgatatgac ccctgagtgc  49560
ctcagtttcc tcctcttcag gatagggatg acagcgcagg tgcttctgat gtgtggccag  49620
gctcagatca gggagtggtg gcaggggtca ccagccacag tgatgccagc cactatgtat  49680
cacacgtact gggccaggtg ccttactggg atgatctcat ctgatcctca caactcatgt  49740
tgtagggtac tgttattatc cccattttgc aggtgaggaa atgaaggcac agagaagtta  49800
agcaactgtc cgaggtcaca cagctagcaa atggccgagc tagggctgca aaccaggcca  49860
accactgtac tttactgact ccttagtaat agctactatt aattaagaaa taataacaat  49920
gatgatggct gggtgcggtg gctcacatct gtaatcccag cactttggga ggccaaggcg  49980
ggcagatcac ttgaggccag gagttcgaga ccagcctggc caatttgtga aaccctgttt  50040
ctactaaaaa tataaaaaat tagccgggct tggtggcagg cacctgtaat cccagctact  50100
cgggtggctg aggcaggaga attgcttgaa cccgggatat gtaggttgca gtgaactgag  50160
atcgtaccac tgcactccag cctgggcgac agagcaagac tctgtctcaa aaaaaaaaaa  50220
ataaataaaa aaaataaata aataataaag cactttcctt gctgttacca agtaaatctt  50280
tgactctggt agacaggcaa ttttaatttt aaaataggat cagaattcct ggaggaattt  50340
taccttagac ctaaggagaa gacgggaact ggtgagagct gagttttgcg tgaggaaggc  50400
ctggtgtttc ttcacactaa cacgggtgct ttttctctgg agcagcaaag ccaaagagct  50460
gaaggaccgg caccgggact tcccagacgt gatctcagga gcgtatataa ttgaagtaat  50520
tcctgatacc ccagcagaag cgtgagttgg agtcgttttc tcttttccca atattcttgt  50580
tgttcctgtg gggtagcag gaagagggag cgctgttcct tttctactgg ctcagatgat  50640
tatgttgatc cttgacagac gtggtcggac gttgcttgtc attcctgctg gccaggcctt  50700
ccgacctggc tcggctcggg actcatccat aggagggtgc cttctgtctt caaaagtcct  50760
tgctccacga ggaccctcca gatggacaga gcaatagcag actcgtaatg agtctctgag  50820
```

-continued

```
atggcccggc tggccagaga gagggtttca ggaacagtgt ccccaagccc tcacttggtg  50880
gtccttttct aggcttcagg acccttctct tcctggagtc ttccagaatg tctctgacaa  50940
ttaggcccat acctgtcaac acctccagaa aaataaccca agtgatatca aagtaacatg  51000
acaagaagta gctcaaccat ccatcagggt ttgttacctg tattggcgga atatccagag  51060
aaaagtgcga gaccagggac cagcaaatgt gccttggggg ctggatctgg cccactgcct  51120
gcttttatat ggagctgtgg gctaagaata gtttttgcat tttattttta tttttactta  51180
ttttttattt tcataggttt ttgggggaac aggtggtatt tggttacatg agtaagttct  51240
ttggtggtga tttgtgaggt tttggtgcac ccatcaccca agcagtgtac actgaaccca  51300
atttgtagtc ttttatccct catccctgtc ccagcctttc cccttgagtc cccagagtcc  51360
attgtatcat tcttatgcct ttgtgtcctc gtagcttagt tcccacttat gagaacattt  51420
aaatggttga aaaaatcctg aaataagaat agtattttgt gacatgttaa atttgtatga  51480
aattcaaatt tcagtgtcca ctgtaatttg gtttatgaca tctatggtgg cttttgtgct  51540
ggaacagcag agttgagtag cttcaacaga gaccatatgt actgcaaagc ctaaaatatt  51600
tcctatggag ccctttacag aaaaagtttg cagacccttg tgctagccca tgaaggacca  51660
tgacagcgtt ttgacgctga gctatataag agctacagtt atagtggcaa ccacacaaag  51720
gaagtgcctc ttaacagaaa cattccgccc accoctatag gaactgcatt ctgagttgca  51780
atacccatta taagcaagtt ggccagatag tggccaacta tctggcagat atctggccaa  51840
ctacgtggca gatagtacct ggtacatcct tccccacttt ggggtcaatc ttgacctttg  51900
atctccttgg ggtcataaag ccacacaagt gttagtaggc atttctacag tggacacaat  51960
ggatgattta gcctaaaaat ctcaaaagga gcccagcatc ctggcacatg catgtaatcc  52020
cagctactca ggaggctgaa gcagaaggat cccttgagcc caggagttcg agactagctt  52080
gggcaacaat tgagacccca tctcaaaaaa aaaaaaaaaa aaaaaaaaag agtggggaaa  52140
aaagaacatt attaaaaaaa aaaaccttaa aaagtaatcc aatctaccga tggtttattt  52200
tttattttat tttatttttt ttgagatgga atcccactct gtcacccagg ctggagtgca  52260
gtggcacaat cttggctcac tgcaacctcc acctcctggg ttcaagtgaa tctcttgcct  52320
cagcctctga gtagctggga ttacaggtgc ccaccaccaa acctggctct tttttttttt  52380
ttttttgtaa ttttagtaga gacggggctt caccatgttg gccaggctgg tcttgaactc  52440
ctgacctcag gtgatccacc tgcctcagcc tcccaaagtg ctgggattac aggcatgagc  52500
caccgtgcct gacccactga tggtttgaat tattctaagt tcgccaccgt ccaatcctgt  52560
ttgctctggg cttttaggtt ctaagctgtg cctctgtcca tgtaaagtca gaccaggagg  52620
aatggaaaca cgaaacattg ccattgtgtt tccctttgtg ttgcagtggt ggtctcaagg  52680
aaaacgacgt cataatcagc atcaatggac agtccgtggt ctccgccaat gatgtcagcg  52740
acgtcattaa aagggaaagc accctgaaca tggtggtccg caggggtaat gaagatatca  52800
tgatcacagt gattcccgaa gaaattgacc cataggcaga ggcatgagct ggacttcatg  52860
tttccctcaa agactctccc gtggatgacg gatgaggact ctgggctgct ggaataggac  52920
actcaagact tttgactgcc attttgtttg ttcagtggag actccctggc caacagaatc  52980
cttcttgata gtttgcaggc aaaacaaatg taatgttgca gatccgcagg cagaagctct  53040
gcccttctgt atcctatgta tgcagtgtgc tttttcttgc cagcttgggc cattcttgct  53100
tagacagtca gcatttgtct cctcctttaa ctgagtcatc atcttagtcc aactaatgca  53160
```

-continued

```
gtcgatacaa tgcgtagata gaagaagccc cacgggagcc aggatgggac tggtcgtgtt  53220

tgtgcttttc tccaagtcag cacccaaagg tcaatgcaca gagaccccgg gtgggtgagc  53280

gctggcttct caaacggccg aagttgcctc ttttaggaat ctctttggaa ttgggagcac  53340

gatgactctg agtttgagct attaaagtac ttcttacaca ttgc                  53384


<210> SEQ ID NO 11
<211> LENGTH: 18
<212> TYPE: DNA
<213> ORGANISM: artificial
<220> FEATURE:
<223> OTHER INFORMATION: Oligonucleotide sequence motif

<400> SEQUENCE: 11

caaatattta cctggttg                                                   18


<210> SEQ ID NO 12
<211> LENGTH: 16
<212> TYPE: DNA
<213> ORGANISM: artificial
<220> FEATURE:
<223> OTHER INFORMATION: Oligonucleotide sequence motif

<400> SEQUENCE: 12

tttacctggt tgttgg                                                     16


<210> SEQ ID NO 13
<211> LENGTH: 18
<212> TYPE: DNA
<213> ORGANISM: artificial
<220> FEATURE:
<223> OTHER INFORMATION: Oligonucleotide sequence motif

<400> SEQUENCE: 13

ccaaatattt acctggtt                                                   18


<210> SEQ ID NO 14
<211> LENGTH: 20
<212> TYPE: DNA
<213> ORGANISM: artificial
<220> FEATURE:
<223> OTHER INFORMATION: Oligonucleotide sequence motif

<400> SEQUENCE: 14

ccaaatattt acctggttgt                                                 20


<210> SEQ ID NO 15
<211> LENGTH: 18
<212> TYPE: DNA
<213> ORGANISM: artificial
<220> FEATURE:
<223> OTHER INFORMATION: Oligonucleotide sequence motif

<400> SEQUENCE: 15

atatttacct ggttgttg                                                   18


<210> SEQ ID NO 16
<211> LENGTH: 16
<212> TYPE: DNA
<213> ORGANISM: artificial
<220> FEATURE:
<223> OTHER INFORMATION: Oligonucleotide sequence motif

<400> SEQUENCE: 16

tatttacctg gttgtt                                                     16
```

-continued

<210> SEQ ID NO 17
<211> LENGTH: 16
<212> TYPE: DNA
<213> ORGANISM: artificial
<220> FEATURE:
<223> OTHER INFORMATION: Oligonucleotide sequence motif

<400> SEQUENCE: 17
atatttacct ggttgt 16

<210> SEQ ID NO 18
<211> LENGTH: 17
<212> TYPE: DNA
<213> ORGANISM: artificial
<220> FEATURE:
<223> OTHER INFORMATION: Oligonucleotide sequence motif

<400> SEQUENCE: 18
atatttacct ggttgtt 17

<210> SEQ ID NO 19
<211> LENGTH: 11
<212> TYPE: DNA
<213> ORGANISM: artificial
<220> FEATURE:
<223> OTHER INFORMATION: Oligonucleotide sequence motif

<400> SEQUENCE: 19
tttacctggt t 11